United States Patent
Kerber et al.

(10) Patent No.: US 9,220,771 B2
(45) Date of Patent: Dec. 29, 2015

(54) PEPTIDE FOR USE IN THE TREATMENT OF BREAST CANCER AND/OR BONE METASTASES

(75) Inventors: Anne Kerber, Langen (DE); Tobias Baeuerle, Heidelberg (DE)

(73) Assignee: MERCK PATENT GMBH, Darmstadt (DE)

( * ) Notice: Subject to any disclaimer, the term of this patent is extended or adjusted under 35 U.S.C. 154(b) by 93 days.

(21) Appl. No.: 13/810,593

(22) PCT Filed: Jul. 8, 2011

(86) PCT No.: PCT/EP2011/003429
§ 371 (c)(1),
(2), (4) Date: Jan. 16, 2013

(87) PCT Pub. No.: WO2012/007137
PCT Pub. Date: Jan. 19, 2012

(65) Prior Publication Data
US 2013/0115210 A1  May 9, 2013

Related U.S. Application Data

(60) Provisional application No. 61/364,900, filed on Jul. 16, 2010.

(51) Int. Cl.
| | | |
|---|---|---|
| *A61K 39/395* | (2006.01) | |
| *A61K 38/12* | (2006.01) | |
| *A61K 45/06* | (2006.01) | |
| *A61K 33/24* | (2006.01) | |
| *C07K 7/64* | (2006.01) | |
| *A61K 31/4188* | (2006.01) | |
| *A61K 31/475* | (2006.01) | |

(52) U.S. Cl.
CPC ....... *A61K 39/39558* (2013.01); *A61K 31/4188* (2013.01); *A61K 31/475* (2013.01); *A61K 33/24* (2013.01); *A61K 38/12* (2013.01); *A61K 45/06* (2013.01); *C07K 7/64* (2013.01)

(58) Field of Classification Search
None
See application file for complete search history.

(56) References Cited

U.S. PATENT DOCUMENTS

| 5,866,540 | A  * | 2/1999 | Jonczyk et al. | 514/21.1 |
| 2007/0155750 | A1 * | 7/2007 | Neamati et al. | 514/249 |
| 2009/0226431 | A1 * | 9/2009 | Habib | 424/133.1 |

FOREIGN PATENT DOCUMENTS

WO  WO 2010/136108 A2  12/2010

OTHER PUBLICATIONS

Bäuerle et al., "Cilengitide inhibits progression of experimental breast cancer bone metastases as imaged noninvasively using VCT, MRI and DCE-MRI in a longitudinal in vivo study," *Int. J. Cancer*, 128:2453-2462 (2011).
Bradley et al., "Cilengitide (EMD 121974, NSC 707544) in asymptomatic metastatic castration resistant prostate cancer patients: a randomized phase II trial by the prostate cancer clinical trials consortium," *Invest New Drugs*, 29:1432-1440 (2011).
Bretschi et al., "Cilengitide inhibits metastatic bone colonization in a nude rat model," *Oncology Reports*, 26:843-851 (2011).
Burke et al., "Cliengitide Targeting of $\alpha_v\beta_3$ Integrin Receptor Synergizes with Radioimmunotherapy to increase Efficacy and Apoptosis in Breast Cancer Xenografts," *Cancer Research*, 62:4263-4272 (Aug. 1, 2002).
Cheng et al., "Evaluation of treatment response of cilengitide in an experimental model of breast cancer bone metastasis using dynamic PET with $^{18}$F-FDG," *Hellenic Journal of Nuclear Medicine*, 14(1):15-20 (2011).
Eskens et al., "Phase I and pharmacokinetic study of continuous twice weekly intravenous administration of Cilengitide (EMD 121974), a novel inhibitor of the integrins αvβ3 and αvβ5 in patients with advanced solid tumours," *European Journal of Cancer*, 39:917-926 (2003).
International Search Report, International Application No. PCT/EP2011/003429 (published as WO 2012/007137 A1), 8 pages (Oct. 31, 2011).

* cited by examiner

*Primary Examiner* — Thomas S Heard
(74) *Attorney, Agent, or Firm* — Ronald J. Kamis; Debora Plehn-Dujowich

(57) ABSTRACT

The invention relates to the use of the Peptide of the formula Cyclo-(Arg-Gly-Asp-DPhe-NMe-Val) and/or the pharmaceutically acceptable derivatives, solvates and/or salts thereof, for the manufacture of a medicament for the treatment of breast cancer and/or bone metastases in humans, wherein the medicament is optionally to be used in combination with one or more cancer cotherapeutic agents, preferably selected from a) hormone modulating agents, b) osteoclast activity modulating agents, c) cancer chemotherapeutic agents, and/or d) radiotherapy, alone, concurrently or not in the dosage regime of the present invention.

13 Claims, 29 Drawing Sheets

Fig. 6A, B. Quantification of histological analysis. Values of fractional mean area stained for smooth muscle actin (SMA) and collagen IV (Col. IV) are expressed as percent total area examined (A), while the blood vessel diameters are presented as mean values in μm (B). Error bars, SEM; *, $p<0.05$; **, $p<0.01$.
548x152mm (72 x 72 DPI)

Dark square represents survival of non irradiated animals.

NSCLC (A549)

Squares – Chemotherapeutic alone
Triangles – Chemotherapeutic plus Cilengitide 6 uM constant Squares – Chemotherapeutic alone
Triangles – Chemotherapeutic plus Cilengitide 0.2 uM constant Cilengitide in combination with paclitaxel on NSCLC cell line Calu 6

Cilengitide in combination with Vinblastine/Paclitaxel on NSCLC cell line H460

Serially dilute Vinblastine/Paclitaxel (squares) in presence of 10 uM cilengitide (triangles)

5-FU or Paxlitaxel on Renal cell line ACHN; Cilengitide constant at 2 µM

5-FU or Paxlitaxel on Renal cell line A498; Cilengitide constant at 2 µM

5-FU or Paxlitaxel on Renal cell line Caki 1; Cilengitide constant at 2 µM

Serially dilute 5-FU/Paclitaxel (squares) in presence of Cilengitide (triangles)

Etoposide

Etoposide $1 \times EC_{50} = 1$ uM
Cilengitide $1 \times EC_{50} = 4$ uM
Values used to generate constant ratio curve shown above

Isobologram Etoposide

Combination Index = 0.2

● Dm for the Combination

Dm for the single agents:
  Cilengitide = 11 uM
  Etoposide = 1.6 uM

Dm = drug concentration at median effect according to CalcuSyn software analysis

Figure 29
Fig. 29 A
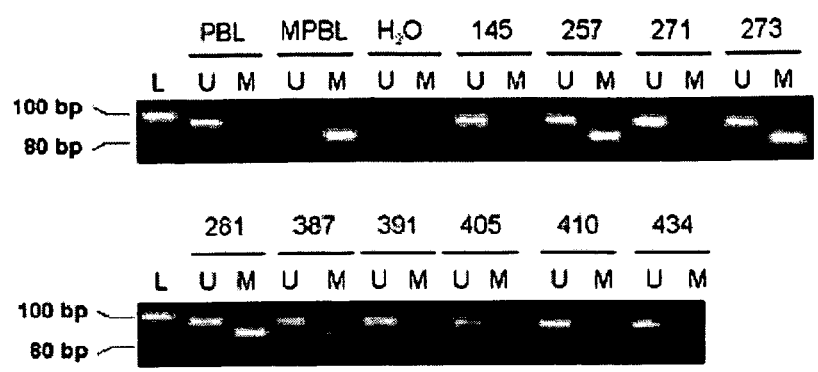
Fig. 29 B
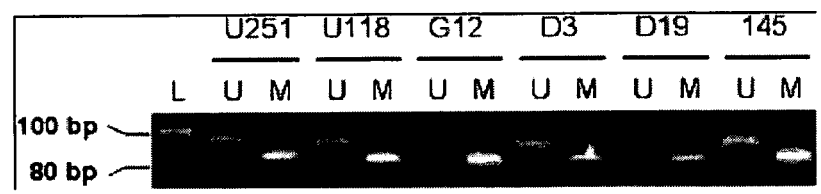

PEPTIDE FOR USE IN THE TREATMENT OF BREAST CANCER AND/OR BONE METASTASES

This application is a 371 national stage entry of International Application No. PCT/EP2011/003429 filed Jul. 8, 2011, which claims the benefit of U.S. Provisional Application No. 61/1364,900 filed Jul. 16, 2010, each of which applications is herein incorporated by reference in its entirety.

INCORPORATION OF SEQUENCE LISTING

This application contains a sequence listing submitted electronically via EFS-web, which serves as both the paper copy and the computer readable form (CRF) and consists of a file entitled "09097-8028.U.S.00$_{13}$seqlist.txt", which was created on Jan. 9, 2013, which is 4,096 bytes in size, and which is herein incorporated by reference in its entirety.

TECHNICAL FIELD OF THE INVENTION

The invention relates to a specific therapy form for the treatment of cancer, especially tumors (or tumours) and tumor metastases, comprising the administration of a Peptide of the formula Cyclo-(Arg-Gly-Asp-DPhe-NMe-Val) and/or the pharmaceutically acceptable dervatives, solvates and/or salts thereof for use in the treatment of breast cancer and/or bone metastases in humans, optionally together with cancer cotherapeutic agents or other cancer cotherapeutic therapy forms that preferably enhance, additively or synergistically, the efficacy when administered together with said Peptide, such as chemotherapeutic agents, immunotherapeutics, including antibodies, radioimmunoconjugates and immunocytokines and or radiation therapy. More specifically, the instant invention relates to the use of at least one Peptide of the formula Cyclo-(Arg-Gly-Asp-DPhe-NMe-Val) and/or the pharmaceutically acceptable dervatives, solvates and/or salts thereof, for the manufacture of a medicament for the treatment of breast cancer and/or bone metastases in humans, wherein the medicament is optionally to be used in combination with a) hormone modulating agents,
b) osteoclast activity modulating agents,
c) cancer chemotherapeutic agents, and/or
d) radiotherapy. Additionally, the instant invention relates to methods of treatment, using said medicament. Preferably, the administration of the medicament can be done in a timely controlled manner. The therapy using one or more cancer cotherapeutic agents or other cancer cotherapeutic therapy forms will preferably result in a synergistic potential increase of the inhibition effect of each individual therapeutic on tumor cell and tumor endothelial cell proliferation, preferably yielding a more effective treatment than found by administering an individual component alone, together or in another therapy regime but the regime of the present invention.

Preferably, said Peptide of the formula Cyclo-(Arg-Gly-Asp-DPhe-NMe-Val) and/or the pharmaceutically acceptable dervatives, solvates and/or salts thereof are preferred examples of the term "specific integrin ligand" as used herein.

BACKGROUND OF THE INVENTION

Vascular endothelial cells are known to contain at least three RGD-dependent integrins, including the vitronectin receptors $\alpha_v\beta_3$ or $\alpha_v\beta_5$ as well as the collagen types I and IV receptors $\alpha_v\beta_1$ and $\alpha_2\beta_1$, the laminin receptors $\alpha_6\beta_1$ and $\alpha_3\beta_1$, and the fibronectin receptor $\alpha_5\beta_1$ (Davis et al., 1993, J. Cell. Biochem. 51, 206). The smooth muscle cell is known to contain at least six RGD-dependent integrins, including $\alpha_v\beta_3$ and $\alpha_v\beta_5$.

Inhibition of cell adhesion in vitro using monoclonal antibodies immunospecific for various integrin α or β subunits have implicated the vitronectin receptor $\alpha_v\beta_3$ in cell adhesion processes of a variety of cell types including microvascular endothelial cells (Davis et al., 1993, J. Cell. Biol. 51, 206).

Integrins are a class of cellular receptors known to bind extracellular matrix proteins, and mediate cell-extracellular matrix and cell-cell interactions, referred generally to as cell adhesion events. The integrin receptors constitute a family of proteins with shared structural characteristics of non-covalenty associated heterodimeric glycoprotein complexes formed of α and β subunits. The vitronectin receptor, named for its original characteristic of preferential binding to vitronectin, is now known to refer to four different integrins, designated $\alpha_v\beta_1$, $\alpha_v\beta_3$, $\alpha_v\beta_5$ and $\alpha_v\beta_8$. $\alpha_v\beta_1$ binds fibronectin and vitronectin. $\alpha_v\beta_3$ binds a large variety of ligands, including fibrin, fibrinogen, laminin, thrombospondin, vitronectin and von Willebrand's factor. $\alpha_v\beta_5$ binds vitronectin. It is clear that there are different integrins with different biological functions as well as different integrins and subunits having shared biological specificity and function. One important recognition site in a ligand for many integrins is the Arg-Gly-Asp (RGD) tripeptide sequence. RGD is found in all of the ligands identified above for the vitronectin receptor integrins. The molecular basis of RGD recognition by $\alpha_v\beta_3$ has been identified (Xiong et al., 2001) This RGD recognition site can be mimicked by linear and cyclic (poly)peptides that contain the RGD sequence. Such RGD peptides are known to be inhibitors or antagonists, respectively, of integrin function. It is important to note, however, that depending upon the sequence and structure of the RGD peptide, the specificity of the inhibition can be altered to target specific integrins. Various RGD polypeptides of varying integrin specificity have been described, for example, by Cheresh, et al., 1989, Cell 58, 945, Aumailley et al., 1991, FEBS Letts. 291, 50, and in numerous patent applications and patents (e.g. U.S. Pat. Nos. 4,517,686, 4,578,079, 4,589,881, 4,614,517, 4,661,111, 4,792,525; EP 0770 622).

The generation of new blood vessels, or angiogenesis, plays a key role in the growth of malignant disease and this has generated much interest in developing agents that inhibit angiogenesis.

Nevertheless, although various combination therapies utilizing potential angiogenesis inhibitors are under investigation, in clinical trials and on the market, the outcome of these therapies are not fruitful enough. Therefore, there still exists a need in the art to develop further combinations which can show increased efficacy and reduced side-effects.

It is known today that tumor vasculature is different from vasculature of healthy tissue. The vasculature is characteristic for the tumor and distinct from the stable, dormant vasculature of healthy tissue. It is often characterized by an increased expression and priming of specific cell adhesion molecules of the alpha-v-integrin series especially $\alpha_v\beta_3$ and $\alpha_v\beta_5$. When activated these integrins enhance the cellular response to growth factors that drive angiogenesis, for example VEGFA and FGF2: VEGFA was originally termed vascular permeability factor, and it acts via the SRC kinase pathway to increase local vascular permeability. VEGRF2, when activated, increases the activity of $\alpha_v\beta_3$ integrin.

Further, solid tumors depend on an induced and cooped vasculature from the host to develop. This vasculature has unusual molecular properties that distinguish it from the normal host vasculature: it tends to be activated, i.e. progressing through cell cycle under the influence of tumor-derived factors like VEGFs, FGFs and others, and expresses endothelial activation markers like ICAM, VCAM and alpha-v-series Integrins, e.g. $\alpha_v\beta_3$ and $\alpha_v\beta_5$, in a ligand competent state. It has a defective extracellular matrix, and is classically described as leaky. It is notable that tumors often resist therapies systemically applied via the blood stream, due to abnormal nature of tumor vasculature.

The metastatic process is a multistep event and represents the most dreadful aspect of cancer. At the moment of diagnosis, cancers are frequently far advanced in their natural history, and the presence of metastases is a common event. In fact, approximately 30% of patients have detectable metastases at the moment of clinical diagnosis and a further 30% of patients have occult metastases. Metastases can be disseminated and they can infest different organs at the same time, or localize to a specific organ. In the case of localized disease, surgery is the treatment of choice; however recurrence and prognosis depend on many criteria such as: resectability, patient's clinical situation, and number of metastases.

After resection, recurrence is common, suggesting that micrometastatic foci are present at the moment of diagnosis. Systemic chemotherapy is an ideal setting but only few patients are cured by it, and in the majority systemic chemotherapy fails. Many physiological barriers and pharmacokinetic parameters contribute to decrease its efficacy.

Liver, lungs and lymph nodes are filtration organs and therefore inclined to metastasization. The poor chemosensitivity of metastases, peculiarly those of colorectal origin has forced many researchers to use methods for increasing the time and the concentration of drugs. The need for decreasing or limiting the side effects for this important and delicate organ led to the development of the technique of liver isolation for perfusion of antineoplastic agents. (K. R. Aigner, Isolated liver perfusion. In: Morris D L, McArdle C S, Onik G M, eds. Hepatic Metastases. Oxford: Butterworth Heinemann, 1996. 101-107). Since 1981, modifications and technical improvements have been continuously introduced. Liver metastases may be of different origin and their chemosensitivity may vary according to the histological type and their response in presence of heat.

There still exists a growing need in the art in order to develop new therapeutics trategies for treating cancer, especially metastases systemically. The object of the present invention therefore was to develop such a new strategy. It should be applicable to systemic treatment, and it should lower the dose and/or increase the efficiency of the cancer therapeutical agents to be applied. A further object was to normalize tumor vasculature to increase delivery of systemic therapeutics of tumor, i.e. to reset the tumor vasculature to the functionality of the vasculature of non-tumor tissue.

Thus, it is a preferred objective of the instant invention to provide a more effective, better tolerated treatment for humans, especially human cancer patients suffering from breast cancer and/or bone metastases, preferably breast cancer and/or bone metastases independent from their origin, thus preferably leading to enhanced overal survival (OS), progression-free survival (PFS), quality of life (QOL) and/or increased median survival.

SUMMARY OF THE INVENTION

The present inventions preferably describe for the first time a novel pharmaceutical treatment which is based on a new concept in breast cancer and/or bone metastases therapy to administer to an individual in a therapeutically effective amount a specific integrin ligand which is the Peptide of the formula Cyclo-(Arg-Gly-Asp-DPhe-NMe-Val) and the pharmaceutically acceptable dervatives, solvates and/or salts thereof, optionally in combination with one or more specified chemotherapeutic agents and/or cancer cotherapeutic agents as described herein. Advantagously, this can preferably be done according to one or more of the regimens as described herein.

Thus, subject of the instant invention is the use of Peptide of the formula Cyclo-(Arg-Gly-Asp-DPhe-NMe-Val) and the pharmaceutically acceptable dervatives, solvates and/or salts thereof for the manufacture of a medicament for the treatment of breast cancer and/or bone metastases, wherein the medicament is optionally to be used in combination with one or more cancer cotherapeutic agents other than said Peptide, said cancer cotherapeutic agents preferably being selected from the group consisting of:

a) hormone modulating agents,
b) osteoclast activity modulating agents,
c) cancer chemotherapeutic agents, and
d) radiotherapy, and methods of treating breast cancer and/or bone metastases using said medicament. Said hormone modulating agents, osteoclast activity modulating agents and/or cancer chemotherapeutic agents are preferably as described below.

Surprisingly, it can be shown that the tumor vasculature can be functionally normalized by systemically applied Peptides of the formula Cyclo-(Arg-Gly-Asp-DPhe-NMe-Val) and the pharmaceutically acceptable dervatives, solvates and/or salts thereof as defined herein. Said Peptide and/or the pharmaceutically acceptable dervatives, solvates and/or salts thereof preferably increase the amount of cancer cotherapeutic agents as described herein and especially the amount of cancer cotherapeutic agents selected from the group consisting of hormone modulating agents, osteoclast activity modulating agents and cancer chemotherapeutic agents, entering the tumor. Said hormone modulating agents, osteoclast activity modulating agents and/or cancer chemotherapeutic agents are preferably as described below. In addition, the Peptide and/or the pharmaceutically acceptable dervatives, solvates and/or salts thereof can preferably be shown to enhance the numbers of leukocytes entering the tumor following systemic immunocytokines therapy, and may directly or indirectly increase the amounts of antibodies entering the tumor compartment on anti-tumor antibody therapy, or increase access to anti-tumor vaccines.

Furthermore, it is believed that this functional normalization of the tumor vasculature will lead to changes in the metabolism of the tumor, e.g. a higher oxygen concentration in the tumor, and thus allows oxygen dependent therapies, like external beam radiotherapy, to become more effective. The increased local amount of the cancer cotherapeutic agents is believed to help to overcome tumor resistance mechanisms, and enhances therapeutic index.

In one embodiment the present invention relates to a composition comprising as the cotherapeutic agent therapeutically active compounds, preferably selected from the group consisting of cytotoxic agents, chemotherapeutic agents and immunotoxic agents, and as the case may be other pharmacologically active compounds which may enhance the efficacy of said agents or reduce the side effects of said agents.

According to the present invention therapeutically active compositions may also be provided by means of a pharmaceutical kit comprising a package comprising at least a Peptide of the formula Cyclo-(Arg-Gly-Asp-DPhe-NMe-Val) and/or the pharmaceutically acceptable dervatives, solvates and/or salts thereof, and one or more cancer cotherapeutic agents, preferably as described herein, e.g. hormone modulating agents, osteoclast activity modulating agents and/or cancer chemotherapeutic agents as described herein, in single packages or in separate containers. The therapy with these combinations may include optionally further treatment with radiation. Said hormone modulating agents, osteoclast activity modulating agents and/or cancer chemotherapeutic agents are preferably as described below.

The invention relates furthermore to a new therapy form for treating breast cancer and/or bone metastases in humans, comprising the administration of a Peptide of the formula Cyclo-(Arg-Gly-Asp-DPhe-NMe-Val) and/or the pharmaceutically acceptable dervatives, solvates and/or salts thereof prior to or after radiotherapy, preferably prior to radiotherapy.

In this new therapy form for treating breast cancer and/or bone metastases in humans comprising the administration of a Peptide of the formula Cyclo-(Arg-Gly-Asp-DPhe-NMe-Val) and/or the pharmaceutically acceptable dervatives, solvates and/or salts thereof prior to radiotherapy, it is a preferred feature that said Peptide and/or the pharmaceutically acceptable dervatives, solvates and/or salts thereof is administered prior to the further cancer cotherapeutic agent. In this context, according to the present invention, radiation, or, radiotherapy has to be understood as a cancer cotherapeutic agent.

Generally, this prior application takes place 1 to 8 hours (h), preferably 1 to 5 h, and more preferably 1 to 3 h before the application of the further cancer cotherapeutic agent. Even more preferably, this prior application takes place 2 to 8 hours (h), preferably 2 to 6 h, and more preferably 2 to 4 h before the application of the further cancer cotherapeutic agent, such as 1 to 2 h, 2 to 3 h, 3 to 6 h, 2 to 5 h or 3 to 7 h before the application of the further cancer therapeutic agent. With respect to the invention, this prior application or administration is also referred to as "timed administration" or "timed application".

As is shown by the data contained in this application, the effect according to the invention is achieved in non-human animals, especially rats, if this prior application preferably takes place 1 to 8 hours (h), preferably 1 to 5 h, and more preferably 1 to 3 h before the application of the further cancer cotherapeutic agent; and even more preferably this prior application takes place 2 to 8 hours (h), preferably 2 to 6 h, and more preferably 2 to 4 h before the application of the further cancer cotherapeutic agent, such as 1 to 2 h, 2 to 3 h, 3 to 6 h, 2 to 5 h or 3 to 7 h before the application of the further cancer therapeutic agent. With respect to the invention, this prior application or administration is also referred to as "timed administration" or "timed application".

However, the data from experiments with human animals preferably shows that the time of the above/below described and discussed "prior application" can be delayed or multiplied by the factor 1 to 4 and especially 2 to 4. This difference in the response or response time between non-human animals, especially rodents, such as rats, and human animals is known and extensively discussed in the art. While the applicant wishes not to be bound by this theory, he believes that this difference is at least in part caused by the different pharmacokinetic behavior of the different species, which i. a. reflects in different halflives ($t_{1/2}$) in the different kinds of animals. For example, for compounds such as cyclopeptides, the halflives in rats usually are in the range of 10-30 minutes, whereas the halflives in human animals for the same compounds are within 2 to 6 hours and especially 3 to 4 hours.

Accordingly, a subject of this application is a method of treatment and/or a method of manufacture as described above/below, wherein the prior application preferably takes place 1 to 32 hours (h), preferably 2 to 32 h, more preferably 2 to 24 h, even more preferably 4 to 24 h, even more preferably 6 to 20 h and especially 6 to 16 h, before the application of the further cancer cotherapeutic agent; or alternatively preferably this prior application takes place 6 to 32 hours (h), preferably 10 to 24 h, and more preferably 12 to 20 h before the application of the further cancer cotherapeutic agent. With respect to the invention, this prior application or administration is also referred to as "timed administration" or "timed application"

A further subject of this application is a method of treatment and/or a method of manufacture as described above/below, wherein the prior application preferably takes place 18 to 23 h hours (h), preferably 20 to 23 h, more preferably 20 to 22 h before the application of the further cancer cotherapeutic agent; or alternatively preferably this prior application takes place 25 to 32 h hours (h), preferably 25 to 30 h, and more preferably 26 to 30 h before the application of the further cancer cotherapeutic agent. With respect to the invention, this prior application or administration is also referred to as "timed administration" or "timed application"

However, in a more preferred aspect of the instant invention, the timed administration (regardless of whether the patient is a human or nonhuman animal) of the specific integrin ligand takes place 1 to 10 hours (h), preferably 2 to 8 h, more preferably 2 to 6 h, even more preferably 3 to 8 h, even more preferably 3 to 6 h and especially 4 to 8 h prior to the application of the one or more cancer cotherapeutic agents, e.g. 1 to 2 h, 1 to 3 h, 1 to 4 h, 2 to 3 h, 2 to 4 h, 2 to 6 h, 2 to 8 h, 2 to 10 h, 3 to 4 h, 3 to 10 h, 4 to 6 h, 4 to 10 h, 5 to 8 or 5 to 10 h. This is especially preferred if the one or more cancer cotherapeutic agents comprise external beam radiation or consist of external beam radiation. With respect to the invention, this prior application or administration is also referred to as "timed administration" or "timed application".

With respect to said timed administration or timed application (of said Peptide and/or the pharmaceutically acceptable dervatives, solvates and/or salts thereof), the hours given for said prior administration or application preferably refer to the beginning or start of the respective administration or application. Accordingly, for example, an administration of the specific integrin ligand starting three hours before the application of the respective cancer cotherapeutic agent is to be regarded as a timed administration or timed application 3 h prior to the application of the one or more cancer cotherapeutic agents according to the invention, even if the specific integrin ligand is administered by i. v. Infusion that takes an hour or two hours to be completed. This definition of prior application/prior administration is in perfect concordance with the understanding of the ones skilled in the art.

If said Peptide and/or the pharmaceutically acceptable dervatives, solvates and/or salts thereof is administered to the patient in a timed administration as described herein, it is preferably timed with respect to the one or more cancer cotherapeutic agents it is combined with. With respect to the timed administration of said Peptide and/or the pharmaceutically acceptable dervatives, solvates and/or salts thereof in combination with two or more cancer cotherapeutic agents, it is preferably timed with respect to the two or more cancer cotherapeutic agents, more preferably timed with respect to at least one of the cancer cotherapeutic agents. If the one or more cancer cotherapeutic agents comprise radiotherapy, especially radiotherapy as described herein, the timed administration preferably refers at least to the radiotherapy.

Especially preferably, the timed administration of said Peptide and/or the pharmaceutically acceptable dervatives, solvates and/or salts thereof refers to radiotherapy as the time-relevant cancer cotherapeutic. Accordingly, in the timed administration, the prior administration of said Peptide and/or the pharmaceutically acceptable dervatives, solvates and/or salts thereof preferably refers to a time prior to the administration of radiotherapy. However, in many cases, it can be advantageous also to administer the one or more further cancer cotherapeutic agents other than radiotherapy within the time window given by the timed administration of said Peptide and/or the pharmaceutically acceptable dervatives, solvates and/or salts thereof and the administration or delivery of the radiotherapy.

More preferably, the timed administration of said Peptide and/or the pharmaceutically acceptable dervatives, solvates and/or salts thereof refers to the administration of said Peptide and/or the pharmaceutically acceptable dervatives, solvates and/or salts thereof and of the radiotherapy, and the additional cancer cotherapeutic agent is preferably administered after the administration of said Peptide and/or the pharmaceutically acceptable dervatives, solvates and/or salts thereof, such as 1 to 2 or 1 to 3 hours after the administration of this Peptide and/or the pharmaceutically acceptable dervatives, solvates and/or salts thereof, but preferably before the administration or delivery of the radiotherapy, preferably at least within one hour before the administration or delivery of the radiotherapy, and more preferably at least 1 hour before radiotherapy, for example 1 to 2 or 1 to 3 h prior to the administration or delivery of the radiotherapy.

It should be understood, however, that the administration of any combination of the present invention can optionally be accompanied by radiation therapy, wherein radiation treatment can preferably be done after the administration of said Peptide and/or the pharmaceutically acceptable dervatives, solvates and/or salts thereof. The administration of the different agents of the combination therapy according to the invention can optionally also be achieved substantially concurrently or sequentially.

It is known that tumors elicit alternative routes for their development and growth. If one route is blocked they often have the capability to switch to another route by expressing and using other receptors and signaling pathways. Therefore, the pharmaceutical combinations of the present invention may block several of such possible development strategies of the tumor and thus preferably provide various therapeutic benefits. The combinations according to the present invention are preferably useful in treating and preventing tumors, tumor-like and neoplasia disorders and tumor metastases, more preferably tumors, tumor-like and neoplasia disorders of the breast and tumor metastases, even more preferably tumors, tumor-like and neoplasia disorders of the breast and tumor metastases thereof, and especially such which develop and grow by activation of their relevant hormone receptors which are present on the surface of the tumor cells. Preferably, the different combined agents of the present invention are administered at a low dose, that is, at a dose lower than has been conventionally used in clinical situations. A benefit of lowering the dose of the compounds, compositions, agents and therapies of the present invention administered to an individual includes a decrease in the incidence of adverse effects associated with higher dosages. For example, by the lowering the dosage of an agent described above and below, a reduction in the frequency and the severity of nausea and vomiting will result when compared to that observed at higher dosages. By lowering the incidence of adverse effects, an improvement in the quality of life of a cancer patient is expected. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects. Alternatively, the methods and combination of the present invention can also maximize the therapeutic effect at higher doses.

Tumors, preferably such which show an increased expression and priming of specific cell adhesion molecules of the alpha-v-integrin series, especially $\alpha_v\beta_3$ and $\alpha_v\beta_5$ in their vasculature, may be successfully treated by the combinations and therapeutic regimen according to the invention. The combinations within the pharmaceutical treatment according to the invention preferably show an astonishing synergetic effect. In administering the combination of drugs real tumor shrinking and disintegration could be observed during clinical studies while no significant adverse drug reactions were detectable.

Further embodiments of the present invention preferably relate to:

A method for the production of a medicament for the timed and combined use as a combination therapy for the treatment of cancer, the medicament comprising, preferably in two distinct (discrete) application forms, a composition containing at least one specific integrin ligand, and a composition containing one or more alkylating chemotherapeutic agents, and optionally at least one further cancer cotherapeutic agent different from the at least one specific integrin ligand of a) and from the one or more alkylating chemotherapeutic agents of b).

A method for the treatment of cancer in a subject, comprising a) administering to the subject at least one specific integrin ligand, b) administering to the subject one or more alkylating chemotherapeutic agents, and optionally c) administering to the subject at least one further cancer cotherapeutic agent different from the at least one specific integrin ligand of a) and from the one or more alkylating chemotherapeutic agents of b).

A said medicament or method, wherein the at least one integrin ligand is selected from the group consisting of $\alpha_v$ integrin inhibitors, preferably $\alpha_v\beta_3$ inhibitors, most preferably cyclo-(Arg-Gly-Asp-DPhe-NMeVal), the pharmaceutically acceptable dervatives, solvates and/or salts thereof. A said medicament or method, wherein the at least one cancer-cotherapeutic agent is selected from the group consisting of chemotherapeutical agents, cytotoxic agents, immunotoxic agents and radiotherapy.

A set for the treatment of breast cancer and/or bone metastases in humans comprising independent dosage forms of:

a) a therapeutically effective amount of the Peptide of the formula Cyclo-(Arg-Gly-Asp-DPhe-NMe-Val) and/or the pharmaceutically acceptable dervatives, solvates and/or salts thereof, more preferably of cyclo-(Arg-Gly-Asp-DPhe-NMeVal), b) and optionally one or more cancer cotherapeutic agents selected from the group consisting of:
 i) hormone modulating agents,
 ii) osteoclast activity modulating agents,
 and/or
 iii) cancer chemotherapeutic agents, optionally wherein a) is to be administered 1 to 8 hours (h), preferably 2 to 7 h, and most preferably 1 to 3 h prior to the application of at least one cancer cotherapeutic agent according b). Said hormone modulating agents, osteoclast activity modulating agents and/or cancer chemotherapeutic agents are preferably as described below.

Said set is further characterized in that it will be advantageous to give detailed instructions to and how to use said Peptide and/or the pharmaceutically acceptable dervatives, solvates and/or salts thereof, and/or detailed instructions to and how to use the one or more cancer cotherapeutic agent, in connection with said Peptide and/or the pharmaceutically acceptable dervatives, solvates and/or salts thereof, preferably in form of a specific packaging, specific package inserts and similar.

Therefore, a further preferred embodiment of the present invention is a medicament consisting of said Peptide and/or the pharmaceutically acceptable dervatives, solvates and/or salts thereof, as one active ingredient, designed for use in the treatment of breast cancer and/or bone metastases in humans, optionally for use in combination with a further cancer cotherapeutic agent, preferably prior to the further cancer cotherapeutic agent, e.g. in the case of radiotherapy, and contained in a container or similar, the container giving in form of writing detailed instructions and/or other technical information on how to use said medicament in said treatment and optionally how to use said medicament in combination with one or more cancer cotherapeutic agents, e.g. with respect to the above application schedule.

A further preferred embodiment of the present invention is the use of the Peptide of the formula Cyclo-(Arg-Gly-Asp-DPhe-NMe-Val) and/or the pharmaceutically acceptable dervatives, solvates and/or salts thereof, more preferably of cyclo-(Arg-Gly-Asp-DPhe-NMeVal) for the manufacture of a medicament for the treatment of cancer in humans, wherein the medicament is to be used in combination with one or more cancer cotherapeutic agents, preferably two or more cancer cotherapeutic agents, more preferably three or more cancer cotherapeutic agents, and especially in combination with one, two, three or four cancer cotherapeutic agents,
wherein the cancer cotherapeutic agents are selected from the group consisting of:
i) hormone modulating agents,
ii) osteoclast activity modulating agents,
and/or
iii) cancer chemotherapeutic agents.

In said embodiment, said hormone modulating agents, osteoclast activity modulating agents and/or cancer chemotherapeutic agents are preferably as described below. In said embodiment, said Peptide and/or the pharmaceutically acceptable dervatives, solvates and/or salts thereof, more preferably of cyclo-(Arg-Gly-Asp-DPhe-NMeVal), and the one or more cancer cotherapeutic agents are provided and/or formulated in(to) discrete application forms. In said embodiment, the cancer is preferably as described herein and more preferably selected from breast cancer, bone metastases, breast cancer and bone metastases thereof, bone metastases of breast cancer, bone metastases of solid cancers other than breast cancer, and myeloma and/or bone lesions thereof.

Another further preferred embodiment of the present invention relates the use of a pharmaceutical composition or a pharmaceutical kit as defined above, below and in the claims, for the manufacture of a medicament to treat breast cancer and/or bone metastases in humans.

The pharmaceutical treatment using the pharmaceutical compositions and kits according to the invention may be accompanied, concurrently or sequentially, by a radiation therapy.

The pharmaceutical combinations and methods of the present invention provide various benefits. The combinations according to the present invention are preferably useful in treating and preventing tumors, tumor-like and neoplasia disorders. Preferably, the different combined agents of the present invention are administered in combination at a low dose, that is, at a dose lower than has been conventionally used in clinical situations. A benefit of lowering the dose of the compounds, compositions, agents and therapies of the present invention administered to a mammal includes a decrease in the incidence of adverse effects associated with higher dosages. For example, by the lowering the dosage of a chemotherapeutic agent such as methotrexate, doxorubicin, gemcitabine, docetaxel, paclitaxel, bleomycin, cisplatin and/or Melphalan, a reduction in the frequency and the severity of nausea and vomiting will result when compared to that observed at higher dosages. Similar benefits are contemplated for the compounds, compositions, agents and therapies in combination with the integrin antagonists of the present invention. By lowering the incidence of adverse effects, an improvement in the quality of life of a cancer patient is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

BRIEF DESCRIPTION OF THE FIGURES

FIG. 29 A shows the methylation status of the MGMT promoter in GBM biopsy specimens, as determined by a nested methylation-specific PCR assay.

FIG. 29 B shows the methylation status of the MGMT promoter in GBM cell-lines, as determined by a nested methylation-specific PCR assay.

DETAILED DESCRIPTION OF THE INVENTION

Figure 1:
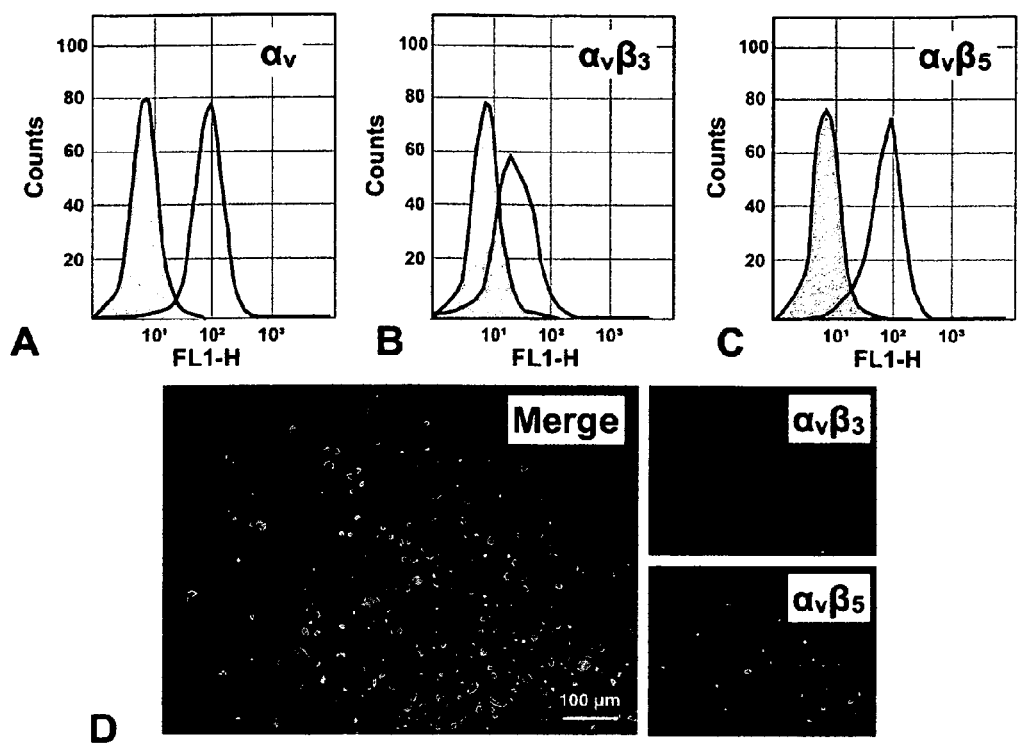
FIG. 1 consists of FIG. 1 A-D and shows expression of integrins of MDA-231 cells in vitro (A-C) and in bone metastases (D). MDA-MB-231 cells were stained with antibodies recognising the $\alpha v$ chains (17E6; A), $\alpha v\beta 3$ (LM609); B) or $\alpha v\beta 5$ (P1 F6; C) integrin complexes and expression was evaluated by flow cytometry (open curves), staining due to the second layer reagent was minimal (closed curves). The raw data curves have been smoothed for presentation. Immunohistology section (D) of the soft tissue component from a control animal staining for $\alpha v\beta 3$ (red), $\alpha v\beta 5$ (green) and DAPI (blue). A merged image ($\alpha v\beta 3$, $\alpha v\beta 5$, DAPI) is shown as well as single channels for $\alpha v\beta 3$ and $\alpha v\beta 5$. Bar, 100 µm. 539×396 mm (72×72 DPI). (See Example 1).

If not otherwise pointed out, the terms and phrases used in this invention preferably have the meanings and definitions as given below. Moreover, these definitions and meanings describe the invention in more detail, preferred embodiments included.

If not otherwise pointed out, the reference to a compound to be used according according tothe invention preferably includes the reference to the pharmaceutically acceptable derivatives, solvates and/or salts thereof. If not otherwise pointed out, the reference to the integrin ligands, integrin antagonists, integrin agonists, as well as the reference to the cancer-cotherapeutic agents that are compounds, preferably chemically derived compounds, preferably includes the pharmaceutically acceptable derivatives, solvates and salts thereof. Even more preferably, the reference to the integrin ligand cyclo-(Arg-Gly-Asp-DPhe-NMeVal) also includes the pharmaceutically acceptable dervatives, solvates and salts thereof, more preferably the pharmaceutically solvates and salts thereof and especially preferably the pharmaceutically acceptable salts thereof, if not indicated otherwise.

By "combination therapy" is preferably meant a combination of at least two distinct compounds, agents or therapy forms so combined as to form a single therapeutical concept, preferably in a consecutive and/or simultaneous manner. A combination therapy thus can comprise two or more compounds, agents or therapy forms, three or more compounds, agents or therapy forms, four or more compounds, agents or therapy forms, such as two, three, four, five or six compounds, agents or therapy forms, In a preferred embodiment of the present invention this means the combination of said Peptide and/or the pharmaceutically acceptable dervatives, solvates and/or salts thereof, with one, two, three or four, preferably one, two or three, further cotherapeutic agents. It is important to note that "combination therapy" preferably does not mean a distinct and/or single pharmaceutical composition or medicament. By way of contrast, in a preferred embodiment of the present invention said Peptide and the further cotherapeutic agent(s) are provided in discrete containers, packages, medicaments, formulations or equivalents. Equally, the combination of said Peptide with radiotherapy or radiation therapy preferably lies within the meaning of "combination therapy" of the present invention.

"Therapy forms" preferably are any means, uses and/or formulations for treating cancer known in the art. By the term "distinct therapy forms" therefore it is meant that two different means, uses and/or formulations for treating cancer are combined. In the context of the present invention it is preferred that the first to be applied therapy form has anti-integrin activity (synonym: integrin ligand) and is preferably said Peptide, and is applied prior to the second therapy form, preferably following the schedule as detailed above.

The term "composition comprising radiotherapy" preferably simply means that subsequent to said Peptide radiotherapy is applied. Therefore, the term "composition comprising radiotherapy" in the context of the present invention preferably does not apply to a pharmaceutical composition as such, but to a pharmaceutical composition to be used in combination with radiotherapy.

With "cancer-cotherapeutic agent" or "cancer cotherapeutic agent" preferably a cytotoxic, chemotherapeutical or immunotoxic agent is meant. more preferably, each cancer cotherapeutic agent for use according to the invention is independently selected from
i) hormone modulating agents,
ii) osteoclast activity modulating agents,
iii) cancer chemotherapeutic agents,
and/or
iv) radiotherapy.

Accordingly, a preferred example of a cancer cotherapeutic agent for use according to the invention is radiotherapy. The terms "cancer-cotherapeutic agent" and/or "cancer cotherapeutic agent" preferably also include targeted therapeutics, targeted specific therapeutics and/or targeted specific agents. However the terms "cancer-cotherapeutic agent" and/or "cancer cotherapeutic agent" as used herein are preferably different from the specific integrin ligands as described herein and thus preferably do not include such specific integrin ligands.

The terms "cancer-cotherapeutic agent" and/or "cancer cotherapeutic agent" as used herein are preferably different from the Peptide of the formula Cyclo-(Arg-Gly-Asp-DPhe-NMe-Val) and/or the pharmaceutically acceptable dervatives, solvates and/or salts thereof described herein and thus preferably do not include the Peptide of the formula Cyclo-(Arg-Gly-Asp-DPhe-NMe-Val) and/or the pharmaceutically acceptable dervatives, solvates and/or salts thereof ligands.

A "receptor" or "receptor molecule" is preferably a soluble or membrane bound or membrane associated protein or glycoprotein comprising one or more domains to which a ligand binds to form a receptor-ligand complex. By binding the ligand, which may be an agonist or an antagonist the receptor is activated or inactivated and may initiate or block pathway signaling. By "ligand" or "receptor ligand" is preferably meant a natural or synthetic compound which binds a receptor molecule to form a receptor-ligand complex. The term ligand includes agonists, antagonists, and compounds with partial agonist/antagonist activity.

An "agonist" or "receptor agonist" is preferably a natural or synthetic compound which binds the receptor to form a receptor-agonist complex by activating said receptor and receptor-agonist complex, respectively, initiating a pathway signaling and further biological processes.

By "antagonist" or "receptor antagonist" is preferably meant a natural or synthetic compound that has a biological effect opposite to that of an agonist. An antagonist binds the receptor and blocks the action of a receptor agonist by competing with the agonist for receptor. An antagonist is defined by its ability to block the actions of an agonist. A receptor antagonist may be also an antibody or an immunotherapeutically effective fragment thereof. Preferred antagonists according to the present invention are cited and discussed below.

The term "integrin antagonists/inhibitors" or "integrin receptor antagonists/inhibitors" preferably refers to a natural or synthetic molecule, preferably a synthetic molecule, that blocks and inhibit an integrin receptor. In some cases, the term includes antagonists directed to the ligands of said integrin receptors (such as for $\alpha_v\beta_3$: vitronectin, fibrin, fibrinogen, von Willebrand's factor, thrombospondin, laminin; for $\alpha_v\beta_5$: vitronectin; for $\alpha_v\beta_1$: fibronectin and vitronectin; for $\alpha_v\beta_6$: fibronectin). Antagonists directed to the integrin receptors are preferred according to the invention. Integrin (receptor) antagonists may be natural or synthetic peptides, non-peptides, peptidomimetica, immunoglobulins, such as antibodies or functional fragments thereof, or immunoconjugates (fusion proteins). Preferred integrin inhibitors of the invention are directed to receptor of $\alpha_v$ integrins (e.g. $\alpha_v\beta_3$, $\alpha_v\beta_5$, $\alpha_v\beta_6$ and sub-classes). Preferred integrin inhibitors are $\alpha_v$ antagonists, and in particular $\alpha_v\beta_3$ antagonists. Preferred $\alpha_v$ antagonists according to the invention are RGD peptides, peptidomimetic (non-peptide) antagonists and anti-integrin receptor antibodies such as antibodies blocking $\alpha_v$ receptors.

Exemplary, non-immunological $\alpha_v\beta_3$ antagonists are described in the teachings of U.S. Pat. Nos. 5,753,230 and 5,766,591. Preferred antagonists are linear and cyclic RGD-containing peptides. Cyclic peptides are, as a rule, more stable and elicit an enhanced serum half-life. The most preferred integrin antagonist of the invention is, however, cyclo-(Arg-Gly-Asp-DPhe-NMeVal) (EMD 121974, Cilengitide®, Merck KGaA, Germany; EP 0770 622) which is efficacious in blocking the integrin receptors $\alpha_v\beta_3$, $\alpha_v\beta_1$, $\alpha_v\beta_6$, $\alpha_v\beta_8$, $\alpha_{IIb}\beta_3$, and preferably especially efficacious with respect to integrin receptors $\alpha_v\beta_3$ and/or $\alpha_v\beta_5$. As is clear to the ones skilled in the art, the cyclo-(Arg-Gly-Asp-DPhe-NMeVal) can be also applied in the context of the instant invention in the form of a physiologically functional derivative, physiologically acceptable derivative, a solvate and/or a salt thereof. The same preferably also applies to all other compounds or active ingredients to be used in the context of the present invention.

The term "antibody" or "immunoglobulin" herein is preferably used in the broadest sense and specifically covers intact monoclonal antibodies, polyclonal antibodies, multi-specific antibodies (e.g. bispecific antibodies) formed from at least two intact antibodies, and antibody fragments, so long as they exhibit the desired biological activity. The term generally includes heteroantibodies which are composed of two or more antibodies or fragments thereof of different binding specificity which are linked together.

Depending on the amino acid sequence of their constant regions, intact antibodies can be assigned to different "antibody (immunoglobulin) classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$ and $\mu$ respectively. Preferred major class for antibodies according to the invention is IgG, in more detail IgG1 and IgG2.

Antibodies are usually glycoproteins having a molecular weight of about 150,000, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. The variable regions comprise hypervariable regions or "CDR" regions, which contain the antigen binding site and are responsible for the specificity of the antibody, and the "FR" regions, which are important with respect to the affinity/avidity of the antibody. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)) .The "FR" residues (frame work region) are those variable domain residues other than the hypervariable region residues as herein defined. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains. The "light chains" of antibodies from any vertebrate species can be assigned to one of two clearly distinct types, called kappa ($\kappa$) and lambda ($\lambda$), based on the amino acid sequences of their constant domains.

The term "monoclonal antibody" as used herein preferably refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well known recombinant DNA methods (see, e.g., U.S. Pat. No. 4,816,567). Monoclonal antibodies may also be isolated from phage antibody libraries using the techniques described in Clackson et al., *Nature*, 352:624-628 (1991) and Marks et al., *J. Mol. Biol.*, 222:58, 1-597(1991), for example. The term "chimeric antibody" preferably means antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g.: U.S. Pat. No. 4,816,567; Morrison et al., Proc. Nat. Acad. Sci., USA, 81:6851-6855 (1984)). Methods for making chimeric and humanized antibodies are also known in the art. For example, methods for making chimeric antibodies include those described in patents by Boss (Celltech) and by Cabilly (Genentech) (U.S. Pat. Nos. 4,816,397; 4,816,567).

"Humanized antibodies" preferably are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397). "Antibody fragments" preferably comprise a portion of an intact antibody, preferably comprising the antigen-binding or variable region thereof. Examples of antibody fragments include Fab, Fab', F(ab')$_2$, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3. Preferably, the intact antibody has one or more effector functions. Papain digestion of antibodies produces two identical antigen-binding fragments, called "Fab" fragments, each comprising a single antigen-binding site and a CL and a CH1 region, and a residual "Fc" fragment, whose name reflects its ability to crystallize readily. The "Fc" region of the antibodies comprises, as a rule, a CH2, CH3 and the hinge region of an IgG1 or IgG2 antibody major class. The hinge region is a group of about 15 amino acid residues which combine the CH1 region with the CH2-CH3 region. Pepsin treatment yields an "F(ab')2" fragment that has two antigen-binding sites and is still capable of cross-linking antigen. "Fv" is the minimum antibody fragment which contains a complete antigen-recognition and antigen-binding site. This region consists of a dimer of one heavy chain and one light chain variable domain in tigh, non-covalent association. It is in this configuration that the three hypervariable regions (CDRs) of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH1) of the heavy chain. "Fab" fragments differ from Fab fragments by the addition of a few residues at the carboxy terminus of the heavy chain CH1 domain including one or more cysteines from the antibody hinge region. F(ab')2 antibody fragments originally were produced as pairs of Fab' fragments which have hinge cysteines between them. Other chemical couplings of antibody fragments are also known (see e.g. Hermanson, Bioconjugate Techniques, Academic Press, 1996; U.S. Pat. No. 4,342,566). "Single-chain Fv" or "scFv" antibody fragments preferably comprise the V, and V, domains of antibody, wherein these domains are present in a Single polypeptide chain. Preferably, the Fv polypeptide further comprises a polypeptide linker between the VH and VL domains which enables the scFv to form the desired structure for antigen binding. Single-chain FV antibodies are known, for example, from Plückthun (*The Pharmacology of Monoclonal Antibodies*, Vol. 113, Rosenburg and Moore eds., Springer-Verlag, New York, pp. 269-315 (1994)), WO93/16185; U.S. Pat. Nos. 5,571,894; 5,587,458; Huston et al. (1988, Proc. Natl. Acad. Sci. 85, 5879) or Skerra and Plueckthun (1988, Science 240, 1038). "Bispecific antibodies" preferably are single, divalent antibodies (or immunotherapeutically effective fragments thereof) which have two differently specific antigen binding sites. For example the first antigen binding site is directed to an angiogenesis receptor (e.g. integrin or VEGF receptor), whereas the second antigen binding site is directed to an ErbB receptor (e.g. EGFR or Her 2). Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. Further methods are described in WO 91/00360, WO 92/05793 and WO 96/04305. Bispecific antibodies can also be prepared from single chain antibodies (see e.g., Huston et al. (1988) Proc. Natl. Acad. Sci. 85, 5879; Skerra and Plueckthun (1988) Science 240, 1038). These are analogues of antibody variable regions produced as a single polypeptide chain. To form the bispecific binding agent, the single chain antibodies may be coupled together chemically or by genetic engineering methods known in the art. It is also possible to produce bispecific antibodies according to this invention by using leucine zipper sequences. The sequences employed are derived from the leucine zipper regions of the transcription factors Fos and Jun (Landschulz et al., 1988, Science 240, 1759; for review, see Maniatis and Abel, 1989, Nature 341, 24). Leucine zippers are specific amino acid sequences about 20-40 residues long with leucine typically occurring at every seventh residue. Such zipper sequences form amphipathic α-helices, with the leucine residues lined up on the hydrophobic side for dimer formation. Peptides corresponding to the leucine zippers of the Fos and Jun proteins form heterodimers preferentially (O'Shea et al., 1989, Science 245, 646). Zipper containing bispecific antibodies and methods for making them are also disclosed in WO 92/10209 and WO 93/11162. A bispecific antibody according the invention may be an antibody, directed to VEGF receptor and αvβ3 receptor as discussed above with respect to the antibodies having single specificity.

"Heteroantibodies" preferably are two or more antibodies or antibody-binding fragments which are linked together, each of them having a different binding specificity. Heteroantibodies can be prepared by conjugating together two or more antibodies or antibody fragments. Preferred heteroantibodies are comprised of cross-linked Fab/Fab' fragments. A variety of coupling or crosslinking agents can be used to conjugate the antibodies. Examples are protein A, carboimide, N-succinimidyl-S-acetyl-thioacetate (SATA) and N-succinimidyl-3-(2-pyridyldithio) propionate (SPDP) (see e.g., Karpovsky et al. (1984) J. EXP. Med. 160,1686; Liu et a. (1985) Proc. Natl. Acad. Sci. USA 82, 8648). Other methods include those described by Paulus, Behring Inst. Mitt., No. 78, 118 (1985); Brennan et a. (1985) Science 30 Method: 81 or Glennie et al. (1987) J. Immunol. 139, 2367. Another method uses o-phenylenedimaleimide (oPDM) for coupling three Fab' fragments (WO 91/03493). Multispecific antibodies are in context of this invention also suitable and can be prepared, for example according to the teaching of WO 94/13804 and WO 98/50431.

The term "fusion protein" preferably refers to a natural or synthetic molecule consisting of one ore more proteins or peptides or fragments thereof having different specificity which are fused together optionally by a linker molecule. As specific embodiment the term includes fusion constructs, wherein at least one protein or peptide is a immunoglobulin or antibody, respectively or parts thereof ("immunoconjugates").

The term "immunoconjugate" preferably refers to an antibody or immunoglobulin respectively, or a immunologically effective fragment thereof, which is fused by covalent linkage to a non-immunologically effective molecule. Preferably this fusion partner is a peptide or a protein, which may be glycosylated. Said non-antibody molecule can be linked to the C-terminal of the constant heavy chains of the antibody or to the N-terminals of the variable light and/or heavy chains. The fusion partners can be linked via a linker molecule, which is, as a rule, a 3-15 amino acid residues containing peptide. Immunoconjugates according to the invention consist of an immunoglobulin or immunotherapeutically effective fragment thereof, directed to a receptor tyrosine kinase, preferably an ErbB (ErbB1/ErbB2) receptor and an integrin antagonistic peptide, or an angiogenic receptor, preferably an integrin or VEGF receptor and TNFα or a fusion protein consisting essentially of TNFα and IFNγ or another suitable cytokine, which is linked with its N-terminal to the C-terminal of said immunoglobulin, preferably the Fc portion thereof. The term includes also corresponding fusion constructs comprising bi- or multi-specific immunoglobulins (antibodies) or fragments thereof.

The term "functionally intact derivative" means according to the understanding of this invention preferably a fragment or portion, modification, variant, homologue or a de-immunized form (a modification, wherein epitopes, which are responsible for immune responses, are removed) of a compound, peptide, protein, antibody (immunoglobulin), immunconjugate, etc., that has principally the same biological and/or therapeutic function as compared with the original compound, peptide, protein, antibody (immunoglobulin), immunconjugate, etc. However, the term includes also such derivatives, which elicit a reduced or enhanced efficacy.

The term "cytokine" is preferably a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; mouse gonadotropin-associated peptide; inhibin; activin; vascular endothelial growth factor (VEGF); integrin; thrombopoietin (TPO); nerve growth factors such as NGFβ; platelet-growth factor; transforming growth factors (TGFs) such as TGFα and TGFβ; erythropoietin (EPO); interferons such as IFNα, IFNβ, and IFNγ; colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12; and TNFα or TNFβ. Preferred cytokines according to the invention are interferons and TNFα.

The term "cytotoxic agent" as used herein preferably refers to a substance that inhibits or prevents the function of cells and/or causes destruction of cells. The term is preferably intended to include radioactive isotopes, chemotherapeutic agents, and toxins such as enzymatically active toxins of bacterial, fungal, plant or animal origin, or fragments thereof. The term may include also members of the cytokine family, preferably IFNγ as well as anti-neoplastic agents having also cytotoxic activity.

The term "chemotherapeutic agent", "chemotherapeutical agent" or "anti-neoplastic agent" is regarded according to the understanding of this invention preferably as a member of the class of "cytotoxic agents", as specified above, and includes chemical agents that exert anti-neoplastic effects, i.e., prevent the development, maturation, or spread of neoplastic cells, directly on the tumor cell, e.g., by cytostatic or cytotoxic effects, and not indirectly through mechanisms such as biological response modification. Suitable chemotherapeutic agents according to the invention are preferably natural or synthetic chemical compounds, but biological molecules, such as proteins, polypeptides etc. are not expressively excluded. There are large numbers of anti-neoplastic agents available in commercial use, in clinical evaluation and in pre-clinical development, which could be included in the present invention for treatment of tumors/neoplasia by combination therapy with TNFα and the anti-angiogenic agents as cited above, optionally with other agents such as EGF receptor antagonists. It should be pointed out that the chemotherapeutic agents can be administered optionally together with above-said drug combination. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. Preferred chemotherapeutic agents or chemotherapy include amifostine (ethyol), cisplatin and/or other platinum compounds, preferably including carboplatin and/or oxaliplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

The term "immunotoxic" preferably refers to an agent which combines the specifity of a immunomolecule, e.g. an antibody or a functional equivalent thereof with a toxic moiety, e.g. a cytotoxic function as defined above.

Further examples of cancer cotherapeutic agents and preferably of chemotherapeutical agents, cytotoxic agents, immunomodulating agents and/or immunotoxic agents preferably include antibodies against one or more target, preferably selected from the group consisting of HER, HER2, PDGF, PDGFR, EGF, EGFR, VEGF, VEGFR and/or VEGFR2, wherein said antibodies are preferably selected from Herceptin, Bevacizumab (rhuMAb-VEGF, Avastin®), Cetuximab (Erbitux®), Panitumumab and/or Nimotuzumab, and more preferably selected from Herceptin, Bevacizumab (rhuMAb-VEGF, Avastin®), Cetuximab (Erbitux®) and Panitumumab, and preferably small molecules or NCEs against one or more of said targets, preferably selected from the group consisting of Sorafenib (Nexavar®), Sunitinib (Sutent®), ZD6474 (ZACTIMA™), Gefitinib and Erlotinib, and more preferably selected from the group consisting of Sorafenib (Nexavar®), Sunitinib (Sutent®) and ZD6474 (ZACTIMA™) and/or selected from the group consisting of Gefitinib and Erlotinib.

In a preferred aspect of the instant invention, the cancer cotherapeutic agents, preferably including, but not limited to chemotherapeutical agents, cytotoxic agents, immunomodulating agents and/or immunotoxic agents, are selected from one or more of the following groups:
a) alkylating agents,
b) antibiotics,
c) antimetabolites,
d) biologicals and immunomodulators,
e) hormone modulating agents, including hormones and antagonists thereof,
f) mustard gas derivatives,
g) alkaloids,
h) osteoclast activity modulating agents, and/or
i) protein kinase inhibitors.

In a more preferred aspect of the instant invention, the cancer cotherapeutic agents, preferably including, but not limited to chemotherapeutical agents, cytostatic agents, cytotoxic agents, immunomodulating agents and/or immunotoxic agents are selected from one or more of the following groups:
a) alkylating agents, selected from busulfan, melphalan, carboplatin, cisplatin, cyclophosphamide, dacarbazine, carmustine (BCNU), nimustin (ACNU), lomustine (CCNU), ifosfamide, temozolomide and altretamine,
b) antibiotics, selected from leomycin, doxorubicin, adriamycin, idarubicin, epirubicin and plicamycin,
c) antimetabolites, selected from sulfonamides, folic acid antagonists, gemcitabine, 5-fluorouracil (5-FU), leucovorine, leucovorine with 5-FU, 5-FU with calcium folinate, and leucovorin, capecitabine, mercaptopurine, cladribine, pentostatine, methotrexate, raltitrexed, pemetrexed, thioguanine, camptothecin derivates (topotecan, irinotecan)
d) biologicals and immunomodulators, selected from interferon a2A, interleukin 2 and levamisole,
e) hormone modulating agents, including the antiestrogens Afimoxifene, Arzoxifene, Bazedoxifene, Lasofoxifene, Ormeloxifene, Raloxifene, Tamoxifen, Toremifene and Fulvestrant, the aromatase inhibitors Anastrozole (e.g. Arimidex), Letrozole (e.g. Femara), Exemestane (e.g. Aromasin), Vorozole (e.g. Rivizor), Formestane (e.g. Lentaron) and Fadrozole (e.g. Afema), the GnRH analoga Leuprorelin (e.g. Eligard®, Enantone®), Goserelin (e.g. Zoladex®) and Buserelin (e.g. Profact®), and/or the hormones and antagonists thereof, such as flutamide, goserelin, mitotane and tamoxifen,
f) mustard gas derivatives, selected from melphalan, carmustine and nitrogen mustard,
g) alkaloids, selected from taxanes, docetaxel, paclitaxel, etoposide, vincristine, vinblastine and vinorelbine
h) osteoclast activity modulating agents, selected from the bisphosphonates Etidronate (e.g. Didronel), Clodronate (e.g. Bonefos, Loron), Tiludronate (e.g. Skelid), Pamidronate (e.g. APD, Aredia), Neridronate, Olpadronate, Alendronate (e.g. Fosamax), Ibandronate (e.g. Boniva), Risedronate (e.g. Actonel) and Zoledronate (e.g. Zometa, Aclasta), and the RANK/RANKL/OPG modulator Denosumab (e.g. Prolia®).

The cancer chemotherapeutic agents agents for use according to the invention preferably include, but are not limited to, one or more, two or more, three or more or four or more compounds, selected from alkylating chemotherapeutic agents, cytotoxic antibiotics, antimetabolites, cytostatic alkaloids, cytostatic Enzymes, VEGF/VEGFR inhibitors, PARP inhibitors, and EGF/EGFR inhibitors.

Alkylating chemotherapeutic agents in this respect preferably comprise:
N-Lost-Derivatives, more preferably selected from the N-Lost derivatives Busulfane and Chlorambucil;
Nitroso urea derivatives, more preferably selected from the Nitroso urea derivatives Nimustine, Carmustine and Lomustine;
Oxazaphosphorines, more preferably selected from the Oxazaphosphorines Cyclophosphamide, Ifosfamide and Trofosfamide;
Platin derivatives, more preferably selected from the Platin derivatives Cisplatin, Carboplatin and Oxaliplatin;
Tetrazines, more preferably selected from the Tetrazines Dacarbacine and Temozolomide;
Aziridines, more preferably Thiotepa, and others, preferably selected from Amsacrine, Estramustinphosphate Procarbazine and Treosulfane;
and pharmaceutically acceptable dervatives, salts and/or solvates thereof.

Cytotoxic antibiotics in this respect preferably comprise:
Anthracyclines, more preferably selected from the Anthracyclines Daunorubicine, Doxorubicine, Epirubicine and Idarubicine;
Anthracendiones, more preferably Mitoxantrone, and others, preferably selected from Actinomycin-D, Bleomycine and Mitomycin-C;
and pharmaceutically acceptable dervatives, salts and/or solvates thereof.

Antimetabolites in this respect preferably comprise:
Antifolates, more preferably selected from the antifolates Methotrexate, Raltitrexed, and Pemetrexed;
Purine antagonists, more preferably selected from the purine antagonists 6-Mercaptopurine, 6-Thioguanine, 2'-Desoxycoformicine, Fludarabinphospate and 2-Chlordeoxyadenosine;
Pyrimidine antagonists, more preferably selected from pyrimidine antagonists 5-Fluorouracil, Gemcitabine, Capecitabine, Cytosinarabinoside and Difluorodesoxycytidine; and
Ribonucleotide reductase inhibitors (RNR inhibitors), more preferably Hydroxyurea;
and pharmaceutically acceptable dervatives, salts and/or solvates thereof.

Cytostatic alkaloids in this respect preferably comprise:

Podophyllotoxinderivatives, more preferably selected from the podophyllotoxinderivatives Etoposide and Teniposide;

Vinca alkaloids, more preferably selected from the vinca alkaloids Vinflunine, Vinblastine, Vincristine, Vindesine and/or Vinorelbine, even more preferably selected from the vinca alkaloids Vinblastine, Vincristine, Vindesine and Vinorelbine;

Taxanes, more preferably selected from the taxanes Docetaxel, Paclitaxel, Cabazintaxel and/or Abraxane, even more preferably selected from the taxanes Docetaxel and Paclitaxel; and Camptothecin derivatives, more preferably selected from the Camptothecin derivatives Irinotecane and Topotecane;

and pharmaceutically acceptable dervatives, salts and/or solvates thereof. Preferably, the term taxanes as used herein preferably also includes protein-bound Docetaxel and/or protein-bound paclitaxel, and especially preferably also includes Abraxane.

Cytostatic Enzymes in this regard preferably comprise:

L-asparaginase;

and pharmaceutically acceptable dervatives, salts and/or solvates thereof.

EGF/EGFR inhibitors in this respect preferably comprise:

Anti-EGFR biologicals, more preferably selected from the anti-EGFR biologicals cetuximab, panitumumab, zalutumumab, nimotuzumab and matuzumab; and anti-EGFR chemically derived compounds, more preferably selected from the anti-EGFR chemically derived compounds gefitinib, erlotinib and lapatinib;

and pharmaceutically acceptable dervatives, salts and/or solvates thereof.

Dosings and preferably standard administration schedules for the above and/or below given cancer cotherapapeutic agents are known in the art.

The terms "cancer" and "tumor" preferably refer to or describe the physiological condition in mammals and especially in humans that is typically characterized by unregulated cell growth. Cancers in this respect are preferably selected from solid cancers, preferably including metastases thereof, bone metastases of solid cancers, myeloma, such as multiple myeloma, and bone lesions thereof. By means of the pharmaceutical compositions according of the present invention cancers or tumors can be treated selected from cancers or tumors of the breast, heart, lung, small intestine, colon, spleen, kidney, bladder, head and neck, ovary, prostate, brain, pancreas, skin, bone, bone marrow, blood, thymus, uterus, testicles, cervix, and liver. More specifically the tumor is selected from the group consisting of adenoma, angio-sarcoma, astrocytoma, epithelial carcinoma, germinoma, glioblastoma, glioma, hamartoma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and teratoma.

In detail, the tumor/cancer is selected from the group consisting of acral lentiginous melanoma, actinic keratoses, adenocarcinoma, adenoid cyestic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangio-carcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adeno-carcinoma, pineal cell, pituitary tumors, plasmacytoma, pseudo-sarcoma, pulmonary blastoma, renal cell carcinoma, retinoblastoma, rhabdomyo-sarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. More preferably, the tumor/cancer is selected from the group consisting of intracerebral cancer, head-and-neck cancer, rectal cancer, astrocytoma, preferably astrocytoma grade II, III or IV, glioblastoma, preferably glioblastoma multiforme (GBM), small cell lung cancer (SCLC) and non-small cell lung cancer (NSCLC), preferably non-small cell lung cancer (NSCLC), metastatic melanoma, metastatic androgen independent prostate cancer (AIPCa), metastatic androgen dependent prostate cancer (ADPCa) and breast cancer. Even more preferably, the tumor/cancer is selected from the group consisting of astrocytoma, preferably astrocytoma grade II, III or IV, glioblastoma, preferably glioblastoma multiforme, small cell lung cancer (SCLC) and non-small cell lung cancer (NSCLC), preferably non-small cell lung cancer (NSCLC), metastatic melanoma, metastatic androgen independent prostate cancer (AIPCa), metastatic androgen dependent prostate cancer (ADPCa). Also more preferably, the tumor/cancer is selected from metastases, preferably brain metastases, of small cell lung cancer (SCLC) and non-small cell lung cancer (NSCLC), preferably non-small cell lung cancer (NSCLC), metastatic melanoma, metastatic androgen independent prostate cancer (AIPCa), metastatic androgen dependent prostate cancer (ADPCa) and breast cancer.

Preferred solid cancers according to the invention include cancers of breast, heart, lung, small intestine, colon, spleen, kidney, bladder, head and neck, ovary, prostate, brain, pancreas, skin, bone, thymus, uterus, testicles, cervix, and/or liver.

Preferred bone metastases to be treated according to the invention preferably include bone metastases of solid cancers, more preferably bone metastases of solid cancers ot the breast, heart, lung, small intestine, colon, spleen, kidney, bladder, head and neck, ovary, prostate, brain, pancreas, skin, bone, thymus, uterus, testicles, cervix, and/or liver.

More preferred bone metastases to be treated according to the invention preferably include bone metastases of cancers ot the breast, lung, head and neck, colon and/or prostate.

More preferred bone metastases to be treated according to the invention preferably also include bone lesions, preferably osteolytic and/or osteoplastic bone lesions, more preferably osteolytic bone lesions, even more preferably bone lesions of myeloma, malignant myeloma and/or multiple myeloma, and especially osteolytic bone lesions of myeloma, malignant myeloma and/or multiple myeloma.

The "pharmaceutical compositions" of the invention can comprise agents that reduce or avoid side effects associated with the combination therapy of the present invention ("adjunctive therapy"), including, but not limited to, those agents, for example, that reduce the toxic effect of anticancer drugs, e.g., bone resorption inhibitors, cardioprotective agents. Said adjunctive agents prevent or reduce the incidence of nausea and vomiting associated with chemotherapy, radiotherapy or operation, or reduce the incidence of infection associated with the administration of myelosuppressive anticancer drugs. Adjunctive agents are well known in the art. The immunotherapeutic agents according to the invention can additionally administered with adjuvants like BCG and immune system stimulators. Furthermore, the compositions may include immunotherapeutic agents or chemotherapeutic agents which contain cytotoxic effective radio labeled isotopes, or other cytotoxic agents, such as a cytotoxic peptides (e.g. cytokines) or cytotoxic drugs and the like.

The term "pharmaceutical kit" as used here in preferably refers to a package and, as a rule, instructions for using the reagents in methods to treat cancers or tumors as described herein and especially to treat breast cancer and/or bone metastases in humans. A reagent in a kit of this invention is typically formulated as a therapeutic composition, for example as described herein, and therefore can be in any of a variety of forms suitable for distribution in a kit. Such forms can include a liquid, solution, powder, tablet, suspension and the like formulation for providing the specific compounds or agents for use according to the invention. The formulations, compounds or agents may be provided in separate containers suitable for administration separately according to the present methods, or alternatively may be provided combined in a composition in a single container in the package. The package may contain an amount sufficient for one or more dosages of reagents according to the treatment methods described herein. A kit of this invention also contains "instruction for use" of the materials contained in the package.

As used herein. the terms "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared. The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as. for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred is the HCl salt when used in the preparation of cyclic polypeptide αv antagonists. Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin. vegetable oils such as cottonseed oil, and water-oil emulsions.

Typically, a therapeutically effective amount of an immunotherapeutic agent in the form of a, for example, antibody or antibody fragment or antibody conjugate is an amount such that when administered in physiologically tolerable composition is sufficient to achieve a plasma concentration of from about 0.01 microgram (µg) per milliliter (ml) to about 100 µg/ml, preferably from about 1 µg/ml to about 5 µ/ml and usually about 5 µg/ml. Stated differently the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily for one or several days. Where the immunotherapeutic agent is in the form of a fragment of a monoclonal antibody or a conjugate, the amount can readily be adjusted based on the mass of the fragment/conjugate relative to the mass of the whole antibody. A preferred plasma concentration in molarity is from about 2 micromolar (µM) to about 5 millimolar (mM) and preferably, about 100 µM to 1 mM antibody antagonist. A therapeutically effective amount of an agent according of this invention which is a non-immunotherapeutic peptide or a protein polypeptide (e.g. IFN-alpha), or other similarly-sized small molecule, is typically an amount of polypeptide such that when administered in a physiologically tolerable composition is sufficient to achieve a plasma concentration of from about 0.1 microgram (µg) per milliliter (ml) to about 200 µg/ml, preferably from about 1 µg/ml to about 150 µg/ml. Based on a polypeptide having a mass of about 500 grams per mole, the preferred plasma concentration in molarity is from about 2 micromolar (µM) to about 5 millimolar (mM) and preferably about 100 µM to 1 mM polypeptide antagonist. The typical dosage of an active agent, which is a preferably a chemical antagonist or a (chemical) chemotherapeutic agent according to the invention (neither an immunotherapeutic agent nor a non-immunotherapeutic peptide/protein) is 10 mg to 1000 mg, preferably about 20 to 200 mg, and more preferably 50 to 100 mg per kilogram body weight per day. The preferred dosage of an active agent, which is a preferably a chemical antagonist or a (chemical) chemotherapeutic agent according to the invention (neither an immunotherapeutic agent nor a non-immunotherapeutic peptide/protein) is 0.5 mg to 3000 mg per patient and day, more preferably 10 to 2500 mg per patient and per day, and especially 50 to 1000 mg per patient and per day, or, per kilogram body weight, preferably about 0.1 to 100 mg/kg, and more preferably 1 mg to 50 mg/kg, preferably per dosage unit and more preferably per day, or, per square meter of the bodysurface, preferably 0.5 mg to 2000 mg/m$^2$, more preferably 5 to 1500 mg/m², and especially 50 to 1000 mg/m², preferably per dosage unit and more preferably per day.

The term "therapeutically effective" or "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by overall survival (OS) or progression free survival (PFS), by assessing the time to disease progression (UP) and/or determining the response rate (RR). Alternatively preferably, the efficacy can, for example, can be measured by assessing the time to disease progression (TTP) and/or determining the response rate (RR).

As used herein, the term "physiologically functional derivative" preferably refers to any pharmaceutically acceptable derivative of a compound to be used according to the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" preferably refers to a complex of variable stoichiometry formed by a solute (in this invention, said Peptide (and/or the pharmaceutically acceptable dervatives, solvates and/or salts thereof) and/or a cancer cotherapeutic agent (or a salt or physiologically functional derivative thereof)) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Preferred examples of suitable pharmaceutically acceptable solvents are water and/or ethanol. Most preferably the solvent used is water. Pharmaceutically acceptable salts of compounds to be used according to the invention and their preparation is known in the art. If the compound itself is not a salt, it can be easily transferred into a salt by addition of a pharmaceutically acceptable acid or of a pharmaceutically acceptable base. Pharmaceutically acceptable acids and bases are known in the art, for example from the literature cited herein.

The compounds to be used according to the invention, preferably including the Peptide of the formula Cyclo-(Arg-Gly-Asp-DPhe-NMe-Val) and/or the pharmaceutically acceptable dervatives, solvates and/or salts thereof, and/or one or more cancer cotherapeutic agents as defined herein, can generally be administered to the patient in a form and in a way or manner that is known in the art for the respective compounds or class of compounds, for example as described herein or as described in the literature cited herein.

The Peptide of the formula Cyclo-(Arg-Gly-Asp-DPhe-NMeVal) is preferably applied as a pharmaceutically acceptable salt, more preferably the pharmacologically acceptable hydrochloride salt, and especially preferably applied as the inner (or internal) salt, which is the compound cyclo-(Arg-Gly-Asp-DPhe-NMeVal) as such.

With regard to the Peptide of the formula cyclo-(Arg-Gly-Asp-DPhe-NMeVal), the following kinds of writing the name are preferably to be regarded as equivalent:
Cyclo-(Arg-Gly-Asp-DPhe-NMeVal)=cyclo-(Arg-Gly-Asp-DPhe-NMeVal)=cyclo-(Arg-Gly-Asp-DPhe-[NMe]Val) =cyclo-(Arg-Gly-Asp-DPhe-[NMe]-Val)=cyclo-(Arg-Gly-Asp-DPhe-NMeVal)=cyclo-(Arg-Gly-Asp-DPhe-NMe- Val)=cyclo(Arg-Gly-Asp-DPhe-NMeVal)=cyclo (Arg-Gly-Asp-DPhe-NMe-Val)=cRGDfNMeV=c (RGDfNMeV).

The Peptide of the formula cyclo-(Arg-Gly-Asp-DPhe-NMeVal) is also referred to as Cilengitide, which is the INN (International Non-propriety Name) of said compound.

The Peptide of the formula cyclo-(Arg-Gly-Asp-DPhe-NMeVal) is also described in EP 0 770 622 A, U.S. Pat. No. 6,001,961, WO 00/15244 and PCT/US07/01446 of the same applicant, the disclosure of which is explicitly incorporated into the instant application by reference.

Recent results show that inhibiting integrins, especially $\alpha v \beta 3$ and/or $\alpha v \beta 5$, commonly expressed in various cancerous cells, can significantly decrease the resistance to chemotherapeutic agents and/or ionising radiation of otherwise chemo- or radioresistant cancerous cells and/or can induce an increased sensitivity of cancerous cells towards chemotherapeutic agents and/or ionising radiation.

Accordingly, specific integrin ligands, especially integrin ligands specific to $\alpha_v \beta_3$ and/or $\alpha_v \beta_5$ integrins according to the invention and especially the Peptide of the formula cyclo-(Arg-Gly-Asp-DPhe-NMeVal) and/or the pharmaceutically acceptable dervatives, solvates and/or salts thereof can be successfully applied to improve the efficacy of various cancer cotherapeutic agents.

For example, a phase I clinical study used cilengitide treatment in a dose escalation study on various brain tumors (NABT 9911). In some of the GBM patients in this study, an indication of response was seen. Cilengitide (=cyclo-(Arg-Gly-Asp-DPhe-NMe-Val), in very marked contrast to most cancer therapeutics currently in use has a very innocuous side effect profile, with no known MTD in humans—and is very well tolerated.

In addition to the essentially 100% mortality in GBM patients (2-year survival rate about 25%), the morbidity from neurological complications also rapidly degrades the quality of life (QOL).

For example, the standard of treatment of glioblastoma multiforme, associating radiotherapy and temozolomide, has only increased the median survival of resected patients by 2.5 months (12.1→14.6 months) compared to radiotherapy alone (Stupp et al., 2005). However, in combination with at least one specific integrin ligand according to the invention, preferably selected from Vi taxin, Abegrin, CNTO95 and cyclo-(Arg-Gly-Asp-DPhe-NMe-Val), more preferably selected from Vitaxin, Abegrin and cyclo-(Arg-Gly-Asp-DPhe-NMe-Val) and especially preferably cyclo-(Arg-Gly-Asp-DPhe-NMe-Val), this standard treatment shows significantly improved efficacy with respect to an increased median survival and quality of life. The literature cited in this paragraph is explicitly incorporated into the disclosure of the instant application by reference.

Breast Cancer:

The term breast cancer or malignant breast neoplasm is commonly used as the generic name for cancers originating from breast tissue, most commonly from the inner lining of milk ducts or the lobules that supply the ducts with milk. Cancers originating from ducts are often referred to as ductal carcinomas; those originating from lobules are often referred to as lobular carcinomas. However, there are many different types of breast cancer, with different stages (spread), aggressiveness, and genetic makeup; survival varies greatly depending on those factors. Breast cancer is about 100 times more common in women than in men, although males tend to have poorer outcomes due to delays in diagnosis.

Breast cancer (BRCA) ist the most common cancer in women worldwide, accounting for ~30% of all female cancers. It represents a major public health problem mainly due to its high incidence, excess mortality and therapeutic challenges. More than 1.1 million women are diagnosed with BRCA each year worldwide, and more than 400.000 succumb to this disease. Approximately 75% of all newly diagnosed patients are women with early stage BRCA.

Generally, treatment options include surgery, drug based therapy, including but not limited to hormonal therapy and/or chemotherapy, and radiation. Some breast cancers require hormones to grow, such as estrogen and/or progesterone, and have receptors for those hormones. After surgery those cancers are treated with drugs that interfere with those hormones and/or shut off the production of said hormones in the ovaries or elsewhere. Such drugs are generally referred to as hormone antagonists or hormone blockers.

However, despite surgery and the use of adjuvant treatments such as chemotherapy, hormonal therapy, radiotherapy and targeted drugs, such as trastuzumab, many of these patients will die as a result of local or distant recurrence. The 5-year survival rate for metastatic breast cancer is in the range of 25%.

As can be seen from the above, management of BRCA has been difficult and it still is difficult. For example, treatment of early BRCA includes combined modality therapy with surgery, followed by adjuvant radiotherapy, chemotherapy, hormonal therapy, or biologic/targeted therapy, such as trastuzumab, for most women. Decision-making regarding the use of adjuvant treatment is based on the risk of disease recurrence. According to the St. Gallen criteria the risk of recurrence depends on the nodal status, tumor stage, grade, tumor invasion of lymphatic or blood vessels, HER2 amplification, age and hormone receptor status.

For advanced (metastatic, locally advanced or recurrent) BRCA there is no clearly defined standard of care. Hormonal treatment, various combinations of chemotherapeutic agents and targeted drugs such as trastuzumab and bevacizumab are currently used to treat these patients. As advanced BRCA is regarded as an potentially incurable disease, treatment is mainly palliative in nature and aims especially at improving quality of life, progression-free and overall survival.

Hormonal Treatment

Hormonal therapy or endocrine therapy is widely accepted as a treatment modality for women with hormone-sensitive, estrogen-receptor positive (ER+) and/or progesterone-receptor positive (PR+) breast cancer (ca. 70%). Especially for postmenopausal women with limited visceral involvement and metastases mainly in skin, soft-tissue, bone and a limited number of pulmonary metastases endocrine therapy is the first-line treatment of choice.

For premenopausal women a combination of GnRH-Analoga and tamoxifen is currently the treatment of choice. Postmenopausal women can be treated with either tamoxifen, aromatase inhibitors (such as exemestane, letrozole and anastrozole), selective estrogen-receptor modulators (such as fulvestran) or—in exceptional cases—with gestagenes. First line endocrine treatment is reported to result in remission rates of ~30% and median progression-free survival of 6-10 months with aromatase inhibitors being superior to tamoxifen in terms of progression-free survival and remission rates, e.g. by Mouridsen et al., Journal of Clinical Oncology, Vol 21, No 11 (June 1), 2003: pp 2101-2109, the disclosure of which is included in its entirety into this application. In contrast thereto, clinical activity of 2nd line endocrine treatment is reported to be far inferior, with remission rates of 10-20% and median time to progression of only 3-6 months, e.g. by Buzdar et al., Journal of Clinical Oncology, Vol 19, No 14 (Jul. 15), 2001: pp 3357-3366, the disclosure of which is included in its entirety into this application.

All women receiving hormonal treatment for advanced disease will eventually develop hormone-resistant disease requiring chemotherapeutic treatment. Chemotherapy is generally associated with substantial systemic toxicity compared to endocrine treatment, therefore new treatment options prolonging the time to first chemotherapy and improving overall survival are highly warranted.

Chemotherapy

Chemotherapy is indicated for women with advanced BRCA with either ER- and PR-negative disease or women, who have progressed on one or several lines of prior endocrine treatment. In principal, chemotherapy can be administered as mono- or polychemotherapy including two or more drug combinations.

For women with slow or moderate progression of disease monotherapy is preferably indicated. For women with poor prognosis, rapid progression or extended visceral involvement with a high medical need for fast remission, polychemotherapy should be considered. The most commonly used drugs include anthrazyklines, especially liposomal anthrazyklines, taxanes, vinorelbine, capecitabine, mitoxantron, gemcitabine and/or platinum-derivates. Remission rates and time to progression for monotherapy with taxanes in the 1st line setting are reported to be in the range of 20-30% and 3-6 months, respectively, e.g. by Jones et al., Journal of Clinical Oncology, Vol 23, No 24 (Aug. 20), 2005: pp 5542-5551), the disclosure of which is included in its entirety into this application. For polychemotherapy reported remission rates are higher (50-70%), however these do not necessarily improve progression-free and overall survival as compared to monotherapy. In general, polychemotherapy is associated with higher hematologic and non-hematologic toxicity.

HER2-Targeting Drugs

Women with HER2-positive advanced BRCA (determined preferably either by INC 3+ or FISH analysis) should be treated with HER2-targeting drugs. These include currently monocloncal antibodies, such as trastuzumab, and tyrosinkinase-inhibitors, such as lapatinib.

Trastuzumab, for example, can be administered as monotherapy (remission rate ~20%), more often however in combination with chemotherapy, preferably selected from taxanes and vinorelbine. The combination of trastuzumab with chemotherapy is reported to result in a significant improvement in progression-free and overall survival compared to chemotherapy alone e.g. by Slamon et al., N Engl J Med, Vol. 344, No. 11 (Mar. 15, 2001) 783-792), the disclosure of which is included in its entirety into this application.

Women with hormone-sensitive, HER2-positive advanced BRCA also benefit, if endocrine therapy (e.g. aromatase inhibitors) is combined with trastuzumab (reported e.g. by Kaufmann et al., Journal of Clinical Oncology, Vol 27, No 33 (Nov. 20), 2009: pp 5529-5537, the disclosure of which is included in its entirety into this application). Lapatinib is especially indicated for 2nd line treatment in combination with capecitabine. By this combination, median time to progression is reported to be improved by 4 months compared to capecitabine alone, e.g. by Geyer et al., N Engl J Med 2006; 355:2733-43, the disclosure of which is included in its entirety into this application.

Anti-Angiogenic Treatment

Especially for women with HER2-negative disease, bevacizumab has shown to improve progression-free survival when combined with docetaxel (reported, e.g. by Miles et al., Journal of Clinical Oncology, 2008 ASCO Annual Meeting Proceedings (Post-Meeting Edition) Vol 26, No 15S (May 20 Supplement), 2008: LBA1011, the disclosure of which is included in its entirety into this application) or paclitaxel (Miller et al., N Engl J Med 2007;357:2666-76, the disclosure of which is included in its entirety into this application). However, no improvement in overall survival has been shown for the combination treatment so far. Recent data support the activity of bevacizumab regarding improvement on progression-free survival for various drug combinations (reported, e.g. by Robert et al., 2009 ASCO Annual Meeting Abstract No: 1005; Citation: J Clin Oncol 27:15s, 2009 (suppl; abstr 1005), the disclosure of which is included in its entirety into this application).

Accordingly, development of new drugs and especially new targeted drugs aiming at an improvement in overall survival in women with advanced BRCA is highly needed.

Supportive Treatment

70% of women with advanced breast cancer develop bone metastases in the course of their disease. These significantly impact on quality of life and are associated with a high morbidity in the affected women. Most frequent complications are pain, pathologic fractures and cord compression, all potentially leading to immobility. These complications elicit the need for interventions such as surgery and/or radiotherapy.

Current standard of care for all women with bone metastases are bisphosphonates, which are shown to be able able to reduce the incidence of the above mentioned skeletal-related events. The rather novel monoclonal RANKL-antibody denosumab might be superior to bisphosphonates according to recently published phase III data of Stopeck et al., European Journal of Cancer Supplements, Vol. 7, No 3, September 2009, Page 2, the disclosure of which is included in its entirety into this application.

However, there remains a high unmet medical need to reduce morbidity caused by bone metastases, especially in women with advanced BRCA.

Treatment Alternatives

After surgery, low-risk, hormone-sensitive breast cancers may be treated with hormone therapy and radiation alone. Breast cancers without hormone receptors, or which have spread to the lymph nodes, or which express certain genetic characteristics, are higher-risk, and thus are generally treated more aggressively. For example, one standard regimen, popular mainly in the U.S., is the combination of cyclophosphamide plus doxorubicin (Adriamycin), known as CA. Sometimes, a taxane drug, such as docetaxel, is added, and the regime is then known as CAT. An equivalent treatment, popular mainly in Europe, is the combination of cyclophosphamide with methotrexate and/or fluorouracil (also known as CM, CF or CMF, respectively). In many cases, radiation is added to the surgical bed to control cancer cells that were missed by the surgery, which usually extends survival.

Bone Metastases:

Cancer metastases to the bone are a major clinical concern that significantly limits the patient's quality of life and life expectancy. Patients with bone metastases frequently have reduced mobility, pain, and bone weakness that predisposes them to pathologic fractures, spinal epidural compression, and bone marrow failure.

Bone metastases, preferably also referred to as bone lesions, metastatic lesions or just lesions, are often multiple at the time of diagnosis. In adults, the bone metastases or lesions generally occur in the axial skeleton and other sites with residual red marrow, although the bone metastases or lesions may be found anywhere in the skeletal system. Common sites for bone metastases or lesions are the vertebrae, pelvis, proximal parts of the femur, ribs, proximal part of the humerus, and skull. More than 90% of the bone metastases or lesions are found in this distribution.

Imaging has an important role in the detection, diagnosis, prognostication, treatment planning, and follow-up monitoring of bone metastases or lesions. The true incidence of bone metastases is the subject of much debate, and it is not fully known. The probability of bone metastasis originating from a primary site can be assessed only by knowing the prevalence of the cancer and its predilection for bone. Therefore, the frequency of bone metastases depends on the prevalence of the cancer in a particular community. The incidence of bone metastases also depends on the source of the data. For example, results from autopsy studies and from bone scintigraphic studies are different for newly diagnosed, established, and end-stage cancers. The bone microenvironment and the ECM (extracellular matrix) in particular, play a major role in the preferential metastasis to bone by certain cancers, mainly prostate and breast cancer. Types of cancer that most commonly metastasize to bone include prostate, breast, and lung cancers, although all types of cancer are capable of doing so.

As a metastatic lesion grows in the medullary cavity, the surrounding bone is remodeled by means of either osteoclastic or osteoblastic processes. All are a result of dysregulation of the normal bone remodeling mechanisms, caused by tumor-host cell interactions. Osteoblastic tumors cause an abnormal formation of bone by direct secretion of bone extracellular matrix (ECM) proteins and by indirect stimulation of osteoblasts. Osteolytic tumors cause abnormal resorption of bone by proteolytic enzymes and through actions on osteoclasts. Osteolysis can release sequestered growth factors from the ECM, resulting in a cyclical feedback loop that leads to further stimulation of osteoclasts and continued bone resorption. As bone mass is lost, tumors can then continue to proliferate in their place and grow in size.

Local radiotherapy, chemotherapy, and osteoclast activity modulating agents, including bisphosphonates and/or RANK/RANKL/OPG modulators, may be used, depending on the type of the primary tumor. If the cancer has spread to bone in only one spot, radiation may be given to treat the bone. In general, this will relieve the pain and prevent fractures at this site. If cancer has spread to several places in the bones, radiation treatment to all of the sites may not be possible because of limitations in the total amount of radiation that can be given safely. Patients experiencing bone pain should be given pain medication. Bisphosphonates and/or RANK/RANKL/OPG modulators encourage osteoclasts to undergo apoptosis and therefore used for the treatment of cancers that spread to bone. However, generally these treatments for bone metastasis are palliative.

Multiple Myeloma

Multiple myeloma, also known as MM, myeloma, plasma cell myeloma, or as Kahler's disease is a cancer of the white blood cells known as plasma cells. Multiple myeloma is a clonal expansion of terminally differentiated B-lymphocytes (plasma cell), characterized by monoclonal immunglobulins ("paraprotein"), oesteolysis, renal dysfunction, and immunodeficiency. Multiple myeloma is the second most prevalent blood cancer (10%) after non-Hodgkin's lymphoma. It represents approximately 1% of all cancers and 2% of all cancer deaths. Although the peak age of onset of multiple myeloma is 65 to 70 years of age, recent statistics indicate both increasing incidence and earlier age of onset.

Multiple myeloma is generally thought to be incurable, but remissions may be induced by therapeutic strategies including, but not limited to steroids, chemotherapy, thalidomide, lenalidomide, bortezomib and/or stem cell transplants.

Treatment for multiple myeloma is focused on disease containment and suppression. If the disease is completely asymptomatic, called smoldering multiple myeloma, (i.e. there is a paraprotein and an abnormal bone marrow population but no end-organ damage), treatment may be deferred. These patients are closely monitored for progression to multiple myeloma. Patients whose multiple myeloma is not stable generally require immediate treatment. Initial treatment choices depend on the severity of the patient's condition (high-risk versus standard-risk based) and on eligibility for stem-cell transplantation. Transplant eligibility is determined by the patient's age and general health. Some patients may have the opportunity to participate in novel clinical trials.

Patients who do not qualify for stem-cell transplantation are usually given combination chemotherapy with one of three commonly used regimens. These include, but are not limited to:
i) Melphalan, prednisone, thalidomide (also referred to as MPT),
ii) Bortezomib (Velcade), melphalan, prednisone (also referred to as VMP),
and
iii) Lenalidomide plus low-dose dexamethasone.

The choice depends on the patient's clinical condition and risk status of the disease. Elderly patients or weakened patients, who may not tolerate these therapies, are often prescribed a different drug combination or excerpts from the above discussed regimens, such as melphalan and prednisone only (also referred to as MP).

If a patient qualifies for bone-marrow transplant, the hematologist may recommend it as an initial treatment or suggests that other treatments be tried first. Recent studies have shown that survival may be similar whether transplantation occurs early (after initial chemotherapy) or is delayed and performed when the disease first returns (first relapse). The patient's needs and wishes are taken into account when choosing early versus delayed transplantation. Whether transplantation is immediate or delayed, transplant candidates typically begin with four rounds of chemotherapy to kill cancer cells. After the initial chemotherapy treatments, stem cells are collected from the patient's bone marrow. Chemotherapy may then resume for patients who wish to delay transplantation.

Autologous stem-cell therapy involves transfusion of the patient's own immature blood cells to replace diseased or damaged marrow. Although stem-cell transplantation cannot cure myeloma, it can prolong survival. Patients who do not respond fully to a first transplant may be offered a second. Patients who achieve a complete or very good response from an initial transplantation are observed or sometimes offered the option of a clinical trial investigating maintenance therapy. A second transplant is reserved as an option in case of relapse.

Treatment of Relapsed Myeloma

Almost all patients with myeloma eventually relapse. If relapse occurs more than six months after stopping therapy, the initial chemotherapy regimen is usually restarted. Transplantation may be recommended for patients who previously had stem cells collected and preserved. The drugs recommended for relapse vary, depending on its severity. Because myeloma cannot be cured, patients with relapsed disease generally continue on one drug or regimen until relapse or adverse side effects, and then try the next option.

Supportive Treatment

In addition to chemotherapy, localized radiotherapy and osteoclast activity modulating agents, including bisphosphonates and/or RANK/RANKL/OPG modulators, may be used for treatment of bone lesions due to multiple myeloma.

SCCHN:

Squamous Cell Cancer of the Head and Neck (also Referred to as Squamous Cell Carcinoma of the Head and Neck):

The annual worldwide incidence of squamous cell cancer of the head and neck is estimated at 500,000 patients; in the United States and Europe, 118.000 new patients are diagnosed annually. SCCHN is more predominant in males with a male:female ratio of 2:1-4:1. There is a positive relationship between smoking habits, alcohol consumption, and head and neck cancer. Approximately 90% of all head and neck malignancies are of squamous cell histology (SCCHN). Most patients are diagnosed with SCCHN at an age of 50-70 years.

A majority of patients (75%) have locally advanced disease at diagnosis. Those patients are mainly treated with radiotherapy and in some cases surgery. Newer strategies such as induction chemotherapy or chemoradiotherapy could provide better survival; however, the 5-year survival rate remains around 30%, and 60% of subjects will experience a locoregional or distant relapse within 2 years of initial treatment.

The group of subjects with recurrent disease and/or with newly diagnosed distant metastases, e.g. bone metastases, has very heterogeneous disease characteristics. Their median survival time, however, remains around 6-8 months with a poor quality of life. This dismal prognosis has not changed in the past 30 years.

The standard chemotherapeutic treatments for recurrent and/or metastatic SCCHN include drugs such as methotrexate, bleomycin, 5-fluorouracil (5-FU), and platinum compounds. Promising phase II results with new agents such as taxanes could not be confirmed in phase III studies. Cisplatin is the most widely used drug for the treatment of recurrent and/or metastatic SCCHN and, as such, is considered the standard treatment in this indication. Overall, all published randomized trials suggest that cisplatin and 5-FU in combination produced higher response rates compared to single agents and most of the other combinations. In general, combination therapy was associated with higher hematological and non-hematological toxicity. The combination of cisplatin plus 5-FU produced a small but questionable improvement over monotherapy with a median survival of 6 to 8 months. Carboplatin+5-FU containing regimens are also frequently used because of their better safety profile (lower renal, otologic, neurologic, and gastrointestinal toxicity than cisplatin). Response rates and survival are not statistically different from cisplatin-based regimens. Carboplatin is therefore approved for the treatment of SCCHN in several European countries. The epidermal growth factor receptor (EGFR) is expressed in nearly all SCCHN. EGFR expression carries a strong prognostic significance, providing the rationale for using EGFR-targeted agents, such as cetuximab (Erbitux®), in this indication (Burtness, JCO 2005; Bourhis, JCO 2006). Erbitux is approved in the U.S. for monotherapy of metastatic disease, and in combination with radiotherapy for unresectable SCCHN, where it has demonstrated a prolongation of survival by 20 months.

A phase III trial with the combination of Cis- or Carboplatinum, 5-FU and Erbitux has been demonstrated to significantly prolong the median survival time in patients with locally recurrent/metastatic SCCHN. The observed median survival time of 10.1 months is among the longest ever reported in a phase III trial for these patients. The literature cited in this paragraph is explicitly incorporated into the disclosure of the instant application by reference.

NSCLC: Non-Small Cell Lung Cancer

Lung cancer is the leading cause of cancer deaths worldwide. About 170,000 new cases of lung cancer and 160,000 deaths due to this disease per year occur in the United States alone. NSCLC accounts for approximately 80% of all lung cancers.

At the time of diagnosis, approximately 30% of NSCLC patients present with locally advanced, and 40% with metastatic disease, including disease having metastasized to the bone. Surgical results in earlier stages are poor compared to other tumor types (about 40% of recurrence in stages I-II). In metastatic disease, chemotherapy is the treatment of choice, but survival benefits have been modest, resulting in one-year survival of 40%, and five-year survival of less than 15%.

It is commonly accepted that the standard treatment for advanced disease (stage IV and IIIb with malignant pleural effusion) consists of platin-based (cisplatin or carboplatin) chemotherapy. However, there are many open questions in the management of these patients, such as the role of combination therapy regimen including more than two drugs, non-platinum-based therapies, and new targeted therapeutical approaches.

Currently, response rates of about 20%-30% and median survival times of 6 to 11 months have been observed in the treatment of metastatic NSCLC. Several chemotherapy combinations are used with comparable efficacy. The combinations of cis-/carboplatin plus vinorelbine, gemcitabine, paclitaxel, or docetaxel are among the regimens most commonly used for first-line therapy of metastatic NSCLC.

A phase III trial has been initiated based on the results of a randomized phase II trial in 86 patients treated with cisplatin/vinorelbine plus cetuximab versus cisplatin/vinorelbine alone. The phase II trial revealed an advantage of the cetuximab combination with regard to overall response rate (53% in the experimental arm and 32% in the control arm [Gatzemeier, ASCO 2003, abstract #2582]). The phase III trial planned to include 1100 patients (550 per arm), and was powered to demonstrate an increase in median overall survival from 7 months (standard arm) to 10 months (combination with Erbitux). This study has already finished enrollment, and first results are expected soon. The literature cited in this paragraph is explicitly incorporated into the disclosure of the instant application by reference.

SCLC: Small Cell Lung Cancer

Small cell lung cancer (SCLC) accounts for 15-20% of all lung cancer cases in the world, equating to approximately 80,000 new patients every year. A recent analysis of the Surveillance, Epidemiology and End Results database confirmed that in the United States, the proportion of small cell lung cancer patients has decreased from about 20% to 13.8% in 1998, likely due to the implementation of smoking cessation programs. This success, however, is to some extent outweighed by the high and rising prevalence of tobacco smoking in other parts of the world.

SCLC is typically disseminated at the time of presentation, with approximately 60% to 70% of patients having disseminated (extensive-stage) disease at presentation. Thus, surgery is rarely an option, and applies only to patients with localized (limited) disease. Relapse and death from SCLC is imminent even in patients who are treated with surgical resection. Without other therapy than surgery, survival was 2 months for patients with extensive-stage SCLC and 3 months for patients with limited-stage SCLC (Green, Am J Med 1969).

Systemic combination chemotherapy remains the mainstay of SCLC treatment, both in limited and extensive stage of their disease. For more than 20 years, etoposide and cis-/carboplatin are considered the current standard agents used in combination for the first-line treatment of patients with SCLC in the Western world. Combination therapy with more than two drugs in clinical trials has resulted in higher response rates, but also higher toxicity, and did not result in a clinically relevant overall survival benefit. A combination regimen consisting of cyclophosphamide, doxorubicin, and vincristine was shwn to be equally effective as the platinum/etoposide combination, but has a more unfavourable toxicity profile due to the inclusion of an anthracycline. In Japan, cisplatin plus irinotecan is used more frequently for the first-line treatment of SCLC after a Japanese trial has yielded favourable overall survival. Studies in the Western hemisphere, however, were not able to confirm those results, thus, this regimen is not used as widely in that part of the world.

In extensive stage SCLC, overall response rates to chemotherapy range from 40% to 70%. Time to progression is short, with the majority of patients progressing within 3 months of completing chemotherapy or even within 3-5 months after the start of the chemotherapy. The median survival is 7 to 11 months. Less than 5% of patients survive longer than 2 years. Especially grim is the prognosis for patients that develop bone metastases. The literature cited in this paragraph is explicitly incorporated into the disclosure of the instant application by reference.

Thus, even in view of the results achieved within the last years, the prognosis of the patients regarding most cancerous diseases is still very grim. This holds especially true for metastatic cancerous diseases and especially those which already have metastasized to the bone. Thus, there is a need for improved medicaments, therapy methods and treatment regimen.

It is an objective of the instant invention to provide such improved medicaments, therapy methods and treatment regimens.

Thus, subject of the instant invention is:

[1] A Peptide of the formula Cyclo-(Arg-Gly-Asp-DPhe-NMe-Val) and/or the pharmaceutically acceptable derivatives, solvates and/or salts thereof, preferably Cyclo-(Arg-Gly-Asp-DPhe-NMe-Val), for use in the treatment of breast cancer and/or bone metastases in humans.

A Peptide of the formula Cyclo-(Arg-Gly-Asp-DPhe-NMe-Val) and/or the pharmaceutically acceptable dervatives, solvates and/or salts thereof, preferably Cyclo-(Arg-Gly-Asp-DPhe-NMe-Val), for use in the treatment of breast cancer and/or bone metastases thereof in humans.

The meaning of the term breast cancer is well known and understood in the art and preferably used herein in accordance with the art. Preferably, in the context of the instant invention, it refers to tumors, tumor-like and neoplasia disorders of the breast, more preferably malignant tumors, tumor-like and neoplasia disorders of the breast, and metastases thereof, preferably including bone metastases thereof.

The meaning of the term bone metastases is well known and understood in the art and preferably used herein in accordance with the art. Preferably, in the context of the instant invention and if not indicated explicitly otherwise, it refers to metastases of any origin in the bone compartment of the subject, preferably the human subject. Preferably, the origin of the bone metastasis can be any cancer or tumour, more preferably any solid cancer or tumour. The meaning of the term solid cancer or tumour is well known and understood in the art and preferably used herein in accordance with the art. Preferably, in the context of the instant invention, term solid cancer or tumour refers to cancers or tumours of the breast, heart, lung, small intestine, colon, spleen, kidney, bladder, head and neck, ovary, prostate, brain, pancreas, skin, bone, bone marrow, thymus, uterus, testicles, cervix and/or liver, more preferably of the breast, heart, lung, small intestine, colon, spleen, kidney, bladder, head and neck, ovary, prostate, brain, pancreas, skin, thymus, uterus, testicles, cervix and/or liver, even more preferably breast, lung, colon, kidney, head and neck, ovary, prostate, brain, pancreas, skin, uterus, testicles, cervix and/or liver. However, in the context of the present invention, bone lesions, preferably osteolytic and/or osteoplastic bone lesions, more preferably osteolytic bone lesions, are preferably also regarded as bone metastases. In the context of the present invention, bone lesions, preferably osteolytic and/or osteoplastic bone lesions, more preferably osteolytic bone lesions, of cancers are preferably also regarded as bone metastases. Especially preferably, bone lesions, preferably osteolytic and/or osteoplastic bone lesions, more preferably osteolytic bone lesions, of cancers selected from a group consisting of myeloma, metastatic melanoma, multiple myeloma and/or morbus Waldenström, are regarded as bone metastases in the context of the instant invention.

[2] For use in the treatment of breast cancer and/or bone metastases as described herein, said treatment preferably comprises the administration of the Cyclo-(Arg-Gly-Asp-DPhe-NMe-Val), the pharmaceutically acceptable dervatives, solvates and/or salts thereof to said humans in an amount of 500 mg to 12500 mg per week (and per human), more preferably in an amount of 1000 mg to 10000 mg per week (and per human), even more preferably 1800 mg to 8000 mg per week (and per human), even more preferably 2500 mg to 6000 mg per week (and per human) and especially 3000 mg to 5000 mg per week (and per human), such as about 600 mg per week, about 800 mg per week, about 1600 mg per week, about 2000 mg per week, about 3200 mg per week, about 4000 mg a week or about 6000 mg a week. The given amounts are preferably to be regarded as "flat" amounts, i.e. without an adaptation or factor regarding the size, body weight and/or body surface of the subject to be treated. Preferably, the above given amounts are administered to human subjects 12 years or older, more preferably 16 years or older and especially 18 years or older. Especially preferably, the given amounts are suitable for adult human subjects. If the Peptide of the formula Cyclo-(Arg-Gly-Asp-DPhe-NMe-Val) is applied, partially or totally, as a pharmaceutically acceptable dervative, solvate and/or salt thereof, said amounts are is preferably calculated on the amount of Cyclo-(Arg-Gly-Asp-DPhe-NMe-Val) contained in said pharmaceutically acceptable dervative, solvate and/or salt thereof.

[3] For use in the treatment of breast cancer and/or bone metastases as described herein, said treatment preferably comprises the administration of the Cyclo-(Arg-Gly-Asp-DPhe-NMe-Val), the pharmaceutically acceptable dervatives, solvates and/or salts thereof to said human at least once a week and more preferably at least twice a week or at least three times a week, for at least 3 consecutive weeks, more preferably at least six consecutive weeks and especially at least 16 consecutive weeks.

Preferred regimens with respect to the weekly amounts given, the number of administrations per week and/or with respect to the duration of said consecutive weekly administrations are specified in more detail below.

[4] For use in the treatment of breast cancer and/or bone metastases as described herein, said treatment preferably additionally comprises the administration of one or more cancer cotherapeutic agents to the respective human subject.

Suitable cancer cotherapeutic agents are in principle known in the art, for example from existing or currently developed therapies for the treatment of breast cancer and/or bone metastases. It is believed, that the Peptide of the formula cyclo-(Arg-Gly-Asp-DPhe-NMe-Val) and/or the pharmaceutically acceptable dervatives, solvates and/or salts thereof for use in the treatment of breast cancer and/or bone metastases can add advantageous and preferably a synergistic effects to any therapeutic regimen currently available or currently developed.

Preferred are combinations of said Peptide and/or the pharmaceutically acceptable dervatives, solvates and/or salts thereof with one or more, two or more, three or more or four or more cancer cotherapeutic agents as described herein.

[5] More preferred for combining it with said Peptide and/or the pharmaceutically acceptable dervatives, solvates and/or salts thereof are cancer cotherapeutic agents selected from the group consisting of:
a) hormone modulating agents,
b) osteoclast activity modulating agents,
c) cancer chemotherapeutic agents, and
d) radiotherapy.

If two or more cancer cotherapeutic agents are selected from said group a) to d), the selection is preferably done in a way that only one or two cancer cotherapeutic agents are selected from the same group out of the groups a) to d). For example, if a total number of two cancer cotherapeutic agents are selected from the groups and the first cancer cotherapeutic agents selected is a hormone modulating agents according to a), the second cancer cotherapeutic agent to be selected can be either
i) another hormone modulating agent (but a different one than the first one) according to a), or
ii) one cancer cotherapeutic agent selected out of the osteoclastic activity modulating agents according to b), out of the cancer chemotherapeutic agents according to c) or out of the radiotherapy according to d).

If three or more cancer cotherapeutic agents are selected from said group a) to d), the same preferably applies, i.e. only one or two cancer cotherapeutic agents are selected from the same group out of the groups a) to d), and the other ones are selected each time from a different group of the remaining groups.

Normally, said treatment does not comprise the combination of two different kinds of radiotherapy selected out of d). However, if therapeutically required or favourable, different kinds of radiotherapy can be combined, such as the application of radio isotopes in combination with external beam radiation, and the like.

Hormone modulating agents for use in the treatment of breast cancer and/or bone metastases, preferably hormone receptor positive breast cancer and/or hormone receptor positive metastases, are known in the art. Preferred hormone modulating agents for use in the treatment according this invention preferably comprise one or more compounds selected from the group consisting of antiestrogens, aromatase inhibitors and GnRH analoga. If hormone modulating agents are selected for use in the treatment according this invention, preferably only one or two hormone modulating agents are used at one time in the treatment according this invention. If two hormone modulating agents are selected for use in the treatment according this invention, preferably either two different antiestrogens are selected for use at one time in the treatment according this invention, or a combination of one antiestrogen and one GnRH analogon is selected for use at one time in the treatment according this invention.

Antiestrogens for use in the treatment of breast cancer and/or bone metastases, preferably hormone receptor positive breast cancer and/or hormone receptor positive metastases, are known in the art. Preferred antiestrogens for use according to the invention are preferably selected from the group consisting of Afimoxifene, Arzoxifene, Bazedoxifene, Lasofoxifene, Ormeloxifene, Raloxifene, Tamoxifen, Toremifene and Fulvestrant and especially preferably selected from Tamoxifen and/or Fulvestrant, and preferably the pharmaceutically acceptable dervatives, solvates and/or salts thereof. If antiestrogens are selected for use in the treatment according this invention, preferably only one or two antiestrogens are used at one time in the treatment according this invention. If antiestrogens are selected for use in the treatment according this invention, more preferably only one antiestrogen is used at one time in the treatment according this invention.

Aromatase inhibitors for use in the treatment of breast cancer and/or bone metastases, preferably hormone receptor positive breast cancer and/or hormone receptor positive metastases, are known in the art. Preferred aromatase inhibitors for use according to the invention are preferably selected from the group consisting of Anastrozole (e.g. Arimidex®), Letrozole (e.g. Femara®), Exemestane (e.g. Aromasin®), Vorozole (e.g. Rivizor®), Formestane (e.g. Lentaron®) and Fadrozole (e.g. Afema®) and especially preferably selected from Anastrozole, Letrozole and/or Exemestane, and preferably the pharmaceutically acceptable dervatives, solvates and/or salts thereof. If aromatase inhibitors are selected for use in the treatment according this invention, preferably only one or two aromatase inhibitors are used at one time in the treatment according this invention. If aromatase inhibitors are selected for use in the treatment according this invention, more preferably only one aromatase inhibitor is used at one time in the treatment according this invention.

GnRH analoga for use in the treatment of breast cancer and/or bone metastases, preferably hormone receptor positive breast cancer and/or hormone receptor positive bone metastases, are known in the art. Preferred GnRH analoga for use according to the invention are preferably selected from the group consisting of Leuprorelin (e.g. Eligard®, Enantone®), Goserelin (e.g. Zoladex®) and Buserelin (e.g. Profact®) and especially preferably selected from Leuprorelin and/or Goserelin, and preferably the pharmaceutically acceptable dervatives, solvates and/or salts thereof. If GnRH analoga are selected for use in the treatment according this invention, preferably only one or two GnRH analoga are used at one time in the treatment according this invention. If GnRH analoga are selected for use in the treatment according this invention, more preferably only one GnRH analogon is used at one time in the treatment according this invention.

Osteoclast activity modulating agents for use in the treatment of breast cancer and/or bone metastases, preferably bone metastases, said bone metastases preferably including bone lesions of myeloma, are known in the art. Preferred osteoclast activity modulating agents for use in the treatment according this invention preferably comprise one or more compounds selected from the group consisting of bisphosphonates and RANK/RANKL/OPG modulators. If osteoclast activity modulating agents are selected for use in the treatment according this invention, preferably only one or two osteoclast activity modulating agents are used at one time in the treatment according this invention. If two osteoclast activity modulating agents are selected for use in the treatment according this invention, preferably either two different bisphosphonates are selected for use at one time in the treatment according this invention, or a combination of one bisphosphonate and one RANK/RANKL/OPG modulator is selected for use at one time in the treatment according this invention.

Bisphosphonates for use in the treatment of breast cancer and/or bone metastases, preferably bone metastases, said bone metastases preferably including bone lesions of myeloma, are known in the art. Preferred bisphosphonates for use according to the invention are preferably selected from the group consisting of Etidronate (e.g. Didronel®), Clodronate (e.g. Bonefos®, Loron®), Tiludronate (e.g. Skelid®), Pamidronate (e.g. APD, Aredia®), Neridronate, Olpadronate, Alendronate (e.g. Fosamax®), Ibandronate (e.g. Boniva®), Risedronate (e.g. Actonel®) and Zoledronate (e.g. Zometa®, Aclasta®) and especially preferably selected from Clodronate, Pamidronate, Ibandronate and/or Zoledronate, and preferably the pharmaceutically acceptable dervatives, solvates and/or salts thereof. If bisphosphonates are selected for use in the treatment according this invention, preferably only one or two bisphosphonates are used at one time in the treatment according this invention. If bisphosphonates are selected for use in the treatment according this invention, more preferably only one bisphosphonate is used at one time in the treatment according this invention.

RANK/RANKL/OPG modulators for use in the treatment of breast cancer and/or bone metastases, preferably bone metastases, said bone metastases preferably including bone lesions of myeloma, are known in the art. RANK/RANKL/OPG modulators for use according to the invention are preferably selected from the group consisting of Denosumab (e.g. Prolia®), and preferably the pharmaceutically acceptable dervatives, solvates and/or salts thereof. If RANK/RANKL/OPG modulators are selected for use in the treatment according this invention, preferably only one RANK/RANKL/OPG modulator is used at one time in the treatment according this invention.

Cancer chemotherapeutic agents for use in the treatment of breast cancer and/or bone metastases are known in the art. Preferred cancer chemotherapeutic agents for use in the treatment according this invention are preferably selected from the chemotherapeutic agents described herein. More preferably, the cancer chemotherapeutic agents for use in the treatment according this invention preferably comprise one or more compounds compounds selected from the group consisting of alkylating chemotherapeutic agents, VEGF/VEGFR inhibitors, EGF/EGFR inhibitors, PARP inhibitors, cytostatic alkaloids, cytotoxic antibiotics and antimetabolites. Even more preferably, the cancer chemotherapeutic agents for use in the treatment according this invention preferably comprise at least one compound, at least two compounds or at least three compounds selected from the group consisting of alkylating chemotherapeutic agents, VEGF/VEGFR inhibitors, EGF/EGFR inhibitors, PARP inhibitors, cytostatic alkaloids, cytotoxic antibiotics and antimetabolites. If two or more compounds are selected from said group, preferably only one or two compounds of the respective subgroups, namely the subgroups alkylating chemotherapeutic agents, VEGF/VEGFR inhibitors, EGF/EGFR inhibitors, PARP inhibitors, cytostatic alkaloids, cytotoxic antibiotics and antimetabolites, are selected, e.g. one alkylating chemotherapeutic agent is combined with one cytostatic alkaloid (i.e. a combination comprising two cancer chemotherapeutic agents), two EGF/EGFR inhibitors are combined (i.e. a combination comprising two cancer chemotherapeutic agents), one EGF/EGFR inhibitor is combined with one cytotoxic antibiotic and one antimetabolite (i.e. a combination comprising three cancer chemotherapeutic agents), or two EGF/EGFR inhibitors are combined with cytostatic alkaloid (i.e. a combination comprising three cancer chemotherapeutic agents). If two or more compounds are selected from said group, more preferably only one compound of the respective subgroups, namely the subgroups alkylating chemotherapeutic agents, VEGF/VEGFR inhibitors, EGF/EGFR inhibitors, PARP inhibitors, cytostatic alkaloids, cytotoxic antibiotics and antimetabolites, is selected, e.g. one alkylating chemotherapeutic agent is combined with one cytostatic alkaloid (i.e. a combination comprising two cancer chemotherapeutic agents), one EGF/EGFR inhibitor is combined with one cytotoxic antibiotic and one antimetabolite (i.e. a combination comprising three cancer chemotherapeutic agents).

Alkylating chemotherapeutic agents for use in the treatment of breast cancer and/or bone metastases are known in the art. Preferred alkylating chemotherapeutic agents for use in the treatment according this invention are preferably selected from the alkylating chemotherapeutic agents described herein. More preferably, the alkylating chemotherapeutic agents for use in the treatment according this invention preferably comprise one or more compounds compounds selected from the group consisting of cisplatin, carboplatin, oxaliplatin, cyclophosphamide, ifosfamide and trofosfamide, more preferably cisplatin, carboplatin, oxaliplatin, cyclophosphamide and especially preferably selected from carboplatin and/or cyclophosphamide, and preferably the pharmaceutically acceptable dervatives, solvates and/or salts thereof. If alkylating chemotherapeutic agents are selected for use according to the invention, preferably one or two, more preferably only one alkylating chemotherapeutic agent is used at one time in the treatment according this invention.

VEGF/VEGFR inhibitors for use in the treatment of breast cancer and/or bone metastases are known in the art. Preferred VEGF/VEGFR inhibitors for use in the treatment according this invention are preferably selected from the VEGF/VEGFR inhibitors described herein. More preferably, the VEGF/VEGFR inhibitors for use in the treatment according this invention preferably comprise one or more compounds compounds selected from the group consisting of Bevacizumab (rhuMAb-VEGF, Avastin®), Sorafenib (Nexavar®), Sunitinib (Sutent®), Vandetanib (ZD6474, Zactima®) and especially preferably selected from Bevacizumab, and preferably the pharmaceutically acceptable dervatives, solvates and/or salts thereof. If VEGF/VEGFR inhibitors are selected for use in the treatment according this invention, preferably only one or two VEGF/VEGFR inhibitors are used at one time in the treatment according this invention. If VEGF/VEGFR inhibitors are selected for use in the treatment according this invention, more preferably only one VEGF/VEGFR inhibitor is used at one time in the treatment according this invention.

EGF/EGFR inhibitors for use in the treatment of breast cancer and/or bone metastases are known in the art. Preferred EGF/EGFR inhibitors for use in the treatment according this invention are preferably selected from the EGF/EGFR inhibitors described herein. More preferably, the EGF/EGFR inhibitors for use in the treatment according this invention preferably comprise one or more compounds compounds selected from the group consisting of Trastuzumab (e.g. Herceptin®), cetuximab, panitumumab, zalutumumab, nimotuzumab, matuzumab, gefitinib, erlotinib and lapatinib and especially preferably selected from Trastuzumab and/or lapatinib, and preferably the pharmaceutically acceptable dervatives, solvates and/or salts thereof. If EGF/EGFR inhibitors are selected for use in the treatment according this invention, preferably one or two EGF/EGFR inhibitors are used at one time in the treatment according this invention. If EGF/EGFR inhibitors are selected for use in the treatment according this invention, more preferably Trastuzumab and/or lapatinib is used at one time in the treatment according this invention.

PARP inhibitors for use in the treatment of breast cancer and/or bone metastases are known in the art. Preferred PARP inhibitors for use in the treatment according this invention are preferably selected from the PARP inhibitors described herein. More preferably, the PARP inhibitors for use in the treatment according this invention preferably comprise one or more compounds compounds selected from the group consisting of Olaparib and Iniparib (BSI-201), and preferably the pharmaceutically acceptable dervatives, solvates and/or salts thereof. If PARP inhibitors are selected for use according to the invention, preferably only one PARP inhibitor is used at one time in the treatment according this invention.

Cytostatic alkaloids for use in the treatment of breast cancer and/or bone metastases are known in the art. Preferred cytostatic alkaloids for use in the treatment according this invention are preferably selected from the cytostatic alkaloids described herein. More preferably, the cytostatic alkaloids for use in the treatment according this invention preferably comprise one or more compounds compounds selected from the group consisting of Etoposide, Teniposide, Vinblastine, Vincristine, Vindesine, Vinorelbine, Docetaxel, Paclitaxel, Irinotecane, Topotecane and Ixabepilone, more preferably Etoposide, Vinblastine, Vincristine, Vinorelbine, Docetaxel, Paclitaxel, Irinotecane, Topotecane and Ixabepilone and especially preferably selected from Vinorelbine, Docetaxel, Paclitaxel, and/or Ixabepilone, and preferably the pharmaceutically acceptable dervatives, solvates and/or salts thereof. If cytostatic alkaloids are selected for use in the treatment according this invention, preferably one or two cytostatic alkaloids are used at one time in the treatment according this invention. If cytostatic alkaloids are selected for use in the treatment according this invention, more preferably one cytostatic alkaloid is used at one time in the treatment according this invention.

Cytotoxic antibiotics for use in the treatment of breast cancer and/or bone metastases are known in the art. Preferred cytotoxic antibiotics for use in the treatment according this invention are preferably selected from the cytotoxic antibiotics described herein. More preferably, the cytotoxic antibiotics for use in the treatment according this invention preferably comprise one or more compounds compounds selected from the group consisting of Daunorubicine, Doxorubicine, Epirubicine, Idarubicine, Mitoxantrone, Actinomycin-D, Bleomycine and Mitomycin-C, more preferably Daunorubicine, Doxorubicine, Epirubicine, Idarubicine, Mitoxantrone and Bleomycine and especially preferably selected from Doxorubicine, Epirubicine and/or Mitoxantrone, and preferably the pharmaceutically acceptable dervatives, solvates and/or salts thereof. If cytotoxic antibiotics are selected for use in the treatment according this invention, preferably only one or two cytotoxic antibiotics are used at one time in the treatment according this invention. If cytotoxic antibiotics are selected for use in the treatment according this invention, more preferably only one cytotoxic antibiotic is used at one time in the treatment according this invention.

Antimetabolites for use in the treatment of breast cancer and/or bone metastases are known in the art. Preferred antimetabolites for use in the treatment according this invention are preferably selected from the antimetabolites described herein. More preferably, the antimetabolites for use in the treatment according this invention preferably comprise one or more compounds compounds selected from the group consisting of Methotrexate, Raltitrexed, Pemetrexed, 6-Mercaptopurine, 6-Thioguanine, 2'-Desoxycoformicine, Fludarabinphospate, 2-Chlordeoxyadenosine, 5-Fluorouracil, Capecitabine, Gemcitabine (e.g. Gemzar®), Cytosinarabinoside, Difluorodesoxycytidine and Hydroxyurea, more preferably Methotrexate, Raltitrexed, Pemetrexed, Fludarabinphospate, 5-Fluorouracil, Capecitabine, Gemcitabine (e.g. Gemzar®), Cytosinarabinoside, Difluorodesoxycytidine and Hydroxyurea and especially preferably selected from Methotrexate, Pemetrexed, 5-Fluorouracil, Capecitabine and/or Gemcitabine, and preferably the pharmaceutically acceptable derivatives, solvates and/or salts thereof. If antimetabolites are selected for use in the treatment according this invention, preferably only one or two antimetabolites are used at one time in the treatment according this invention. If antimetabolites are selected for use in the treatment according this invention, more preferably only one antimetabolites is used at one time in the treatment according this invention. If two antimetabolites are used at one time, the combination of Methotrexate and 5-Fluorouracil is especially preferred.

[6] Even more preferred for combining it with said Peptide and/or the pharmaceutically acceptable derivatives, solvates and/or salts thereof are cancer cotherapeutic agents, wherein
i) the hormone modulating agents according to a) comprise one or more compounds selected from the group consisting of antiestrogens, aromatase inhibitors and GnRH analoga,
ii) the osteoclast activity modulating agents according to b) comprise one or more compounds selected from the group consisting of bisphosphonates and RANK/RANKL/OPG modulators,
iii) the cancer chemotherapeutic agents according to c) comprise one or more compounds selected from the group consisting of alkylating chemotherapeutic agents, VEGF/VEGFR inhibitors, EGF/EGFR inhibitors, PARP inhibitors, cytostatic alkaloids, cytotoxic antibiotics, and antimetabolites, and/or
iv) the radiotherapy is selected from external beam radiotherapy/radiation, brachytherapy, and systemic radioisotope therapy.

[7] Especially preferred for combining it with said Peptide and/or the pharmaceutically acceptable derivatives, solvates and/or salts thereof are cancer cotherapeutic agents, wherein
i) the hormone modulating agents according to a) comprise:
α) one or more compounds selected from the antiestrogens Afimoxifene, Arzoxifene, Bazedoxifene, Lasofoxifene, Ormeloxifene, Raloxifene, Tamoxifen, Toremifene and Fulvestrant,
β) one or more compounds selected from the aromatase inhibitors Anastrozole (e.g. Arimidex), Letrozole (e.g. Femara), Exemestane (e.g. Aromasin), Vorozole (e.g. Rivizor), Formestane (e.g. Lentaron) and Fadrozole (e.g. Afema), and/or
γ) one or more compounds selected from the GnRH analoga Leuprorelin (e.g. Eligard®, Enantone®), Goserelin (e.g. Zoladex®) and Buserelin (e.g. Profact®);
ii) the osteoclast activity modulating agents according to b) comprise: δ) one or more compounds selected from the bisphosphonates Etidronate (e.g. Didronel), Clodronate (e.g. Bonefos, Loron), Tiludronate (e.g. Skelid), Pamidronate (e.g. APD, Aredia), Neridronate, Olpadronate, Alendronate (e.g. Fosamax), Ibandronate (e.g. Boniva), Risedronate (e.g. Actonel) and Zoledronate (e.g. Zometa, Aclasta), and/or ε) the RANK/RANKL/OPG modulator Denosumab (e.g. Prolia®); and/or
iii) the cancer chemotherapeutic agents according to c) comprise:
ζ) one or more compounds selected from the alkylating chemotherapeutic agents cisplatin, carboplatin, oxaliplatin, cyclophosphamide, ifosfamide and trofosfamide,
η) one or more compounds selected from the VEGF/VEGFR inhibitors Bevacizumab (rhuMAb-VEGF, e.g. Avastin®), Sorafenib (e.g. Nexavar®), Sunitinib (e.g. Sutent®), Vandetanib (e.g. ZD6474, Zactima®),
θ) one or more compounds selected from the EGF/EGFR inhibitors Trastuzumab (e.g. Herceptin®), cetuximab, panitumumab, zalutumumab, nimotuzumab, matuzumab, gefitinib, erlotinib and lapatinib,
ι) one or more compounds selected from the PARP inhibitors Olaparib and Iniparib (BSI-201),
κ) one or more compounds selected from the cytostatic alkaloids Etoposide, Teniposide, Vinblastine, Vincristine, Vindesine, Vinorelbine, Docetaxel, Paclitaxel, Irinotecane, Topotecane and Ixabepilone,
λ) one or more compounds selected from the cytotoxic antibiotics Daunorubicine, Doxorubicine, Epirubicine, Idarubicine, Mitoxantrone, Actinomycin-D, Bleomycine and Mitomycin-C, and/or
μ) one or more compounds selected from the antimetabolites Gemcitabine, Methotrexate, Raltitrexed, Pemetrexed, 6-Mercaptopurine, 6-Thioguanine, 2'-Desoxycoformicine, Fludarabinphospate, 2-Chlordeoxyadenosine, 5-Fluorouracil, Capecitabine, Cytosinarabinoside, Difluorodesoxycytidine and Hydroxyurea;
nd/or the pharmaceutically acceptable derivatives, solvates and/or salts thereof.

Generally, the Peptide of the formula Cyclo-(Arg-Gly-Asp-DPhe-NMe-Val) and/or the pharmaceutically acceptable derivatives, solvates and/or salts thereof and/or the one or more cancer cotherapeutic agents (including the radiotherapy) can be administered or applied to said human in an amount and/or a regimen as it is known in the art for the respective compound and/or therapy form.

Preferably, the Peptide of the formula Cyclo-(Arg-Gly-Asp-DPhe-NMe-Val) and/or the pharmaceutically acceptable derivatives, solvates and/or salts thereof and/or the one or more cancer cotherapeutic agents (including the radiotherapy) can be administered or applied to said human in an amount and/or a regimen as it is described above and/or below for the respective compound and/or therapy form.

The term "breast cancer" as used in the context of the present invention preferably includes:
hormone receptor negative breast cancer,
hormone receptor positive breast cancer,
HER2 negative breast cancer,
HER2 positive breast cancer,
hormone receptor negative, HER2 negative breast cancer,
hormone receptor positive, HER2 negative breast cancer,
hormone receptor negative, HER2 positive breast cancer, and/or
hormone receptor positive, HER2 positive breast cancer.

The term "breast cancer" as used in the context of the present invention preferably includes "normal" breast cancer" or "non-metastatic breast cancer", and/or "metastatic breast cancer".

The term "non-metastatic breast cancer" preferably includes:
non-metastatic hormone receptor negative breast cancer,
non-metastatic hormone receptor positive breast cancer,
non-metastatic HER2 negative breast cancer, non-metastatic HER2 positive breast cancer,
non-metastatic hormone receptor negative, HER2 negative breast cancer,
non-metastatic hormone receptor positive, HER2 negative breast cancer,
non-metastatic hormone receptor negative, HER2 positive breast cancer,
and/or
nonmetastatic hormone receptor positive, HER2 positive breast cancer.

The term "metastatic breast cancer" is preferably selected from:
   metastatic hormone receptor negative breast cancer,
   metastatic hormone receptor positive breast cancer,
   metastatic HER2 negative breast cancer,
   metastatic HER2 positive breast cancer,
   metastatic hormone receptor negative, HER2 negative breast cancer,
   metastatic hormone receptor positive, HER2 negative breast cancer,
   metastatic hormone receptor negative, HER2 positive breast cancer, and/or
   metastatic hormone receptor positive, HER2 positive breast cancer.

Preferably, the Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), is advantageous for use in the treatment of one or more of the above given breast cancer types and especially advantageous for use in the treatment of substantially all of the above given breast cancer types.

Preferably, the Peptide of the formula Cyclo-(Arg-Gly-Asp-DPhe-NMe-Val) and/or the pharmaceutically acceptable dervatives, solvates and/or salts thereof, is advantageous for the treatment of bone metastases, and more preferably advantageous for the treatment of bone metastases from breast cancer.

[8] A preferred subject is thus a Peptide of the formula Cyclo-(Arg-Gly-Asp-DPhe-NMe-Val) and/or the pharmaceutically acceptable dervatives, solvates and/or salts thereof, for use in the treatment
i) breast cancer,
ii) hormone-receptor positive, HER2 negative breast cancer,
iii) hormone-receptor positive, HER2 positive breast cancer,
iv) hormone-receptor negative, HER2 negative breast cancer, and
v) hormone-receptor negative, HER2 positive breast cancer; and/or
vi) bone metastases thereof.

Thus, a preferred subject of the instant invention is the Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), for use in the treatment of breast cancer and/or bone metastases thereof.

Accordingly, a more preferred subject of the instant invention is the Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), for use in the treatment of metastatic breast cancer and/or the bone metastases thereof.

Accordingly, an especially preferred subject of the instant invention is the Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), for use in the treatment of bone metastases of metastatic breast cancer, preferably including bone metastases of:
   metastatic hormone receptor negative breast cancer,
   metastatic hormone receptor positive breast cancer,
   metastatic HER2 negative breast cancer,
   metastatic HER2 positive breast cancer,
   metastatic hormone receptor negative, HER2 negative breast cancer,
   metastatic hormone receptor positive, HER2 negative breast cancer,
   metastatic hormone receptor negative, HER2 positive breast cancer, and/or
   metastatic hormone receptor positive, HER2 positive breast cancer.

(1) A preferred subject of the instant invention is a method of treating breast cancer in humans, more preferably hormone receptor positive breast cancer, even more preferably hormone receptor positive and HER2 negative breast cancer and especially preferably metastatic hormone receptor positive and HER2 negative breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and optionally
b) one or more hormone modulating agents or two or more hormone modulating agents, preferably hormone modulating agents selected from
i) the antiestrogens Afimoxifene, Arzoxifene, Bazedoxifene, Lasofoxifene, Ormeloxifene, Raloxifene, Tamoxifen, Toremifene and Fulvestrant,
ii) the aromatase inhibitors Anastrozole (Arimidex), Letrozole (Femara), Exemestane (Aromasin), Vorozole (Rivizor), Formestane (Lentaron) and Fadrozole (Afema), and/or
iii) the GnRH analoga Leuprorelin (Eligard®, Enantone®), Goserelin (Zoladex®) and Buserelin (Profact®).

(2) More preferred is a method of treating method of treating breast cancer in humans, more preferably hormone receptor positive breast cancer, even more preferably hormone receptor positive and HER2 negative breast cancer and especially preferably metastatic hormone receptor positive and HER2 negative breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
b) one hormone modulating agent, preferably one hormone modulating agent selected from
i) the antiestrogens Afimoxifene, Arzoxifene, Bazedoxifene, Lasofoxifene, Ormeloxifene, Raloxifene, Tamoxifen, Toremifene and Fulvestrant,
ii) the aromatase inhibitors Anastrozole (Arimidex), Letrozole (Femara), Exemestane (Aromasin), Vorozole (Rivizor), Formestane (Lentaron) and Fadrozole (Afema), and/or
iii) the GnRH analoga Leuprorelin (Eligard®, Enantone®), Goserelin (Zoladex®) and Buserelin (Profact®).

(3) More preferred is a method of treating breast cancer in humans, more preferably hormone receptor positive breast cancer and especially preferably hormone receptor positive and HER2 negative breast, comprising administering to said human:

a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
b) two hormone modulating agents, which are
i) one antiestrogen, preferably one antiestrogen selected from Afimoxifene, Arzoxifene, Bazedoxifene, Lasofoxifene, Ormeloxifene, Raloxifene, Tamoxifen, Toremifene and Fulvestrant, and especially preferably Tamoxifen; and
ii) one GnRH analogon, preferably one GnRH analogon selected from Leuprorelin (Eligard®, Enantone®), Goserelin (Zoladex®) and Buserelin (Profact®), and especially Leuprorelin or Goserelin.

(4) Even more preferred is a method of treating breast cancer in humans, more preferably hormone receptor positive breast cancer, even more preferably hormone receptor positive and HER2 negative breast cancer and especially preferably metastatic hormone receptor positive and HER2 negative breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
b) two hormone modulating agents, which are
i) one antiestrogen, preferably one antiestrogen selected from Afimoxifene, Arzoxifene, Bazedoxifene, Lasofoxifene, Ormeloxifene, Raloxifene, Tamoxifen, Toremifene and Fulvestrant, and especially preferably Tamoxifen; and
ii) one GnRH analogon, preferably one GnRH analogon selected from Leuprorelin (Eligard®, Enantone®), Goserelin (Zoladex®) and Buserelin (Profact®), and especially Leuprorelin or Goserelin.

The four above given methods are preferred in the treatment of hormone receptor positive breast cancer and especially hormone receptor positive and HER2 negative breast cancer, and/or bone metastases thereof. The four above given methods are even more preferred in the treatment of metastatic hormone receptor positive breast cancer and especially metastatic hormone receptor positive and HER2 negative breast cancer, and/or bone metastases thereof.

In the case of the presence of bone metastases, said methods can preferably combined with the administration of one or more osteoclast activity modulating agents, preferably osteoclast activity modulating agents as described herein.

(5) A preferred subject of the instant invention is a method of treating breast cancer in humans, more preferably HER2 positive breast cancer and especially metastatic HER2 positive breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), optionally in combination with
b) one or more EGF/EGFR inhibitors, preferably one or more EGF/EGFR inhibitors selected from the group consisting of Trastuzumab (Herceptin®), cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab and/or lapatinib.

(6) A preferred subject of the instant invention is a method of treating breast cancer in humans, more preferably HER2 positive breast cancer, even more preferably HER2 positive and hormone receptor positive breast cancer and especially metastatic HER2 positive and hormone receptor positive breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
b) one or more EGF/EGFR inhibitors, preferably one or more EGF/EGFR inhibitors selected from the group consisting of Trastuzumab (Herceptin®), cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab and/or lapatinib,
optionally in combination with
b) one or more hormone modulating agents or two or more hormone modulating agents, preferably hormone modulating agents selected from
i) the antiestrogens Afimoxifene, Arzoxifene, Bazedoxifene, Lasofoxifene, Ormeloxifene, Raloxifene, Tamoxifen, Toremifene and Fulvestrant,
ii) the aromatase inhibitors Anastrozole (Arimidex), Letrozole (Femara), Exemestane (Aromasin), Vorozole (Rivizor), Formestane (Lentaron) and Fadrozole (Afema), and/or
iii) the GnRH analoga Leuprorelin (Eligard®, Enantone®), Goserelin (Zoladex®) and Buserelin (Profact®).

(7) A preferred subject of the instant invention is a method of treating breast cancer in humans, more preferably HER2 positive breast cancer, even more preferably HER2 positive and hormone receptor positive breast cancer and especially metastatic HER2 positive and hormone receptor positive breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
b) one or more EGF/EGFR inhibitors, preferably one or more EGF/EGFR inhibitors selected from the group consisting of Trastuzumab (Herceptin®), cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab and/or lapatinib,
optionally in combination with
b) one or more hormone modulating agents, preferably one or more hormone modulating agents selected from
i) the aromatase inhibitors Anastrozole (Arimidex), Letrozole (Femara), Exemestane (Aromasin), Vorozole (Rivizor), Formestane (Lentaron) and Fadrozole (Afema), more preferably Anastrozole (Arimidex), Letrozole (Femara) and Exemestane (Aromasin), and/or
ii) Tamoxifen.

Preferably, only one hormone modulating agent is selected.

The three above given methods (methods (4) to (7)) are preferred in the treatment of HER2 positive breast cancer and especially HER2 positive and hormone receptor positive breast cancer, and/or bone metastases thereof.

The three above given methods are even more preferred in the treatment of metastatic HER2 positive breast cancer and especially metastatic HER2 positive and hormone receptor positive breast cancer, and/or bone metastases thereof.

In the case of the presence of bone metastases, said methods can preferably combined with the administration of one or more osteoclast activity modulating agents, preferably osteoclast activity modulating agents as described herein.

(8) A preferred subject of the instant invention is a method of treating breast cancer in humans, more preferably hormone receptor positive breast cancer, even more preferably hormone receptor positive and HER2 negative breast cancer and especially preferably metastatic hormone receptor positive and HER2 negative breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), optionally in combination with
b) one or more hormone modulating agents or two or more hormone modulating agents, preferably hormone modulating agents selected from
i) the antiestrogens Afimoxifene, Arzoxifene, Bazedoxifene, Lasofoxifene, Ormeloxifene, Raloxifene, Tamoxifen, Toremifene and Fulvestrant,
ii) the aromatase inhibitors Anastrozole (Arimidex), Letrozole (Femara), Exemestane (Aromasin), Vorozole (Rivizor), Formestane (Lentaron) and Fadrozole (Afema), and/or
iii) the GnRH analoga Leuprorelin (Eligard®, Enantone®), Goserelin (Zoladex®) and Buserelin (Profact®),
and/or
c) one or more compounds selected from the VEGF/VEGFR inhibitors, preferably selected from the VEGF/VEGFR inhibitors Bevacizumab (rhuMAb-VEGF, Avastin®), Sorafenib (Nexavar®), Sunitinib (Sutent®), Vandetanib (ZD6474, Zactima®), and especially Bevacizumab.

(9) A preferred subject of the instant invention is a method of treating breast cancer in humans, more preferably hormone receptor positive breast cancer, even more preferably hormone receptor positive and HER2 negative breast cancer and especially preferably metastatic hormone receptor positive and HER2 negative breast cancer, comprising administering to said human:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), optionally in combination with
b) one or more hormone modulating agents or two or more hormone modulating agents, preferably hormone modulating agents selected from the aromatase inhibitors Anastrozole (Arimidex), Letrozole (Femara), Exemestane (Aromasin), Vorozole (Rivizor), Formestane (Lentaron) and Fadrozole (Afema), and especially Letrozole,
and/or
c) one or more compounds selected from the VEGF/VEGFR inhibitors, preferably selected from the VEGF/VEGFR inhibitors Bevacizumab (rhuMAb-VEGF, Avastin®), Sorafenib (Nexavar®), Sunitinib (Sutent®), Vandetanib (ZD6474, Zactima®), and especially Bevacizumab.

(10) A preferred subject of the instant invention is a method of treating breast cancer in humans comprising the administration of chemotherapy, preferably in a first line treatment setting, said method comprising the administration of:
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
and
b) one or more cancer chemotherapeutic agents, preferably at least two or at least three cancer chemotherapeutic agents, more preferably one, two or three cancer chemotherapeutic agents, preferably cancer chemotherapeutic agents selected from the groups consisting of:
i) one or more alkylating chemotherapeutic agents, preferably one alkylating chemotherapeutic agent, preferably alkylating chemotherapeutic agents as described herein and more preferably alkylating chemotherapeutic agents selected from the group consisting of cisplatin, carboplatin, oxaliplatin, cyclophosphamide, ifosfamide and trofosfamide, and especially cyclophosphamide,
ii) one or more cytostatic alkaloids, preferably one cytostatic alkaloids or two cytostatic alkaloids, preferably cytostatic alkaloids as described herein and more preferably cytostatic alkaloids selected from the group consisting of Etoposide, Teniposide, Vinblastine, Vincristine, Vindesine, Vinorelbine, Docetaxel, Paclitaxel, Irinotecane, Topotecane and Ixabepilone, and especially Docetaxel or Paclitaxel,
iii) one or more cytotoxic antibiotics, preferably one cytotoxic antibiotic or two cytotoxic antibiotics, preferably cytotoxic antibiotics as described herein and more preferably cytotoxic antibiotics selected from the group consisting of Daunorubicine, Doxorubicine, Epirubicine, Idarubicine, Mitoxantrone and Bleomycine, and especially Doxorubicine, Epirubicine or Mitoxantrone,
and/or
iv) one or more antimetabolites, preferably one antimetabolite or two antimetabolites, preferably antimetabolites as described herein and more preferably antimetabolites selected from the group consisting of Gemcitabine, Methotrexate, Raltitrexed, Pemetrexed, Fludarabinphospate, 5-Fluorouracil and Capecitabine, and especially Methotrexate and/or 5-Fluorouracil,
to said human.

This method is preferably applied in the treatment of humans with metastatic breast cancer, hormone receptor positive and HER2 negative breast cancer, hormone receptor negative and HER2 negative breast cancer, metastatichormone receptor positive and HER2 negative breast cancer, and/or metastatic hormone receptor negative and HER2 negative breast cancer, preferably in a first line treatment setting. This method can be combined with the administration of one VEGF/VEGFR inhibitor, preferably one VEGF/VEGFR inhibitor as described herein, more preferably one VEGF/VEGFR inhibitor selected from the group consisting of Bevacizumab (rhuMAb-VEGF, Avastin®), Sorafenib (Nexavar®), Sunitinib (Sutent®) and Vandetanib (ZD6474, Zactima®), and especially with the administration of Bevacizumab to said human.

The three above given methods (methods (8) to (10)) are preferred in the treatment of HER2 negative breast cancer, more preferably hormone receptor positive and HER2 negative breast cancer and especially preferably hormone receptor positive, HER2 negative and/or VEGF/VEGFR positve breast cancer, and/or bone metastases thereof. The three above given methods (methods (8) to (10)) are even more preferred in the treatment of metastatic HER2 negative breast cancer, more preferably metastatic hormone receptor positive and HER2 negative breast cancer and especially preferably metastatic hormone receptor positive, HER2 negative and/or VEGF/VEGFR positve breast cancer, and/or bone metastases thereof. In the case of the presence of bone metastases, said methods can preferably combined with the administration of one or more osteoclast activity modulating agents, preferably osteoclast activity modulating agents as described herein.

(11) A preferred subject of the instant invention is a method of treating breast cancer in humans, preferably comprising the administration of chemotherapy, preferably in a first line treatment setting, said method comprising the administration of:

(I)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
  b) Docetaxel or Paclitaxel, and/or the pharmaceutically acceptable dervatives, solvates and/or salts thereof, and
  c) Doxorubicine, Epirubicine or Mitoxantrone, and/or the pharmaceutically acceptable dervatives, solvates and/or salts thereof;

(II)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
  b) Docetaxel or Paclitaxel, and/or the pharmaceutically acceptable dervatives, solvates and/or salts thereof,
  optionally in combination with
  c) Bevacizumab, and/or the pharmaceutically acceptable dervatives, solvates and/or salts thereof;

(III)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
  b) Doxorubicine, Epirubicine or Mitoxantrone, and/or the pharmaceutically acceptable dervatives, solvates and/or salts thereof,
  optionally in combination with
  c) Bevacizumab, and/or the pharmaceutically acceptable dervatives, solvates and/or salts thereof;

(IV)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
  b) an alkylating chemotherapeutic agent, preferably an alkylating chemotherapeutic agent as described herein and especially an alkylating chemotherapeutic agent selected from a group consisting of Cyclophosphamide, Cisplatin and Carboplatin and more preferably selected from a group consisting of Cyclophosphamide and Carboplatin, and/or the pharmaceutically acceptable dervatives, solvates and/or salts thereof, and
  c) one or two antimetabolites, preferably one or two antimetabolites as described herein and especially one or two antimetabolites selected from Methotrexate and 5-Fluorouracil, and/or the pharmaceutically acceptable derivatives, solvates and/or salts thereof;

(V)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
  b) an alkylating chemotherapeutic agent, preferably an alkylating chemotherapeutic agent as described herein and especially an alkylating chemotherapeutic agent selected from a group consisting of Cyclophosphamide, Cisplatin and Carboplatin and more preferably selected from a group consisting of Cyclophosphamide and Carboplatin, and/or the pharmaceutically acceptable dervatives, solvates and/or salts thereof,
  optionally in combination with
  c) a cytotoxic antibiotic, preferably a cytotoxic antibiotic as described herein, more preferably a cytotoxic antibiotic selected from the group consisting of Doxorubicine, Epirubicine and Mitoxantrone, and especially Doxorubicine or Epirubicine, and/or the pharmaceutically acceptable dervatives, solvates and/or salts thereof
  and/or
  d) one or two antimetabolites, preferably one or two antimetabolites as described herein and especially one or two antimetabolites selected from Methotrexate and 5-Fluorouracil, and/or the pharmaceutically acceptable dervatives, solvates and/or salts thereof;

(VI)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
  b) an alkylating chemotherapeutic agent, preferably an alkylating chemotherapeutic agent as described herein and especially an alkylating chemotherapeutic agent selected from a group consisting of Cyclophosphamide, Cisplatin and Carboplatin and more preferably selected from a group consisting of Cyclophosphamide and Carboplatin, and/or the pharmaceutically acceptable dervatives, solvates and/or salts thereof,
  optionally in combination with
  c) a cytotoxic antibiotic, preferably a cytotoxic antibiotic as described herein, more preferably a cytotoxic antibiotic selected from the group consisting of Doxorubicine, Epirubicine and Mitoxantrone, and especially Doxorubicine or Epirubicine, and/or the pharmaceutically acceptable dervatives, solvates and/or salts thereof
  and/or
  d) a cytostatic alkaloid, preferably a cytostatic alkaloid as described herein and especially a cytostatic alkaloid selected from Docetaxel and Paclitaxel, and/or the pharmaceutically acceptable dervatives, solvates and/or salts thereof;

(VII)
  a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
  b) Cyclophosphamide, and/or the pharmaceutically acceptable dervatives, solvates and/or salts thereof,
  c) Methotrexat, and/or the pharmaceutically acceptable dervatives, solvates and/or salts thereof, and
d) 5-Fluorouracil, and/or the pharmaceutically acceptable dervatives, solvates and/or salts thereof;

(VIII)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Cyclophosphamide, and/or the pharmaceutically acceptable dervatives, solvates and/or salts thereof,
c) Doxirubicine, and/or the pharmaceutically acceptable dervatives, solvates and/or salts thereof,
and
d) 5-Fluorouracil, and/or the pharmaceutically acceptable dervatives, solvates and/or salts thereof;

(IX)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Cyclophosphamide, and/or the pharmaceutically acceptable dervatives, solvates and/or salts thereof,
c) Doxirubicine, and/or the pharmaceutically acceptable dervatives, solvates and/or salts thereof,
and
d) Docetaxel, and/or the pharmaceutically acceptable dervatives, solvates and/or salts thereof;

(X)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Cyclophosphamide, and/or the pharmaceutically acceptable dervatives, solvates and/or salts thereof, and
c) Doxirubicine, and/or the pharmaceutically acceptable dervatives, solvates and/or salts thereof;

(XI)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b ) Cyclophosphamide, and/or the pharmaceutically acceptable dervatives, solvates and/or salts thereof,
and
c) Epirubicine, and/or the pharmaceutically acceptable dervatives, solvates and/or salts thereof;

or (XII)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Cyclophosphamide, and/or the pharmaceutically acceptable dervatives, solvates and/or salts thereof,
c) Epirubicine, and/or the pharmaceutically acceptable dervatives, solvates and/or salts thereof,
and
d) 5-Fluorouracil, and/or the pharmaceutically acceptable dervatives, solvates and/or salts thereof;
to said human.

The methods (I) to (XII) are preferred treatment regimen options that are preferably advantageous in the treatment of metastatic breast cancer, hormone receptor positive breast cancer, hormone receptor negative breast cancer, hormone receptor positive HER2 negative breast cancer and/or hormone receptor negative HER2 negative breast cancer, more preferably metastatic breast cancer, hormone receptor negative HER2 negative breast cancer, hormone receptor positive HER2 negative breast cancer and especially metastatic breast cancer and/or hormone receptor negative HER2 negative breast cancer. They are especially preferred in a first line therapy setting.

(12) A preferred subject of the instant invention is a method of treating breast cancer in humans, preferably comprising the administration of EGF/EGFR and/or HER2 targeting compounds, preferably in a first line treatment setting, said method comprising the administration of:

(XIII)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more EGF/EGFR inhibitors, preferably one or more EGF/EGFR inhibitors as described herein and especially preferably EGF/EGFR inhibitors selected from the group consisting of Trastuzumab (Herceptin®), cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab and/or lapatinib,
optionally in combination with
c) a cytostatic alkaloid, preferably a cytostatic alkaloid as described herein and especially a cytostatic alkaloid selected from Docetaxel and Paclitaxel, and/or the pharmaceutically acceptable dervatives, solvates and/or salts thereof;

(XIV)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more EGF/EGFR inhibitors, preferably one or more EGF/EGFR inhibitors as described herein, and especially preferably Trastuzumab, and/or the pharmaceutically acceptable dervatives, solvates and/or salts thereof,
in combination with
c) Docetaxel, and/or the pharmaceutically acceptable dervatives, solvates and/or salts thereof;

or (XV)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more EGF/EGFR inhibitors, preferably one or more EGF/EGFR inhibitors as described herein, and especially preferably Trastuzumab, and/or the pharmaceutically acceptable dervatives, solvates and/or salts thereof,
in combination with
c) Paclitaxel, and/or the pharmaceutically acceptable dervatives, solvates and/or salts thereof;
to said human.

(13) A preferred subject of the instant invention is a method of treating breast cancer in humans, preferably comprising the administration of chemotherapy, preferably in a second line or higher treatment setting, said method comprising the administration of:

(XVI)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- in combination with
- b) one or more cytostatic alkaloids, preferably one or more cytostatic alkaloids as described herein and more preferably one or more cytostatic alkaloid selected from Etoposide, Vinblastine, Vincristine, Vinorelbine, Docetaxel, Paclitaxel, Irinotecane and Ixabepilone, and especially Vinorelbine, Docetaxel, Paclitaxel or Ixabepilone, and/or the pharmaceutically acceptable dervatives, solvates and/or salts thereof;
- and/or
- c) one or two antimetabolites, preferably one or two antimetabolites as described herein and especially one or two antimetabolites selected from the group consisting of Methotrexate, Raltitrexed, Pemetrexed, 5-Fluorouracil, Gemcitabine and Capecitabine, and especially Gemcitabine and/or Capecitabine, and/or the pharmaceutically acceptable dervatives, solvates and/or salts thereof;

(XVII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- in combination with
- b) one or more compounds selected from PARP inhibitors, preferably PARP inhibitors as described herein and especially one or two PARP inhibitors, selected from Olaparib and Iniparib (BSI-201), and/or the pharmaceutically acceptable dervatives, solvates and/or salts thereof;

(XVIII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- and
- b) one or more compounds selected from PARP inhibitors, preferably PARP inhibitors as described herein, more preferably PARP inhibitors selected from the group consisting of Olaparib and Iniparib (BSI-201), and especially Iniparib (BSI-201), and/or the pharmaceutically acceptable dervatives, solvates and/or salts thereof;
- in combination with
- c) an alkylating chemotherapeutic agent, preferably an alkylating chemotherapeutic agent as described herein, more preferably n alkylating chemotherapeutic agent selected from a group consisting of Cyclophosphamide, Cisplatin and Carboplatin, and especially, Cisplatin or Carboplatin, and/or the pharmaceutically acceptable derivatives, solvates and/or salts thereof,
- and/or
- d) one or two antimetabolites, preferably one or two antimetabolites as described herein and especially one or two antimetabolites selected from the group consisting of Methotrexate, Raltitrexed, Pemetrexed, 5-Fluorouracil, Gemcitabine and Capecitabine, and especially Gemcitabine, and/or the pharmaceutically acceptable derivatives, solvates and/or salts thereof;

(XIX)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- and
- b) Ixabepilone, and/or the pharmaceutically acceptable dervatives, solvates and/or salts thereof;

(XX)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Ixabepilone, and/or the pharmaceutically acceptable dervatives, solvates and/or salts thereof,
- and/or
- c) Capecitabine, and/or the pharmaceutically acceptable dervatives, solvates and/or salts thereof;

(XXI)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- and
- b) one or more compounds, more preferably one, two or three compounds, selected from the group consisting of Paclitaxel, Docetaxel, Vinorelbine and Capecitabine, and/or the pharmaceutically acceptable dervatives, solvates and/or salts thereof;

(XXII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- and
- b) Paclitaxel, Paclitaxel-Albumin, Docetaxel, Vinorelbine or Capecitabine;

(XXIII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Vinorelbine, and/or the pharmaceutically acceptable dervatives, solvates and/or salts thereof;
- and
- c) Capecitabine, and/or the pharmaceutically acceptable dervatives, solvates and/or salts thereof;

(XXIV)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Vinorelbine, and/or the pharmaceutically acceptable dervatives, solvates and/or salts thereof;
- and
- c) Gemcitabine, and/or the pharmaceutically acceptable dervatives, solvates and/or salts thereof;

(XXV)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Gemcitabine, and/or the pharmaceutically acceptable dervatives, solvates and/or salts thereof; and
- c) Paclitaxel or Docetaxel, and/or the pharmaceutically acceptable derivatives, solvates and/or salts thereof;

(XXVI)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Capecitabine, and/or the pharmaceutically acceptable derivatives, solvates and/or salts thereof; and
- c) Paclitaxel or Docetaxel, and/or the pharmaceutically acceptable derivatives, solvates and/or salts thereof;

(XXVII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
- b) Olaparib, and/or the pharmaceutically acceptable dervatives, solvates and/or salts thereof;

or (XXVIII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Iniparib (BSI-201), and/or the pharmaceutically acceptable derivatives, solvates and/or salts thereof;
- c) Cyclophosphamide, Cisplatin or Carboplatin, preferably Cisplatin or Carboplatin, and/or the pharmaceutically acceptable dervatives, solvates and/or salts thereof, and
- d) 5-Fluorouracil, Gemcitabine or Capecitabine, preferably Gemcitabine, and/or the pharmaceutically acceptable derivatives, solvates and/or salts thereof;

to said human.

(14) A preferred subject of the instant invention is a method of treating breast cancer in humans, preferably comprising the administration of EGF/EGFR inhibitors, preferably in a second line or higher treatment setting, said method comprising the administration of:

(XXIX)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) one or more EGF/EGFR inhibitors, preferably one or more EGF/EGFR inhibitors as described herein and especially preferably EGF/EGFR inhibitors selected from the group consisting of Trastuzumab (e.g. Herceptin®), cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab and/or Lapatinib, optionally in combination with
- c) one or two antimetabolites, preferably one or two antimetabolites as described herein and especially one or two antimetabolites selected from the group consisting of Methotrexate, Raltitrexed, Pemetrexed, 5-Fluorouracil, Gemcitabine and Capecitabine, and especially Capecitabine, and/or the pharmaceutically acceptable derivatives, solvates and/or salts thereof;

(XXX)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Trastuzumab, and/or the pharmaceutically acceptable derivatives, solvates and/or salts thereof, and
- c) Lapatinib, and/or the pharmaceutically acceptable dervatives, solvates and/or salts thereof;

(XXXI)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val), and
- b) Trastuzumab, and/or the pharmaceutically acceptable derivatives, solvates and/or salts thereof;

(XXXII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Trastuzumab, and/or the pharmaceutically acceptable derivatives, solvates and/or salts thereof, and
- c) Capecitabine, and/or the pharmaceutically acceptable derivatives, solvates and/or salts thereof;

or (XXXIII)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) Lapatinib, and/or the pharmaceutically acceptable dervatives, solvates and/or salts thereof, and
- c) Capecitabine, and/or the pharmaceutically acceptable derivatives, solvates and/or salts thereof;

to said human.

(15) A preferred subject of the instant invention is a method of treating breast cancer in humans, preferably comprising the administration of hormone modulating agents, preferably in a first line or higher treatment setting, said method comprising the administration of:

(XXXIV)
- a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
- b) one or more antioestrogens, preferably one or more antioestrogens as described herein, more preferably one or more antioestrogens selected from the group consisting of Afimoxifene, Arzoxifene, Bazedoxifene, Lasofoxifene, Ormeloxifene, Raloxifene, Tamoxifen, Toremifene and Fulvestrant, and especially Tamoxifen and/or Fulvestrant, and/or the pharmaceutically acceptable dervatives,solvates and/or salts thereof
and
c) one or more GnRH analoga, preferably one or more GnRH analoga as described herein, more preferably one or more GnRH analoga selected from the group consisting of Leuprorelin, Goserelin and Buserelin, and especially Leuprorelin or Goserelin, and/or the pharmaceutically acceptable dervatives, solvates and/or salts thereof;
(XXXV)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more aromatase inhibitors, preferably one or more aromatase inhibitors as described herein, more preferably one or more aromatase inhibitors selected from the group consisting of Anastrozole, Letrozole, Exemestane, Vorozole, Formestane and Fadrozole, and especially Anastrozole (Arimidex), Letrozole or Exemestane, and/or the pharmaceutically acceptable dervatives, solvates and/or salts thereof;
(XXXVI)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Tamoxifen, and/or the pharmaceutically acceptable dervatives, solvates and/or salts thereof,
and
c) Leuprorelin or Goserelin, and/or the pharmaceutically acceptable dervatives, solvates and/or salts thereof;
(XXXVII)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more aromatase inhibitors, preferably one or more aromatase inhibitors as described herein, more preferably one or more aromatase inhibitors selected from the group consisting of Anastrozole, Letrozole, Exemestane, Vorozole, Formestane and Fadrozole, and especially Anastrozole, Letrozole or Exemestane, and/or the pharmaceutically acceptable dervatives, solvates and/or salts thereof,
and
c) one or more EGF/EGFR inhibitors, preferably one or more EGF/EGFR inhibitors as described herein and especially preferably EGF/EGFR inhibitors selected from the group consisting of Trastuzumab, cetuximab, panitumumab, zalutumumab, nimotuzumab, matuzumab, gefitinib, erlotinib and lapatinib, more preferably selected from the group consisting of Trastuzumab, panitumumab, zalutumumab, nimotuzumab, gefitinib, erlotinib and lapatinib, and especially Trastuzumab or Lapatinib, and/or the pharmaceutically acceptable dervatives, solvates and/or salts thereof;
(XXXVIII)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-OPhe-NMe-Val),
b) Anastrozole, Letrozole or Exemestane, and/or the pharmaceutically acceptable dervatives, solvates and/or salts thereof,
and
c) Trastuzumab, and/or the pharmaceutically acceptable dervatives, solvates and/or salts thereof,
(XXXIX)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Anastrozole, Letrozole or Exemestane, and/or the pharmaceutically acceptable dervatives, solvates and/or salts thereof, and
c) Lapatinib, and/or the pharmaceutically acceptable dervatives, solvates and/or salts thereof;
(XL)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) one or more aromatase inhibitors, preferably one or more aromatase inhibitors as described herein, more preferably one or more aromatase inhibitors selected from the group consisting of Anastrozole, Letrozole, Exemestane, Vorozole, Formestane and Fadrozole, and especially Anastrozole, Letrozole or Exemestane, and/or the pharmaceutically acceptable dervatives, solvates and/or salts thereof,
and
c) one VEGF/VEGFR inhibitor, preferably one VEGF/VEGFR inhibitor as described herein, more preferably one VEGF/VEGFR inhibitor selected from the group consisting of Bevacizumab, Sorafenib, Sunitinib and Vandetanib, and especially Bevacizumab, and/or the pharmaceutically acceptable dervatives, solvates and/or salts thereof;
or (XLI)
a) a Peptide of the formula Cyclo-(Arg-Gly-Asp-DPhe-NMe-Val) and/or the pharmaceutically acceptable dervatives, solvates and/or salts thereof, more preferably the Peptide of the formula Cyclo-(Arg-Gly-Asp-DPhe-NMe-Val),
b) Anastrozole, Letrozole or Exemestane, and/or the pharmaceutically acceptable dervatives, solvates and/or salts thereof,
and
c) Bevacizumab, and/or the pharmaceutically acceptable dervatives, solvates and/or salts thereof;
to said humans.

In the case of the presence of bone metastases, said methods can preferably combined with the administration of one or more osteoclast activity modulating agents, preferably osteoclast activity modulating agents as described herein.

A preferred subject of the instant invention is a method of treating bone metastases, preferably bone metastases in humans, comprising administering a Peptide of the formula Cyclo-(Arg-Gly-Asp-DPhe-NMe-Val) and/or the pharmaceutically acceptable dervatives, solvates and/or salts thereof, to a subject, preferably a human subject.

The meaning of the term "bone metastases" is well known and understood in the art. Generally, the term includes bone metastases of any origin. According to the instant invention, the term bone metastases preferably includes, but is not limited to, bone metastases of cancers as described herein, more preferably of solid cancers, more preferably cancers selected from the group consisting of cancers of the breast, heart, lung, small intestine, colon, spleen, kidney, bladder, head and neck, ovary, prostate, brain, pancreas, skin, bone, thymus, uterus, testicles, cervix, and/or liver. According to the instant invention, the term bone metastases preferably also includes bone lesions, preferably osteolytic and/or osteoplastic bone lesions, more preferably osteolytic bone lesions, even more preferably bone lesions of myeloma, malignant myeloma and/or multiple myeloma, and especially osteolytic bone lesions of myeloma, malignant myeloma and/or multiple myeloma.

According to the instant invention, the term bone metastases preferably also includes bone lesions of Morbus Waldenström, preferably osteolytic and/or osteoplastic bone lesions of Morbus Waldenström, more preferably osteolytic bone lesions of Morbus Waldenström .

Bone metastases according to the invention more preferably include bone metastases of cancers selected from the group consisting of breast cancer, lung cancer, colon cancer, colorectal cancer, kidney cancer, bladder cancer, head and neck cancer, ovary cancer, prostate cancer, brain cancer, pancreas cancer, skin cancer, thymus cancer, uterus cancer, testicle cancer, cervix cancer and liver cancer.

Bone metastases according to the invention even more preferably include bone metastases of cancers selected from the group consisting of breast cancer, lung cancer, preferably NSCLC and/or SCLC, head and neck cancer, preferably SCCHN, colon cancer, colorectal cancer, prostate cancer and multiple myeloma.

Bone metastases according to the invention epecially preferably include bone metastases of breast cancer, or consist of bone metastases of breast cancer.

A more preferred subject of the instant invention is a method of treating bone metastases, preferably bone metastases in humans, comprising administering
a) a Peptide of the formula Cyclo-(Arg-Gly-Asp-DPhe-NMe-Val) and/or the pharmaceutically acceptable dervatives, solvates and/or salts thereof,
and
b) one or more osteoclast activity modulating agents, preferably one or more osteoclast activity modulating agents as described herein and especially preferably one or more osteoclast activity modulating agents selected from the group consisting of bisphosphonates and RANK/RANKL/OPG modulators, preferably bisphosphonates and RANK/RANKL/OPG modulators
as described herein,
to a subject, preferably a human subject.

A more preferred subject of the instant invention is a method of treating bone metastases, preferably bone metastases in humans, comprising administering
a) a Peptide of the formula Cyclo-(Arg-Gly-Asp-DPhe-NMe-Val) and/or the pharmaceutically acceptable dervatives, solvates and/or salts thereof,
and
b) one or more osteoclast activity modulating agents, preferably one or two osteoclast activity modulating agents, selected from the group consisting of the bisphosphonates Etidronate, Clodronate, Tiludronate, Pamidronate, Neridronate, Olpadronate, Alendronate, Ibandronate, Risedronate and Zoledronate and the RANK/RANKL/OPG modulator Denosumab, and/or the pharmaceutically acceptable dervatives, solvates and/or salts thereof, to a subject, preferably a human subject.

An even more preferred subject of the instant invention is a method of treating bone metastases, preferably bone metastases in humans, comprising administering
a) a Peptide of the formula Cyclo-(Arg-Gly-Asp-DPhe-NMe-Val) and/or the pharmaceutically acceptable dervatives, solvates and/or salts thereof,
and
b) one or more osteoclast activity modulating agents, preferably one or two osteoclast activity modulating agents, selected from the group consisting of the bisphosphonates Etidronate, Clodronate, Tiludronate, Pamidronate, Neridronate, Olpadronate, Alendronate, Ibandronate, Risedronate and Zoledronate, more preferably Clodronate, Ibandronate, Pamidronate and Zoledronate, and/or the pharmaceutically acceptable dervatives, solvates and/or salts thereof,
to a subject, preferably a human subject.

An also more preferred subject of the instant invention is a method of treating bone metastases, preferably bone metastases in humans, comprising administering
a) a Peptide of the formula Cyclo-(Arg-Gly-Asp-DPhe-NMe-Val) and/or the pharmaceutically acceptable dervatives, solvates and/or salts thereof,
and
b) Denosumab, and/or the pharmaceutically acceptable dervatives, solvates and/or salts thereof,
to a subject, preferably a human subject.

However, in the treatment of bone metastases, it can be necessary or advantageous not only to treat the bone metastases according to the above described methods, but to additionally treat or suppress the activity of the primary source of the disease e.g. the primary tumour, and/or other metastases thereof than bone metastases.

Accordingly, it can be necessary or advantageous to combine the herein described method of treating bone metastases with one or more, preferably one of the herein described treatment regimens that do not comprise
a) the administration of the Peptide of the formula Cyclo-(Arg-Gly-Asp-DPhe-NMe-Val) and/or the pharmaceutically acceptable dervatives, solvates and/or salts thereof, and/or
b) the administration of osteoclast activity modulating agents, preferably osteoclast activity modulating agents as described herein.

Thus, a preferred aspect relates to a method of treating of bone metastases, preferably bone metastases as described herein, comprising or additionally comprising the administration of one or more osteoclast activity modulating agents, preferably one or two osteoclast activity modulating agents, preferably osteoclast activity modulating agents as described herein. This method is especially preferred in human subjects.

Thus, a more preferred aspect relates to a method of treating of bone metastases, preferably bone metastases as described herein, comprising additionally administering one or more osteoclast activity modulating agents, preferably one or two osteoclast activity modulating agents, preferably osteoclast activity modulating agents as described herein, to a treatment regimen described herein, preferably a treatment regimen described herein that does not already comprise the administration of osteoclast activity modulating agents, preferably, preferably osteoclast activity modulating agents as described herein. This method is especially preferred in human subjects.

An even more preferred method of treating bone metastases, preferably bone metastases as described herein, comprises the application of
a) one or more treatment regimens as described in the methods (I) to (XLI),
and
b) the administration of one or more osteoclast activity modulating agents, preferably one or more osteoclast activity modulating agents as described herein and especially preferably one or more osteoclast activity modulating agents selected from the group consisting of bisphosphonates and RANK/RANKL/OPG modulators, preferably bisphosphonates and RANK/RANKL/OPG modulators as described herein, to a subject, preferably a human subject.

An even more preferred method of treating bone metastases, preferably bone metastases as described herein, comprises f
a) the application one or more treatment regimens as described in the methods (I) to (XLI),
and
b) the administration of one or more osteoclast activity modulating agents, preferably one or two osteoclast activity modulating agents, selected from the group consisting of the bisphosphonates Etidronate, Clodronate, Tiludronate, Pamidronate, Neridronate, Olpadronate, Alendronate, Ibandronate, Risedronate and Zoledronate and the RANK/RANKL/OPG modulator Denosumab, and/or the pharmaceutically acceptable dervatives, solvates and/or salts thereof,
to a subject, preferably a human subject.

An even more preferred method of treating bone metastases, preferably bone metastases as described herein, comprises
a) the application of a treatment regimen selected from
i) the methods (I) to (XII),
ii) the methods (XIII) to (XV),
iii) the methods (XVI) to (XXVIII),
iv) the methods (XXIX) to (XXXIII), and/or
v) the methods (XXXIV) to (XLI)
and
b) the administration of one or more osteoclast activity modulating agents, preferably one or two osteoclast activity modulating agents, selected from the group consisting of the bisphosphonates Etidronate, Clodronate, Tiludronate, Pamidronate, Neridronate, Olpadronate, Alendronate, Ibandronate, Risedronate and Zoledronate and the RANIVRANKUOPG modulator Denosumab, and/or the pharmaceutically acceptable dervatives, solvates and/or salts thereof,
to a subject, preferably a human subject.

Especially preferred osteoclast activity modulating agents in this regard are selected from the group consisting of Clodronate, Ibandronate, Pamidronate, Zoledronate and Denosumab, nd/or the pharmaceutically acceptable dervatives, solvates and/or salts thereof.

The above described methods for the treatment of breast cancer and/or bone metastases, preferably the treatment of breast cancer and/or bone metastases in humans, can be advantageously combined with the application of radiotherapy to the respective subject, preferably respective human subject. Preferred kinds of radiotherapy applied to the said subject include, but are not limited to external beam radiotherapy or external beam radiation, brachytherapy, and/or systemic radioisotope therapy.

[9] Thus, subject is a Peptide of the formula Cyclo-(Arg-Gly-Asp-DPhe-NMe-Val) and/or the pharmaceutically acceptable dervatives, solvates and/or salts thereof for use in the treatment of breast cancer and/or bone metastases, preferably bone metastases and especially bone metastases of breast cancer, wherein the treatment comprises or additionally comprises the administration of:
a) or more cancer cotherapeutic agents, selected from the group consisting of osteoclast activity modulating agents, preferably osteoclast activity modulating agents as described herein,
and/or
b) radiotherapy, preferably radiotherapy as described herein and especially radiotherapy selected from the group consisting of external beam radiotherapy or external beam radiation, brachytherapy, and systemic radioisotope therapy,
to a subject, preferably a human subject.

An even more preferred subject is a Peptide of the formula Cyclo-(Arg-Gly-Asp-DPhe-NMe-Val) and/or the pharmaceutically acceptable dervatives, solvates and/or salts thereof for use in the treatment of breast cancer and/or bone metastases, preferably bone metastases and especially bone metastases of breast cancer, wherein the treatment comprises or additionally comprises the administration of:
a) one or more osteoclast activity modulating agents, preferably one or two osteoclast activity modulating agents, selected from the group consisting of Etidronate, Clodronate, Tiludronate, Pamidronate, Neridronate, Olpadronate, Alendronate, Ibandronate, Risedronate, Zoledronate and Denosumab, more preferably the group consisting of Clodronate, Pamidronate, Ibandronate, Zoledronate and Denosumab, and/or the pharmaceutically acceptable dervatives, solvates and/or salts thereof,
and/or
b) radiotherapy, preferably radiotherapy as described herein and especially radiotherapy selected from the group consisting of external beam radiotherapy or external beam radiation, brachytherapy, and systemic radioisotope therapy
to a subject, preferably a human subject.

[12] Preferably, said treatment of the bone metastases comprises or additionally comprises the administration of:
one or more cancer cotherapeutic agents, selected from the group consisting cisplatin, carboplatin, oxaliplatin, cyclophosphamide, ifosfamide and trofosfamide, and/or the pharmaceutically acceptable dervatives, solvates and/or salts thereof,
to a subject, preferably a human subject.

[10] Preferably, the treatment of the hormone-receptor positive breast cancer comprises the administration of Peptide of the formula Cyclo-(Arg-Gly-Asp-DPhe-NMe-Val) and/or the pharmaceutically acceptable dervatives, solvates and/or salts thereof and additionally comprises the administration of:
i) at least one compound, preferably one or two compounds, selected from the group consiting of Afimoxifene, Arzoxifene, Bazedoxifene, Lasofoxifene, Ormeloxifene, Raloxifene, Tamoxifen, Toremifene, Fulvestrant, Anastrozole (e.g. Arimidex), Letrozole (e.g. Femara), Exemestane (e.g. Aromasin), Vorozole (e.g. Rivizor), Formestane (e.g. Lentaron) and Fadrozole (e.g. Afema), Leuprorelin, (e.g. Eligard®, Enantone®), Goserelin, (e.g. Zoladex®) and Buserelin (e.g. Profact®);
optionally in combination with
ii) at least one compound selected from the group consisting of Bevacizumab rhuMAb-VEGF, (e.g. Avastin®), panitumumab, zalutumumab, nimotuzumab, matuzumab, gefitinib, erlotinib and lapatinib, Trastuzumab (e.g. Herceptin®), cetuximab, panitumumab, zalutumumab, nimotuzumab, matuzumab, gefitinib, erlotinib and lapatinib;
and/or
iii) radiotherapy;
to a subject, preferably a human subject.

Preferably, the Leuprorelin can be administered as Leuprorelinacetat and/or the Goserelin can be administered as Goserelinacetat.

[11] Preferably, the treatment of the hormone-receptor negative breast cancer comprises the administration of the Peptide of the formula Cyclo-(Arg-Gly-Asp-DPhe-NMe-Val) and/or the pharmaceutically acceptable dervatives, solvates and/or salts thereof and additionally comprises the administration of:
i) at least one compound selected from the group consisting of Bevacizumab (rhuMAb-VEGF, e.g. Avastin®), panitumumab, azlutumumab, nimotuzumab, matuzumab, gefitinib, erlotinib and lapatinib, Trastuzumab (e.g. Herceptin®), cetuximab, panitumumab, zalutumumab, nimotuzumab, matuzumab, gefitinib, erlotinib and lapatinib;
optionally in combination with
ii) at least one compound selected from the group consisting of Daunorubicine, Doxorubicine, Epirubicine, Idarubicine, Mitoxantrone, Actinomycin-D, Bleomycine and Mitomycin-C,
iii) at least one compound selected from the group consisting of Etoposide, Teniposide, Vinblastine, Vincristine, Vindesine, Vinorelbine, Docetaxel, Paclitaxel, Irinotecane, Topotecane and Ixabepilone,
iv) at least one compound selected from the group consisting of Olaparib and Iniparib (BSI-201),
and/or
v) one or more compounds selected from the antimetabolites Gemcitabine, Methotrexate, Raltitrexed, Pemetrexed, 6-Mercaptopurine, 6-Thioguanine, 2'-Desoxycoformicine, Fludarabinphospate, 2-Chlordeoxyadenosine, 5-Fluorouracil, Capecitabine, Cytosinarabinoside, Difluorodesoxycytidine and Hydroxyurea;
to a subject, preferably a human subject.

A further and especially preferred aspect of the instant application is
a) method of reducing bone resorption, preferably reduced osteoclast-mediated bone resorption, in a subject, preferably a human subject,
b) a method of inducing new bone formation, preferably new bone formation in osteolytic lesions,
c) a method for the regulation or normalisation of the osteoclast activity,
d) a method for the resumption of bone formation,
and/or
e) a method of inducing regrowth of bone or partial regroth of the bone, in a subject, preferably a human subject, more preferably a subject suffering from bone metastases and especially a humansubject suffering from bone metastases, said method comprising or consisting of the administration of the Peptide of the formula Cyclo-(Arg-Gly-Asp-DPhe-NMe-Val) and/or the pharmaceutically acceptable dervatives, solvates and/or salts thereof.

Optionally, said method(s) can comprise or additionally comprise the administration of one or more cancer cotherapeutic agents, preferably one or more cancer cotherapeutic agents. In said method(s), the bone metastases are preferably as described herein.

According to the invention, the one or more one alkylating chemotherapeutic agents preferably comprise one or more compounds, selected from the group consisting of platinum containing chemotherapeutic agents and/or selected from a group consisting of oxazaphosphorines.

According to one embodiment of the instant invention, the breast cancer and/or the bone metastases are EGF/EGFR dependant.

According to one embodiment of the instant invention, the breast cancer and/or the bone metastases are VEGF/VEGFR dependent.

According to one embodiment of the instant invention, the breast cancer and/or the bone metastasized thereof are HER2 dependent.

According to one embodiment of the instant invention, the bone metastases to be treated are bone metastases of breast cancer, lung cancer and/prostate cancer.

According to one embodiment of the instant invention, the bone metastases to be treated are bone metastases cancer is head and neck cancer, preferably squamous cell cancer of the head and neck (SCCHN).

Preferably, the Peptide of the formula Cyclo-(Arg-Gly-Asp-DPhe-NMe-Val) and/or the pharmaceutically acceptable dervatives, solvates and/or salts thereof, and/or the one or more cancer cotherapeutic agents are administered in an amount and/or a regimen as it is described herein for the respective compound and preferably for the respective cancer and/or bone metastases.

Preferably, the breast cancer as described herein also includes metastases in other organs or parts of the body of the subject. Examples of other organs or parts of the body of a subject that are prone to developing metastases include, but are not limited to lung, bone, liver, brain, kidney, adrenal gland, lymph nodes (including lymphangiosis carcinomatosa), heart and skin, more preferably lung, liver, brain, kidney, adrenal gland, lymph nodes (including lymphangiosis carcinomatosa), heart and skin.

According to the invention, the one or more alkylating chemotherapeutic agents preferably comprise one or more compounds, selected from the group consisting the platinum containing compounds cisplatin, carboplatin and oxaliplatin, and/or selected from the group consisting of the oxazaphosphorines cyclophosphamide, ifosfamide and trofosfamide.

Preferably, the cancer cotherapeutic agents for use in the treatments/treatment methods described herein comprise one or more compounds selected from the group consisting of:
i) EGF/EGFR inhibitors,
ii) VEGF/VEGFR inhibitors
iii) cytostatic alkaloids,
iv) cytotoxic antibiotics, and
v) antimetabolites,
and pharmaceutically acceptable dervatives, salts and/or solvates thereof.

Preferably, the cancer cotherapeutic agents for use in the treatments/treatment methods described herein comprise one or more compounds selected from the group consisting of:
i) EGF/EGFR inhibitors, selected from anti-EGFR biologicals and chemically derived compounds,
ii) cytostatic alkaloids, selected from podophylotoxines, vinca alkaloids, taxanes and campthothecines,
iii) cytotoxic antibiotics, selected from anthracyclines, and
iv) antimetabolites, selected from pyrimidin antagonists and antifolates,
and pharmaceutically acceptable dervatives, salts and/or solvates thereof.

Anti-EGFR biologicals in this respect are preferably selected from trastuzumab, cetuximab, panitumumab, zalutumumab, nimotuzumab and matuzumab;

Anti-EGFR chemically derived compounds in this respect are preferably selected from gefitinib, erlotinib and lapatinib;

Podophyllotoxinderivatives in this respect are preferably selected from Etoposide and Teniposide;

Vinca alkaloids in this respect are preferably selected from Vinblastine, Vincristine, Vindesine and Vinorelbine;

Taxanes in this respect are preferably selected from Docetaxel and Paclitaxel; Camptothecin derivatives in this respect are preferably selected from Irinotecane and Topotecane;

Anthracyclines in this respect are preferably selected from Daunorubicine, Doxorubicine, Epirubicine and Idarubicine;

Antifolates in this respect are preferably selected from Methotrexate, Raltitrexed, and Pemetrexed;

Pyrimidine antagonists in this respect are preferably selected from 5-Fluorouracil, Gemcitabine, Capecitabine, Cytosinarabinoside and Difluorodesoxycytidine;

and pharmaceutically acceptable dervatives, salts and/or solvates thereof.

More preferably, the cancer cotherapeutic agents for use in the treatments/treatment methods described herein comprise one or more compounds selected from the group consisting of:
i) EGF/EGFR inhibitors, selected from the group consisting of cetuximab, panitumumab, zalutumumab, nimotuzumab and matuzumab and/or the group consisting of gefitinib, erlotinib and lapatinib,
ii) cytostatic alkaloids, selected from the group consisting of etoposide, vinblastine and teniposide, the group consisting of vinorelbine, vincristine and vindesine, the group consisting of docetaxel and paclitaxel, and/or the group consisting of irinotecan and topotecan,
iii) cytotoxic antibiotics, selected from the group consisting of doxorubicin, idarubicin, daunorubicin, epirubicin and valrubicin, and
iv) antimetabolites, selected from the group consisting of 5-fluorouracil, capecitabine, cytosinarabinosid and difluorodesoxycytidin and/or the group consisting of pemetrexed, methotrexat and raltitrexed,
and pharmaceutically acceptable dervatives, salts and/or solvates thereof.

Preferably, the Peptide of the formula cyclo-(Arg-Gly-Asp-DPhe-NMe-Val), and/or the pharmaceutically acceptable dervatives, solvates and/or salts thereof, preferably the Peptide of formula cyclo-(Arg-Gly-Asp-DPhe-NMe-Val), is administered to a subject, preferably a human subject and especially a patient, in an amount of 250 mg to 12500 mg per week, More preferably in an amount of 500 mg to 10000 mg per week, even more preferably 900 mg to 9000 mg per week, even more preferably 1200 mg to 7000 mg per week and especially 2000 to 6000 mg per week, such as 2500 mg to 5000 mg per week.

Preferably, the platinum containing chemotherapeutic agents cisplatin, carboplatin and oxaliplatin are administered to the subject, preferably human subject and especially patient, in an amount of 100 to 1000 mg in one or more portions within a time period of 2 to 4 weeks.

The treatment of cancer, at least the treatment of cancer with chemotherapeutic agents in the broadest sense, is a protracted issue. Thus, the treatment of cancer with chemotherapeutic agents generally includes a prolonged exposure to the one or more respective chemotherapeutic agents. Taking into account that most of the chemotherapeutic agents, when applied in an efficient dose, are toxic for the body of the patient, the chemotherapeutic agents (unless they show any or hardly any acute toxicity) are generally applied over a certain, limited time, followed by a time period without the administration of the respective chemotherapeutic agent, during which time the patient's body is allowed to recover from the toxicity of said chemotherapeutic agent. generally, this treatment regimen comprising the application time period of the respective chemotherapeutic agent and the recovery time period after the application of the respective chemotherapeutic agent is repeated one or more times, preferably several times. This kind of regimen is usually referred to by the skilled artisan as "cycles", each cycle comprising the application time period of the respective chemotherapeutic agent and the recovery time period after the application of the respective chemotherapeutic agent. The duration of the application time period and/or the recovery time period after the application of the chemotherapeutic are usually depending on the properties of the respective chemotherapeutic agent. Accordingly, different chemotherapeutic agents can have different durations of the application time period and/or the recovery time period after the of the chemotherapeutic. Thus, the length or duration of a cycle can be different for different chemotherapeutic agents. Generally, the length of a cycle is in between one week and 12 weeks, more preferably one week to six weeks and especially 2 to 4 weeks. Preferably, the dosing of the respective chemotherapeutic agent is given in an amount per cycle, allowing the the physicist to adapt the actual administration to the status of the patient, i.e. whether the amount per cycle is given in one single administration or divided into two or more portions administered at different times within the cycle. In the setting of a combination treatment comprising two or more chemotherapeutic agents, generally two or more cycles (having the same or a different length) run in parallel. If the chemotherapeutic agent is administered to the patient in two or more portions within one cycle, each portion is preferably given on a different day within said cycle. With respect to each of the chemotherapeutics administered, generally more than one cycle, preferably two or more cycles, even more preferably three or more cycles are applied to the patient, preferably substantially with out a pause. Generally, not more than 24 cycles are applied to the patient substantially without a pause. The application of about six cycles substantially without a pause to the patient for each of the chemotherapeutics administered is generally a standard for of many of the chemotherapeutics described herein.

Accordingly, the time period of 2 to 4 weeks referred to herein wherein the platinum containing chemotherapeutic agents cisplatin, carboplatin and oxaliplatin are administered to the patient in an amount of 100 to 1000 mg in one or more portions (within said time period of 2 to 4 weeks) is preferably to be regarded as one cycle. More preferably, the time period or cycle, wherein the platinum containing therapeutic agent is administered is about three weeks (about 21 days). With respect to oxaliplatin, following administration is also preferred: oxaliplatin is preferably administered to the patient in an amount of 50 to 500 mg in one or more portions, preferably one portion, within a time period of about two weeks. Accordingly, the duration of a cycle with respect to oxaliplatin is preferably about two weeks.

Generally, the cisplatin can be administered to the patient as is known in the art.

Preferably, cisplatin is administered to the patient in an amount of 50 mg to 500 mg within one cycle, more preferably 80 mg to 300 mg within one cycle. Preferably, the amount of cisplatin is administered to the patient is given in mg per square metre of the by the surface of the patient, i.e. in mg/m$^2$. Accordingly, cisplatin is preferably administered to the patient in an amount of 50 to 150 mg/m², more preferably 80 to 120 mg/m² and especially about 100 mg/m² within one cycle.

The amount cisplatin can be administered in one or more portions, more preferably 1 to 5 portions, even more preferred 1 to 3 and especially preferably in one portion on one day. Generally, cisplatin is administered as an i. V. infusion.

Generally, the carboplatin can be administered to the patient as is known in the art.

Preferably, carboplatin is administered to the patient in an amount of 200 mg to 1000 mg within one cycle, more preferably 300 mg to 800 mg within one cycle and especially 400 to 700 mg within one cycle. Even more preferably, the carboplatin is administered to the patient in an AUC (Area Under the Curve) regimen, more specifically an AUC 4-8 regimen (4-8 mg/ml/min), preferably an AUC 5-7 regimen (5-7 mg/ml/min). The principles of the AUC regimen or dosing are known in the art. Preferably, the amounts to be administered to the patient in the AUC regimen according to the invention are calculated using the Calvert formula and/or the Chatelut formula, preferably the Calvert formula.

Calvert Formula:

Carboplatin dose (mg)=AUC×(CrCl (ml/min)+25);

wherein:
AUC=Area Under the Curve ((mg/ml×min))
x=multiplied
CrCl=Creatinin Clearence (of the respective patient)
Chatelut formula:

Carboplatin dosage (mg)=AUC (mg/ml×min)×carboplatin clearance (ml/min);

wherein:
AUC=Area Under the Curve

Formula suitable for estimation of the carboplatin clearance of a patient for use in the Chatelut formula:

for Males=(0.134×weight)+(218×weight×(1−0.00457×age)/serum creat.)

for Females=(0.134×weight)+0.686×(218×weight×(1−0.00457×age)/serum creat.)

Age=age in years
x=multiplied
weight=weight in kg serum creat.=the serum concentration of creatinine The amount carboplatin can be administered in one or more portions, more preferably 1 to 5 portions, even more preferred 1 to 3 and especially preferably in one portion on one day. Generally, carboplatin is administered as an i. V. infusion.

Generally, the oxaliplatin can be administered to the patient as is known in the art.

Preferably, oxaliplatin is administered to the patient in an amount of 50 mg to 500 mg within one cycle, more preferably 80 mg to 300 mg within one cycle. If the duration of the cycle is about three or about five weeks, the oxaliplatin is preferably administered to the patient in an amount of 100 to 500 mg. If the duration of the cycle is about two weeks, the oxaliplatin is preferably administered to the patient in an amount of 50 to 250 mg. Preferably, the amount of oxaliplatin is administered to the patient is given in mg per square metre of the by the surface of the patient, i.e. in mg/m². Accordingly, oxaliplatin is preferably administered to the patient in an amount of 80 to 150 mg/m² within one cycle, for example about 130 mg/m² within one cycle, especially if the duration of the cycle is about three or about four weeks. Alternatively, the oxaliplatin is preferably administered to the patient in an amount of 50 to 100 mg/m² within one cycle, for example about 85 mg/m² within one cycle, especially if the duration of the cycle is about two weeks.

The amount oxaliplatin can be administered in one or more portions, more preferably 1 to 5 portions, even more preferred 1 to 3 and especially preferably in one portion on one day. Generally, oxaliplatin is administered as an i. V. infusion.

Dosings and preferably standard administration schedules for the above and/or below given cancer cotherapapeutic agents are preferably known in the art.

Even more preferably, the cancer cotherapapeutic agents can generally be administered to the patient in a form and in a way or manner that is known in the art for the respective compounds or class of compounds, for example as described herein or as described in the literature cited herein.

The antiestrogens, preferably the antioestrogens selected from the group consisting of Afimoxifene, Arzoxifene, Bazedoxifene, Lasofoxifene, Ormeloxifene, Raloxifene, Tamoxifen, Toremifene and Fulvestrant, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Tamoxifen and/or the pharmaceutically acceptable dervatives, solvates and/or salts thereof, preferably Tamoxifen, is administered to the subject in an amount of 100 mg to 1000 mg within one cycle, more preferably 300 mg to 700 mg within one cycle. Preferably, the amount of Tamoxifen and/or the pharmaceutically acceptable dervatives, solvates and/or salts thereof, preferably Tamoxifen, is administered to the subject in about daily doses of 10 to 30 mg (flat) and especially about 20 mg (flat) on about every day or about every second day within the cycle. A cycle in this regard preferably consists of 2 to 4 weeks (14 to 28 days) and especially of about three weeks (about 21 days). Preferably, Tamoxifen and/or the pharmaceutically acceptable dervatives, solvates and/or salts thereof, preferably Tamoxifen, is administered to the subject per orally (p.o.). Especially preferably, Tamoxifen is administered to the subject per orally (p.o.) in an amount of about 20 mg per day about every day, preferably about every day during a cycle, more preferably per day about every day during a cycle of about 3 weeks.

Preferably, Fulvestrant and/or the pharmaceutically acceptable dervatives, solvates and/or salts thereof, preferably Fulvestrant, is administered to the subject in an amount of 100 mg to 1000 mg within one cycle or within one month, more preferably 200 mg to 600 mg and especially 250 to 500 mg within one cycle or within one month. Preferably, the amount of Fulvestrant and/or the pharmaceutically acceptable dervatives, solvates and/or salts thereof, preferably Fulvestrant, is administered to the subject once within the cycle or within the month in an amount 200 mg to 600 mg and especially 250 to 500 mg (flat), preferably on day one of said cycle or month. A cycle in this regard preferably consists of 2 to 4 weeks (14 to 28 days) and a month preferably consists of 29 to 31 days. Fulvestrant is preferably administered orally or by injection, preferably intramuscularly (i.m.). Preferably, Fulvestrant and/or the pharmaceutically acceptable dervatives, solvates and/or salts thereof, preferably Fulvestrant, is administered intramuscularly (i.m.).

Especially preferably, Fulvestrant is administered intramuscularly (i.m.) in an amount of 250 to 500 mg on one day, preferably the first day, every about 29 days.

The aromatase inhibitors, preferably the aromatase inhibitors selected from the group consisting of Anastrozole (Arimidex), Letrozole (Femara), Exemestane (Aromasin), Vorozole (Rivizor), Formestane (Lentaron) and Fadrozole (Afema), and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Exemestane and/or the pharmaceutically acceptable dervatives, solvates and/or salts thereof, preferably Exemestane, is administered to the subject in an amount of 100 mg to 1000 mg within one cycle, more preferably 300 mg to 700 mg within one cycle. Preferably, the amount of Exemestane and/or the pharmaceutically acceptable dervatives, solvates and/or salts thereof, preferably Exemestane, is administered to the subject in about daily doses of 15 to 35 mg (flat) and especially about 25 mg (flat) on about every day or about every second day within the cycle. A cycle in this regard preferably consists of 2 to 4 weeks (14 to 28 days) and especially of about three weeks (about 21 days). Preferably, Exemestane and/or the pharmaceutically acceptable dervatives, solvates and/or salts thereof, preferably Exemestane, is administered to the subject per orally (p.o.). Especially preferably, Exemestane is administered to the subject per orally (p.o.) in an amount of about 25 mg per day about every day, preferably about every day during a cycle, more preferably per day about every day during a cycle of about 3 weeks.

Preferably, Anastrozole and/or the pharmaceutically acceptable dervatives, solvates and/or salts thereof, preferably Anastrozole, is administered to the subject in an amount of 10 mg to 50 mg within one cycle, more preferably 15 mg to 40 mg within one cycle. Preferably, the amount of Anastrozole and/or the pharmaceutically acceptable dervatives, solvates and/or salts thereof, preferably Anastrozole, is administered to the subject in about daily doses of 0.5 to 2 mg (flat) and especially about 1 mg (flat) on about every day or about every second day within the cycle. A cycle in this regard preferably consists of 2 to 4 weeks (14 to 28 days) and especially of about three weeks (about 21 days). Preferably, Anastrozole and/or the pharmaceutically acceptable dervatives, solvates and/or salts thereof, preferably Anastrozole, is administered to the subject per orally (p.o.). Especially preferably, Anastrozole is administered to the subject per orally (p.o.) in an amount of about 1 mg per day about every day, preferably about every day during a cycle, more preferably per day about every day during a cycle of about 3 weeks.

Preferably, Letrozole and/or the pharmaceutically acceptable dervatives, solvates and/or salts thereof, preferably Letrozole, is administered to the subject in an amount of 25 mg to 120 mg within one cycle, more preferably 35 mg to 90 mg within one cycle. Preferably, the amount of Letrozole and/or the pharmaceutically acceptable dervatives, solvates and/or salts thereof, preferably Letrozole, is administered to the subject in about daily doses of 1.5 to 3.5 mg (flat) and especially about 2.5 mg (flat) on about every day or about every second day within the cycle. A cycle in this regard preferably consists of 2 to 4 weeks (14 to 28 days) and especially of about three weeks (about 21 days). Preferably, Letrozole and/or the pharmaceutically acceptable dervatives, solvates and/or salts thereof, preferably Letrozole, is administered to the subject per orally (p.o.). Especially preferably, Letrozole is administered to the subject per orally (p.o.) in an amount of about 2.5 mg per day about every day, preferably about every day during a cycle, more preferably per day about every day during a cycle of about 3 weeks.

The GnRH analoga, preferably the GnRH analoga selected from the group consisting of Leuprorelin (Eligard®, Enantone®), Goserelin (Zoladex®) and Buserelin, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Goserelin and/or the pharmaceutically acceptable dervatives, solvates and/or salts thereof, preferably Goserelin, is administered to the subject in an amount of 1 mg to 5 mg within one cycle or within one month, more preferably 2.5 mg to 4.5 mg and especially about 3.6 mg within one cycle or within one month. Preferably, the amount of Goserelin and/or the pharmaceutically acceptable dervatives, solvates and/or salts thereof, preferably Goserelin, is administered to the subject once within the cycle or within the month in an amount 2.5 mg to 4.5 mg and especially about 3.6 mg (flat), preferably on day one of said cycle or month. A cycle in this regard preferably consists of 2 to 4 weeks (14 to 28 days) and a month preferably consists of 29 to 31 days. Goserelin is preferably administered orally or by injection, preferably subcutaneously (s.c.). Preferably, Goserelin and/or the pharmaceutically acceptable dervatives, solvates and/or salts thereof, preferably Goserelin, is administered subcutaneously (s.c.). Especially preferably, Goserelin is administered subcutaneously (s.c.) in an amount of about 3.6 mg on one day, preferably the first day, every about 29 days.

Preferably, Leuprorelin and/or the pharmaceutically acceptable dervatives, solvates and/or salts thereof, preferably Leuprorelinacetate, is administered to the subject in an amount of 5 mg to 15 mg within 70 to 90 days, more preferably 9 mg to 14 mg and especially about 11.3 mg within the within 70 to 90 days. Preferably, the amount of Leuprorelin and/or the pharmaceutically acceptable dervatives, solvates and/or salts thereof, preferably Leuprorelinacetate, is administered to the subject once within 70 to 90 days in an amount 10 mg to 12 mg and especially about 11.3 mg (flat), preferably on day one of said 70 to 90 days and more preferably 80 to 90 days. Leuprorelin or Leuprorelinacetate is preferably administered orally or by injection, preferably subcutaneously (s.c.) or intramuscularly (i.m.). Preferably, Leuprorelin and/or the pharmaceutically acceptable dervatives, solvates and/or salts thereof, preferably Leuprorelinacetate, is administered subcutaneously (s.c.) or intramuscularly (i.m.). Especially preferably, Leuprorelinacetate is administered intramuscularly (i.m.) or subcutaneously (s.c.) in an amount of about 11.3 mg on one day, preferably the first day, every about 84 days.

The bisphosphonates, preferably the bisphosphonates selected from the group consisting of Afimoxifene, Arzoxifene, Bazedoxifene, Lasofoxifene, Ormeloxifene, Raloxifene, Tamoxifen, Toremifene and Fulvestrant, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Clodronate and/or the pharmaceutically acceptable dervatives, solvates and/or salts thereof, preferably Clodronate, is administered to the subject in an amount of 15000 mg to 50000 mg within one cycle, more preferably 25000 mg to 40000 mg within one cycle. Preferably, the amount of Clodronate and/or the pharmaceutically acceptable dervatives, solvates and/or salts thereof, preferably Clodronate, is administered to the subject in about daily doses of 1000 to 2500 mg (flat) and especially about 1600 mg (flat) on about every day or about every second day within the cycle. A cycle in this regard preferably consists of 2 to 4 weeks (14 to 28 days) and especially of about three weeks (about 21 days). Preferably, Clodronate and/or the pharmaceutically acceptable dervatives, solvates and/or salts thereof, preferably Clodronate, is administered to the subject per orally (p.o.). Especially preferably, Clodronate is administered to the subject per orally (p.o.) in an amount of about 1600 mg per day about every day, preferably about every day during a cycle, more preferably per day about every day during a cycle of about 3 or about 4 weeks.

Preferably, Zoledronate and/or the pharmaceutically acceptable dervatives, solvates and/or salts thereof, preferably Zoledronate, is administered to the subject in an amount of 1 mg to 10 mg within one cycle, more preferably 2 mg to 6 mg within one cycle. Preferably, the amount of Zoledronate and/or the pharmaceutically acceptable dervatives, solvates and/or salts thereof, preferably Zoledronate, is administered to the subject once or twice, preferably once in an amout 2 mg to 6 mg (flat) and especially about 4 mg (flat) on one day or two days, preferably one day, within the cycle, preferably on day one of said cycle. A cycle in this regard preferably consists of 2 to 4 weeks (14 to 28 days) and especially of about three weeks (about 21 days). Preferably, Zoledronate and/or the pharmaceutically acceptable dervatives, solvates and/or salts thereof, preferably Zoledronate, is administered to the subject per orally (p.o.) or by injection, more preferably intravenously (i.v.). Especially preferably, Zoledronate is administered to the subject intravenously (i.v.) in an amount of about 4 mg per day on one day, preferably a on one day during a cycle, more preferably on one day during a cycle of about 3 or 4 weeks, preferably on day one of said cycle.

Preferably, Ibandronate and/or the pharmaceutically acceptable dervatives, solvates and/or salts thereof, preferably Ibandronate, is administered to the subject in an amount of 2 mg to 12 mg within one cycle, more preferably 4 mg to 8 mg within one cycle. Preferably, the amount of Ibandronate and/or the pharmaceutically acceptable dervatives, solvates and/or salts thereof, preferably Ibandronate, is administered to the subject once or twice, preferably once in an amout 4 mg to 8 mg (flat) and especially about 6 mg (flat) on one day or two days, preferably one day, within the cycle, preferably on day one of said cycle. A cycle in this regard preferably consists of 2 to 4 weeks (14 to 28 days) and especially of about three weeks (about 21 days). Preferably, Ibandronate and/or the pharmaceutically acceptable dervatives, solvates and/or salts thereof, preferably Ibandronate, is administered to the subject per orally (p.o.) or by injection, more preferably intravenously (i.v.). Especially preferably, Ibandronate is administered to the subject intravenously (i.v.) in an amount of about 6 mg per day on one day, preferably a on one day during a cycle, more preferably on one day during a cycle of about 3 or 4 weeks, preferably on day one of said cycle. Ibandronate and/or the pharmaceutically acceptable dervatives, solvates and/or salts thereof are especially preferred in the treatment of metatases of breast cancer.

Preferably, Pamidronate and/or the pharmaceutically acceptable dervatives, solvates and/or salts thereof, preferably Pamidronate, is administered to the subject in an amount of 70 mg to 120 mg within one cycle, more preferably 80 mg to 100 mg within one cycle. Preferably, the amount of Pamidronate and/or the pharmaceutically acceptable dervatives, solvates and/or salts thereof, preferably Pamidronate, is administered to the subject once or twice, preferably once in an amout 80 mg to 100 mg (flat) and especially about 90 mg (flat) on one day or two days, preferably one day, within the cycle, preferably on day one of said cycle. A cycle in this regard preferably consists of 2 to 4 weeks (14 to 28 days) and especially of about three weeks (about 21 days). Preferably, Pamidronate and/or the pharmaceutically acceptable dervatives, solvates and/or salts thereof, preferably Pamidronate, is administered to the subject per orally (p.o.) or by injection, more preferably intravenously (i.v.). Especially preferably, Pamidronate is administered to the subject intravenously (i.v.) in an amount of about 90 mg per day on one day, preferably a on one day during a cycle, more preferably on one day during a cycle of about 3 or 4 weeks, preferably on day one of said cycle.

The RANK/RANKL/OPG modulators, preferably the RANK/RANKL/OPG modulator Denosumab and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Denosumab and/or the pharmaceutically acceptable dervatives, solvates and/or salts thereof, preferably Denosumab, is administered to the subject in an amount of 30 mg to 200 mg within one cycle, more preferably 40 mg to 150 mg within one cycle. Preferably, the amount of Denosumab and/or the pharmaceutically acceptable dervatives, solvates and/or salts thereof, preferably Denosumab, is administered to the subject once or twice, preferably once in an amout 40 mg to 150 mg (flat) and especially 60-120 mg (flat) on one day or two days, preferably one day, within the cycle, preferably on day one of said cycle. A cycle in this regard preferably consists of 2 to 4 weeks (14 to 28 days) and especially of about three weeks (about 21 days). Preferably, Denosumab and/or the pharmaceutically acceptable dervatives, solvates and/or salts thereof, preferably Denosumab, is administered to the subject per orally (p.o.) or by injection, more preferably subcutaneously (s.c.). Especially preferably, Denosumab is administered subcutaneously (s.c.) in an amount of about 60 to 120 mg per day on one day, preferably a on one day during a cycle, more preferably on one day during a cycle of about 3 or 4 weeks, preferably on day one of said cycle.

The VEGF/VEGFR inhibitors, preferably the VEGF/VEGFR inhibitors selected from the group consisting of Bevacizumab (rhuMAb-VEGF, Avastin®), Sorafenib (Nexavar®), Sunitinib (Sutent®), Vandetanib (ZD6474, Zactima® and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Bevacizumab and/or the pharmaceutically acceptable dervatives, solvates and/or salts thereof, preferably Bevacizumab, is administered to the subject in an amount of 750 mg to 2000 mg within one cycle, more preferably 900 mg to 1500 mg within one cycle. Preferably, the amount of Bevacizumab and/or the pharmaceutically acceptable dervatives, solvates and/or salts thereof, preferably Bevacizumab, is administered to the subject once or twice, preferably once in an amout 5 mg/kg to 25 mg/kg; more preferably 10 to 20 mg/kg and especially about 15 mg/kg on one day or two days, preferably one day, within the cycle, preferably on day one of said cycle. A cycle in this regard preferably consists of 2 to 4 weeks (14 to 28 days) and especially of about three weeks (about 21 days). Preferably, Bevacizumab and/or the pharmaceutically acceptable dervatives, solvates and/or salts thereof, preferably Bevacizumab, is administered to the subject per orally (p.o.) or by injection, more preferably intravenously (i.v.). Especially preferably, Bevacizumab is administered to the subject intravenously (i.v.) in an amount of about 15 mg/kg per day on one day, preferably on one day during a cycle, more preferably on one day during a cycle of about 3 weeks, preferably on day one of said cycle.

The EGF/EGFR inhibitors, preferably the EGF/EGFR inhibitors selected from the group consisting of Trastuzumab (Herceptin®), cetuximab, panitumumab, zalutumumab, nimotuzumab, matuzumab, gefitinib, erlotinib and lapatinib, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Trastuzumab and/or the pharmaceutically acceptable dervatives, solvates and/or salts thereof, preferably Trastuzumab, is administered to the subject in an amount of 350 mg to 2000 mg within one cycle, more preferably 500 mg to 1600 mg within one cycle. Preferably, the amount of Trastuzumab and/or the pharmaceutically acceptable dervatives, solvates and/or salts thereof, preferably Trastuzumab, is administered to the subject once or twice, preferably once in an amount 1 mg/kg to 10 mg/kg; more preferably 1 to 10 mg/kg and especially about 6 or 8 mg/kg on one day or two days, preferably one day, within the cycle, preferably on day one of said cycle. A cycle in this regard preferably consists of 2 to 4 weeks (14 to 28 days) and especially of about three weeks (about 21 days).

Alternatively preferably, the amount of Trastuzumab and/or the pharmaceutically acceptable dervatives, solvates and/or salts thereof, preferably Trastuzumab, is administered to the subject once a week, preferably in an amout 1 mg/kg to 10 mg/kg, more preferably 2 to 6 mg/kg and especially about 2 or 8 mg/kg once a week, every week within the cycle, preferably on day one of said week. Preferably, Trastuzumab and/or the pharmaceutically acceptable dervatives, solvates and/or salts thereof, preferably Trastuzumab, is administered to the subject per orally (p.o.) or by injection, more preferably intravenously (i.v.). Especially preferably, Trastuzumab is administered to the subject intravenously (i.v.) in an amount of about 4, 6 or 8 mg/kg per day on one day, preferably on one day during a cycle, more preferably on one day during a cycle of about 3 weeks, preferably on day one of said cycle. Alternatively preferably, Trastuzumab is administered to the subject intravenously (i.v.) in an amount of about 2 or about 4 mg/kg on one day per week, preferably on one day during said, more preferably on one day during a cycle of about 3 weeks, preferably each week of said cycle.

Preferably, Lapatinib and/or the pharmaceutically acceptable dervatives, solvates and/or salts thereof, preferably Lapatinib, is administered to the subject in an amount of 15000 mg to 50000 mg within one cycle, more preferably 20000 mg to 35000 mg within one cycle. Preferably, the amount of Lapatinib and/or the pharmaceutically acceptable dervatives, solvates and/or salts thereof, preferably Lapatinib, is administered to the subject in about daily doses of 900 to 2000 mg (flat) and especially about 1250 mg (flat) on about every day or about every second day within the cycle. A cycle in this regard preferably consists of 2 to 4 weeks (14 to 28 days) and especially of about three weeks (about 21 days). Preferably, Lapatinib and/or the pharmaceutically acceptable dervatives, solvates and/or salts thereof, preferably Lapatinib, is administered to the subject per orally (p.o.). Especially preferably, Lapatinib is administered to the subject per orally (p.o.) in an amount of about 1250 mg per day about every day, preferably about every day during a cycle, more preferably per day about every day during a cycle of about 3 or about 4 weeks.

The PARP inhibitors, preferably the PARP inhibitors selected from the group consisting of Olaparib and Iniparib (BSI-201), and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Olaparib and/or the pharmaceutically acceptable dervatives, solvates and/or salts thereof, preferably Olaparib, is administered to the subject in an amount of 1500 mg to 40000 mg within one cycle, more preferably 3000 mg to 25000 mg within one cycle. Preferably, the amount of Olaparib and/or the pharmaceutically acceptable dervatives, solvates and/or salts thereof, preferably Olaparib, is administered to the subject in about daily doses of 100 to 900 mg (flat) and especially about 100 mg or about 400 mg (flat), preferably once a day or twice a day, more preferably twice a day, on about every day within the cycle. A cycle in this regard preferably consists of 2 to 4 weeks (14 to 28 days) and especially of about three weeks (about 21 days). Preferably, Olaparib and/or the pharmaceutically acceptable dervatives, solvates and/or salts thereof, preferably Olaparib, is administered to the subject per orally (p.o.). Especially preferably, Olaparib is administered to the subject per orally (p.o.) in an amount of about 100 or about 400 mg twice a day about every day, preferably about every day during a cycle, more preferably per day about every day during a cycle of about 3 or about 4 weeks.

Preferably, Iniparib (BSI-201) and/or the pharmaceutically acceptable dervatives, solvates and/or salts thereof, preferably Iniparib (BSI-201), is administered to the subject in an amount of 800 mg to 3000 mg within one cycle, more preferably 1000 mg to 2000 mg within one cycle. Preferably, the amount of Iniparib (BSI-201) and/or the pharmaceutically acceptable dervatives, solvates and/or salts thereof, preferably Iniparib (BSI-201), is administered to the subject in doses of 3 to 10 mg/kg and especially about 5.6 mg/kg per day on about about 3 to 5 days within the cycle, more preferably 4 days within said cycle and especially on days 1, 4, 8 and 11 of said cycle. A cycle in this regard preferably consists of 2 to 4 weeks (14 to 28 days) and especially of about three weeks (about 21 days). Preferably, Iniparib (BSI-201) and/or the pharmaceutically acceptable dervatives, solvates and/or salts thereof, preferably lniparib (BSI-201), is administered to the subject per orally (p.o.) or by injection, more preferably intravenously (i.v.). Especially preferably, Iniparib (BSI-201) is administered to the subject intravenously (i.v.) in an amount of about 5.6 mg/kg per day on days 1, 4, 8 and 11 during a cycle, more preferably a cycle of about 3 weeks.

The cytotoxic antibiotics, preferably the cytotoxic antibiotics selected from the group consisting of Daunorubicine, Doxorubicine, Epirubicine, Idarubicine, Mitoxantrone, Actinomycin-D, Bleomycine and Mitomycin-C, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Epirubicine and/or the pharmaceutically acceptable derivatives, solvates salts thereof, preferably Epirubicine, is administered to the subject intravenously or orally, more preferably intravenously, in an amount of 50 to 150 mg/m$^2$, more preferably 75 to 135 mg/m$^2$, preferably every three or four weeks, which preferably makes up for a cycle according to the invention. Alternatively preferably, Epirubicine and/or the pharmaceutically acceptable derivatives, solvates salts thereof, preferably Epirubicine, is administered to the subject intravenously or orally, more preferably intravenously, in an amount of 10 to 50 mg/m$^2$, more preferably 20 to 30 mg/m$^2$, every week, preferably every week within a cycle. A cycle in this regard preferably consists of 2 to 4 weeks (14 to 28 days) and especially of about three weeks (about 21 days) or about four weeks (about 28 days).

Preferably, Mitoxantrone and/or the pharmaceutically acceptable derivatives, solvates salts thereof, preferably Mitoxantrone, is administered to the subject intravenously or orally, more preferably intravenously, in an amount of 5 to 25 mg/m$^2$, more preferably 12 to 14 mg/m$^2$, preferably every three or four weeks, which preferably makes up for a cycle according to the invention.

The cytostatic alkaloids, preferably the cytostatic alkaloids selected from the group consisting of Etoposide, Teniposide, Vinblastine, Vincristine, Vindesine, Vinorelbine, Docetaxel, Paclitaxel, Irinotecane, Topotecane and Ixabepilone, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Ixabepilone and/or the pharmaceutically acceptable dervatives, solvates salts thereof, preferably Ixabepilone, is administered to the subject intravenously or orally, more preferably intravenously, in an amount of 20 to 60 mg/m$^2$, more preferably about 40 mg/m$^2$, preferably every three or four weeks and more preferably 3 weeks, which preferably makes up for a cycle according to the invention.

The antimetabolites, preferably the antimetabolites selected from the group consisting of Gemcitabine, Methotrexate, Raltitrexed, Pemetrexed, 6-Mercaptopurine, 6-Thioguanine, 2'-Desoxycoformicine, Fludarabinphospate, 2-Chlordeoxyadenosine, 5-Fluorouracil, Capecitabine, Cytosinarabinoside, Difluorodesoxycytidine and Hydroxyurea, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Capecitabine and/or the pharmaceutically acceptable dervatives, solvates salts thereof, preferably Capecitabine, is administered to the subject orally in an amount of 2000 to 3000 mg/m$^2$, more preferably about 2500 mg/m$^2$, preferably every every day on days 1 to 14 within three or four weeks and more preferably 3 weeks, and even more preferably every every day on days 1 to 14 every three weeks, which preferably makes up for a cycle according to the invention.

The alkylating chemotherapeutic agents, preferably the alkylating chemotherapeutic agents selected from the group consisting of cisplatin, carboplatin, oxaliplatin, cyclophosphamide, ifosfamide and trofosfamide, and/or the pharmaceutically acceptable dervatives, solvates and/or salts thereof, can generally be administered to the patient in a form and in a way or manner that is known in the art for the respective compounds or class of compounds, or can be derived from the art without undue experimentation, for example as described herein or as described in the literature cited herein.

Preferably, Cyclophosphamide and/or the pharmaceutically acceptable dervatives, solvates salts thereof, preferably Cyclophosphamide, is administered to the subject orally in an amount of 80 to 120 mg/m$^2$, more preferably about 100 mg/m$^2$, preferably every every day on days 1 to 14 within three or four weeks and more preferably 3 weeks, which preferably makes up for a cycle according to the invention. Alternatively preferably, Cyclophosphamide and/or the pharmaceutically acceptable dervatives, solvates salts thereof, preferably Cyclophosphamide, is administered to the subject orally in an amount of 500 to 700 mg/m$^2$, more preferably about 600 mg/m$^2$, preferably on days 1 and 8 within three or four weeks, and more on days 1 and 8 every three or four weeks, which preferably make up for a cycle according to the invention.

Generally, the cyclo-(Arg-Gly-Asp-DPhe-NMe-Val), the pharmaceutically acceptable dervatives, solvates and/or salts thereof, preferably cyclo-(Arg-Gly-Asp-DPhe-NMe-Val), can be administered to the patient as it is known in the art.

Preferably, cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val), is administered to the patient in an amount of 250 mg to 12500 mg, more preferably 450 to 10500 mg, within a time period of one week. This is also referred to as the weekly administration with respect to cyclo-(Arg-Gly-Asp-DPhe-NMe-Val). Preferably, a weekly administration of the given amounts takes place two or more times, preferably two or three times, within a time period of about three weeks. Preferably, a weekly administration of the given amounts takes place two or more times, preferably two, three or four times, within a time period of about four weeks. Preferably, the weekly administration with respect to cyclo-(Arg-Gly-Asp-DPhe-NMe-Val) takes place during two or more weeks within the cycle or the cycles with respect to the a) one or more cancer cotherapeutic agents or further cancer cotherapeutic agents, more preferably one or more cancer chemotherapeutic agents, and/or b) radiotherapy.

Even more preferably, the weekly administration with respect to cyclo-(Arg-Gly-Asp-DPhe-NMe-Val) takes place during every week within the cycle or the cycles with respect to the a) one or more cancer cotherapeutic agents or further cancer cotherapeutic agents, more preferably one or more cancer chemotherapeutic agents, and/or b) radiotherapy.

The amount of cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) to be administered in the weekly administration with respect to cyclo-(Arg-Gly-Asp-DPhe-NMe-Val) can be a the same or different in each week.

The following dosings or regimen are preferred in this respect:

(A) The cyclo-(Arg-Gly-Asp-DPhe-NMe-Val), the pharmaceutically acceptable dervatives, solvates and/or salts thereof and preferably cyclo-(Arg-Gly-Asp-DPhe-NMe- Val) is preferably administered to the subject, preferably human subject and especially patient in an amount of about 500 mg or about 2000 mg once a week each week during the cycle or the cycles with respect to the
a) one or more cancer cotherapeutic agents or further cancer cotherapeutic agents, more preferably one or more cancer chemotherapeutic agents,
and/or
b) radiotherapy.
(B) The cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) is preferably administered to the subject, preferably human subject and especially patient in an amount of about 500 mg or about 2000 mg twice a week each week during the cycle or the cycles with respect to the
a) one or more cancer cotherapeutic agents or further cancer cotherapeutic agents, more preferably one or more cancer chemotherapeutic agents,
and/or
b) radiotherapy.
(C) The cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) is preferably administered to the subject, preferably human subject and especially patient in an amount of about 500 mg each day on five consecutive days within one first week and in an amount of about 500 mg on one day within each further week during the cycle or the cycles with respect to the
a) one or more cancer cotherapeutic agents or further cancer cotherapeutic agents, more preferably one or more cancer chemotherapeutic agents,
and/or
b) radiotherapy.
(D) Alternatively preferably, the cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) is preferably administered to the subject, preferably human subject and especially patient in an amount of about 2000 mg each day on three consecutive days within one first week and in an amount of about 2000 mg on one day within each further week during the cycle or the cycles with respect to the
a) one or more cancer cotherapeutic agents or further cancer cotherapeutic agents, more preferably one or more cancer chemotherapeutic agents,
and/or
b) radiotherapy.
(E) Preferably, the cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) is administered to the subject, preferably human subject and especially patient in an amount of about 2000 mg once a week each week during the cycle or the cycles with respect to the
a) one or more cancer cotherapeutic agents or further cancer cotherapeutic agents, more preferably one or more cancer chemotherapeutic agents,
and/or
b) radiotherapy.

Preferably, more than one cycle with respect to the
a) one or more cancer cotherapeutic agents or further cancer cotherapeutic agents, more preferably one or more cancer chemotherapeutic agents,
and/or
b) radiotherapy,
is applied to the patient. More preferably 2 to 12 cycles and especially about 6 cycles are applied to the subject, preferably human subject and especially patient, preferably comprising one or more of the regimen (A) to (E).

Even more preferably, more than one cycle with respect to the one or more cancer cotherapeutic agents or further cancer cotherapeutic agents and especially with respect to one or more cancer chemotherapeutic agents, is applied to the subject, preferably human subject and especially patient. More preferably 2 to 12 cycles and especially about 6 cycles are applied to the patient, preferably comprising one or more of the regimen (A) to (E).

Preferably, the more than one cycles comprise only one of the regimen selected from (A) to (E), i.e. the same regimen selected from (A) to (E) is applied to the subject, preferably human subject and especially patient in each of the cycles. More preferably the same regimen selected from (A) to (E) is applied to the patient in each of the about 6 cycles.

Alternatively preferably, the more than one cycles comprise two or more of the regimen selected from (A) to (E), i.e. in different cycles different regimen selected from (A) to (E) are applied to the patient.

Preferably, in cases wherein more than one cycle with respect to the
a) one or more cancer cotherapeutic agents or further cancer cotherapeutic agents, more preferably one or more cancer chemotherapeutic agents,
and/or
b) radiotherapy
is applied to the subject, preferably human subject and especially patient, combinations of one or more of the dosings or regimen (A) to (E) are also or preferred in this respect:
(F) Regimen (C) is applied to the subject, preferably human subject and especially patient for the first cycle, followed by regimen (A) for 1 to 11 cycles and especially about 5 cycles. Preferably, during the regimen (A), the weekly administration consists of about 500 mg.
(G) Regimen (D) is applied to the subject, preferably human subject and especially patient for the first cycle, followed by regimen (A) for 1 to 11 cycles and especially about 5 cycles. Preferably, during the regimen (A), the weekly administration consists of about 2000 mg.

Preferably in this respect and especially with respect to one or more of the regimen (A) to (G), the duration of one cycle, preferably each cycle, is about three weeks (about 21 days) or about four weeks (about 28 days), more preferably about three weeks (about 21 days).

However, due to the extremely low toxicity of the cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val), it can be also applied to the subject, preferably human subject and especially patient outside the cycles with respect to the
a) one or more cancer cotherapeutic agents or further cancer cotherapeutic agents, more preferably one or more cancer chemotherapeutic agents,
and/or
b) radiotherapy,
preferably in a dosing or regimen as described above and/or below. This is especially advantageous as a maintenance therapy consisting of or comprising, preferably consisting of the administration of the cyclo-(Arg-Gly-Asp-DPhe-NMe-Val), the pharmaceutically acceptable dervatives, solvates and/or salts thereof and preferably cyclo-(Arg-Gly-Asp-DPhe-NMe-Val) for one or months, for example for up to 24 months, even substantially without a pause.

Cisplatin, carboplatin, oxaliplatin, cyclo-(Arg-Gly-Asp-DPhe-NMe-Val), cetuximab, matuzumab, doxorubicine, irinotecane, vincristine, cyclophamide, gemcitabine, paclitaxel, docetaxel, pemetrexed and/or 5-fluorouracil are typically administered as an i. V. infusion.

Etoposide, cyclophosphamide and vinorelbine are typically administered either orally or as an i. V. infusion.

However, other administration forms can generally be applied according to the invention, if available.

Generally, the Peptide of the formula Cyclo-(Arg-Gly-Asp-DPhe-NMe-Val) and/or the pharmaceutically acceptable dervatives, solvates and/or salts thereof and/or the one or more cancer cotherapeutic agents or further cancer cotherapeutic agents, more preferably the one or more cancer chemotherapeutic agents, can be administered in an amount and/or a regimen as it is known in the art for the respective compound.

Preferably, the Peptide of the formula Cyclo-(Arg-Gly-Asp-DPhe-NMe-Val) and/or the pharmaceutically acceptable dervatives, solvates and/or salts thereof and/or the one or more cancer cotherapeutic agents or further cancer cotherapeutic agents, more preferably the one or more cancer chemotherapeutic agents, are administered in an amount and/or a regimen as it is described above and/or below for the respective compound.

Alkylating chemotherapeutic agents are preferably selected from:

Oxazaphosphorines, more preferably from the Oxazaphosphorines Cyclophosphamide, Ifosfamide and Trofosfamide;

Platin derivatives, more preferably from the Platin derivatives Cisplatin, Carboplatin and Oxaliplatin;

and pharmaceutically acceptable dervatives, salts and/or solvates thereof.

Cytotoxic antibiotics are preferably selected from:

Anthracyclines, more preferably from the Anthracyclines Daunorubicine, Doxorubicine, Epirubicine and Idarubicine;

Anthracendiones, more preferably Mitoxantrone, and others, preferably selected from Actinomycin-D, Bleomycine and Mitomycin-C;

and pharmaceutically acceptable dervatives, salts and/or solvates thereof.

Cytostatic alkaloids are preferably selected from:

Podophyllotoxinderivatives, more preferably from the podophyllotoxin-derivatives Etoposide and Teniposide;

Vinca alkaloids, more preferably from the vinca alkaloids Vinblastine, Vincristine, Vindesine and Vinorelbine;

Taxanes, more preferably from the taxanes Docetaxel and Paclitaxel; and

Camptothecin derivatives, more preferably from the Camptothecin derivatives Irinotecane and Topotecane;

and pharmaceutically acceptable dervatives, salts and/or solvates thereof.

Preferably, the platinum containing chemotherapeutic agent is selected from the group consisting of cisplatin, carboplatin and oxaliplatin, more preferably consisting of cisplatin and carboplatin, ii) the oxazaphosphorine is cyclophosphamide, iii) the cytostatic alkaloid is selected from the group consisting of podophylotoxines, vinca alkaloids and campthothecines, and iv) the cytotoxic antibiotic is selected from anthracyclines, and the pharmaceutically acceptable dervatives, salts and/or solvates thereof.

Podophyllotoxinderivatives are preferably selected from Etoposide and Teniposide;

and the pharmaceutically acceptable dervatives, salts and/or solvates thereof.

Vinca alkaloids are preferably selected from Vinblastine, Vincristine, Vindesine and Vinorelbine;

and the pharmaceutically acceptable dervatives, salts and/or solvates thereof.

Camptothecin derivatives are preferably selected from Irinotecane and Topotecane;

and the pharmaceutically acceptable dervatives, salts and/or solvates thereof.

Anthracyclines are preferably selected from Daunorubicine, Doxorubicine, Epirubicine and Idarubicine;

and pharmaceutically acceptable dervatives, salts and/or solvates thereof.

According to one embodiment, the cytostatic alkaloid is selected from the group consisting of etoposide, Irinotecan and vincristine, preferably etoposide, and/or the cytotoxic antibiotic is selected from the group consisting of doxorubicine and idarubicine, preferably doxorubicine;

and the pharmaceutically acceptable dervatives, salts and/or solvates thereof.

Generally, the etoposide, Irinotecan, vincristine, doxorubicine and idarubicine can be administered to the patient as it is known in the art.

Preferably, etoposide is administered to the patient in an amount of 300 mg to 1000 mg, more preferably 500 to 900 mg, within a time period of 2 to 4 weeks and preferably within a time period of about three weeks, which time periods are preferably to be regarded as one cycle. More preferably, the amount of etoposide administered to the patient is given in mg per square metre of the by the surface of the patient, i.e. in $mg/m^2$. Accordingly, more preferably the etoposide is administered to the patient in an amount of 200 $mg/m^2$ to 600 $mg/m^2$, more preferably 250 $mg/m^2$ to 450 $mg/m^2$, for example in an amount of about 300 $mg/m^2$, within a time period of 2 to 4 weeks and preferably within a time period of about three weeks, which time periods are preferably to be regarded as one cycle. Even more preferably, the amount of etoposide to be administered to the patient is divided into three about equal portions that are administered to the patient on three different days, preferably three consecutive days and more preferably three consecutive days at the beginning of one cycle with respect to the etoposide. Especially preferably, the etoposide is administered to the patient in an amount of about 100 $mg/m^2$ per day on the days 1, 2 and 3 of a cycle consisting of about 21 days. Preferably, 2 to 12 cycles, more preferably 4 to 8 cycles and especially about 6 cycles are applied to the patient with respect to etoposide, preferably substantially without a pause. The whole procedure/regimen described above with respect to the etoposide can be repeated one or more times, preferably one to 12 times and especially 2 to 6 times, for example about 5 times, preferably with a pause in between each repetition of the procedure/regimen.

Preferably, vincristine is administered to the patient in an amount of 1 mg to 50 mg, more preferably 2 to 10 mg, within a time period of 2 to 4 weeks and preferably within a time period of about three weeks, which time periods are preferably to be regarded as one cycle. More preferably, the amount of vincristine administered to the patient is given in mg per square metre of the by the surface of the patient, i.e. in $mg/m^2$. Accordingly, more preferably the vincristine is administered to the patient in an amount of 1 $mg/m^2$ to 10 $mg/m^2$, more preferably 1 $mg/m^2$ to 2 $mg/m^2$, for example in an amount of about 1.4 $mg/m^2$, within a time period of 2 to 4 weeks and preferably within a time period of about three weeks, which time periods are preferably to be regarded as one cycle. Especially preferably, the vincristine is administered to the patient in an amount of about 1.4 $mg/m^2$ per day, preferably on day 1 of a cycle consisting of about 21 days. Preferably, 2 to 12 cycles, more preferably 4 to 8 cycles and especially about 6 cycles are applied to the patient with respect to vincristine, preferably substantially without a pause. The whole procedure/regimen described above with respect to the vincristine can be repeated one or more times, preferably one to 12 times and especially 2 to 6 times, for example about 5 times, preferably with a pause in between each repetition of the procedure/regimen.

Preferably, doxorubicine is administered to the patient in an amount of 20 mg to 300 mg, more preferably 40 to 200 mg, within a time period of 2 to 4 weeks and preferably within a time period of about three weeks, which time periods are preferably to be regarded as one cycle. More preferably, the amount of doxorubicine administered to the patient is given in mg per square metre of the by the surface of the patient, i.e. in $mg/m^2$. Accordingly, more preferably the doxorubicine is administered to the patient in an amount of 30 $mg/m^2$ to 100 $mg/m^2$, more preferably 40 $mg/m^2$ to 60 $mg/m^2$, for example in an amount of about 50 $mg/m^2$, within a time period of 2 to 4 weeks and preferably within a time period of about three weeks, which time periods are preferably to be regarded as one cycle. Even more preferably, the amount of doxorubicine to be administered to the patient is administered to the patient on one day, preferably at the beginning of one cycle with respect to the doxorubicine. Especially preferably, the doxorubicine is administered to the patient in an amount of about 40 $mg/m^2$ to 60 $mg/m^2$ per day on day 1 of a cycle consisting of about 21 days. Preferably, 2 to 12 cycles, more preferably 4 to 8 cycles and especially about 6 cycles are applied to the patient with respect to doxorubicine, preferably substantially without a pause. The whole procedure/regimen described above with respect to the doxorubicine can be repeated one or more times, preferably one to 12 times and especially 2 to 6 times, for example about 5 times, preferably with a pause in between each repetition of the procedure/regimen.

Preferably, Irinotecan is administered to the patient in an amount of 20 mg to 300 mg, more preferably 40 to 200 mg, within a time period of 2 to 4 weeks and preferably within a time period of about three weeks, which time periods are preferably to be regarded as one cycle. More preferably, the amount of Irinotecan administered to the patient is given in mg per square metre of the by the surface of the patient, i.e. in $mg/m^2$. Accordingly, more preferably the Irinotecan is administered to the patient in an amount of 30 $mg/m^2$ to 100 $mg/m^2$, more preferably 50 $mg/m^2$ to 70 $mg/m^2$, for example in an amount of about 60 $mg/m^2$, within a time period of 2 to 4 weeks and preferably within a time period of about three weeks, which time periods are preferably to be regarded as one cycle. Even more preferably, the amount of Irinotecan to be administered to the patient is administered to the patient on one day, preferably at the beginning of one cycle with respect to the Irinotecan. Especially preferably, the Irinotecan is administered to the patient in an amount of about 40 $mg/m^2$ to 60 $mg/m^2$ per day on days 1 of a cycle consisting of about 21 days. Preferably, 2 to 12 cycles, more preferably 4 to 8 cycles and especially about 6 cycles are applied to the patient with respect to Irinotecan, preferably substantially without a pause. The whole procedure/regimen described above with respect to the Irinotecan can be repeated one or more times, preferably one to 12 times and especially 2 to 6 times, for example about 5 times, preferably with a pause in between each repetition of the procedure/regimen.

Preferably, the cisplatin, carboplatin, oxaliplatin, etoposide, vinblastine and teniposide are administered to the patient as it is known in the art and even more preferably as it is described above and/or below. More preferably, the cisplatin, carboplatin and/or oxaliplatin is administered to the patient as it is described herein.

According to one embodiment, the cyclo-(Arg-Gly-Asp-DPhe-NMe-Val) is preferably administered to a subject, preferably human subject and especially patient in an amount of 800 mg to 8000 mg per week or 1500 mg to 7000 mg per week.

The cyclo-(Arg-Gly-Asp-DPhe-NMe-Val) and/or the pharmaceutically acceptable dervatives, solvates and/or salts thereof, more preferably is administered to a subject, preferably human subject and especially patient in a twice weekly to four times weekly administration scheme, preferably consisting of about 500 mg or about 2000 mg per administration.

According to one embodiment, the cisplatin is administered to the patient in an amount of 50 mg to 500 mg within one cycle, more preferably 80 mg to 300 mg within one cycle. Preferably, the amount of cisplatin is administered to the patient is given in mg per square metre of the by the surface of the patient, i.e. in $mg/m^2$. Accordingly, cisplatin is preferably administered to the patient in an amount of 50 to 150 $mg/m^2$, more preferably 80 to 120 $mg/m^2$ and especially about 100 $mg/m^2$ within one cycle.

The amount cisplatin can be administered in one or more portions, more preferably 1 to 5 portions, even more preferred 1 to 3 and especially preferably in one portion on one day. Generally, cisplatin is administered as an i. V. infusion.

Another especially preferred subject of the instant invention relates to the use of cyclo-(Arg-Gly-Asp-DPhe-NMe-Val), the pharmaceutically acceptable dervatives, solvates and/or salts thereof, preferably cyclo-(Arg-Gly-Asp-DPhe-NMe-Val), for the manufacture of a medicament to be used in the methods of treatment described above.

According to one embodiment, the EGF/EGFR inhibitor is selected from the group consisting of trastuzumab, cetuximab, panitumumab, zalutumumab, nimotuzumab and matuzumab and/or the group consisting of gefitinib, erlotinib and lapatinib, the cytostatic alkaloid is selected from the group consisting of vinorelbine and vincristine and/or the group consisting of ixabepilone, paclitaxel and docetaxel, and the antimetabolite is selected from the group consisting of gemcitabine, capecitabine, 5-FU and methotrexat, and/or the pharmaceutically acceptable dervatives, solvates and/or salts thereof.

Generally, the EGF/EGFR inhibitors selected from the group consisting of trastuzumab, cetuximab, panitumumab, zalutumumab, nimotuzumab and matuzumab and/or the group consisting of gefitinib, erlotinib and lapatinib, can be administered to the patient as it is known in the art.

Preferably, cetuximab is administered to the patient in an amount of 500 mg to 3000 mg, more preferably 800 to 2500 mg, within a time period of 2 to 4 weeks and preferably within a time period of about three weeks or about four weeks weeks, which time periods are preferably to be regarded as one cycle. More preferably, the amount of cetuximab administered to the patient is given in mg per square metre of the by the surface of the patient, i.e. in $mg/m^2$. Accordingly, more preferably the cetuximab is administered to the patient in an amount of 500 $mg/m^2$ to 2000 $mg/m^2$, more preferably 750 $mg/m^2$ to 1500 $mg/m^2$, and especially 750 $mg/m^2$ to 1000 $mg/m^2$, for example in an amount of about 750 $mg/m^2$, about 1000 $mg/m^2$, about 900 $mg/m^2$, about 1000 $mg/m^2$, about 1150 $mg/m^2$ or about 1600 $mg/m^2$, within a time period of 2 to 4 weeks and preferably within a time period of about three weeks or about four weeks, more preferably three weeks, which time periods are preferably to be regarded as one cycle. Even more preferably, the amount of cetuximab to be administered to the patient is divided into three or four portions that are administered to the patient on three or four different days, preferably selected from one day within one week for three or four consecutive weeks and more preferably on each day 1 of three or four consecutive weeks, preferably beginning with day 1 within the first week of one cycle with respect to the cetuximab. Especially preferably, the amount of cetuximab to be administered to the patient is divided into three or four portions comprising or consisting of 200 to 500 mg/m$^2$ that are administered to the patient on three or four different days, preferably selected from one day within one week for three or four consecutive weeks and more preferably on each day 1 of three or four consecutive weeks, preferably beginning with day 1 within the first week of one cycle with respect to the cetuximab. Especially preferably in this regimen, the cetuximab is administered to the patient in an amount of about 250 mg/m$^2$ or about 400 mg/m$^2$ per day on a day one during the first week of the three or four consecutive weeks consecutive, followed by an administration of about 250 mg/m$^2$ per day on a day during each of the consecutively following two or three further weeks of a cycle consisting of about three weeks (about 21 days) or consisting of about four weeks (about 28 days). Preferably the cycle starts with the first administration on day 1 of the first week.

Even more preferably, the cetuximab is administered to the patient in an amount of about 400 mg/m$^2$ per day on day 1 and in an amount of about 250 mg/m$^2$ per day on days 8 and 15 of a cycle consisting of about 21 days.

Alternatively, the cetuximab is administered to the patient in an amount of about 250 mg/m$^2$ per day on the days 1, 8 and 15.

Preferably, matuzumab is administered to the patient in an amount of 500 mg to 3000 mg, more preferably 800 to 2500 mg, within a time period of 2 to 4 weeks and preferably within a time period of about three weeks or about four weeks weeks, which time periods are preferably to be regarded as one cycle. More preferably, the amount of matuzumab administered to the patient is given in mg per square metre of the by the surface of the patient, i.e. in mg/m$^2$. Accordingly, more preferably the matuzumab is administered to the patient in an amount of 500 mg/m$^2$ to 2000 mg/m$^2$, more preferably 750 mg/m$^2$ to 1750 mg/m$^2$, and especially 800 mg/m$^2$ to 1600 mg/m$^2$, for example in an amount of about 600 mg/m$^2$, about 800 mg/m$^2$, about 1000 mg/m$^2$, about 1200 mg/m$^2$ or about 1600 mg/m$^2$, within a time period of 2 to 4 weeks and preferably within a time period of about three weeks or about four weeks, more preferably three weeks, which time periods are preferably to be regarded as one cycle. Even more preferably, the amount of matuzumab to be administered to the patient is either divided into two or three portions that are administered to the patient on two or three different days, preferably selected from one day within one week for two or three consecutive weeks and more preferably on each day 1 of two or three consecutive weeks, preferably beginning with day 1 within the first week of one cycle with respect to the matuzumab, or the whole amount to be administerd within a time period of about three weeks or about four weeks is administered on one day within one first week of said time period, preferablly on day 1 of said first week. Especially preferably, the amount of matuzumab to be administered to the patient is divided into two portions comprising or consisting of 600 to 1000 mg/m$^2$, for example about 800 mg/m$^2$, that are administered to the patient on two different days, preferably selected from one day within one week for two consecutive weeks (i.e. on one day within one first week and on one day within one second week) and more preferably on each day 1 two consecutive weeks, preferably beginning with day 1 within the first week of one cycle with respect to the matuzumab. Alternatively preferably the matuzumab is administered to the patient in an amount of about 1600 mg/m$^2$ per day on a day one during the first week of three or four consecutive weeks. Thus, a cycle with respect to matuzumab preferably consists of about three weeks (about 21 days) or about four weeks (about 28 days), more preferably about three weeks (about 21 days). Preferably, the cycle starts with the first administration on day 1 of the first week.

Even more preferably, the matuzumab is administered to the patient in an amount of about 800 mg/m$^2$ per day on days 1 and 8 of a cycle consisting of about 21 days.

Alternatively more preferably, the matuzumab is administered to the patient in an amount of of 1600 mg/m$^2$, per day on the day 1 of a cycle consisting of about 21 days.

Generally, cytostatic alkaloids, especially cytostatic alkaloids selected from the group consisting of vinorelbine, vincristine, paclitaxel and docetaxel, can can be administered to the patient as it is known in the art.

Preferably, vinorelbine is administered to the patient in an amount of 25 mg to 250 mg, more preferably 50 to 150 mg, within a time period of 2 to 4 weeks and preferably within a time period of about three weeks, which time periods are preferably to be regarded as one cycle. More preferably, the amount of vinorelbine administered to the patient is given in mg per square meter of the by the surface of the patient, i.e. in mg/m$^2$. Accordingly, more preferably the vinorelbine is administered to the patient in an amount of 20 mg/m$^2$ to 100 mg/m$^2$, more preferably 40 mg/m$^2$ to 60 mg/m$^2$, for example in an amount of about 25 mg/m$^2$, within a time period of 2 to 4 weeks and preferably within a time period of about three weeks, which time periods are preferably to be regarded as one cycle. Even more preferably, the amount of vinorelbine to be administered to the patient is divided into two about equal portions that are administered to the patient on two different days, preferably one day within one first week and one day within one second week, preferably day 1 of one first week and day 1 of one second week, e.g. on day 1 and day 8 of one cycle with respect to the vinorelbine. Especially preferably, the vinorelbine is administered to the patient in an amount of about 25 mg/m$^2$ per day on the days 1 and 8 of a cycle consisting of about 21 days. Preferably, 2 to 12 cycles, more preferably 4 to 8 cycles and especially about 6 cycles are applied to the patient with respect to vinorelbine, preferably substantially without a pause. The whole procedure/regimen described above with respect to the vinorelbine can be repeated one or more times, preferably one to 12 times and especially 2 to 6 times, for example about 5 times, preferably with a pause in between each repetition of the procedure/regimen.

Preferably, docetaxel is administered to the patient in an amount of 50 mg to 500 mg, more preferably 100 to 250 mg, within a time period of 2 to 4 weeks and preferably within a time period of about three weeks, which time periods are preferably to be regarded as one cycle. More preferably, the amount of docetaxel administered to the patient is given in mg per square metre of the by the surface of the patient, i.e. in mg/m$^2$. Accordingly, more preferably the docetaxel is administered to the patient in an amount of 25 mg/m$^2$ to 150 mg/m$^2$, more preferably 50 mg/m$^2$ to 100 mg/m$^2$, for example in an amount of about 75 mg/m$^2$, within a time period of 2 to 4 weeks and preferably within a time period of about three weeks, which time periods are preferably to be regarded as one cycle. Even more preferably, the amount of docetaxel to be administered to the patient is administered on one day, preferably on day 1 within one first week, more preferably day 1 of one first week of one cycle with respect to the docetaxel. Especially preferably, the docetaxel is administered to the patient in an amount of about 75 mg/m² per day on day 1 of a cycle consisting of about 21 days. Preferably, 2 to 12 cycles, more preferably 4 to 8 cycles and especially about 6 cycles are applied to the patient with respect to docetaxel, preferably substantially without a pause. The whole procedure/regimen described above with respect to the docetaxel can be repeated one or more times, preferably one to 12 times and especially 2 to 6 times, for example about 5 times, preferably with a pause in between each repetition of the procedure/regimen.

Preferably, paclitaxel is administered to the patient in an amount of 100 mg to 1000 mg, more preferably 200 to 800 mg, within a time period of 2 to 4 weeks and preferably within a time period of about three weeks or about four weeks weeks, which time periods are preferably to be regarded as one cycle. More preferably, the amount of paclitaxel administered to the patient is given in mg per square metre of the by the surface of the patient, i.e. in mg/m². Accordingly, more preferably the paclitaxel is administered to the patient in an amount of 100 mg/m² to 500 mg/m², more preferably 120 mg/m² to 350 mg/m², for example in an amount of about 135 mg/m², about 150 mg/m², about 175 mg/m², about 250 mg/m², about 270 mg/m² or about 300 mg/m², within a time period of 2 to 4 weeks and preferably within a time period of about three weeks or about four weeks, which time periods are preferably to be regarded as one cycle. Even more preferably, the amount of paclitaxel to be administered to the patient is administered on one day, preferably on day 1 within one first week, more preferably day 1 of one first week of one cycle with respect to the paclitaxel.

Alternatively and also preferably, the amount of paclitaxel to be administered to the patient is divided into three about equal portions that are administered to the patient on three different days, preferably selected from one day within one week for three consecutive weeks and more preferably on each day 1 of three consecutive weeks, preferably beginning with day 1 within the first week of one cycle with respect to the paclitaxel. Especially preferably in this regimen, the paclitaxel is administered to the patient in an amount of 80 mg/m² to 100 mg/m² per day on the days 1 of three consecutive weeks of a cycle consisting of about three weeks (about 28 days), preferably starting the administration on day 1 of the first week of the cycle of about four weeks, and ending the cycle with the fourth week without an administration.

Especially preferably, the paclitaxel is administered to the patient in an amount of about 250 mg/m² per day on day 1 of a cycle consisting of about 21 days, in an amount of 135 mg/m² to 175 mg/m² per day on day 1 of a cycle consisting of about 21 days, or in an amount of 80 mg/m² to 100 mg/m² per day on day 1, day 8 and day 15 of a cycle consisting of about 28 days.

For example, the paclitaxel is administered to the patient in an amount of about 250 mg/m² per day on day 1 of a cycle consisting of about 21 days as an i.V. infusion over 16 to 26 h (hours) on the respective day, preferably over about 24 h, in an amount of 135 mg/m² to 175 mg/m² per day on day 1 of a cycle consisting of about 21 days as an i.V. infusion over 1 to 6 hours, preferably over about 3 h on the respective day, or in an amount of 80 mg/m² to 100 mg/m² per day on day 1, day 8 and day 15 of a cycle consisting of about 28 days as an i.V. infusion over 1 to 6 hours, preferably over about 3 h, on the respective days.

Preferably, 2 to 12 cycles, more preferably 4 to 8 cycles and especially about 6 cycles are applied to the patient with respect to paclitaxel, preferably substantially without a pause. The whole procedure/regimen described above with respect to the paclitaxel can be repeated one or more times, preferably one to 12 times and especially 2 to 6 times, for example about 5 times, preferably with a pause in between each repetition of the procedure/regimen.

Generally, cytostatic alkaloids, especially cytostatic alkaloids selected from the group consisting of podophyllotoxin-derivatives, and especially the podophyllotoxinderivative etoposide, can can be administered to the patient as it is known in the art.

Generally, antimetabolites, especially antimetabolites selected from the group consisting of gemcitabine and pemetrexed, can can be administered to the patient as it is known in the art.

Preferably, gemcitabine is administered to the patient in an amount of 800 mg to 8000 mg, more preferably 1200 to 6000 mg, within a time period of 2 to 4 weeks and preferably within a time period of about three weeks, which time periods are preferably to be regarded as one cycle. More preferably, the amount of gemcitabine administered to the patient is given in mg per square metre of the by the surface of the patient, i.e. in mg/m². Accordingly, more preferably the gemcitabine is administered to the patient in an amount of 1000 mg/m² to 5000 mg/m², more preferably 2000 mg/m² to 3000 mg/m², for example in an amount of about 2000 mg/m², within a time period of 2 to 4 weeks and preferably within a time period of about three weeks, which time periods are preferably to be regarded as one cycle. Even more preferably, the amount of gemcitabine to be administered to the patient is divided into two about equal portions that are administered to the patient on two different days, preferably one day within one first week and one day within one second week, preferably day 1 of one first week and day 1 of one second week, e.g. on day 1 and day 8 of one cycle with respect to the gemcitabine. Especially preferably, the gemcitabine is administered to the patient in an amount of about 1000 mg/m² per day on the days 1 and 8 of a cycle consisting of about 21 days. Preferably, 2 to 12 cycles, more preferably 4 to 8 cycles and especially about 6 cycles are applied to the patient with respect to gemcitabine, preferably substantially without a pause. The whole procedure/regimen described above with respect to the gemcitabine can be repeated one or more times, preferably one to 12 times and especially 2 to 6 times, for example about 5 times, preferably with a pause in between each repetition of the procedure/regimen.

Preferably, pemetrexed is administered to the patient in an amount of 500 mg to 2000 mg, more preferably 800 to 1500 mg, within a time period of 2 to 4 weeks and preferably within a time period of about three weeks, which time periods are preferably to be regarded as one cycle. More preferably, the amount of pemetrexed administered to the patient is given in mg per square metre of the by the surface of the patient, i.e. in mg/m². Accordingly, more preferably the pemetrexed is administered to the patient in an amount of 300 mg/m² to 700 mg/m², more preferably 400 mg/m² to 600 mg/m², for example in an amount of about 500 mg/m², within a time period of 2 to 4 weeks and preferably within a time period of about three weeks, which time periods are preferably to be regarded as one cycle. Even more preferably, the amount of pemetrexed to be administered to the patient is administered to the patient on one day within one first week, preferably day 1 of one first week, e.g. on day 1 of one cycle with respect to the pemetrexed. Especially preferably, the pemetrexed is administered to the patient in an amount of about 500 mg/m² per day on day 1 of a cycle consisting of about 21 days. Preferably, 2 to 12 cycles, more preferably 4 to 8 cycles and especially about 6 cycles are applied to the patient with respect to pemetrexed, preferably substantially without a pause. The whole procedure/regimen described above with respect to the pemetrexed can be repeated one or more times, preferably one to 12 times and especially 2 to 6 times, for example about 5 times, preferably with a pause in between each repetition of the procedure/regimen.

In one embodiment, the cyclo-(Arg-Gly-Asp-DPhe-NMe-Val) is administered to a subject, preferably human subject and especially patient, in an amount of 400 mg to 6000 mg per week or in an amount of 1500 mg to 5000 mg per week.

In the methods of treatment described herein, the one or more cycles preferably mean one or more cycles substantially without a pause.

In one embodiment, the pyrimidine antagonists are preferably selected from 5-Fluorouracil, Gemcitabine, Capecitabine, Cytosinarabinoside and Difluorodesoxycytidine, more preferably 5-Fluorouracil;
and pharmaceutically acceptable dervatives, salts and/or solvates thereof.

In one embodiment, the vinca alkaloids are preferably selected from Vinblastine, Vincristine, Vindesine and Vinorelbine, more preferably Vinorelbine;
and pharmaceutically acceptable dervatives, salts and/or solvates thereof.

In one embodiment, the taxanes in this respect are preferably selected from Docetaxel and Paclitaxel, more preferably Paclitaxel;
and pharmaceutically acceptable dervatives, salts and/or solvates thereof.

In one embodiment, the Anti-EGFR biologicals are preferably selected from cetuximab, panitumumab, zalutumumab, nimotuzumab and matuzumab, more preferably from cetuximab and matuzumab;
and pharmaceutically acceptable dervatives, salts and/or solvates thereof.

In one embodiment, the Anti-EGFR chemically derived compounds are preferably selected from gefitinib, erlotinib and lapatinib;
and pharmaceutically acceptable dervatives, salts and/or solvates thereof.

In one embodiment, preferably 2 to 12 cycles, more preferably 4 to 8 cycles and especially about 6 cycles are applied to the patient with respect to paclitaxel, preferably substantially without a pause. The whole procedure/regimen described above with respect to the paclitaxel can be repeated one or more times, preferably one to 12 times and especially 2 to 6 times, for example about 5 times, preferably with a pause in between each repetition of the procedure/regimen.

Generally, the 5-fluorouracil can be administered to the patient as it is known in the art.

Preferably, 5-fluorouracil is administered to the patient in an amount of 2000 mg to 15000 mg, more preferably 3000 to 10000 mg, within a time period of 2 to 4 weeks and preferably within a time period of about three weeks, which time periods are preferably to be regarded as one cycle. More preferably, the amount of 5-fluorouracil administered to the patient is given in mg per square metre of the by the surface of the patient, i.e. in mg/m$^2$. Accordingly, more preferably the 5-fluorouracil is administered to the patient in an amount of 1500 mg/m$^2$ to 8000 mg/m$^2$, more preferably 2500 mg/m$^2$ to 7500 mg/m$^2$, for example in an amount of about 5000 mg/m$^2$, within a time period of 2 to 4 weeks and preferably within a time period of about three weeks, which time periods are preferably to be regarded as one cycle. Even more preferably, the amount of 5-fluorouracil to be administered to the patient is divided into five about equal portions that are administered to the patient on five different days, preferably five consecutive days and more preferably five consecutive days at the beginning of one cycle with respect to the 5-fluorouracil. Especially preferably, the 5-fluorouracil is administered to the patient in an amount of about 1000 mg/m$^2$ per day on the days 1, 2, 3, 4 and 5 of a cycle consisting of about 21 days. Preferably, 2 to 12 cycles, more preferably 4 to 8 cycles and especially about 6 cycles are applied to the patient with respect to 5-fluorouracil, preferably substantially without a pause. The whole procedure/regimen described above with respect to the 5-fluorouracil can be repeated one or more times, preferably one to 12 times and especially 2 to 6 times, for example about 5 times, preferably with a pause in between each repetition of the procedure/regimen.

According to one embodiment, the weekly administration or the weekly administration scheme with respect to the Peptide of the formula Cyclo-(Arg-Gly-Asp-DPhe-NMe-Val) and/or the pharmaceutically acceptable dervatives, solvates and/or salts thereof, is applied 1 to 52 times substantially without a pause.

According to one embodiment, the weekly administration or the weekly administration scheme with respect to the Peptide of the formula Cyclo-(Arg-Gly-Asp-DPhe-NMe-Val) and/or the pharmaceutically acceptable dervatives, solvates and/or salts thereof, is applied 4 to 52 times, preferably 6 to 52 substantially without a pause, or even longer.

In the uses as described above and/or below or the methods of treatment as described above and/or below, said administration to the subject, preferably human subject and especially patient, within a time period of 2 to 4 weeks is preferably repeated 1 to 12 times substantially without a pause.

Preferred are uses as described above and/or below or the methods of treatment as described above and/or below, wherein
a) the weekly administration scheme regarding the Peptide of the formula Cyclo-(Arg-Gly-Asp-DPhe-NMe-Val) and/or the pharmaceutically acceptable dervatives, solvates and/or salts thereof,
and
b) the administration to the subject, preferably human subject and especially patient, within a time period of 2 to 4 weeks regarding
  i) the one or more cancer cotherapeutic agents or further cancer cotherapeutic agents, more preferably one or more cancer chemotherapeutic agents,
  and/or
  b) the radiotherapy,
run in parallel for one or more weeks.

Recent in vitro results show an increase in cell death/deterioration after combination treatment of lung cancer cell lines, such as A549, H157, H322, H460 and/or H1975, with specific integrin ligands, such as Vitaxin, Abegrin, CNTO95 and cyclo-(Arg-Gly-Asp-DPhe-NMe-Val), and cancer cotherapeutic agents, such as Cisplatin, Oxaliplatin, Vinblastin, Taxol, Gemcitabine, Gleevec, Iressa, and radiotherapy, preferably external beam radiation and/or fractionated external beam radiation. The results suggest that cancer cotherapeutic agents, such as radiation, can induce expression of relevant integrins in lung cancer cells, and/or that the specific integrin ligand is acting as an amplifier of efficacy, e.g. as a radio amplifier. Moreover, combined application of at least one specific integrin ligand and at least one cancer cotherapeutic agent, preferably radiation, results in significant cell kill and thus reduced survival curves of the respective treated cells considerably. Accordingly, the combinations appear to effectively induce cell death, likely due to apoptosis and/or mitotic cell death, in endothelial cells and tumour cells, especially in lung cancer cells and especially in non-small cell lung cancer cells. The extent of effect may depend on the degree of target expression, i.e. integrin expression. Thus, the medicaments and/or methods as described herein can be effectively used to treat lung cancer, and especially small cell lung cancer, non-small cell lung cancer and/or metastases thereof.

Subject of the instant invention is the use the Peptide of the formula Cyclo-(Arg-Gly-Asp-DPhe-NMe-Val) and/or the pharmaceutically acceptable dervatives, solvates and/or salts thereof, for the manufacture of a medicament for the treatment of breast cancer and/or bone metastases, wherein the medicament is to be used in combination with a) one or more cancer cotherapeutic agents or further cancer cotherapeutic agents, more preferably one or more cancer chemotherapeutic agents as described herein,
and/or
b) radiotherapy, preferably external beam radiation, wherein said Peptide and/or the pharmaceutically acceptable salts thereof is administered to a patient in an amount of 800 mg to 7000 mg per week, more preferably 1200 milligram to 6000 mg per week, even more preferably 1800 mg to 6000 mg per week, even more preferably 2000 mg to 6000 mg per week and especially 2500 to 5000 mg per week.

Optionally, the amount of cyclo-(Arg-Gly-Asp-DPhe-NMeVal) and/or a pharmaceutically acceptable salt thereof, preferably cyclo-(Arg-Gly-Asp-DPhe-NMeVal), to be administered to a patient per week is administered in about equal amounts of about 500 mg or about 2000 mg for each administration.

Optionally, the amount of cyclo-(Arg-Gly-Asp-DPhe-NMeVal) and/or a pharmaceutically acceptable salt thereof, preferably cyclo-(Arg-Gly-Asp-DPhe-NMeVal), is administered to a patient in an amount of about 1000 mg per week, about 1500 mg per week, about 2500 mg per week, about 4000 mg per week or about 6000 mg per week.

Optionally, the amount of about 1000 mg of cyclo-(Arg-Gly-Asp-DPhe-NMeVal) and/or a pharmaceutically acceptable salt thereof, preferably of is cyclo-(Arg-Gly-Asp-DPhe-NMeVal), per week is administered in a twice weekly administration scheme.

Optionally, the amount of about 4000 mg of cyclo-(Arg-Gly-Asp-DPhe-NMeVal) and/or a pharmaceutically acceptable salt thereof, preferably of cyclo-(Arg-Gly-Asp-DPhe-NMeVal), per week is administered in a twice weekly administration scheme, preferably in about equal amounts of about 2000 mg each.

Optionally, the amount of about 6000 mg of cyclo-(Arg-Gly-Asp-DPhe-NMeVal) and/or a pharmaceutically acceptable salt thereof, preferably of cyclo-(Arg-Gly-Asp-DPhe-NMeVal), per week is administered in a three times weekly administration scheme, preferably in about equal amounts of about 2000 mg each.

In the twice weekly administration scheme, the administration is optionally done on a day one and then on day three or a day four. Thus, the twice weekly administration scheme is optionally done either in an alternating every third day/every fourth day scheme or an alternating every fourth day/every third day scheme, such as an administration on mondays and thursdays (as an example of the 3/4 scheme) or tuesdays and fridays (as a further example of the 3/4 scheme), or on Thursdays and Mondays (as an example of the 4/3 scheme) or on Fridays and Tuesdays (as a further example of the 4/3 scheme).

Optionally, the twice weekly or three times weekly administration scheme, preferably the twice weekly or three times weekly administration scheme as described above, can be applied to the patient once or several times. Optionally, it is applied several times, preferably at least three times or at least six times. For example, the these weekly administration schemes can be applied continuously until healing, stable disease or tumor progression takes place. Optionally, the these weekly administration schemes, preferably the the weekly administration schemes as described above, are applied 4 to 156 times, such as about 4 times, about 8 times, about 16 times, about 24 times, about 35 times, about 70 times or about 104 times. This is preferred with respect to small cell lung cancer (SCLC), non-small cell lung cancer (NSCLC) and squamous cell cancer of the head and neck (SCCHN).

Optionally, the amount of about 1500 mg of cyclo-(Arg-Gly-Asp-DPhe-NMeVal) and/or a pharmaceutically acceptable salt thereof, preferably of cyclo-(Arg-Gly-Asp-DPhe-NMeVal), per week is administered in a three times weekly administration scheme, preferably in about equal amounts of about 500 mg each.

Optionally, the amount of about 6000 mg of cyclo-(Arg-Gly-Asp-DPhe-NMeVal) and/or a pharmaceutically acceptable salt thereof, preferably of cyclo-(Arg-Gly-Asp-DPhe-NMeVal), per week is administered in a three times weekly administration scheme, preferably in about equal amounts of about 2000 mg each.

In the three times weekly administration scheme, the administration is Optionally either done on a day one, on a day three or a day four and then on a day 6, or optionally on a day one, on a day 3 and on a day 5, then followed of two consecutive days off. The latter three times weekly administration scheme, for example, typically starts on a monday, followed by one administration on the following wednesday and one administration on friday, with saturday and sunday off of treatment.

The three times weekly administration scheme, preferably the three times weekly administration scheme as described above, can optionally be applied to the patient once or several times. Preferably, it is applied several times, even more preferably at least three times or at least six times. For example, the three times weekly administration scheme can be applied continuously till healing or tumor progression takes place. Optionally, the twice weekly administration scheme, preferably the twice weekly administration scheme as described above, is applied 4 to 156 times, such as about 4 times, about 8 times, about 16 times, about 24 times, about 35 times, about 70 times or about 104 times.

The three times weekly administration scheme can optionally be combined partially or totally with radiotherapy, preferably radiotherapy as described herein. Optionally, the three times weekly administration scheme is combined partially with radiotherapy.

Optionally, the amount of about 2500 mg of cyclo-(Arg-Gly-Asp-DPhe-NMeVal) and/or a pharmaceutically acceptable salt thereof, preferably of cyclo-(Arg-Gly-Asp-DPhe-NMeVal), per week is administered in a five times weekly administration scheme, preferably in about equal amounts of about 500 mg each. In the five times weekly administration scheme, the administration is preferably done on five consecutive days, preferably followed by 2 days in a row off. This "5 days of consecutive administration followed by 2 consecutive days off" scheme can be repeated once or several times. Preferably, this before described "5 days of consecutive administration followed by 2 consecutive days off" scheme is performed more than once but preferably less than 18 times, more preferably 2 to 12 times, even more preferably 3 to 8 times and especially 4 to 6 times, for example 2 times, 3 times, 4 times, 5 times, 6 times, 8 times or 12 times. Especially preferably, this "5 days of consecutive administration followed by 2 consecutive days off" scheme is applied 6 times.

Optionally, this "5 days of consecutive administration followed by 2 consecutive days off" scheme is combined with radiotherapy as described herein, preferably radiotherapy as described herein that is applied to the patient in an analog "5 days of consecutive application followed by 2 consecutive days off" scheme that preferably runs in parallel to the other scheme, preferably with the same two days off.

Regarding the herein described weekly administration amounts and/or schemes, the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), is optionally administered in a timed administration as described herein, generally 1.5 to 20 hours (h), preferably 2 to 16 h, more preferably 2 to 12 h, even more preferably 2 to 10 h, even more preferably 3 to 10 h and especially 2 to 8 h prior to the application of the radiotherapy. Alternatively, the Peptide according to formula cyclo-(Arg-Gly-Asp-DPhe-NMeVal) and/or the pharmaceutically acceptable salts thereof is administered in a timed administration as described herein, preferably 1 to 10 hours (h), preferably 1 to 6, more preferably 2 to 8, even more preferably 3 to 8 h, even more preferably 3 to 6 and especially 4 to 8 h prior to the application of the radiotherapy.

Optionally, the administration of the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), is combined, partially or totally, preferably partially, with the administration or delivery of radiotherapy, wherein 20 to 50 Gray (Gy), preferably 25 to 40 Gy, more preferably 28 to 25 Gy, for example about 28 Gy, about 30 Gy or about 35 Gy are administered or delivered to the patient, preferably in fractions of 0.5 to 5 Gy, more preferably 0.8 to 3 Gy and especially 1 to 2.5 Gy, for example about 1.0, about 1.3 Gy, about 1.6 Gy, about 1.8 Gy, about 2.0 Gy, about 2.5 Gy or about 3.0 Gy, per administration or delivery, which is preferably also the amount of radiation per day on which the administration or delivery of the radiation takes place. Accordingly, an administration or delivery of 1.5 to 2.5 Gy and preferably 1.8 to 2.2 Gy per day for 2 or 3 days within one week is preferred. Accordingly, an administration or delivery of 0.7 to 1.3 Gy and preferably 0.9 to 1.2 Gy per day for 3 to 6 days, preferably for 5 days and more preferably 5 consequtive days, within one week, is also preferred. Generally, the administration or delivery of 1.0 to 3.0 Gy, preferably about 1.0, about 2.0 Gy or about 3.0 Gy per day for 2 or 3 days within one week is especially preferred. The kind of application of focal radiotherapy as described above is preferred in the treatment of bone metastases, preferably bone metastases of cancer types as described herein, more prferrably cancer types selected from the group consisting of small cell lung cancer and non-small cell lung cancer, preferably non-small cell lung cancer, breast cancer, metastatic melanoma, metastatic androgen independent prostate cancer, metastatic androgen dependent prostate cancer, and myeloma or multiple myeloma.

Typically, both the amounts of about 30 Gy and about 60 Gy are administered or delivered to the patient within about six consecutive weeks.

If fractionated focal radiotherapy is applied with respect to bone metastases, preferably bone metastases of cancer types as described herein, it preferably consists of about 30 to 60 Gy, more preferably 30 to 40 gy, preferably delivered in frations of 1.0 to 3.5, more preferably 1.2 to 2, e. g. about 1.5 Gy or about 2 Gy, preferably over a period of about three to six weeks, preferably 2 to 5 days a week.

With respect to the methods of treatment, administered amounts and/or the administration schemes described herein regarding the Peptide according to formula cyclo-(Arg-Gly-Asp-DPhe-NMeVal) and/or the pharmaceutically acceptable salts thereof, preferably cyclo-(Arg-Gly-Asp-DPhe-NMe-Val), the amounts of (about) 500 mg or (about) 1000 mg to be administered at each administration as well as the amounts of (about) 1000 mg, (about) 1500 mg, (about) 2000 mg, (about) 2500 mg, (about) 4000 mg and (about) 6000 mg given for the weekly administration schemes are preferably calculated on the compound cyclo-(Arg-Gly-Asp-DPhe-NMeVal) as such (which is also referred to as the inner or internal salt of cyclo-(Arg-Gly-Asp-DPhe-NMeVal). Accordingly, if a different form or derivative, such as the pharmacologically acceptable salts and solvates, of the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), is to be administered to the subject, preferably you and subject and especially patient, it is preferably administered in an amount equimolar to the amounts given above for the compound cyclo-(Arg-Gly-Asp-DPhe-NMeVal) as such.

In the context of medicine and in the context of the target of treatment and/or the administration of compounds or medicaments, the terms
i) "subject" or "subjects",
ii) "human subject" or "human subjects"
and/or
iii) "patient" or "patients"
are known and understood in the art.

With respect to the instant invention and in the context of treatment and/or administration as described herein, the terms "subject" and "patient" are preferably synonyms.

With respect to the instant invention, subjects (preferably with regard to administration and/or treatment as described herein) are preferably human subjects.

Accordingly, with respect to the instant invention, patients are preferably humans or human patients.

Thus, the term "human subjects" preferably also means patient and more preferably means human patient.

With respect to the instant invention, patients are especially preferably human patients.

The specific integrin ligands to be used according to the invention surprisingly show an advantageously improved effect on patients that are having increased DNA methylation status, are having a partial or complete methylation of at least one promoter of at least one MGMT gene and/or are having an abnormal level of MGMT protein, especially an abnormal low level of MGMT protein. Accordingly, the invention provides medicaments and methods that can be advantageously used to treat patients associated with one or more of the aforementioned effects or defects.

Therefore, subject of the instant invention is the use of a medicament as described herein and/or a method using said medicament for the treatment of patients, wherein the medicament is to be used in the treatment of patients having an increased DNA methylation status, patients showing partial or complete methylation of at least one promotor of at least one MGMT gene and or patients having an abnormal level of MGMT protein, especially an abnormal low level of MGMT protein. Such patients are preferably referred to as "methylated patients".

These subjects are explained and discussed in more detail below.

Methylation of the DNA-repair gene $O^6$-methylguanine-DNA methyltransferase (MGMT), more correctly called $O^6$-methylguanine-DNA methyltransferase repair gene or short MGMT repair gene, causes gene silencing. This epigenetic modification has been associated with a favourable prognosis in patients with many different cancer types, such as glioblastoma (GBM), who receive alkylating agents, for example, nitrogen mustards, ethyleneimine compounds, alkyl sulphonates and other compounds with an alkylating action, preferably selected from nitrosoureas, preferably ACNU, BCNU and CCNU, busulfan, melphalan, carboplatin, cisplatin, oxaliplatin, cyclophosphamide, dacarbazine, carmustine, ifosfamide and lomustine, temozolomide and altretamine, or campthothecin. Accordingly, there is a relationship between MGMT promoter methylation and the survival rate and sensitivity to alkylating agents, such as temozolomide. The MGMT enzyme removes alkyl groups from the O6 position of guanine, the site of a number of chemotherapy-induced DNA alkylations. These chemotherapy induced alkylations lead to DNA damage in the tumor cells, including DNA double strand breaks and mismatches, which trigger apoptosis and cytotoxicity [5,6]. The MGMT enzyme repairs DNA damage, thus interfering with the therapeutic effects of chemotherapy alkylating agents [7-10]. Methylation of discrete regions of the MGMT promoter CpG island is associated with silencing of the gene and diminished DNA-repair enzyme activity [11-13]. Previous studies have indicated that 30-40% of GBM patients have methylated MGMT promoter [1-4].

The MGMT promoter methylation and thus the methylation status of the MGMT can be advantageously determined using a 2-stage methylation specific PCR analysis on DNA extracted from tumor specimens, such as tumour specimens which have been snap frozen at surgery. The Methylation specific PCR analysis can be easily performed according to methods in the art. Preferably it can be performed by the Method by Hegi et al., NEJM, 2005, 352; 997-1003); the following method has been successfully been used in a Phase III trial assessing the methylation status of a subset of the patients (tissue available):

DNA Extraction and Methylation-Specific Polymerase Chain Reaction

Genomic DNA is isolated from one or two paraffin sections of glioblastoma tissue (Ex-Wax DNA Extraction Kit S4530, Chemicon) (proteinase digestion lasted a maximum of six hours). DNA is denatured with sodium hydroxide in a volume of 35 μl and subjected to bisulfite treatment in a volume of 360 μl (4.4 M sodium bisulfite and 20 mM hydroquinone) for five hours at 55° C. and then purified (Wizard DNA Clean-Up System A7280, Promega). Unmethylated cytosine, but not its methylated counterpart, is modified into uracil by the treatment. The methylation-specific polymerase chain reaction (PCR) is performed in a two-step approach. [Palmisano W A, Divine K K, Saccomanno G, et al. Predicting lung cancer by detecting aberrant promoter methylation in sputum. Cancer Res 2000;60:5954-8.]

The results can be confirmed in an independent experiment, starting with reisolation of DNA from the tumor. The PCR products are separated on 4 percent agarose gels. The investigators who selected and analyzed the glioblastoma samples are blinded to all clinical information.

Alternatively, it can be performed according to the method described by Donson et al. in Journal Pedriatic Blood Cancer, 2006.

According to Donson et al., the MGMT promoter methylation/methylation status of the MGMT can be advantageously determined according to the following procedure:

DNA Extraction and Methylation-specific Polymerase Chain Reaction

Genomic DNA is isolated from snap frozen tumor obtained at surgery (COMIRB 95-500) and GBM cell-lines using a DNeasy kit (Qiagen, Valencia, Calif.). DNA methylation patterns in the CpG island of the MGMT gene are determined by methylation specific PCR. This procedure involves chemical modification of unmethylated, but not methylated cytosines to uracil, followed by a nested, twostage PCR [17]. One microgram of DNA is denatured with sodium hydroxide (final conc. 0.3 M) in a volume of 55 ml and subjected to bisulfite treatment in a volume of 610 ml (3.3 M sodium bisulfite and 0.5 mM hydroquinone) for 16 hr at 55° C. and then purified using the Wizard DNA Clean-Up System (Promega, Madison, Wis.). PCR is performed to amplify a 289-bp fragment of the MGMT gene including a portion of the CpG-rich promoter region. The primers recognize the bisulfite-modified template but do not discriminate between methylated and unmethylated alleles. Primer sequences used in the stage 1 amplification of theMGMTgene are as follows: MGMT-stage 1-Forward, 50-GGATATGTTGGGATAGTT-30; and MGMT-stage 1-Reverse, 50-CCAAAAAC-CCCAAACCC-30. Master Mix (Fermentas, Hanover, Md.). The PCR amplification protocol for stage 1 is as follows: 95° C. for 10 min, then denature at 95° C. for 30 sec, anneal at 52° C. for 30 sec, extension at 72° C. for 30 sec for 40 cycles followed by a 10 min final extension. A 25-ml volume is used in all of the PCR reactions. The stage-1 PCR products are diluted 50-fold, and 5 ml of this dilution is subjected to a stage-2 PCR in which primers specific to methylated or unmethylated template are used. Primer sequences for the stage 2 PCR for the unmethylated reaction are MGMT-stage 2-Forward, 50-TTTGTGTTTTGATGTTTGTAGGTTTTTGT-30 and MGMT-stage 2-Reverse, 50-AACTCCACACTCTTC-CAAAAACAAAACA-30 and for the methylated reaction MGMT-stage 2-forward 50-TTTCGACGTTCGTAG-GTTTTCGC- 30 and MGMT-stage 2-reverse 50-GCACTCTTCCGAAAACGAAACG- 30. The PCR amplification protocol for stage 2 is as follows: 95° C. for 10 min, then denature at 95° C. for 15 sec, anneal at 62° C. for 15 sec, extension at 72° C. for 15 sec for 40 cycles followed by a 10 min final 72° C. extension. DNA from normal human lymphocytes treated in vitro with Sssl methyltransferase (New England Biolabs, Beverly, Mass.) is used as positive control for methylated alleles of MGMT and untreated DNA from normal lymphocytes is used as negative control for methylated alleles of MGMT. Each PCR reaction (10 ml) is directly loaded onto 4% agarose gel, stained with ethidium bromide and visualized under UV illumination. Statistical Analysis can be performed with methods known in the art, such as the methods by Kaplan-Meier, correlation and statistical significance analyses, for example using the Prism statistical analysisprogram (GraphPad Software, Inc., San Diego, Calif.).

Methylguanine-DNA methyltransferase promoter methylation status analysis is performed on snap frozen tissue of the patients. MGMT methylation status can regularly be determined out the tumors. In a part of the patients, the samples tested for MGMT promoter methylation status proved to be partially methylated (FIG. 29 A). None of the samples showed complete methylation. The incomplete methylation observed may be due to tumor heterogeneity, infiltrating peripheral blood lymphocytes and/or vasculature. For comparison purposes, it can be determined whether partial methylation of the tumor MGMT promoter can be responsible for this observation by investigating the MGMT promoter methylation status of 6 GBM cell-lines, including cell-line 145 which is established from a patient who is treated with temozolomide and who's snap frozen tumor is also analyzed in the above study. In four out of the six celllines studied, partial methylation of promoter is observed (FIG. 29 B). The results show that even in pure GBM cell-lines, partial MGMT promoter methylation can exist.

FIG. 29 A shows the Methylation status of the MGMT promoter in GBM biopsy specimens, as determined by a nested methylation-specific PCR assay. DNA from normal peripheral blood lymphocytes (PBL) is used as a control for the unmethylated MGMT promoter (U), enzymatically methylated DNA from PBL (MPBL) served as a positive control for the methylated MGMT promoter (M), and water is used as a negative control for the PCR. A 100-bp marker ladder is loaded to estimate molecular size, as shown on the left scale (L).

FIG. 29 B shows the Methylation status of the MGMT promoter in GBM cell-lines, as determined by a nested methylation-specific PCR assay. A 100-bp marker ladder is loaded to estimate molecular size, as shown on the left scale (L).

The MGMT analysis technique described above has been employed in the majority of recent studies showing MGMT methylation to be a successful predictor of response to alkylating agents [1-3]. This technique has superseded earlier techniques of enzyme activity measurement after it was demonstrated that MGMT methylation was the main cause of loss of MGMT enzymatic activity in GBM.

Patients that are tested as patients showing MGMT methylation or that can be tested as patients showing MGMT methylation, preferably using the above described method, an analog method thereof, or any other method which is equally suitable according to the understanding of the ones skilled in the art, are to be regarded as "methylated patients" according to the invention, more preferably as patients having an increased DNA methylation status and/or as patients showing partial or complete methylation of at least one promotor of at least one MGMT gene. They thus belong to the collective of patients that can be especially advantageously treated by the methods of treatment or the medicaments according to the invention.

However, such techniques, e.g. the method described below, can preferably be used in concordance with the instant invention with respect to the MGMT status.

Chemotherapeutic efficacy, the ability of chemotherapy to eradicate tumor cells without causing lethal host toxicity, depends on drug selectivity. One class of anticancer drugs, alkylating agents, cause cell death by binding to DNA which structurally distorts the DNA helical structure preventing DNA transcription and translation. In normal cells, the damaging action of alkylating agents can be repaired by cellular DNA repair enzymes, in particular $O^6$-methylguanine-DNA methyltransferase (MGMT) also known as $O^6$-alkylguanine-DNA-alkyltransferase (AGAT). The level of MGMT varies in tumor cells, even among tumors of the same type. The gene encoding MGMT is not commonly mutated or deleted. Rather, low levels of MGMT in tumor cells are due to an epigenetic modification; the MGMT promoter region is methylated, thus inhibiting transcription of the MGMT gene and preventing expression of MGMT.

Methylation has been shown by several lines of evidence to play a role in gene expression, cell differentiation, tumorigenesis, X-chromosome inactivation, genomic imprinting and other major biological processes. In eukaryotic cells, methylation of cytosine residues that are immediately 5' to a guanosine, occurs predominantly in cytosine-guanine (CG) poor regions. In contrast, CpG islands remain unmethylated in normal cells, except during X-chromosome inactivation and parental specific imprinting where methylation of 5' regulatory regions can lead to transcriptional repression. Expression of a tumor suppressor gene can also be abolished by de novo DNA methylation of a normally unmethylated CpG.

Hypermethylation of genes encoding DNA repair enzymes can serve as markers for predicting the clinical response to certain cancer treatments. Certain chemotherapeutic agents (including alkylating agents for example) inhibit cellular proliferation by cross-linking DNA, resulting in cell death. Treatment efforts with such agents can be thwarted and resistance to such agents develops because DNA repair enzymes remove the cross-linked structures. In view of the deleterious side effects of most chemotherapeutic drugs, and the ineffectiveness of certain drugs for various treatments, it is desirable to predict the clinical response to treatment with chemotherapeutic agents.

U.S. Pat. No. 6,773,897 discloses methods relating to chemotherapeutic treatment of a cell proliferative disorder. In particular, a method is provided for "predicting the clinical response to certain types of chemotherapeutic agents", including specific alkylating agents. The method entails determination and comparison of the methylation state of nucleic acid encoding a DNA repair enzyme from a patient in need of treatment with that of a subject not in need of treatment. Any difference is deemed "predictive" of response. The method, however, offers no suggestion of how to improve clinical outcome for any patient with an unfavorable "prediction". Temozolomide is an alkylating agent available from Schering Corp. under the trade name of Temodar® in the United States and Temodal® in Europe. Temodar® Capsules for oral administration contain temozolomide, an imidazotetrazine derivative. The chemical name of temozolomide is 3,4-dihydro-3-methyl-4-oxoimidazo[5,1-d]-as-tetrazine-8-carboxamide (see U.S. Pat. No. 5,260,291). The cytotoxicity of temozolomide or metabolite of it, MTIC, is thought to be primarily due to alkylation of DNA. Alkylation (methylation) occurs mainly at the $O^6$ and $N^7$ positions of guanine. Temodar® (temozolomide) Capsules are currently indicated in the United States for the treatment of adult patients with newly diagnosed gliobastoma multiforme as well as refractory anaplastic astrocytoma, i.e. patients at first relapse who have experienced disease progression on a drug regimen containing a nitrosourea and procarbazine. Temodal® is currently approved in Europe for the treatment of patients with malignant glioma, such as glioblastoma multiforme or anaplastic astrocytoma showing recurrence or progression after standard therapy.

According to the invention, alternatively to the method described above, the level of methylation of MGMT gene is assessed by determining the level of MGMT protein in a sample obtained from the patient. The level can be classified as being "Very Low" "Low", "Moderate", or "High", preferably as described in more detail below.

Assessing whether or not the MGMT gene is methylated can be performed using any method known to one skilled in the art. Techniques useful for detecting methylation of a gene or nucleic acid include, but are not limited to those described by Ahrendt et aL, J. Natl. Cancer Inst., 91:332-339 (1999); Belsinky et al., Proc. Natl. Acad. Sci. U.S.A., 95:11891-11896 (1998), Clark et al., Nucleic Acids Res., 22:2990-2997 (1994); Herman et aL, Proc Natl Acad Sd U.S.A., 93:9821-9826 (1996); Xiong and Laird, Nucleic Acids Res., 25:2532-2534 (1997); Eads et aL, Nuc. Acids. Res., 28:e32 (2002); Cottrell et al., Nucleic Acids Res., 32:1-8 (2004). All references cited herein are incorporated herein by reference.

Methylation-specific PCR (MSP; Herman et al., Proc. Natl. Acad Sci. USA, 93(18):9821-9826 (1996); Esteller et al., Cancer Res., 59:793-797 (1999)) see also U.S. Pat. No. 5,786,146, issued Jul. 28, 1998; U.S. Pat. No. 6,017,704, issued Jan. 25, 2000; U.S. Pat. No. 6,200,756, issued Mar. 13, 2001; and U.S. Pat. No. 6,265,171, issued Jul. 24, 2001; U.S. Pat. No. 6,773,897 issued Aug. 10, 2004; the entire contents of each of which is incorporated herein by reference can rapidly assess the methylation status of virtually any group of CpG sites within a CpG island, independent of the use of methylation-sensitive restriction enzymes. This assay entails initial modification of DNA by sodium bisulfite, converting all unmethylated, but not methylated, cytosines to uracil, and subsequent amplification with primers specific for methylated versus unmethylated DNA. MSP requires only small quantities of DNA, is sensitive to 0.1% methylated alleles of a given CpG island locus, and can be performed on DNA extracted from paraffin-embedded samples. MSP eliminates the false positive results inherent to previous PCR-based approaches which relied on differential restriction enzyme cleavage to distinguish methylated from unmethylated DNA. This method is very simple and can be used on small amounts of tissue or a few cells.

An illustrative example of a Western blot assay useful for this embodiment of the invention to measure the level of MGMT protein in patient samples is presented in U.S. Pat. No. 5,817,514 by Li et al., the entire disclosure of which is incorporated herein by reference. Li et al. described monoclonal antibodies able to specifically bind either to native human MGMT protein or to human MGMT protein having an active site which is alkylated. An illustrative example of an immunohistochemical technique useful for this embodiment of the invention to measure the level of MGMT protein in patient samples is presented in U.S. Pat. No. 5,407,804, the entire disclosure of which is incorporated herein by reference. Monoclonal antibodies are disclosed which are able to specifically bind to the MGMT protein in single cell preparations (immunohistochemical staining assays) and in cell-extracts (immunoassays).

The use of fluorescent read out coupled with digitization of the cell image is described and allows for quantitative measurement of MGMT levels in patient and control samples, including but not limited to tumor biopsy samples. Useful techniques for measuring the enzymatic acitivity of MGMT protein include but are not limited to methods described by: Myrnes et al., Carcinogenesis, 5:1061-1 064 (1984); Futscher et al., Cancer Comm., 1: 65-73 (1989); Kreklaw et al., J. Pharmacol. Exper. Ther., 297(2):524-530 (2001); and Nagel et al., Anal. Biochem., 321(1):38-43 (2003), the entire disclosures of which are incorporated herein in their entireties.

According to one mode of this invention, the level of MGMT protein expressed by cells of the patient is assessed by measurement of the MGMT protein, e.g., by Western blot using an antibody specific to MGMT, see for example, U.S. Pat. No. 5,817,514 (supra) by Li et al. for a description of a Western blot assay to determine MGMT level. The level is compared to that expressed by normal lymphocytes known to express MGMT.

Patient MGMT protein levels are preferably classified as follows: Very Low=0-30% of the MGMT expressed by normal lymphocytes; Low=31-70% of the MGMT expressed by normal lymphocytes; Moderate=71-90% and High=91-300% or higher of the MGMT expressed by normal lymphocytes.

Patients that are tested as patients having Moderate or less MGMT protein levels or that can be tested as patients having Moderate or less MGMT protein levels, preferably using the above described method, an analog method thereof, or any other method which is equally suitable according to the understanding of the ones skilled in the art in the art, are to be regarded as "methylated patients" according to the invention. They thus belong to the collective of patients that can be especially advantageously treated by the methods of treatment or the medicaments according to the invention.

Accordingly, patients that have or can be shown to have Moderate (=71-90%), preferably (Low=31-70%) and more preferably Very Low (=0-30%), of the MGMT expressed by normal lymphocytes are preferably to be regarded as "methylated patients" according to the invention, more preferably as patients having an increased DNA methylation status and/or as patients showing partial or complete methylation of at least one promotor of at least one MGMT gene. They thus belong to the collective of patients that can be especially advantageously treated by the methods of treatment or the medicaments according to the invention.

Thus, an especially preferred subject of the invention is a method or a use as described herein, wherein the medicament is to be used in the treatment of patients having an increased DNA methylation status.

Thus, an especially preferred subject of the invention is a method or a use as described herein, wherein the medicament is to be used in the treatment of patients showing partial or complete methylation of at least one promotor of at least one MGMT gene.

Thus, an especially preferred subject of the invention is a method or a use as described herein, wherein the medicament is to be used in the treatment of patients, having a Moderate, preferably a Low and more preferably a Very Low level of MGMT protein, preferably in comparison of the MGMT expressed by normal lymphocytes.

Thus, an especially preferred subject of the invention is a method or a use as described herein, wherein the medicament is to be used in the treatment of patients having an increased DNA methylation status, and wherein said method comprises the administration of one or more alkylating agents, preferably selected from, nitrogen mustards, ethyleneimine compounds, alkyl sulphonates and other compounds with an alkylating action, preferably selected from nitrosoureas, preferably ACNU, BCNU and CCNU, busulfan, melphalan, carboplatin, cisplatin, oxaliplatin, cyclophosphamide, dacarbazine, carmustine, ifosfamide and lomustine, temozolomide and altretamine, or campthothecin.

Thus, an especially preferred subject of the invention is a method or a use as described herein, wherein the medicament is to be used in the treatment of patients showing partial or complete methylation of at least one promotor of at least one MGMT gene and wherein said method comprises the administration of one or more alkylating agents, preferably selected from, nitrogen mustards, ethyleneimine compounds, alkyl sulphonates and other compounds with an alkylating action, preferably selected from nitrosoureas, preferably ACNU, BCNU and CCNU, busulfan, melphalan, carboplatin, cisplatin, oxaliplatin, cyclophosphamide, dacarbazine, carmustine, ifosfamide and lomustine, temozolomide and altretamine, or campthothecin.

Thus, an especially preferred subject of the invention is a method or a use as described herein, wherein the medicament is to be used in the treatment of patients, having a Moderate, preferably a Low and more preferably a Very Low level of MGMT protein, preferably in comparison of the MGMT expressed by normal lymphocytes, and wherein said method comprises the administration of one or more alkylating agents, preferably selected from, nitrogen mustards, ethyleneimine compounds, alkyl sulphonates and other compounds with an alkylating action, preferably selected from nitrosoureas, preferably ACNU, BCNU and CCNU, busulfan, melphalan, carboplatin, cisplatin, oxaliplatin, cyclophosphamide, dacarbazine, carmustine, ifosfamide and lomustine, temozolomide and altretamine, or campthothecin.

In the afore described methods or uses with respect to MGMT, the methods or uses preferably comprise the administration of one or more specific integrin ligands, preferably selected from cyclo-(Arg-Gly-Asp-DPhe-NMe-Val), the pharmaceutically acceptable dervatives, solvates and salts thereof, and especially cyclo-(Arg-Gly-Asp-DPhe-NMe-Val).

Methods to assess an increased DNA methylation status and/or showing partial or complete methylation of at least one promotor of at least one MGMT gene in patients are known in the art. Accordingly, patients to be advantagously treatable by methods or a uses as described herein can readily determined by the ones skilled in the art.

A preferred subject of the instant invention is a method or a use as described herein, wherein the medicament is to be used in the treatment of recurrent cancer, for example in a second line or subsequent treatment setting.

A more preferred subject of the instant invention is a method or a use as described herein, wherein the medicament is to be used in the treatment of recurrent cancer, for example in a second line or subsequent treatment setting, wherein the cancer is as defined herein.

An even more preferred subject of the instant invention is a method or a use as described herein, wherein the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), is to be used in the treatment of newly diagnosed cancer, preferably in a first line treatment setting.

A further subject of the instant invention is a method of treatment of a subject, preferably a human subject, or a use as described herein regarding the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), wherein the subject or human subject is having an increased DNA methylation status.

A further subject of the instant invention is a method of treatment of a subject, preferably a human subject, or a use as described herein regarding the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), wherein the subject or human subject is showing partial or complete methylation of at least one promotor of at least one MGMT gene.

A further subject of the instant invention is a method of treatment of a subject, preferably a human subject, or a use as described herein regarding the Peptide according to formula cyclo-(Arg-Gly-Asp-DPhe-NMeVal) and/or the pharmaceutically acceptable salts thereof, preferably cyclo-(Arg-Gly-Asp-DPhe-NMeVal), wherein the treatment or use concerns newly diagnosed cancer, preferably in a first line chemotherapy setting.

Preferably, a reference to "the Peptide of the formula Cyclo-(Arg-Gly-Asp-DPhe-NMe-Val)" or the reference to "Cyclo-(Arg-Gly-Asp-DPhe-NMe-Val)" includes also the pharmaceutically acceptable dervatives, solvates and/or salts thereof.

Preferably, a reference to "the Peptide" or "said Peptide" preferably means "the Peptide of the formula Cyclo-(Arg-Gly-Asp-DPhe-NMe-Val)" and preferably also includes the pharmaceutically acceptable dervatives, solvates and/or salts thereof.

Thus, a reference to "the Peptide and/or the pharmaceutically acceptable dervatives, solvates and/or salts thereof" or to "said Peptide and/or the pharmaceutically acceptable dervatives, solvates and/or salts thereof" preferably refers to "the Peptide of the formula Cyclo-(Arg-Gly-Asp-DPhe-NMe-Val) and/or the pharmaceutically acceptable dervatives, solvates and/or salts thereof".

The term "without a pause" as used herein, especially used with respect to treatment regimens or treatment durations, is preferably understood to mean that said treatment regimens or durations are performed or applied in a consecutive order. For example, "2 to 8 weeks and especially 6 weeks, preferably without a pause" is preferably intended to mean "2 to 8 weeks and especially 6 weeks, preferably in a consecutive order".

As used herein, the term "about" with respect to numbers, amounts, dosings, hours, times, timings, durations, and the like, is preferably understood to mean "approximately" with respect to said numbers, amounts, dosings, hours, times, timings, durations, and the like.

If not specified otherwise, amounts administered to a subject, human subject or patient given in "mg", such as in 500 mg, 1000 mg, 2000 mg, 4000 mg, 6000 mg, 8000 mg, 10000 mg, 12000 mg and 14000 mg, are preferably intended to mean the respective amounts to be administered "flat", i.e. as a fixed dose that is not adjusted to the bodyweight and/or body surface of the respective subject, human subject or patient.

If not specified otherwise, amounts administered to a human subject, patient or human patient given in "mg", such as in 500 mg, 1000 mg, 2000 mg, 4000 mg, 6000 mg, 8000 mg, 10000 mg, 12000 mg and 14000 mg, are preferably intended to mean the respective amounts to be administered "flat", i.e. as a fixed dose that is not adjusted to the bodyweight and/or body surface of the respective human subject, patient or human patient.

If not explicitly indicated otherweise, the term "one or more" as used herein, e.g. with respect to the number of compounds, agents, cancer cotherapeutic agents, cancer chemotherapeutic agents and the like, preferably means "one or more than one" and thus preferably includes "two or more" (or "two or more than two"), "three or more" (or "three or more than three") and/or "four more" (or "more or more than four"). Accordingly, the term "one or more" as used herein preferably includes the numbers one, two, three, four, five, six and/or higher numbers. With respect to the number of compounds, agents, cancer cotherapeutic agents, cancer chemotherapeutic agents, it especially preferably includes the numbers one, two, three, four and/or five, even more preferably the numbers one, two, three and/or four and especially the numbers one, two and/or three.

Preferably, especially preferred subjects of the instant invention relate to aspects, subjects, uses, methods and/or embodiments, wherein one or more features of two or more of the herein described aspects, subjects, uses, methods and/or embodiments are combined in one subject.

The invention is explained in greater detail below by means of examples. The invention can be carried out throughout the range claimed and is not restricted to the examples given here.

Moreover, the following examples are given in order to assist the skilled artisan to better understand the present invention by way of examplification. The examples are not intended to limit the scope of protection conferred by the claims. The features, properties and advantages examplified for the compounds, compositions, methods and/or uses defined in the examples may be assigned to other compounds, compositions, methods and/or uses not specifically described and/or defined in the examples, but falling under the scope of what is defined in the claims.

Preferably, the features, properties and advantages examplified for the compounds, compositions, methods and/or uses defined in the examples and/or claims may be assigned to other compounds, compositions, methods and/or uses not specifically described and/or defined in the examples and/or claims, but falling under the scope of what is defined in the specification and/or the claims.

EXAMPLES

The following examples are given in order to assist the skilled artisan to better understand the present invention by way of exemplification. The examples are not intended to limit the scope of protection conferred by the claims. The features, properties and advantages exemplified for the compounds and uses defined in the examples and/or the Figures related thereto may be assigned to other compounds and uses not specifically described and/or defined in the examples and/or the Figures related thereto, but falling under the scope of what is defined in the claims.

Example 1

Cilengitide Inhibits Progression of Experimental Breast Cancer Bone Metastases as Imaged Non-invasively Using VCT, MRI and DCE-MRI in a Longitudinal in vivo Study The aim of this study is to investigate the effect of inhibiting $\alpha v\beta 3/\alpha v\beta 5$ integrins by cilengitide in experimentally induced breast cancer bone metastases using non-invasive imaging techniques. For this purpose, nude rats bearing established breast cancer bone metastases are treated with cilengitide, a small molecule inhibitor of $\alpha v\beta 3$ and $\alpha v\beta 5$ integrins (75 mg/kg, five days per week; n=12 rats) and compared to vehicle treated control rats (n=12). In a longitudinal study, conventional magnetic resonance imaging (MRI) and flat panel volumetric computed tomography (VCT) are used to assess the volume of the soft tissue tumor and osteolysis, respectively, and dynamic contrastenhanced (DCE-) MRI is performed to determine functional parameters of the tumor vasculature reflecting blood volume and blood vessel permeability. In rats treated with cilengitide, VCT and MRI shows that osteolytic lesions and the respective bone metastatic soft tissue tumors progress more slowly than in vehicle treated controls. DCE-MRI indicates a decrease in blood volume and an increase in vessel permeability, and immunohistology reveales increased numbers of immature vessels in cilengitidetreated rats compared to vehicle controls. In conclusion, treatment of experimental breast cancer bone metastases with cilengitide results in pronounced anti-resorptive and antitumor effects, suggesting that the achieved $\alpha v\beta 3/\alpha v\beta 5$ inhibition is a a promising therapeutic approach for the treatment of bone metastases.

1. Introduction

Bone metastases occur frequently in many human malignancies including breast, prostate, and lung carcinoma. The stimulation of osteoclasts by tumor cells proliferating within the bone marrow is a feature of the pathogenesis of bone metastases, and both the tumor and the bone microenvironment must be considered when strategies for therapy of bone metastases are developed.[1] Bisphosphonates are potent inhibitors of osteoclast function that have been used over the last decades to treat patients with bone metastases. However, they do not induce regression of bone metastases. This, together with the adverse effects associated with bisphosphonate therapy such as osteonecrosis of the jaw and renal toxicity, emphasize the urgent need for the development of novel therapies that can be applied alternatively and as combination partners to target bone metastases more effectively.

Integrins are a family of 24 transmembrane proteins that integrate extracellular and intracellular activities. Besides their role in promoting physical adhesion, integrin signaling can induce cell spreading, migration, survival, proliferation, and differentiation.[2] The $\alpha v\beta 3$ integrin interacts with several extracellular matrix (ECM) proteins including vitronectin, fibronectin, osteopontin, bone sialoprotein (BSP) and fibrinogen.[3,4] It is strongly expressed on activated tumor endothelial cells while on resting endothelial cells in non-diseased tissues its expression is generally low.[8-7] In the pathogenesis of bone metastases, osteoclasts too express $\alpha v\beta 3$ integrin, and selective $\alpha v\beta 3$ inhibitors have been shown to inhibit osteoclast-mediated bone resorption in experimental prostate carcinoma bone metastases.[8] Furthermore, $\alpha v\beta 3$ integrin over expression on tumor cells stimulated metastasis to bone in experimental models.[9,10] The closely related integrin $\alpha v\beta 5$ is also a vitronectin receptor involved in breast cancer cell migration and invasion, but is less studied in the pathogenesis of bone metastasis, although it is over expressed by osteoclasts and a wide range of cancer cells.[11,12] Together with $\alpha v\beta 5$, $\alpha v\beta 3$ integrin recognizes the arginine-glycine-aspartic acid (RGD) peptide sequence of extracellular ligands.[13] Cilengitide (EMD 121974) is a cyclic pentapeptide containing the sequence RGDf(N-Me)V with high affinity for $\alpha v\beta 3$ and $\alpha v\beta 5$, which inhibits $\alpha v\beta 3/\alpha v\beta 5$-dependent cellular processes.[14-17] As cilengitide inhibits $\alpha v\beta 3$ and $\alpha v\beta 5$ integrin from human, bovine and rat origin, it can be appropriately used in both experimental and clinical studies.[15,16] In recent phase II trials for treatment of glioblastoma multiforme, cilengitide has shown promising results including indications of anti-tumor activity and a good safety profile.[13,19] Cilengitide has anti-angiogenic activity in model systems, correlating with its inhibition of attachment, migration, sprouting, differentiation, and in the induction of anoikis in those endothelial angiogenic cells whose adhesion and survival is dependent on $\alpha v\beta 3/\alpha v\beta 5$.[15,18,20] Nevertheless, targeting $\alpha v$ integrins for therapy remains contentious, and for some tumors growth is accelerated in mice lacking $\alpha v\beta 3$ and $\alpha v\beta 5$ while in others, tumor growth and angiogenesis is accelerated by cilengitide.[21,22] In this study, we have used non-invasive imaging techniques to examine the dynamics of metastatic lesion development under therapy with cilengitide. Computed tomography (CT) and magnetic resonance imaging (MRI) are currently used to determine the extent of the osteolysis and the respective soft tissue component of bone metastases. For in vivo imaging of angiogenesis in bone metastases, dynamic contrast-enhanced MRI (DCE-MRI) allows assessment of functional parameters associated with blood volume and vessel permeability in these skeletal lesions.[23] We recently introduced an in vivo model of experimental breast cancer bone metastasis in which angiogenesis, soft-tissue lesion size and extent of osteolysis can be monitored simultaneously and longitudinally by volumetric CT (VCT), morphologic MRI and DCE-MRI.[23,24] Here we use this model to noninvasively assess the treatment effects of cilengitide inhibiting $\alpha v\beta 3$ and $\alpha v\beta 5$ integrins in breast cancer bone metastases.

2. Materials and Methods 2.1 Cell Lines and Culture Conditions

The human estrogen-independent breast cancer cell line MDA-MB-231 is purchased from American Type Culture Collection. Cells are cultured routinely in RPMI-1640 (Invitrogen, Karlsruhe, Germany), supplemented with 10% FCS (Sigma, Taufkirchen, Germany). All cultures are kept under controlled conditions (humidified atmosphere, 5% CO2, 37° C.) and passaged 2-3 times a week to keep them in logarithmic growth.

2.2 Flow Cytometry

The integrin expression profile of MDA-MB-231 human breast cancer cells is characterized using flow cytometry. Surface integrin staining on live cells is performed as described with minor modifications.[25] Briefly, cells are harvested, rinsed, suspended in PBS-BSA (containing divalent cations), and sequentially incubated with mouse anti-αvβ3 (LM609[26]) mouse anti-αvβ5 (P1F6[27]; Millipore, Schwalbach, Germany), or mouse anti- αv (17E6[25]) followed by staining with fluorescinated goat-anti-mouse IgG and propidium iodide (5 µg/ml). Incubations use 10 µg/ml primary antibody concentrations and are for 45 min on ice. Flow cytometry is performed on a FACScan instrument (Becton-Dickinson, Heidelberg, Germany), gating for viable cells, and collecting 10000 events per staining. The mean fluorescence intensity of the integrin staining is normalized using the staining intensity of the second layer reagent as background.

2.3 Animal Model and Therapy Application

Nude rats (RNU strain) are obtained from Harlan-Winkelmann GmbH (Borchen, Germany) at the age of six weeks and housed in a specific pathogen-free environment in a mini barrier system of the central animal facility. Animals are kept under controlled conditions (21±2° C. room temperature, 60% humidity, 12 h light-dark rhythm) and offered autoclaved food and water ad libitum. Sub-confluent MDAMB-231 cells are harvested using 0.05% Trypsin-EDTA (Gibco®; Invitrogen, Karlsruhe, Germany) counted on a Neubauer's chamber and resuspended in RPMI-1640 to a final concentration of $10^5$ cells in 200 µl. Rats are anesthetized using a mixture of nitrous oxide (1 l/min), oxygen (0.5 l/min) and isoflurane (1.5 vol. %). Arterial branches of the right hind leg are dissected and $10^5$ cells injected into the superficial epigastric artery as described previously.[28] Bone metastases established and are observed exclusively in the femur, tibia and fibula of the right hind leg. 30 days after cancer cell transplantation, rats (n=24) are randomly divided into two groups, one group receiving the cyclic RGD-peptide inhibitor of αvβ3/αvβ5 integrins (cilengitide, EMD 121974[14, 17, 29]; Merck, Darmstadt, Germany) intraperitoneally five times per week in isotonic saline (75 mg/kg; n=12 rats) and the other, sham-treated group, serving as a control (n=12 rats). The observation period of all animals is 55 days and no rat in the study dies ahead of schedule.

2.4 In vivo Imaging

After the inoculation of cancer cells each rat is imaged at days 30, 35, 45 and 55 using (i) a flat-panel equipped volumetric computed tomograph (Volume CT, Siemens, Germany) and (ii) a 1.5T clinical magnetic resonance scanner (Symphony, Siemens, Erlangen, Germany) equipped with a home-built receive-transmit coil (cylindrical volume resonator with an inner diameter of 83 mm and a usable length of 120 mm). Prior to in vivo imaging with VCT and MRI, rats aree anesthetized with nitrous oxide, oxygen and isoflurane as described above.

2.4.1 Volumetric Computed Tomography

VCT imaging is obtained using the following parameters: tube voltage 80 kV, tube current 50 mA, scan time 51 s, rotation speed 10 s, frames per second 120, matrix 512×512, and slice thickness 0.2 mm. Image reconstructions are performed using a modified FDK (Feldkamp Davis Kress) cone beam reconstruction algorithm (kernel H80a; Afra, Erlangen, Germany).

2.4.2 Magnetic Resonance Imaging

T2-weighted imaging is performed using a turbo spin echo sequence (orientation axial, TR 3240 ms, TE 81 ms, matrix 152×256, FOV 90×53.4 mm², slice thickness 1.5 mm, 3 averages, scan time 3 min 40 s). For dynamic contrast-enhanced MRI, a saturation recovery turbo flash sequence through the largest diameter of the tumor (orientation axial, TR 373 ms, TE 1.86 ms, matrix 192×144, FOV 130×97.5 mm, slice thickness 5 mm, measurements 512, averages 1, scan time 6 min 55 s) is used. After 20 s baseline, 0.1 mmol/kg Gd-DTPA (Magnevist; Bayer Schering Pharma, Berlin, Germany) is intravenously infused for a time period of 10 s.

2.5 Postprocessing

Unenhanced VCT images and MRI-acquired T2-weighted images are analyzed using the Medical Imaging Interaction Toolkit (MITK, Heidelberg, Germany) to determine volumes of osteolytic lesions and soft tissue components, respectively. DCE-MRI acquired data is analyzed using the Dynalab workstation (Mevis Research, Bremen, Germany) according to the two-compartment model of Brix to determine the parameters amplitude A and exchange rate constant kep, as described.[23, 30] Briefly, the injected contrast media is distributed in both compartments (intravascular space and extravascular, interstitial space). The accumulation of contrast agent in these compartments over time is characterized by the amplitude A (associated with blood volume), whereas the exchange of contrast agent between the intravascular space and the interstitial space is characterized by the exchange rate constant $k_{ep}$ (associated with vessel permeability). For determination of the respective values of the amplitude A and $k_{ep}$ of bone metastases in our study, a region of interest is placed around the soft tissue component on color maps for A and $k_{ep}$, respectively, using the Dynalab workstation (Mevis Research, Bremen, Germany).

2.6 Histology

At the end of the observation period lower limbs of each animal are amputated and muscular tissue removed. Bones with surrounding soft tissue tumors are stored in 70% ethanol and embedded in a methylmethacrylat-based compound (Technovit® 9100 NEU, Heraeus Kulzer, Hanau, Germany) according to the instructions of the manufacturer. 5 µm-thick sections are cut (Microm HM340e microtome; Thermo Scientific, Waltham, Mass.), mounted on SuperFrost Plus microscope slides and dried overnight at 60° C. Additional freshly removed soft tissue tumors are embedded in optimum cutting temperature compound (OCT, TissueTec, Sakura, Japan) and stored at −80° C. 7 µm thick cryosections (obtained on a Leica CM 3050S) are thaw-mounted, fixed in methanol and acetone and washed in PBS. For immunostaining, the Technovit®-embedded sections are incubated overnight at 4° C. with primary antibodies in PBS containing 12% bovine serum albumin. The following priniary antibodies are used: rabbit anti-collagen IV polyclonal antibody (1:50; Progen Biotechnik GmbH, Heidelberg, Germany) and mouse anti-smooth muscle actin (SMA) polyclonal antibody (1:400; Sigma Aldrich, Saint Louis, Mo.). After washing in PBS, sections are incubated with secondary antibodies for 1 h at room temperature as follows: Texas Red® dye-conjugated donkey anti rabbit IgG (1:100; Jackson Immunoresearch, Suffolk, UK) and Cy™2-conjugated goat anti mouse IgG (1:50, Jackson Immunoresearch, Suffolk, UK). Cryosections are incubated overnight at 4° C. with the following antibodies: mouse anti-human integrin αvβ3 Alexa Fluor® 488 conjugated monoclonal [LM609] antibody (1:100; Millipore GmbH, Schwalbach, Germany) and mouse monoclonal [P1F6] antibody to integrin αvβ5 (Phycoerythrin) (1:100; Abcam, Cambridge, UK). After a nuclear staining step with DAPI (4',6-diamidino-2-phenylindole, Serva, Heidelberg, Germany) sections are mounted in Fluoromount G (Southern Biotech, USA). Sections are examined using a Leica microscope (DMRE Bensheim, Germany) equipped with a digital camera (F-view XS; Soft Imaging System, Münster, Germany). Mean positive area fractions of SMA and collagen IV (in percent) as well as mean vessel diameters (in µm) are determined from 4 representative animals of each group analyzing 10 fields of view chosen randomly from each rat using Analysis Software (cell$^F$; Olympus Soft Imaging Solutions, Münster, Germany). Immunostainings for CD 31 (endothelial cells) and collagen IV (basal lamina) on tumor vessels are seen to be strongly positively correlated in soft tissue components of bone metastases (data not shown).

For light microscopical analysis, sections are stained with Mayer's hematoxylin (Carl Roth, Karlsruhe, Germany) and eosin (Merck, Darmstadt, Germany), mounted using Eukitt mounting medium (O. Kindler, Freiburg, Germany) and analyzed using a microscope (DM LB; Leica, Wetzlar, Germany) equipped with a digital camera (DFC 320; Leica, Wetzlar, Germany).

2.7 Statistical Analyses

For each animal, volumes of the osteolysis and soft tissue component, amplitude A and exchange rate constant $k_{ep}$ are plotted versus time after tumor cell inoculation (due to technical reasons one animal of the control group can not be evaluated for the amplitude A and $k_{ep}$). Normalization of the data to the corresponding initial value at day 30 for each animal is performed and changes are expressed in percent. For statistical comparisons of data from non-invasive imaging and histological analysis, the respective values are compared between the control and treatment groups using the two-sided Wilcoxon-Test; p-values <0.05 are considered significant.

3. Results

MDA-MB-231 Human Breast Cancer Cells Express αvβ5 but Only Low Levels of αvβ3 Integrins in vitro. The entire population of MDA-MB-231 cells in vitro expresses αv integrins as detected by the pan alpha-v reagent 17E6 (FIG. 1A). They show low cell surface expression of αvβ3 integrins by flow cytometry using the standard defining antibodies in the literature (36% of the cells are gated; median intensity 3 fold background), while staining strongly for αvβ5 integrins (100% cells gated; median intensity 10 fold background) (FIG. 1B, C). MDA-MB-231 also expresses α2, α3, α5, α6, and β1, β4, but not α4 or β6 chains (data not shown). In situ immunohistochemistry shows that soft tissue tumors stained strongly and quite uniformly for αvβ5, but has only weak patches of staining for αvβ3 (FIG. 1 D, E).

Treatment With Cilengitide Reduces the Volume of Osteolytic Lesions (OL) and Soft Tissue Components (STC) in Experimental Bone Metastases as assessed in vivo With VCT and MRI. Tumor bearing animals are randomly ssigned to two groups before therapy is begun at day 30. The mean relative volumes of the osteolytic lesions (OL) and the soft tissue components of bone metastases (STC) increase continuously in untreated rats until the end of the observation time (day 55 post tumor cell injection) compared to the initial values at day 30 after cancer cell injection (FIG. 2A). Mean relative values of the OL volumes have increased by 1.9, 4.5 and 9.7 fold in the control group and by 1.5, 2.4 and 3.5 fold in the treatment group (at days 35, 45 and 55, respectively) when compared to initial values at day 30 (FIG. 2A, FIG. 3A). Significant differences between the groups are found at days 45 (p<0.05) and 55 (p<0.01) for the OL (FIG. 2A). The mean volume of STC have increased by 2.3, 10.4 and 22.5 fold in controls at days 35, 45 and 55, respectively (FIG. 2A). The increase in mean relative STC values in bone metastases of the treatment group, however, increases only by 2.2, 4.9 and 6.3 fold for the volume of STC compared to initial values (FIG. 2A, FIG. 3B). Significant differences between the control and on-therapy groups are recorded at days 45 (p<0.05) and 55 (p<0.01; FIG. 2A) for the STC. In the treatment group, three rats (25%) show new bone formation under therapy with cilengitide as imaged by VCT (FIG. 3C). This bone formation is confined to the osteolytic lesion and no excessive increase in bone mass beyond the osteolyis is observed. Such a de novo bone formation further confirmed by histology does not occur in control animals.

Experimental Breast Cancer Bone Metastases Treated With Cilengitide reveal changes in DCE-MRI derived parameters for both, relative blood volume, and for vessel permeability. For the mean relative values of the DCE-MRI parameter amplitude A, a significant decrease is found in animals treated with the αvβ3/αvβ5 inhibitor at days 45 (102% of initial value; p<0.05) and 55 (93% of initial value; p<0.05) as compared to controls (day 45, 125% and day 55, 105% of initial values) but not on day 35 post inoculation (106% in controls vs. 97% in treated rats; p>0.05) (FIG. 2B, FIG. 4A). DCE-MRI parameter exchange rate constant $k_{ep}$ also reveales significant differences at day 55 post inoculation with increased values in treated animals (72% of initial value; p<0.05) compared to controls (40% of initial value), but not on days 35 (controls, 86% and treated animals, 69%; p>0.05) or 45 (controls, 63% and treated animals, 88%; p>0.05) (FIG. 2B, FIG. 4B).

Histological analysis reveals new bone formation, decreased vessel Diameter and reduced co-localization of smooth muscle actin and collagen IV in blood vessels of animals after treatment with cilengitide when compared to untreated controls. In control rats bone metastases contain tumor cells (representing the soft tissue tumor) within areas of bone resorption corresponding to VCT and MR imaging (FIG. 5A). After treatment with cilengitide, newly formed bone is confirmed on hematoxylin/eosin stained sections (FIG. 5B) taken from the proximal tibia of the animal shown in FIG. 3C. Immunofluorescence analysis in control animals reveales irregular vessels with small diameters, indicated by collagen IV staining in the basal lamina of vessels, which are not co-localized with smooth muscle actin (SMA), along with larger vessels showing collagen IV/SMA co-localization (FIG. 5C). After 4 weeks treatment with cilengitide essentially only small and mesh-like vessels are seen, without clear co-localization of SMA and collagen IV (FIG. 5D). Quantification of the immunofluorescent analysis results in significantly decreased mean positive area fractions of SMA (p<0.05) and significantly increased area fractions of collagen IV (p<0.01) in treated animals as compared to controls (FIG. 6A). The ratio of SMA and collagen IV (treated rats: 0.60/3.32; control rats: 0.83/2.37) is significantly decreased in animals after 4 weeks treatment with cilengitide (p<0.01), and the mean vessel diameter in cilengitide-treated bone metastases (6.6 µm) is significantly smaller than in control rats (8.8 µm, p<0.01; FIG. 6B).

4. Discussion

The aim of this study is to assess the effects of the αvβ3/αvβ5 integrin inhibitor cilengitide on breast cancer bone metastases in nude rats transplanted with human MDA-MB-231 breast cancer cells. We use the non-invasive imaging techniques VCT, morphological MRI and DCE-MRI to follow-up longitudinal progression. Our primary findings are that cilengitide treatment, begun a month after tumors are allowed to implant into bone, decreases osteolysis of breast cancer metastases in nude rats and the volume of the soft tissue tumor components. Cilengitide increases intratumoral vascular permeability, reduces the apparent numbers of mature intratumoral vessels, and unexpectedly causes an resumption of bone formation in a quarter of the animals under therapy. We find a significant decrease in osteolysis using VCT during therapy with cilengitide in nude rats. Several studies have reported a decrease of bone resorption in breast cancer bone metastases after inhibition of the integrin $\alpha v \beta 3$.[9, 31, 32] However, these groups have used MDA-MB-231 cells engineered and cloned to over express $\alpha v \beta 3$ or breast cancer cell lines such as MDA-MB-435 that strongly express this integrin. As the MDA-MB-231 cells we use only express low levels of $\alpha v \beta 3$, the anti-resorptive effect observe here may not be primarily due to the inhibition of this integrin on tumor cells, but also of $\alpha v \beta 3$ on osteoclasts and on the intratumoral vasculature, and $\alpha v \beta 5$ integrin on all three compartments.[12, 33] In previous studies osteoclasts which express high levels of the $\alpha v \beta 3$ integrin, bind several RGD-containing ECM proteins including vitronectin, osteopontin, and BSP.[34] By these interactions, $\alpha v \beta 3$ is involved in the regulation of osteoclast activity and the inhibition of this integrin is found to reduce osteoclast-mediated bone resorption.[35] Furthermore, as angiogenesis is required for initiation and maintenance of osteoclastic bone resorption, its inhibition by cilengitide might contribute to the observed decrease of osteolysis we observe after cilengitide treatment.[36] As cilengitide cross reacts with human and rat $\alpha v$ integrins the observed effects in our study are due to the inhibition of $\alpha v \beta 3$ and $\alpha v \beta 5$ integrins on both, MDA-MB-231 as well as on host cells in particular of the vascular and bone compartments. Which compartments are targeted to produce the effects we report here is under investigation.

Interestingly, three animals (25%) treated with cilengitide here show an increase in bone matrix, i.e. new bone formation in the osteolytic lesions, which is not seen in control animals. There are no known therapies in use today for patients suffering from bone metastases, where such an effect is seen. After treatment with bisphosphonates, a sclerotic rim around osteolytic lesions is a common sign for treatment response indicating local bone mineralization, but new bone formation is not seen after this therapy.[37] Both integrins, $\alpha v \beta 3$ and $\alpha v \beta 5$, are expressed by osteoblasts and are associated with osteoblast migration, adhesion and activity.[38] We have previously shown in this model of breast cancer bone metastases, that the inhibition of BSP also resulted in decreased bone resorption and new bone formation.[28, 39] As BSP binds $\alpha v \beta 3$ integrin, the inhibition of either factors, BSP or $\alpha v \beta 3$, might result in osteoblastic bone formation via the same pathway.[46] However, the exact mechanism inducing bone regrowth must still be elucidated.

Not only are there anti-resorptive effects, but also the respective soft tissue components have a lower volume than in the control animals, indicating an anti-tumor effect of Cilengitide. Cilengitide inhibits the growth of several experimental tumors including melanomas and glioblastomas.[41, 42] Due to the high expression of $\alpha v \beta 5$ and the low expression of $\alpha v \beta 3$ of MDA-MB-231 cells, the anti-tumor effect we report here may be a consequence of directly inhibiting $\alpha v \beta 5$ on the surface of the breast cancer cells, combined with the anti-angiogenic effects of inhibiting $\alpha v \beta 3$ and $\alpha v \beta 5$ on the endothelia of tumor vessels.[15] This hypothesis, however, is based only on the integrin expression of MDAMB- 231 cells observed in our study, and has to be verified experimentally in further studies. Chen et al. previously observed that MDA-MB-231 cells expressed $\alpha v \beta 3$ and $\alpha v \beta 5$ integrins at similar levels suggesting that treatment effects of Cilengitide might vary depending on the expression pattern of the respective cell clone used.[43]

Anti-angiogenic effects of cilengitide have been described previously in vitro and in vivo.[15, 18, 41, 44] In our study, cilengitide treatment of experimental breast cancer bone metastases results in a decrease of the amplitude A and an increase of the exchage rate constant $k_{ep}$ as assessed by DCE-MRI. These results indicate a decrease in blood volume and an increase of vessel permeability in these skeletal lesions, compatible with an "antiangiogenic" effect. In experimental glioblastomas and melanomas, a decrease in tumor vascularization and tumor growth followed treatment with cilengitide.[21, 29] It is generally assumed that the anti-angiogenic activity of cilengitide and related inhibitors is due to the experimentally observable inhibition of sprouting and differentiation, and the induction of anoikis of angiogenic endothelial cells relaying on $\alpha v \beta 3$ and $\alpha v \beta 5$ for adhesion and survival.[15, 45] In our immunohistology analysis we observe vessel remodeling after cilengitide treatment including significantly decreased mean vessel diameter and SMA/collagen IV ratio, indicating that smaller vessels lacking pericyte and smooth muscle cells occur more frequently in these animals than in untreated controls. These results of vessel remodeling rather than complete regression of tumor vessels upon cilengitide treatment are in good agreement with the moderate changes of DCE-MRI parameters A and $k_{ep}$. Taken together, we conclude that cilengitide triggeres a decrease in blood volume (assessed by the amplitude A) due to smaller and partly non-functional blood vessels, and increased vessel permeability (assessed by the exchange rate constant $k_{ep}$) is observed due to the increased number of immature vessels that arose after treatment with cilengitide. Increased vessel permeability as seen in our study was previously reported by Alghisi and colleagues, who reported VE-cadherin delocalization from cell-cell contact sites on cilengitide treatment leading to a loss of cellular contacts and an increase of endothelial monolayer permeability.[46] In bone metastases, this effect might improve local drug delivery to these lesions when combining cilengitide with standard treatments such as bisphosphonates or chemotherapy. In comparison to bisphosphonates showing predominantly anti-osteoclastic and chemotherapy exhibiting mainly cytotoxic effects in bone metastases, cilengitide shows anti-resorptive, anti-tumor and anti-angiogenic efficacy in our study. Due to the favorable safety profile of this drug and the alternative mechanism of action compared to currently used treatments, cilengitide emerges as a promising novel therapy for breast cancer metastasis to bone and could be validated either as a single agent, or in combination with bisphosphonates and chemotherapy in further experimental and clinical studies. Cilengitide might also be a suitable combination partner for ionizing radiation in the treatment of skeletal lesions due to its previously reported radio sensitizing effects in various tumors including breast cancer.[47-49] In some rodent tumor models, a lack of $\alpha v \beta 3$ and $\alpha v \beta 35$ integrins, or an inhibition by low concentrations of cilengitide stimulate tumor growth.[50, 51] This appears not to be the case in the breast-tumor-to-bone model we report here. Whether one or other of these experimental contexts better reflects the response of human pathologies to $\alpha v$ integrin inhibitors, however, must remain to be proven by clinical trial.[19] In conclusion, treatment of well established experimental breast cancer bone metastases with cilengitide results in an inhibition of bone resorption and soft tissue tumor growth in these osseous lesions and partial regrowth of bone. Although further experimental and clinical studies are required, cilengitide is a possible option for breast cancer patients suffering from metastases to bone.

5. References

1. Guise T A. Breaking down bone: new insight into site-specific mechanisms of breast cancer osteolysis mediated by metalloproteinases. Genes Dev 2009;23:2117-23.
2. Schwartz M A. Integrin signaling revisited. Trends Cell Biol 2001;11:466-70.
3. Varner J A, Brooks P C, Cheresh D A. The integrin alpha V beta 3: angiogenesis and apoptosis. Cell Adhes Commun 1995;3:367-74.
4. Hynes R O. Integrins: bidirectional, allosteric signaling machines. Cell 2002;110:673-87.
5. Max R, Gerritsen R R, Nooijen P T, Goodman S L, Sutter A, Keilholz U, Ruiter D J, De Waal R M. Immunohistochemical analysis of integrin alpha v beta3 expression on tumorassociated vessels of human carcinomas. Int J Cancer 1997;71:320-4.
6. Nemeth J A, Nakada M T, Trikha M, Lang Z, Gordon M S, Jayson G C, Corringham R, Prabhakar U, Davis H M, Beckman R A. Alpha-v integrins as therapeutic targets in oncology. Cancer Invest 2007;25:632-46.
7. Mulder W J, Castermans K, van Beijnum J R, Oude Egbrink M G, Chin P T, Fayad Z A, Löwik C W, Kaijzel E L , Que I, Storm G, Strijkers G J, Griffioen A W, et al. Molecular imaging of tumor angiogenesis using alphav-beta3-integrin targeted multimodal quantum dots. Angiogenesis 2009;12:17-24.
8. Nemeth J A, Cher M L, Zhou Z, Mullins C, Bhagat S, Trikha M. Inhibition of alpha(v)beta3 integrin reduces angiogenesis, bone turnover, and tumor cell proliferation in experimental prostate cancer bone metastases. Clin Exp Metastasis 2003;20:413-20.
9. Pecheur I, Peyruchaud O, Serre C M, Guglielmi J, Voland C, Bourre F, Margue C, Cohen-Solal M, Buffet A, Kieffer N, Clezardin P. Integrin alpha(v)beta3 expression confers on tumor cells a greater propensity to metastasize to bone. Faseb J 2002;16:1266-8.
10. Sloan E K, Pouliot N, Stanley K L, Chia J, Moseley J M, Hards D K, Anderson R L. Tumor-specific expression of alphavbeta3 integrin promotes spontaneous metastasis of breast cancer to bone. Breast Cancer Res 2006;8:R20.
11. Silvestri I, Longanesi Cattani I, Franco P, Pirozzi G, Botti G, Stoppelli M P, Carriero M V. Engaged urokinase receptors enhance tumor breast cell migration and invasion by upregulating alpha(v)beta5 vitronectin receptor cell surface expression. Int J Cancer 2002;102:562-71.
12. Inoue M, Ross F P, Erdmann J M, Abu-Amer Y, Wei S, Teitelbaum S L. Tumor necrosis factor alpha regulates alpha(v)beta5 integrin expression by osteoclast precursors in vitro and in vivo. Endocrinology 2000;141:284-90.
13. Reardon D A, Nabors L B, Stupp R, Mikkelsen T. Cilengitide: an integrin-targeting arginine-glycine-aspartic acid peptide with promising activity for glioblastoma multiforme. Expert Opin Investig Drugs 2008;17:1225-35.
14. Dechantsreiter M A, Planker E, Matha B, Lohof E, Holzemann G, Jonczyk A, Goodman S L, Kessler H. N-Methylated cyclic RGD peptides as highly active and selective alpha(V)beta(3) integrin antagonists. J Med Chem 1999; 42:3033-40.
15. Nisato R E, Tille J C, Jonczyk A, Goodman S L, Pepper M S. Alpha v beta 3 and alphav beta 5 integrin antagonists inhibit angiogenesis in vitro. Angiogenesis 2003;6:105-19.
16. Patsenker E, Popov Y, Sickel F, Schneider V, Ledermann M, Sägesser H, Niedobitek G, Goodman S L, Schuppan D. Pharmacological Inhibition of Integrin avb3 aggravates experimental liver fibrosis and suppresses hepatic angiogenesis. Hepatology 50:1501-11.
17. Xiong J P, Stehle T, Zhang R, Joachimiak A, Frech M, Goodman S L, Arnaout M A. Crystal structure of the extracellular segment of integrin alpha V beta3 in complex with an Arg-Gly-Asp ligand. Science 2002;296:151-5.
18. Buerkle M A, Pahernik S A, Sutter A, Jonczyk A, Messmer K, Dellian M. Inhibition of the alpha-nu integrins with a cyclic RGD peptide impairs angiogenesis, growth and metastasis of solid tumours in vivo. Br J Cancer 2002;86: 788-95.
19. Reardon D A, Fink K L, Mikkelsen T, Cloughesy T F, O'Neill A, Plotkin S, Glantz M, Ravin P, Raizer J J, Rich K M, Schiff D, Shapiro W R, et al. Randomized phase II study of cilengitide, an integrin-targeting arginine-glycine-aspartic acid peptide, in recurrent glioblastoma multiforme. J Clin Oncol 2008;26:5610-7.
20. Strieth S, Eichhorn M E, Sutter A, Jonczyk A, Berghaus A, Dellian M. Antiangiogenic combination tumor therapy blocking alpha(v)-integrins and VEGF-receptor-2 increases therapeutic effects in vivo. Int J Cancer 2006; 119:423-31.
21. Hodivala-Dilke K. alphavbeta3 integrin and angiogenesis: a moody integrin in a changing environment. Curr Opin Cell Biol 2008;20:514-9.
22. Taverna D, Moher H, Crowley D, Borsig L, Varki A, Hynes R O. Increased primary tumor growth in mice null for beta3- or beta3/beta5-integrins or selectins. Proc Natl Acad Sci USA 2004;101:763-8.
23. Bäuerle T, Bartling S, Berger M, Schmitt-Gräff A, Hilbig H, Kauczor H U, Delorme S, Kiessling F. Imaging anti-angiogenic treatment response with DCE-VCT, DCE-MRI and DWI in an animal model of breast cancer bone metastasis. Eur J Radiol 2010;73:280-7.
24. Bäuerle T, Hilbig H, Bartling S, Kiessling F, Kersten A, Schmitt-Graff A, Kauczor H U, Delorme S, Berger M R. Bevacizumab inhibits breast cancer-induced osteolysis, surrounding soft tissue metastasis, and angiogenesis in rats as visualized by VCT and MRI. Neoplasia 2008;10:511-20.
25. Mitjans F, Sander D, Adan J, Sutter A, Martinez J M, Jaggle C S, Moyano J M, Kreysch H G, Piulats J, Goodman S L. An anti-alpha v-integrin antibody that blocks integrin function inhibits the development of a human melanoma in nude mice. J Cell Sci 1995;108 (Pt 8):2825-38.
26. Cheresh D A, Spiro R C. Biosynthetic and functional properties of an Arg-Gly-Aspdirected receptor involved in human melanoma cell attachment to vitronectin, fibrinogen, and von Willebrand factor. J Biol Chem 1987;262: 17703-11.
27. Weinacker A, Chen A, Agrez M, Cone R I, Nishimura S, Wayner E, Pytela R, Sheppard D. Role of the integrin alpha v beta 6 in cell attachment to fibronectin. Heterologous expression of intact and secreted forms of the receptor. J Biol Chem 1994;269:6940-8.
28. Bäuerle T, Adwan H, Kiessling F, Hilbig H, Armbruster F P, Berger M R. Characterization of a rat model with site-specific bone metastasis induced by MDA-MB- 231 breast cancer cells and its application to the effects of an antibody against bone sialoprotein. Int J Cancer 2005;115:177-86.
29. Yamada S, Bu X Y, Khankaldyyan V, Gonzales-Gomez I, McComb J G, Laug W E. Effect of the angiogenesis inhibitor Cilengitide (EMD 121974) on glioblastoma growth in nude mice. Neurosurgery 2006;59:1304-12.
30. Brix G, Semmler W, Port R, Schad L R, Layer G, Lorenz W J. Pharmacokinetic parameters in CNS Gd-DTPA enhanced MR imaging. J Comput Assist Tomogr 1991;15: 621-8.

31. Harms J F, Welch D R, Samant R S, Shevde L A, Miele M E, Babu G R, Goldberg S F, Gilman V R, Sosnowski D M, Campo D A, Gay C V, Budgeon L R, et al. A small molecule antagonist of the alpha(v)beta3 integrin suppresses MDA-MB-435 skeletal metastasis. Clin Exp Metastasis 2004;21: 119-28.

32. Zhao Y, Bachelier R, Treilleux I, Pujuguet P, Peyruchaud O, Baron R, Clement-Lacroix P, Clezardin P. Tumor alphavbeta3 integrin is a therapeutic target for breast cancer bone metastases. Cancer Res 2007;67:5821-30.

33. Eliceiri B P, Puente X S, Hood J D, Stupack D G, Schlaepfer D D, Huang X Z, Sheppard D, Cheresh D A. Src-mediated coupling of focal adhesion kinase to integrin alpha(v)beta5 in vascular endothelial growth factor signaling. J Cell Biol 2002;157:149-60.

34. Duong L T, Rodan G A. Integrin-mediated signaling in the regulation of osteoclast adhesion and activation. Front Biosci 1998;3:d757-68.

35. Nakamura I, Duong Ie T, Rodan S B, Rodan G A. Involvement of alpha(v)beta3 integrins in osteoclast function. J Bone Miner Metab 2007;25:337-44.

36. Andersen T L, Sondergaard T E, Skorzynska K E, Dagnaes-Hansen F, Plesner T L, Hauge E M, Plesner T, Delaisse J M. A physical mechanism for coupling bone resorption and formation in adult human bone. Am J Pathol 2009;174: 239-47.

37. Hamaoka T, Madewell J E, Podoloff D A, Hortobagyi G N, Ueno N T. Bone imaging in metastatic breast cancer. J Clin Oncol 2004;22:2942-53.

38. Lai C F, Cheng S L. Alphavbeta integrins play an essential role in BMP-2 induction of osteoblast differentiation. J Bone Miner Res 2005;20:330-40.

39. Bäuerle T, Peterschmitt J, Hilbig H, Kiessling F, Armbruster F P, Berger M R. Treatment of bone metastasis induced by MDA-MB-231 breast cancer cells with an antibody against bone sialoprotein. Int J Oncol 2006;28:573-83.

40. Karadag A, Ogbureke K U, Fedarko N S, Fisher L W. Bone sialoprotein, matrix metalloproteinase 2, and alpha (v)beta3 integrin in osteotropic cancer cell invasion. Journal of the National Cancer Institute 2004;96:956-65.

41. Mitjans F, Meyer T, Fittschen C, Goodman S, Jonczyk A, Marshall J F, Reyes G, Piulats J. In vivo therapy of malignant melanoma by means of antagonists of alphav integrins. Int J Cancer 2000;87:716-23.

42. MacDonald T J, Taga T, Shimada H, Tabrizi P, Zlokovic B V, Cheresh D A, Laug W E. Preferential susceptibility of brain tumors to the antiangiogenic effects of an alpha(v) integrin antagonist. Neurosurgery 2001;48:151-7.

43. Chen Q, Manning A D, Millar H, McCabe F L, Ferrante C, Sharp C, Shahied-Arruda L, Doshi P, Nakada M T, Anderson G M. CNTO 95, a fully human anti αv integrin antibody, inhibits cell signalin, migration, invasion, and spontaneous metastasis of human breast cancer cells. Clin Exp Metastasis 2008;25:139-48.

44. Patsenker E, Popov Y, Stickel F, Schneider V, Ledermann M, Sagesser H, Niedobitek G, Goodman S L, Schuppan D. Pharmacological inhibition of integrin alphavbeta3 aggravates experimental liver fibrosis and suppresses hepatic angiogenesis. Hepatology 2009;50:1501-11.

45. Brooks P C, Montgomery A M, Rosenfeld M, Reisfeld R A, Hu T, Klier G, Cheresh D A. Integrin alpha v beta 3 antagonists promote tumor regression by inducing apoptosis of angiogenic blood vessels. Cell 1994;79:1157-64.

46. Alghisi G C, Ponsonnet L, Ruegg C. The integrin antagonist cilengitide activates alphaVbeta3, disrupts VE-cadherin localization at cell junctions and enhances permeability in endothelial cells. PLoS One 2009;4:e4449.

47. Abdollahi A, Griggs D W, Zieher H, Roth A, Lipson K E, Saffrich R, Gröne H J, Hallahan D E, Reisfeld R A, Debus J, Niethammer A G, Huber P E. Inhibition of alpha(v)beta3 integrin survival signaling enhances antiangiogenic and antitumor effects of radiotherapy. Clin Cancer Res 2005; 11:6270-9.

48. Mikkelsen T, Brodie C, Finniss S, Berens M E, Rennert J L, Nelson K, Lemke N, Brown S L, Hahn D, Neuteboom B, Goodman S L. Radiation sensitization of glioblastoma by cilengitide has unanticipated schedule-dependency. Int J Cancer 2009;124:2719-27.

49. Albert J M, Cao C, Geng L, Leavitt L, Hallahan D E, Lu B. Integrin alpha v beta 3 antagonist Cilengitide enhances efficacy of radiotherapy in endothelial cell and non-small-cell lung cancer models. Int J Radiat Oncol Biol Phys 2006;65:1536-43.

50. Reynolds L E, Wyder L, Lively J C, Taverna D, Robinson S D, Huang X, Sheppard D, Hynes R O, Hodivala-Dilke K M. Enhanced pathological angiogenesis in mice lacking beta3 integrin or beta3 and beta5 integrins. Nat Med 2002; 8:27-34.

51. Reynolds A R, Hart I R, Watson A R, Welti J C, Silva R G, Robinson S D, Da Violante G, Gourlaouen M, Salih M, Jones M C, Jones D T, Saunders G, et al. Stimulation of tumor growth and angiogenesis by low concentrations of RGD-mimetic integrin inhibitors. Nat Med 2009;15:392-400.

The disclosure of the above given documents is incorporated into this application by reference in their entirety.

6. Figure Legends

FIG. 1 A-D. Expression of integrins of MDA-MB-231 cells in vitro (A-C) and in bone metastases (D). MDA-MB-231 cells are stained with antibodies recognizing the αv chains (17E6; A), αvβ3 (LM609; B) or αvβ5 (P1F6; C) integrin complexes and expression is evaluated by flow cytometry (open curves), staining due to the second layer reagent is minimal (closed curves). The raw data curves are smoothed for presentation. Immunohistology section (D) of the soft tissue component from a control animal staining for αvβ3 (red), αvβ5 (green) and DAPI (blue). A merged image (αvβ3, αvβ5, DAPI) is shown as well as single channels for αvβ3 and αvβ5. Bar, 100 μm.

Figure 2:
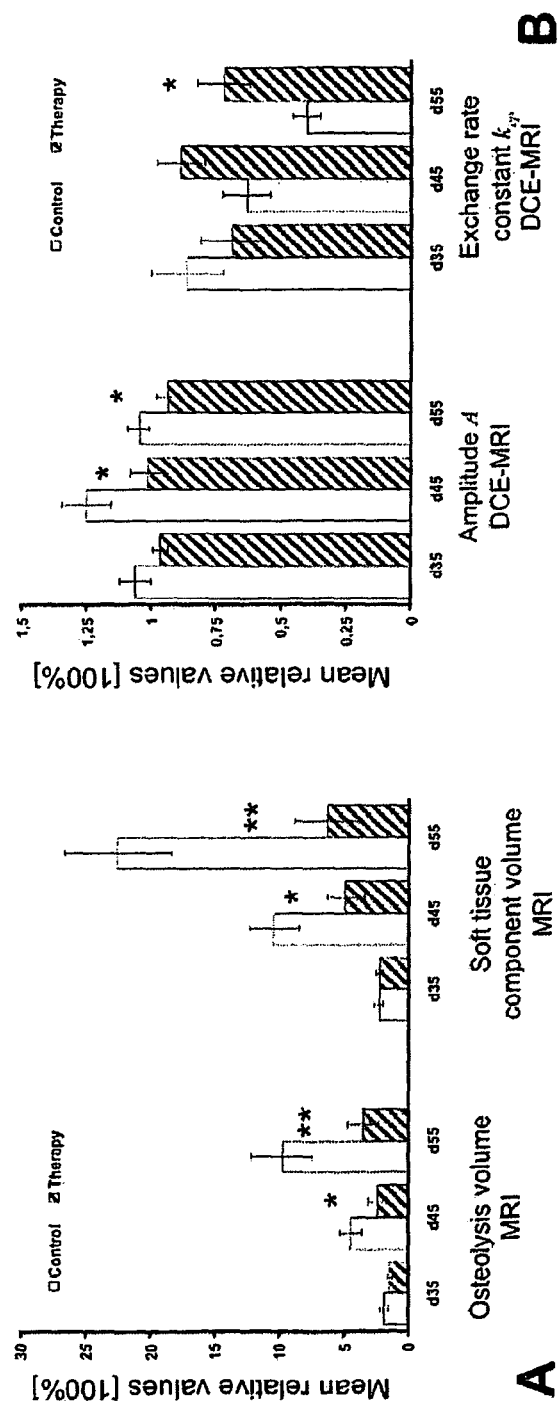
FIG. 2 consists of FIG. 2A, B and shows volumetric analyses of osteolytic lesions and soft tissue tumors (A) as well as quantification of mean relative parameters A and kep (B) from experimental bone metastases: Comparison between untreated and cilengitide-treated rats. Values are given in percent and are presented as mean values relative to initial values determined at day 30 after cancer cell inoculation at which time cilengitide therapy was started. Y-axis, mean relative values in percent (times 100); X-axis, days after cancer cell inoculation; error bars, SEM; *, p<0.05; **, P<0.01. 452×173 mm (72×72 DPI). (See Example 1).

FIG. 2 A, B. Volumetric analyses of osteolytic lesions and soft tissue tumors (A) as well as quantification of mean relative values of parameters A (associated with blood volume) and $k_{ep}$ (associated with vessel permeability) (B) from experimental bone metastases: comparison between untreated and cilengitide-treated rats. Values are given in percent and are presented as mean values relative to initial values determined at day 30 after cancer cell inoculation, at which time cilengitide therapy is started. Y-axis, mean relative values in percent (times 100); X-axis, days (d) after cancer cells inoculation (d35, d45, d55); error bars, SEM; *, p<0.05; **, p<0.01.

Figure 3:
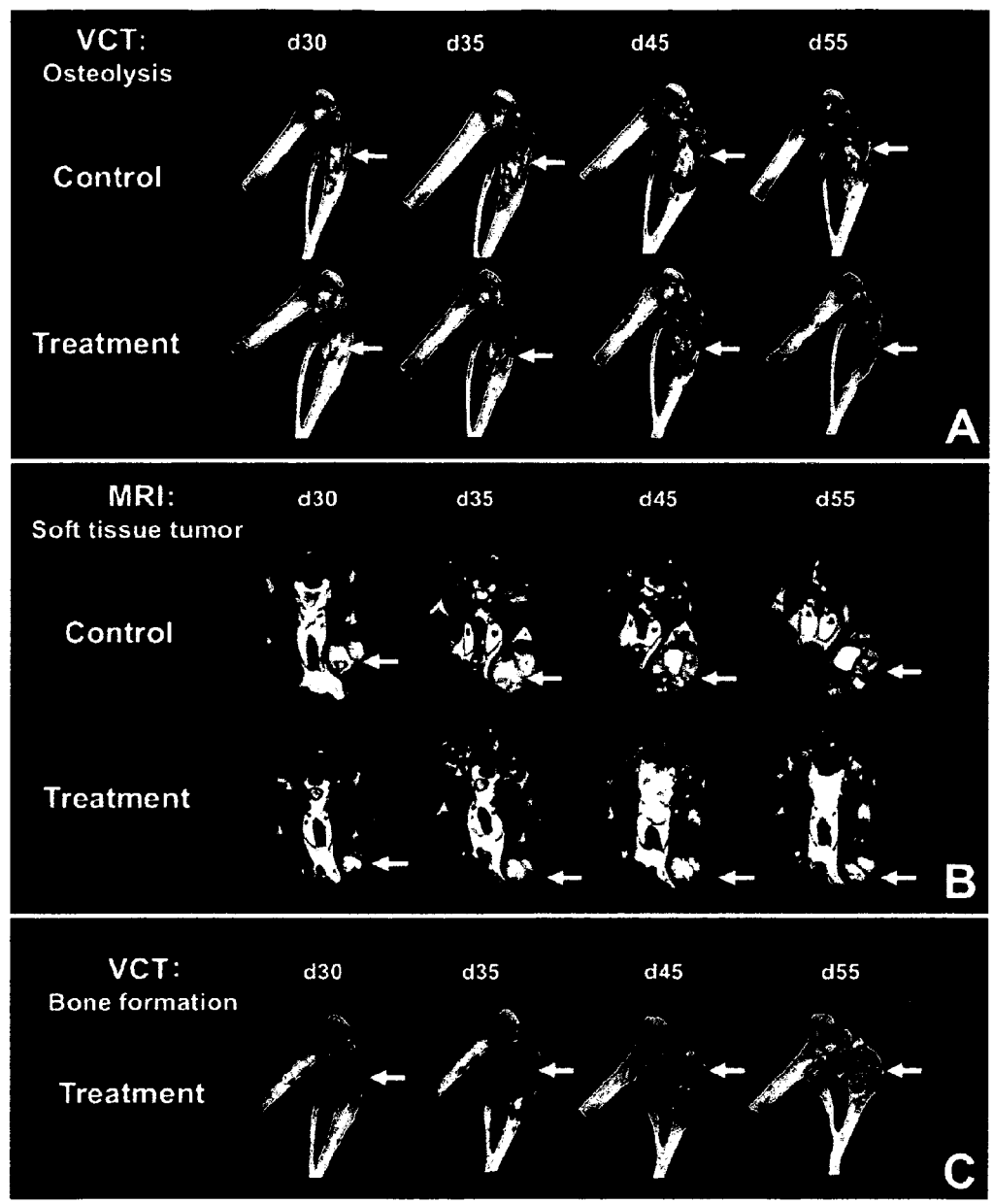
FIG. 3 consists of FIG. 3A-C and shows morphological characteristics of vehicle treated and Cilengitide-treated experimental bone metastases. Volumes of the osteolytic lesions (A, C) and soft tissue tumours (B) were determined by the analysis of images acquired by VCT and MRI, respectively, at days 30, 35, 45 and 55 after cancer cell injection. Therapy with Cilengitide commenced after imaging on day 30. Compare differences in bone loss and soft tumour burden between vehicle treated (A, B: upper rows) as well as Cilengitide-treated animals resulting in inhibition of osteolysis and bone formation (A, B: upper rows; C). Representative VCT images: 3D bone surface reconstructions, and MRI: axial slices from T2-weighted imaging. Arrows, proximal tibia of the hind leg. 323×402 mm (72×72 DPI). (See Example 1)

FIG. 3 A-C. Morphological characteristics of vehicle treated and cilengitide-treated experimental bone metastases. Volumes of the osteolytic lesions (A, C) and soft tissue tumors (B) are determined by the analysis of images acquired by VCT and MRI, respectively, at days 30, 35, 45 and 55 after cancer cell injection. Therapy with cilengitide commences after imaging on day 30. Compare differences in bone loss and soft tumor burden between vehicle treated (A, B: upper rows) as well as cilengitide-treated animals resulting in inhibition of osteolysis and bone formation (A, B: lower rows; C). Representative VCT images: 3D bone surface reconstructions, and MRI: axial slices from T2-weighted imaging. Arrows, proximal tibia of the hind leg.

Figure 4:
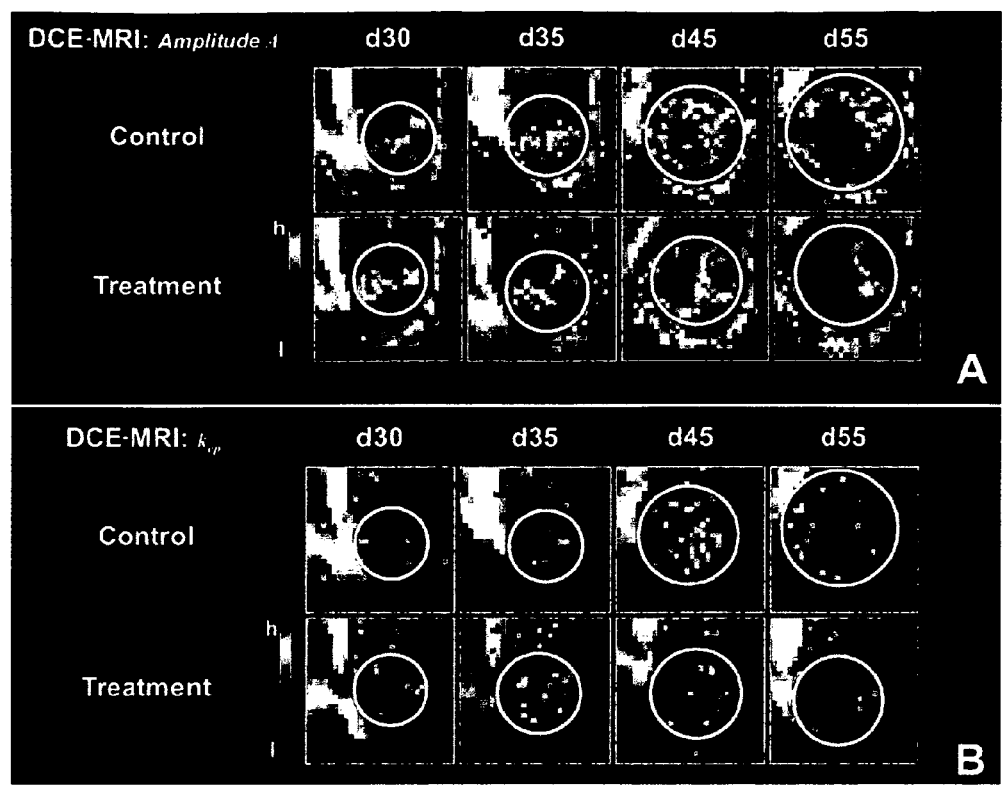
FIG. 4 consist of FIG. 4A, B and shows DCE-MRI-acquired colour maps depicting functional parameters of bone metastases amplitude A (A) and exchange rate constant kep (B): Comparison between untreated and Cilengitide-treated rats at days 30, 35, 45 and 55 after cancer cell inoculation. Cilengitide treatment began following imaging at day 30. Rats bearing MDA-MBE-231 bone metastases were imaged at day 30, and then following control (upper rows) or Cilengitide (lower rows) treatment. These colour maps were calculated by the use of DynaLab software, red colour denotes high (h) values for the given parameters, blue colour denotes low (l) values. The same scaling ranges were used to produce these images for experimental and control animals. 440×351 mm (72×72 DPI). (See Example 1).

FIG. 4 A-B. DCE-MRI-acquired color maps depicting functional parameters of bone metastases amplitude A (associated with blood volume) (A) and exchange rate constant $k_{ep}$ (associated with vessel permeability) (B): comparison between untreated and cilengitide-treated rats at days 30, 35, 45 and 55 after cancer cell inoculation. Cilengitide treatment begins following imaging at day 30. Rats bearing MDAMB-231 bone metastases are imaged at day 30, and then following control (upper rows) or cilengitide (lower rows) treatment. These color maps are calculated by the use of DynaLab software, red color denotes high (h) values for the given parameter, blue color denotes low (l) values. The same scaling ranges are used to produce these images for experimental and control animals.

Figure 5:
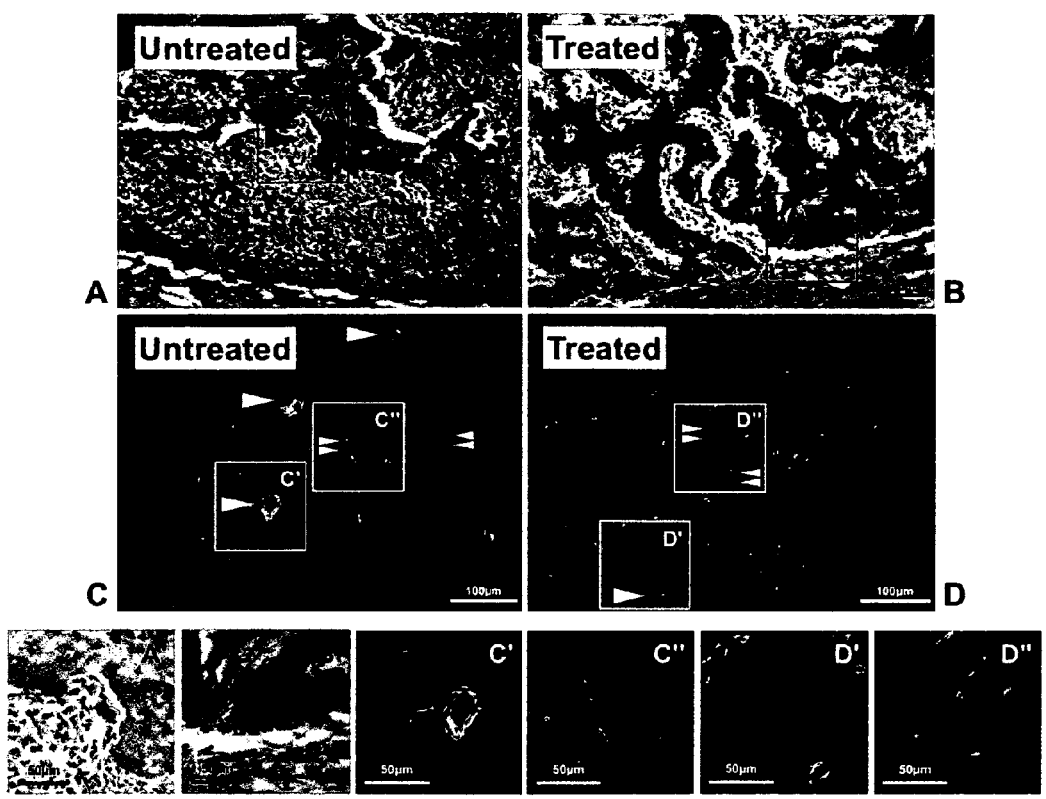
FIG. 5 consists of FIG. 5 A-D and shows histologic analysis of experimental breast cancer bone metastases of untreated and Cilengitide-treated rats. Hematoxylin/eosin stained sections of an osteolytic lesion in a control rat (A; t, tumour cells; b, bone; arrow, osteoclast) and new bone formation in a treated rat (B; b, arrows, osteoclasts). Immunohistology sections of the soft tissue component from a control animal (C) and a Cilengitide-treated rat (D). Green colour shows collagen IV staining whereas red denotes structures staining for smooth muscle actin; blue, cell nuclei. Arrows point at larger vessels with partial co-localisation of smooth muscle actin and collagen IV, while double arrows indicate smaller vessels without clear co-localisation of green and red staining. Enlarged images of the highlighted structures are shown below (A', B', C', C'', D', D''). A-D, bar 100 µm; A'-D'', bar 50 µm. 478×371 mm (72×72 DPI). (See Example 1)

FIG. 5 A-D. Histologic analysis of experimental breast cancer bone metastases of untreated and cilengitide-treated rats. Hematoxylin/eosin stained sections of an osteolytic lesion in a control rat (A; t, tumor cells; b, bone; arrow, osteoclast) and new bone formation in a treated rat (B; b, bone; arrows, osteoblasts). Immunohistology sections of the soft tissue component from a control animal (C) and a cilengitide-treated rat (D). Green color shows collagen IV staining whereas red denotes structures staining for smooth muscle actin; blue, cell nuclei. Arrows point at larger vessels with partial co-localization of smooth muscle actin and collagen IV, while double arrows indicate smaller vessels without clear co-localization of green and red staining. Enlarged images of the highlighted structures are shown below (A', B', C', C'', D', D''). A-D, bar 100 µm; A'-D'', bar 50 µm.

Figure 6:
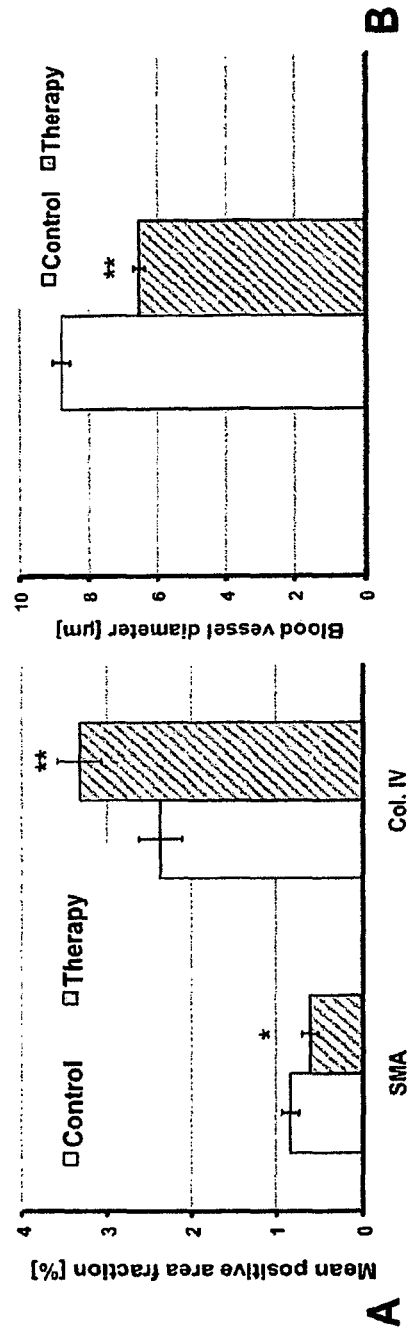
FIG. 6 consist of FIG. 6A, B and shows the quantification of histological analysis. Values of fractional mean area stained for smooth muscle actin (SMA) and collagen IV (Col. IV) are expressed as percent total area examined (A), while the blood vessels by a meters are presented as mean values in µm (B). Error bars, SEM; *, p<0.05; **, p<0.01. 548×152 mm (72×72 DPI). (See Example 1)

FIG. 6 A, B. Quantification of histological analysis. Values of fractional mean area stained for smooth muscle actin (SMA) and collagen IV (Col. IV) are expressed as percent total area examined (A), while the blood vessel diameters are presented as mean values in µm (B). Error bars, SEM; *, $p<0.05$; **, $p<0.01$.

Example 2

Rat Orthotopic Glioblastoma Model Radiotherapy, Cilengitide (=cyclo-(Arg-Gly-Asp-DPhe-NMe-Val)) Scheduling Experiments NIH rnu nude rats are anaesthetized, restrained, and injected intracerebrally 1 mm retro orbitally, 3 mm to the right of the bregma and at a depth of 2.5 mm with 5×10E5 U251 human glioblastoma cells suspended in 10 ul of culture medium, using a #2701 Hamilton syringe fitted with a 26 gauge needle, essentially as previously described (Engebraaten et al., 1999). After 14 days, cilengitide (4 mg/kg) is given as an intraperitoneal bolus in PBS, at various time (8 h, 4 h, 2 h, 1 h) prior to a single treatment with single, collimated, dorsal-ventral beam of 6 MV x-rays, so that 95-100% of the central axis dose of 25 Gy hit the tumor volume (Kim et al., 1999). Each of the 7 subsequent days the animals also received an identical i.p. bolus of cilengitide. The animals are maintained under ad libitum food and drink until they become moribund, or are sampled for tissue analysis (in the t-4 and t-8 h groups, where the animals are healthy past 230 days post tumor injection). A Kaplan-Meier survival curve is calculated and plotted (FIG. 7) from the raw data (Table 2). All animals in the RT monotherapy group died by 120 d.

Reference List

Engebraaten, O., Hjortland, G .O., Hirschberg, H., and Fodstad, O. (1999). Growth of precultured human glioma specimens in nude rat brain. J. Neurosurg. 90, 125-132.

Kim, J. H., Khil, M. S., Kolozsvary, A., Gutierrez, J. A., and Brown, S. L. (1999). Fractionated radiosurgery for 9 L gliosarcoma in the rat brain. Int. J. Radiat. Oncol. Biol. Phys. 45, 1035-1040.

The disclosure of the above given documents is incorporated into this application by reference in their entirety.

Figure 7:
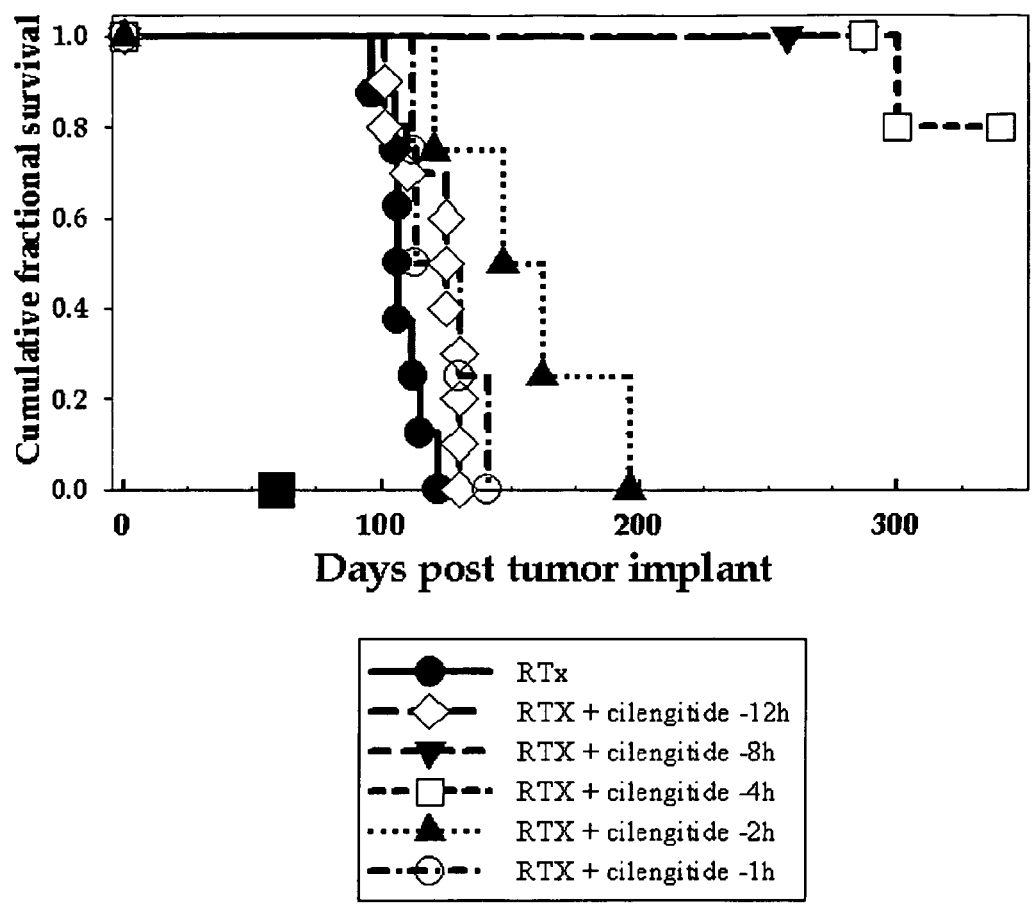
FIG. 7 shows Kaplan Meier survival curves of nude rats bearing orthotopic human glioblastomas U251 derived. Dark square represents survival of non irradiated animals. (See Example 2).

The Results are given in Table 2 below and FIG. 7:

TABLE 2

| 400,000 U251n Cells Inj. | | Animal | | EMD Survival Study | | | Days Post |
| --- | --- | --- | --- | --- | --- | --- | --- |
| Group | Time Pre-Irradiation | # | Trtmnt | Date of Injection | Date of Radiation | Date of Termination | Implant |
| 89 | 8 hours | G89-1 | Rt | Mar. 3, 2005 | Mar. 17, 2005 | (Sick) Jun. 7, 2005 | 96 |
| 89 | 8 hours | G89-2 | Rt | Mar. 3, 2005 | Mar. 17, 2005 | (Sick) Jun. 17, 2005 | 106 |
| 89 | 8 hours | G89-3 | Rt + EMD | Mar. 3, 2005 | Mar. 17, 2005 | (Healthy) Nov. 15, 2005 | 257 |
| 89 | 8 hours | G89-4 | Rt + EMD | Mar. 3, 2005 | Mar. 17, 2005 | (Healthy) Nov. 15, 2005 | 257 |
| 89 | 8 hours | G89-5 | Rt + EMD | Mar. 3, 2005 | Mar. 17, 2005 | (Alive) Dec. 15, 2005 | 287 |
| 89 | 8 hours | G89-6 | Rt + EMD | Mar. 3, 2005 | Mar. 17, 2005 | (Alive) Dec. 15, 2005 | 287 |
| 90 | 4 hours | G90-1 | Rt | Apr. 5, 2005 | Apr. 19, 2005 | (Sick) Jul. 20, 2005 | 106 |
| 90 | 4 hours | G90-2 | Rt | Apr. 5, 2005 | Apr. 19, 2005 | (Sick) Jul. 29, 2005 | 115 |
| 90 | 4 hours | G90-3 | Rt + EMD | Apr. 5, 2005 | Apr. 19, 2005 | (Healthy) Nov. 29, 2005 | 238 |
| 90 | 4 hours | G90-4 | Rt + EMD | Apr. 5, 2005 | Apr. 19, 2005 | (Healthy) Nov. 29, 2005 | 238 |
| 90 | 4 hours | G90-5 | Rt + EMD | Apr. 5, 2005 | Apr. 19, 2005 | (Alive) Dec. 15, 2005 | 254 |
| 90 | 4 hours | G90-6 | Rt + EMD | Apr. 5, 2005 | Apr. 19, 2005 | (Alive) Dec. 15, 2005 | 254 |
| 91 | 2 hours | G91-1 | Rt | Apr. 12 2005 | Apr. 26, 2005 | (Sick) Jul. 26, 2005 | 105 |
| 91 | 2 hours | G91-2 | Rt | Apr. 12, 2005 | Apr. 26, 2005 | (Sick) Aug. 12, 2005 | 122 |
| 91 | 2 hours | G91-3 | Rt + EMD | Apr. 12, 2005 | Apr. 26, 2005 | (Sick) Aug. 10, 2005 | 120 |
| 91 | 2 hours | G91-4 | Rt + EMD | Apr. 12, 2005 | Apr. 26, 2005 | (Sick) Sep. 6, 2005 | 147 |
| 91 | 2 hours | G91-5 | Rt + EMD | Apr. 12, 2005 | Apr. 26, 2005 | (Sick) Sep. 21, 2005 | 162 |
| 91 | 2 hours | G91-6 | Rt + EMD | Apr. 12, 2005 | Apr. 26, 2005 | (Sick) Oct. 25, 2005 | 196 |
| 92 | 1 hour | G92-1 | Rt | May 12, 2005 | May 26, 2005 | (Sick) Aug. 26, 2005 | 106 |
| 92 | 1 hour | G92-2 | Rt | May 12, 2005 | May 26, 2005 | (Sick) Sep. 1, 2005 | 112 |
| 92 | 1 hour | G92-3 | Rt + EMD | May 12, 2005 | May 26, 2005 | (Sick) Sep. 1, 2005 | 112 |
| 92 | 1 hour | G92-4 | Rt + EMD | May 12, 2005 | May 26, 2005 | (Sick) Sep. 2, 2005 | 113 |

TABLE 2-continued

| 400,000 U251n Cells Inj. | | Animal | | EMD Survival Study | | | Days Post |
|---|---|---|---|---|---|---|---|
| Group | Time Pre-Irradiation | # | Trtmnt | Date of Injection | Date of Radiation | Date of Termination | Implant |
| 92 | 1 hour | G92-5 | Rt + EMD | May 12, 2005 | May 26, 2005 | (Sick) Sep. 19, 2005 | 130 |
| 92 | 1 hour | G92-6 | Rt + EMD | May 12, 2005 | May 26, 2005 | (Sick) Sep. 30, 2005 | 141 |

Sick = moribund and removed from study
Healthy = indicates sampled for tissue at date shown, but alive at this point
Alive = surviving at time point shown.
Time pre-irradiation = when cilengitide 4 mg/kg is given.
Rt = radiotherapy 25 Gy
EMD = cilengitide bolus 4 mg/kg American date convention in date of termination column, European date convention in date of radiation column

Example 3

Phase I/IIa Trial of Cilengitide (=cyclo-(Arg-Gly-Asp-DPhe-NMe-Val)) and Temozolomide with Concomitant Radiotherapy, Followed by Temozolomide and Cilengitide Maintenance Therapy in Patients With Newly Diagnosed Glioblastoma (GBM)

Purpose: To evaluate safety, toxicity, and efficacy of the combination of the cyclic RGD pentapeptide Cilengitide (=cyclo-(Arg-Gly-Asp-DPhe-NMe-Val)), an inhibitor of integrins $\alpha v\beta 3$ and $\alpha v\beta 5$, in addition to standard temozolomide (TMZ) and radiotherapy (RT).

Patients and methods: Fifty-two pts (PS 0-1: 92%, 2: 8%; median age 57 yrs) after biopsy (n=9/17%) or tumor resection (n=43/83%) were treated with standard TMZ/RT (Stupp et al. NEJM 2005). In addition Cilengitide (500 mg i.v., 2×/week) was started one week before TMZ/RT and given throughout for the duration of chemotherapy or until progression. Primary endpoint was progression free survival rate at 6 months (target: 65%). Patients were followed with MRI every 2 months. Histopathologic diagnosis and MRI imaging were independently reviewed, MGMT promotor methylation status was assessed in 45 (86.5%) pts.

Results: Forty-six pts (92%) completed RT, ≥90% of concomitant TMZ was received by 42 pts and cilengitide by 45 pts. 20 pts (3 ongoing) completed 6 cycles of maintenance TMZ and cilengitide. Observed haematological grade 3 and 4 toxicity was: lymphopenia (28/52, 53.8%), thrombocytopenia (7/52 pt. 13.4%) and neutropenia (5/52, 9.6%). Treatment related non-hematologic grade 3 toxicities were reported for n=3/52 (5.7%) patients: constitutional symptoms (asthenia, fatigue, anorexia, n=3); elevated liver function tests (n=1), deep venous thrombosis and pulmonary embolism (n=1). One patient with a history of sigmoid diverticulosis experienced sigmoid perforation (grade 2). In total, 34/52 (65.4% [95% Cl, 50.9-78.0%]) of the patients were progression free at 6 months. Pts with $O^6$-Methylguanine-DNA methyltransferase (MGMT) gene-promotor methylation in the tumor were more likely to reach 6 months PFS endpoint. In total, 34/52 (65.4% [95% Cl, 50.9-78.0%]) of the pts were progression free at 6 months. A major contribution to the overall result was provided by a subgroup of patients (23/52 subjects, with methylated MGMT promoter, silencing the DNA repair enzyme MGMT), which showed a strong increase of the PFS-6 rate compared to historical control (91% vs. 69%). The other major subgroup (22/52, unmethylated MGMT promotor) showed a less relevant difference to the historical control (40.9% vs. 40%), which is likely to be significantly improved by a higher dosing of Cilengitide in comparison to the subgroup with methylated MGMT promoter. Overall the study reached its primary endpoint (PFS-6=65.4%)

Figure 8:
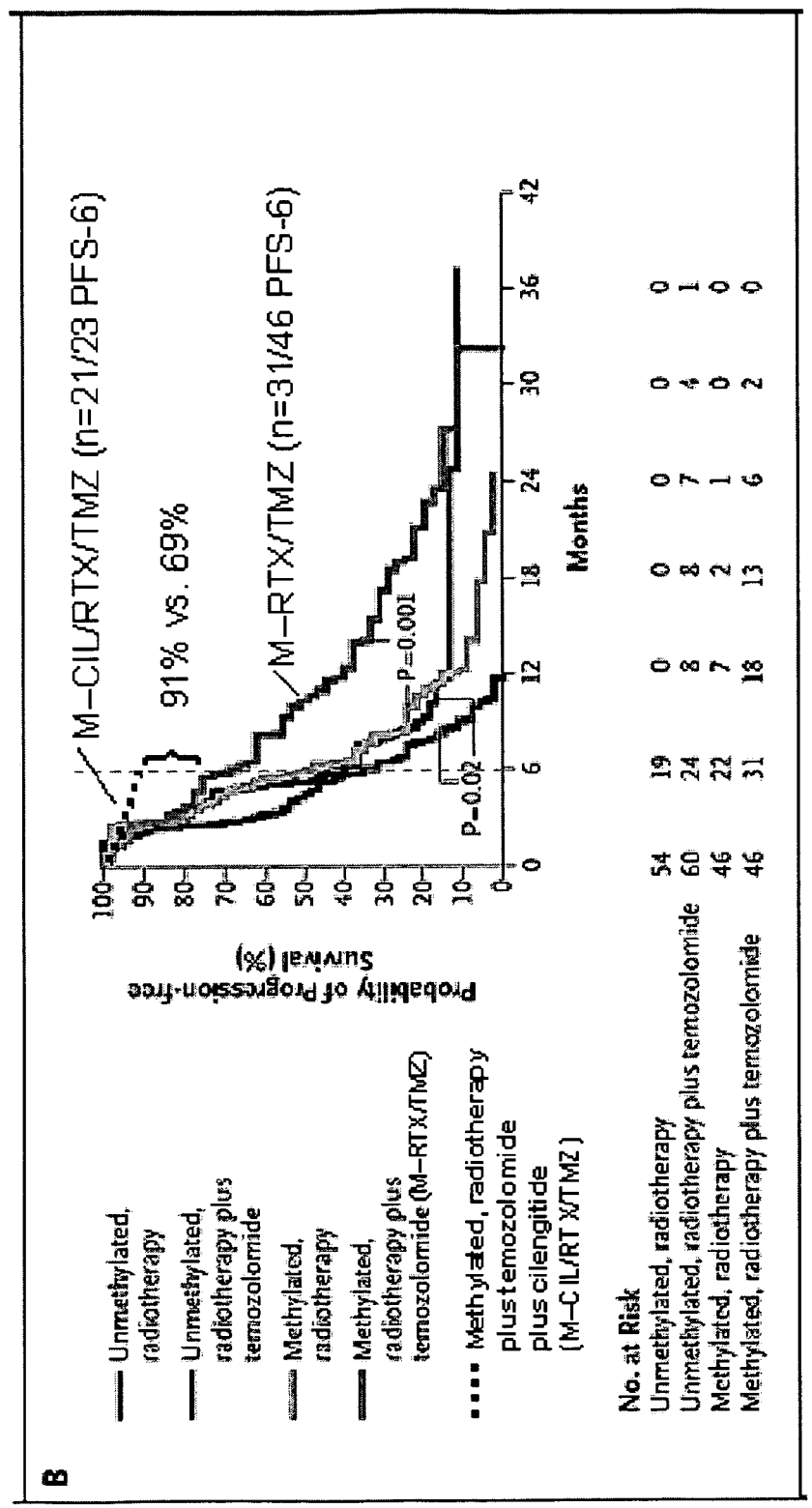
FIG. 8 shows the results of a Phase I/IIa Trial of Cilengitide (=cyclo-(Arg-Gly-Asp-DPhe-NMe-Val)) and Temozolomide with Concomitant Radiotherapy, Followed by Temozolomide and Cilengitide Maintenance Therapy in Patients With Newly Diagnosed Glioblastoma (GBM). The study reached its primary endpoint. The combination of the integrin inhibitor RGD peptide Cilengitide and TMZ/RT was well tolerated, PFS at 6 months is very advantagous. MGMT gene promotor methylation provides for even better prognosis. (See Example 3).

Conclusion: The study reached its primary endpoint. The combination of the integrin inhibitor RGD peptide Cilengitide and TMZ/RT was well tolerated, PFS at 6 months is very advantagous. MGMT gene promotor methylation provides for even better prognosis. The results are summarized in FIG. 8.

Example 4

Proliferation Assays

1 Materials and Methods
1.1 Test System (Biological Materials/Animals)
Carcinoma cell lines are grown in the following media:
A549-DMEM containing 10% FCS (heat-inactivated) plus 2 mM glutamine, HUVEC-DMEM containing 10% FCS (heat-inactivated) plus 2 mM glutamine and 1 mM sodium pyruvate.

All media contains 100 units/ml penicillin and 100 ug/ml streptomycin. Cells are passaged at confluence by washing once in cation-free PBS followed by a 3 minute incubation in trypsin (0.5 ug/ml)/EDTA (0.2 ug/ml) solution in PBS at 37° C. Cells are recovered in medium, centrifuged and taken up in medium and counted.
1.2 Chemicals and Solutions
All cell culture reagents are from GIBCO/InVitrogen with the exception of foetal calf serum which is purchased from BioWhittaker. Dulbecco's PBS with and without cations is from GIBCO/Invitrogen Alamar Blue is from Serotech. Paclitaxel, vinblastin, and oxaliplatin are from Sigma. Cisplatin is purchased from Fluka. Gemcitabine is purchased from LGC Promochem, Heidelberg. Gefitnib from AstraZeneca and imatinib from Novartis are commercially available.

Cilengitide by Merck KGaA. Bovine serum albimun is from VWR. The extracellular matrix components vitronectin and fibronectin are purified from human serum in house according to SOP 6456; fibrinogen according to SOP 6460. Rat tail collagen I is from Serva. Antibodies for FACS analysis: 17E6, 20H9, LM609, P1F6, 11D1, P4C10, MAb P1D6 are are commercially available, e.g. purchased from Chemicon. Goat anti-mouse IgG FITC conjugate is from Becton Dickson.
1.3 Methods
FACS Analysis
Cells are harvested with trypsin as described above. The required number of cells is taken up in PBS containing 0.9 mM CaCl2 and 0.5 mM MgCl2+0.5% BSA (=FACS Buffer) and aliquoted 1×10e6/tube. After centrifugation at 800×g for 4 minutes, the cells are incubated 60 minutes on ice with anti-integrin antibodies at 10 ug/ml in FACS Buffer, 100 ul/tube. After washing to remove unbound antibody, the cells are incubated with goat anti-mouse FITC diluted 1:25 in FACS Buffer. Cells are incubated 30 minutes on ice, washed to remove unbound antibody and a final cell suspension is made in FACS Buffer 500 ul/tube. Cells are analyzed on a FACScan and the mean intensity fluorescence (MIF) is normalized to the MIF of the negative control (no primary antibody).

Attachment Assay

Attachment to extracellular matrix proteins is performed as follows:

Briefly, 2.5×10e4 cells/well in RPMI containing 0.5% BSA and 25 mM Hepes pH 7.4 attached to non-tissue culture treated 96-well plates coated with serially diluted vitronectin, fibronectin, fibrinogen and collagen I for 60 minutes at 37° C. After washing to remove unbound cells the relative cell number is determined by incubation with hexosaminidase substrate. The colormetric reaction is read at 405 nm in a Genios plate reader (SLT). Proliferation assay Non-tissue cultures treated 96 well plates are coated using 100 ul/well of a 2 ug/ml vitronectin solution in PBS incubated overnight at 4° C. Cells are plated at 5×10e3 in 100 ul cell culture medium (as described above for each cell line). After 3 hours at 37° C. serially diluted chemotherapeutic agents are added alone or in the presence of a constant EC50 concentration of alpha V integrin blocker at two-fold concentration in 100 ul/well in cell culture medium. Plates are incubated for 72 hours, after which relative cell number is determined by the addition of 20 ul/well Alamar Blue (Resazurin) (Nakayama et al. 1997). After 4 hours of incubation at 37° C. relative fluorescent intensity is read in a Genios plate reader (SLT) at 535/590 nm (excitation/emission).

1.4 Experimental Design

Points are run in triplicate. Reagent blanks, containing media plus colormetric reagent without cells, are run on each plate. Blank values are subtracted from test values and are routinely 5-10% of uninhibited control values. In FACS analysis 15,000 events analyzed. Single cells are gated out from debris and aggregates and the live cells based on staining with propidium iodide. Markers are set on a negative control population stained with goat anti-mouse FITC alone (no primary antibody). Cells that fell to the right of the marker (higher intensity fluorescence) are considered positively stained.

Figure 9:
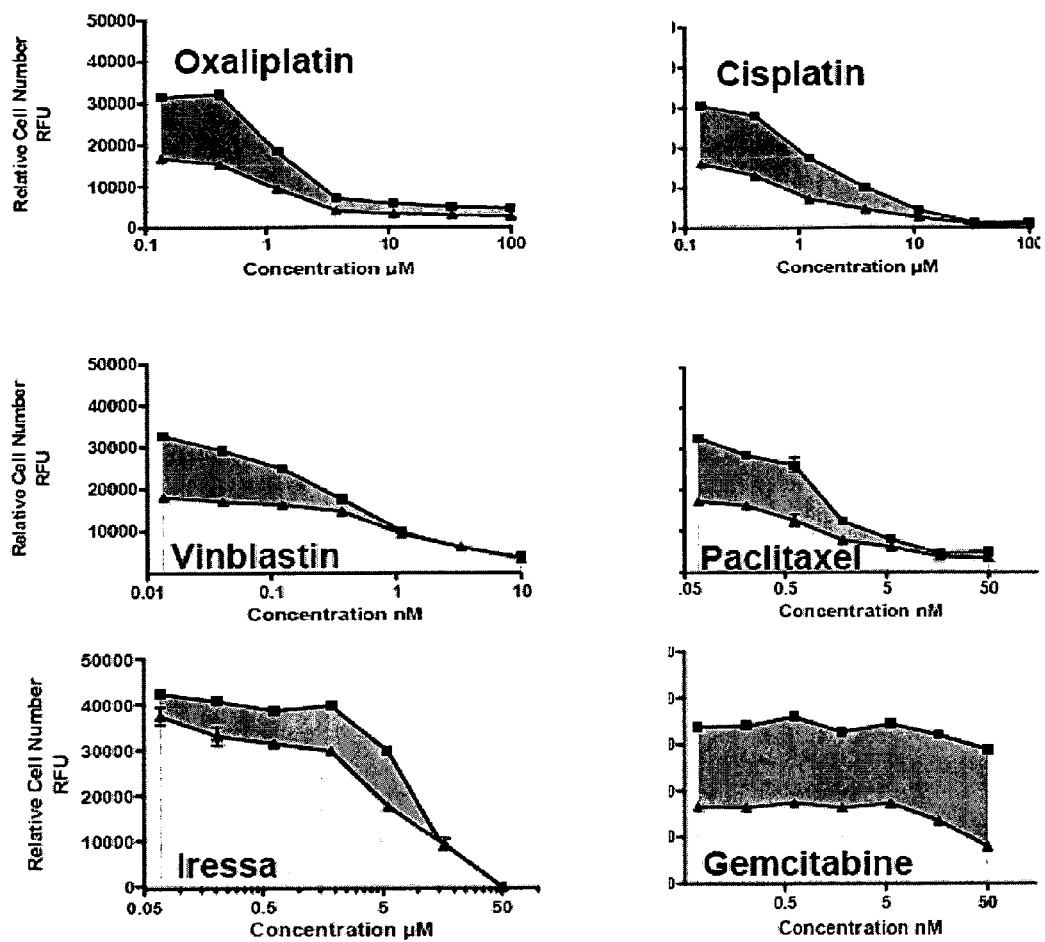
FIGS. 9 and 10 show the results of Proliferation Assays using NSCLC (A549) and Endothelial Cells (HUVEC), respectively. (See Example 4).
Figure 10:
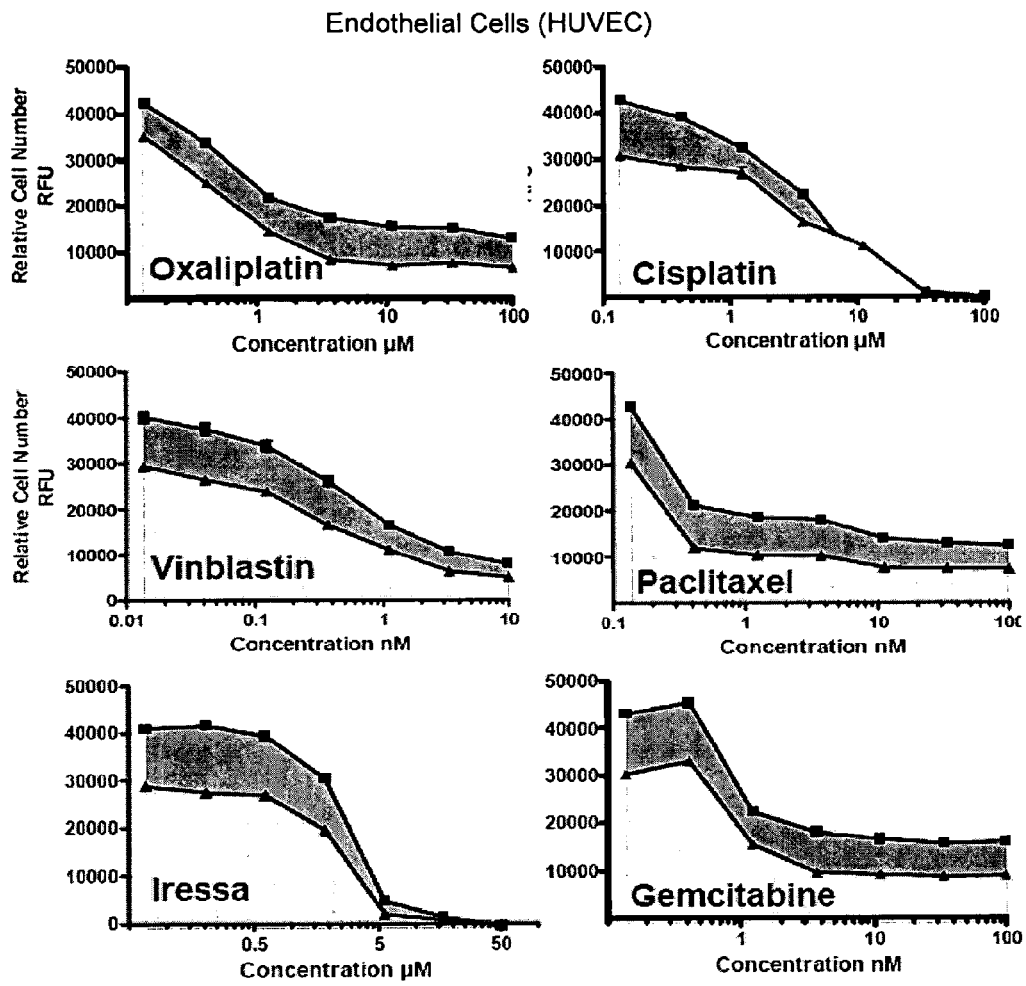

The results are shown in FIG. 9 and FIG. 10, respectively.

Concentration on X-Axis) refers to the respective compound (oxaliplatin, cisplatin, vinblastine, paclitaxel, Iressa (gefitinib) or gemcitabine).

Y-Axis refers to the relative cell number.

Cilengitide concentration is constant (6 nM for NSCLC (A549) and 0.2 nM for Endothelial Cells (HUVEC), respectively).

Figure 11:
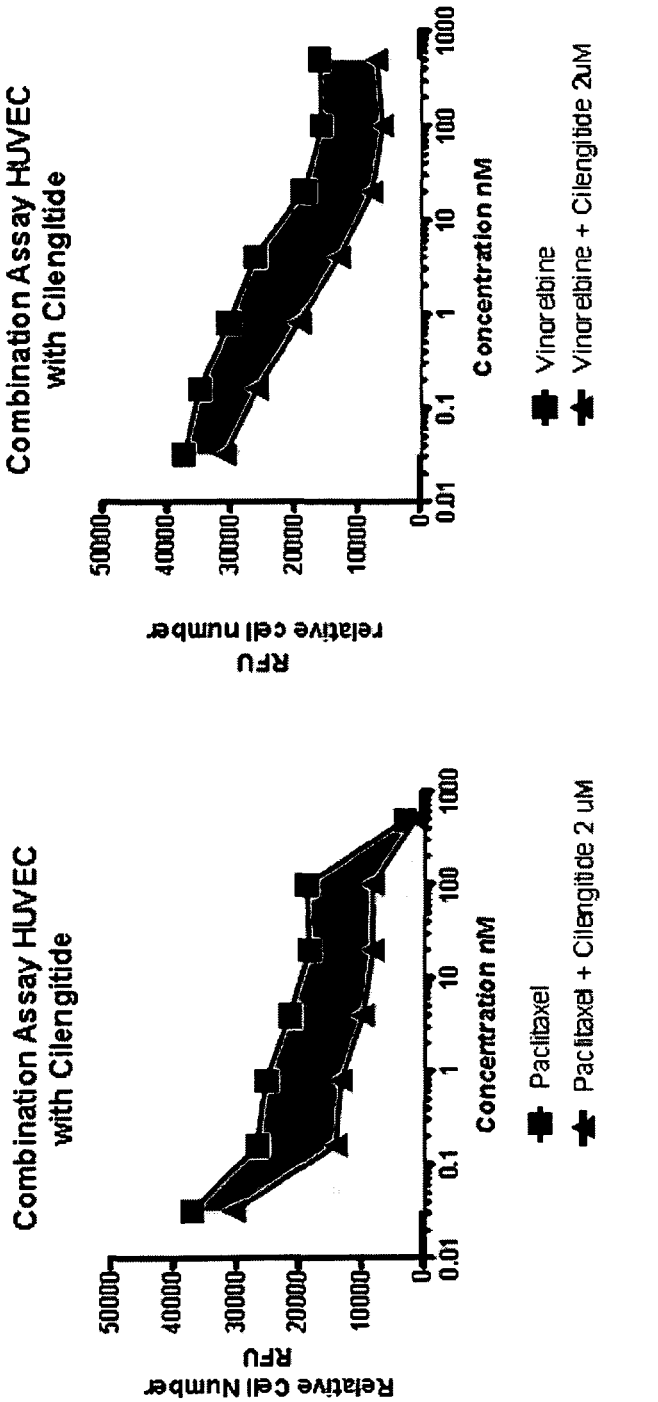
FIG. 11 shows the Effect of αv integrin ligand Cilengitide in combination with paclitaxel or vinorelbine on HUVEC cell proliferation. (See Example 4)
Figure 12:
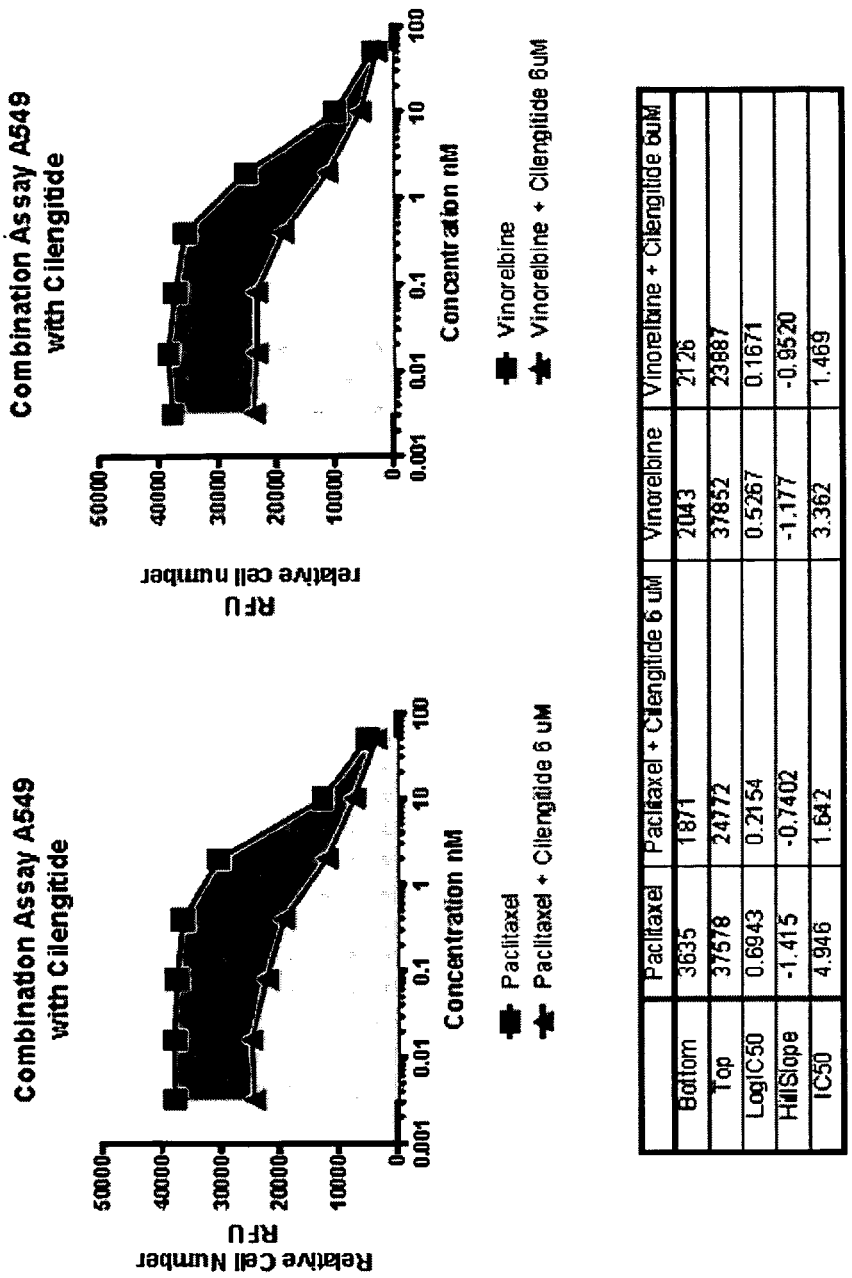
FIG. 12 shows the Effect αv integrin ligand Cilengitide in combination with paclitaxel or vinorelbine on NSCLC cells. (See Example 4).

Results Shown in FIGS. 11 And 12: Effect of Alpha-V Integrin Inhibitors in Combination With Vinorelbine on the Proliferation of Human Carcinoma Cells The effect of integrin alpha V blocker EMD 121974 (Cilengitide) on the viability of human carcinoma cells were tested, in combination with vinorelbine and paclitaxel, respectively, in a cell viability assay, dependent on reduction of Alamar blue dye. Each agent alone could inhibiting carcinoma viability, used together the compounds show an advantagous and preferably synergistic inhibitory effect.

5.1 Test System (Biological Materials/Animals)

5.2 Chemicals and Solutions

Cilengitide, EMD 121974, cyclo-(Arg-Gly-Asp-D-Phe [N-Me]-Val) was synthesized, purified and characterized in house [23]. Cilengitide was stored in sterile apyrogenic solution at 4° C.

Dulbecco's Phosphate Buffered Saline (136.9 mM NaCl, 2.8 mM KCl, 8.1 mM $Na_2HPO_4.H_2O$, 1.5 mM $KH_2PO_4$) without calcium and magnesium, trypsin/EDTA and Medium 199 were from Life Technologies, and other reagents as follows: serum albumin (bovine Fraction V) (VWR); Alamar Blue (Serotec); chemotherapeutic agents paclitaxel, docetaxel, etoposide, and vinorelbine are commercially available. Chemotherapeutic compounds were dissolved in DMSO as stock solutions at 10 mM, stored at 4° C. and used within one month.

5.3 Methods

The methods established and described in detail previously (Goodman and Hahn a; b) were used to measure the effect of combinations of integrin inhibitors and chemotherapeutics on carcinoma cell and human endothelial cell proliferation.

5.4 Experimental Design

Points were run in duplicate or in triplicate. Reagent blanks, containing media plus Alamar Blue without cells, were run on each plate. Blank values were subtracted from test values and were routinely 5-10% of uninhibited control values.

In the growth assay Cilengitide was tested in the range of 50 µM to 0.1 nM. In the Constant Ratio Combination Assay substances were tested at 8-fold, 4-fold, 2-fold 1-fold 0.5-fold and 0.25-fold of the respective $EC_{50}$ concentration.

5.5 Methods of Evaluation and Statistics

Chemotherapeutic agents and αv-integrin blockers were serially diluted alone or together (combination therapy). In some assays the chemotherapeutic agent was serially diluted alone or in combination with of alpha-v integrin blocker. Growth inhibition curves were plotted and a shift of the combination therapy curve to lower concentrations in relation to the single agent curves was interpreted as an additional effect, produced by combination versus monotherapy.

5.6 Results

The αv-integrin competitive inhibitor Cilengitide (EMD 121974) was tested alone and in combination with vinorelbine in a serum growth stimulation assay using human carcinoma cells or human umbilical vein endothelial cells (HUVECs). In these assays cells are cultured in serum, or in an endothelial growth stimulation medium (Goodman & Hahn).

As monotherapies, the chemotherapeutics inhibited the growth of both endothelial and carcinoma cells.

The alpha-v integrin blockers inhibited endothelial cell growth. A typical result using HUVEC is shown in FIG. 1, where the $IC_{50}$ for Cilengitide was 700 nM. For Paclitaxel the $IC_{50}$ of 10 nM was reduced to 0.05 nM in combination with 2 µM Cilengitide. For vinorelbine, the $IC_{50}$ of 20 nM was reduced to 0.8 nM in combination with 2 µM Cilengitide.

Growth of cancer cell lines derived from non-small cell lung carcinoma (NSCLC: A549, renal carcinoma (A498), and squamous cell carcinoma of the head and neck (SCCHN: Detroit 562) were also inhibited by the chemotherapeutics, and specifically by vinorelbine, and in all cases this inhibition was advantagously and preferably synergistically enhanced by the presence of cilengitide.

In conclusion, the combination of the vinorelbine with integrin inhibitors at their $EC_{50}$ concentrations lowered the $EC_{50}$ for these cytotoxics dramatically, preferably at least 5-fold, more preferably at least 10-fold, or even more. As the therapeutic window for such drugs is often extremely narrow, this reduction in $EC_{50}$ appears to be a very valuable addition to the anti-cancer drug battery allowing more prolonged and less aggressive, yet more efficacious therapy regimens to be pursued. The results of these assays or assays performed in an analogous or essentially analogous manner are preferably summarized in FIGS. 9, 10, 11, 12, 13, 14, 15, 16, 17, 18, 19, 22, 23, 24, 25, 26 and/or 27, respectively. Amendments or comments to the assays/results are preferably highlighted in the respective Examples 5, 6, 7, 8, 9, 10, 12, 13, 14, 15, 16 and/or 17 and the corresponding Figures as given below.

5.7 References

1. Chou T C, Talalay P: Quantitative analysis of dose-effect relationships: the combined effects of multiple drugs or enzyme inhibitors. *Adv. Enzyme Regul.* 1984, 22:27-55.: 27-55.
2. Folkman J: Angiogenesis. *Annu. Rev Med.* 2006, 57:1-18.: 1-18.
3. Gasparini G, Longo R, Toi M, Ferrara N: Angiogenic inhibitors: a new therapeutic strategy in oncology. *Nat Clin. Pract. Oncol.* 2005, 2:562-577.
4. Hurwitz H, Fehrenbacher L, Novotny W, Cartwright T, Hainsworth J, Heim W, Berlin J, Baron A, Griffing S, Holmgren E, Ferrara N, Fyfe G, Rogers B, Ross R, Kabbinavar F: Bevacizumab plus irinotecan, fluorouracil, and leucovorin for metastatic colorectal cancer. *N. Engl. J Med.* 2004, 350:2335-2342.
5. MacDonald T J, Taga T, Shimada H, Tabrizi P, Zlokovic B V, Cheresh D A, Laug W E: Preferential susceptibility of brain tumors to the antiangiogenic effects of an alpha(v) integrin antagonist. *Neurosurgery* 2001, 48:151-157.
6. Max R, Gerritsen R R, Nooijen P T, Goodman S L, Sutter A, Keilholz U, Ruiter D J, De Waal R M: Immunohistochemical analysis of integrin alpha vbeta3 expression on tumor-associated vessels of human carcinomas. *Int. J Cancer* 1997, 71:320-324.
7. Albelda S M, Mette S A, Elder D E, Stewart R, Damjanovich L, Herlyn M, Buck C A: Integrin distribution in malignant melanoma: association of the beta 3 subunit with tumor progression. *Cancer Res.* 1990, 50:6757-6764.
8. Friedlander M, Brooks P C, Shaffer R W, Kincaid C M, Varner J A, Cheresh D A: Definition of two angiogenic pathways by distinct alpha v integrins. *Science* 1995, 270: 1500-1502.
9. Schwartz M A, Ginsberg M H: Networks and crosstalk: integrin signalling spreads. *Nat Cell Biol.* 2002, 4:E65-E68.
10. Friedlander M, Theesfeld C L, Sugita M, Fruttiger M, Thomas M A, Chang S, Cheresh D A: Involvement of integrins alpha v beta 3 and alpha v beta 5 in ocular neovascular diseases. *Proc. Natl. Acad. Sci. U.S.A.* 1996, 93:9764-9769.
11. Stromblad S, Becker J C, Yebra M, Brooks P C, Cheresh D A: Suppression of p53 activity and p21WAF1/CIP1 expression by vascular cell integrin alphaVbeta3 during angiogenesis. *J Clin Invest* 1996, 98:426-433.
12. Schiff P B, Fant J, Horwitz S B: Promotion of microtubule assembly in vitro by taxol. *Nature.* 1979, 277:665-667.
13. Madoc-Jones H, Mauro F: Interphase action of vinblastine and vincristine: differences in their lethal action through the mitotic cycle of cultured mammalian cells. *J Cell Physiol.* 1968, 72:185-196.
14. Wozniak A J, Ross W E: DNA damage as a basis for 4'-demethylepipodophyllotoxin-9-(4,6-O-ethylidene-beta-D-glucopyranoside) (etoposide) cytotoxicity. *Cancer Res.* 1983, 43:120-124.
15. Jaxel C, Taudou G, Portemer C, Mirambeau G, Panijel J, Duguet M: Topoisomerase inhibitors induce irreversible fragmentation of replicated DNA in concanavalin A stimulated splenocytes. *Biochemistry.* 1988, 27:95-99.
16. Watring W G, Byfield J E, Lagasse L D, Lee Y D, Juillard G, Jacobs M, Smith M L: Combination Adriamycin and radiation therapy in gynecologic cancers. *Gynecol. Oncol.* 1974, 2:518-526.
17. Pascoe J M, Roberts J J: Interactions between mammalian cell DNA and inorganic platinum compounds. I. DNA interstrand cross-linking and cytotoxic properties of platinum(II) compounds. *Biochem Pharmacol.* 1974, 23:1359-1365.
18. Blommaert F A, van Dijk-Knijnenburg H C, Dijt F J, den E L, Baan R A, Berends F, Fichtinger-Schepman A M: Formation of DNA adducts by the anticancer drug carboplatin: different nucleotide sequence preferences in vitro and in cells. *Biochemistry.* 1995, 34:8474-8480.
19. Baker C H, Banzon J, Bollinger J M, Stubbe J, Samano V, Robins M J, Lippert B, Jarvi E, Resvick R: 2'-Deoxy-2'-methylenecytidine and 2'-deoxy-2',2'-difluorocytidine 5'-diphosphates: potent mechanism-based inhibitors of ribonucleotide reductase. *J Med Chem.* 1991, 34:1879-1884.
20. Hehlgans S, Haase M, Cordes N: Signalling via integrins: implications for cell survival and anticancer strategies. *Biochim. Biophys. Acta.* 2007, 1775:163-180.
21. Yatohgo T, Izumi M, Kashiwagi H, Hayashi M: Novel purification of vitronectin from human plasma by heparin affinity chromatography. *Cell Struct. Funct.* 1988, 13:281-292.
22. Mitjans F, Sander D, Adan J, Sutter A, Martinez J M, Jaggle C S, Moyano J M, Kreysch H G, Piulats J, Goodman S L: An anti-alpha v-integrin antibody that blocks integrin function inhibits the development of a human melanoma in nude mice. *J. Cell Sci.* 1995, 108:2825-2838.
23. Dechantsreiter M A, Planker E, Matha B, Lohof E, Holzemann G, Jonczyk A, Goodman S L, Kessler H: N-methylated cyclic RGD peptides as highly active and selective alpha(v)beta(3) integrin antagonists. *J. Med. Chem.* 1999, 42:3033-3040.
24. Chou T-C., Hayball M. CalcuSyn for Windows, Multiple-drug dose-effect analyzer and manual. 1996. Cambridge Place, Cambridge, United Kingdom, Biosoft.
25. Chou T C: Theoretical basis, experimental design, and computerized simulation of synergism and antagonism in drug combination studies. *Pharmacol Rev.* 2006, 58:621-681.
26. Milkiewicz M, Ispanovic E, Doyle J L, Haas T L: Regulators of angiogenesis and strategies for their therapeutic manipulation. *The International Journal of Biochemistry & Cell Biology* 2006, 38:333-357.
27. Conway E M, Collen D, Carmeliet P: Molecular mechanisms of blood vessel growth. *Cardiovasc. Res.* 2001, 49:507-521.
28. Nakayama G R, Caton M C, Nova M P, Parandoosh Z: Assessment of the Alamar Blue assay for cellular growth and viability in vitro. *J Immunol Methods.* 1997, 204:205-208.
29. Hynes R O: Integrins: bidirectional, allosteric signaling machines. *Cell* 2002, 110:673-687.
30. Zaidel-Bar R, Itzkovitz S, Ma'ayan A, Iyengar R, Geiger B: Functional atlas of the integrin adhesome. *Nat Cell Biol.* 2007, 9:858-867.
31. Katsumi A, Naoe T, Matsushita T, Kaibuchi K, Schwartz M A: Integrin activation and matrix binding mediate cellular responses to mechanical stretch. *J Biol. Chem.* 2005, 280:16546-16549.
32. Friedlander M, Brooks P C, Shaffer R W, Kincaid C M, Varner J A, Cheresh D A: Definition of two angiogenic pathways by distinct alpha v integrins. *Science* 1995, 270: 1500-1502.
33. Stromblad S, Becker J C, Yebra M, Brooks P C, Cheresh D A: Suppression of p53 activity and p21WAF1/CIP1 expression by vascular cell integrin alphaVbeta3 during angiogenesis. *J Clin Invest* 1996, 98:426-433.
34. Diefenbach B. EMD 85189: Cell adhesion inhibition. 1998. Darmstadt, Merck KGaA. EMD 121974.
35. Goodman S L, Hahn D. Endothelial cells: effect of alpha-V integrin inhibitors alone and in combination with chemotherapeutic agents on viability. Merck KGaA, Darmstadt, EMD 121974
36. Goodman S L, Hahn D. Human secondary endothelial cells: the role of av-integrins in modifying sensitivity to radiation compared to NSCLC and melanoma cell lines. Merck KGaA, Darmstadt, EMD 121974

The disclosure of the above given documents is incorporated into this application by reference in their entirety.

5.8 Figures and Tables

TABLE 1

Summary of effect of vinorelbine in combination with cilengitide on various carcinoma cell lines

| EC50 (nM) | Cancer origin NSCLC A549 | Renal A498 |
|---|---|---|
| Paclitaxel | 8 | 100 |
| Paclitaxel + Cilengitide | 0.05 | <0.01 |
| Vinorelbine | 8.00 | 60 |
| Vinorelbine + Cilengitide | 0.2 | <0.01 |

See also Figures relating to the Effect of αv integrin ligand Cilengitide and paclitaxel/vinorelbine on HUVEC cell proliferation and the effect of αv integrin ligand Cilengitide and paclitaxel/vinorelbine on NSCLC (A549) cell proliferation.

Example 5

Figure 13:
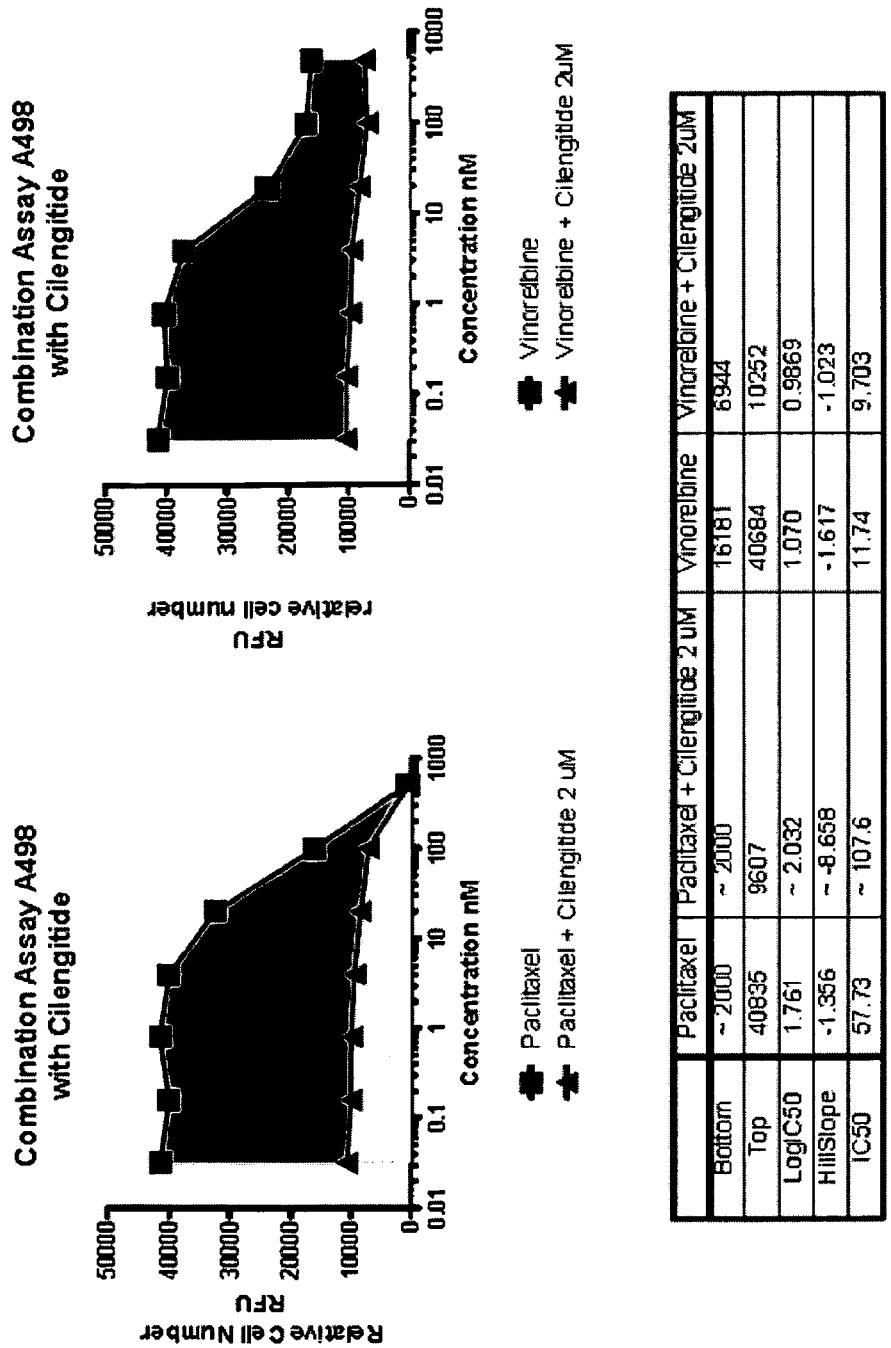
FIG. 13 shows the Effect αv integrin ligand Cilengitide in combination with paclitaxel or vinorelbine on renal carcinoma cell proliferation. (See Example 5).
Figure 14:
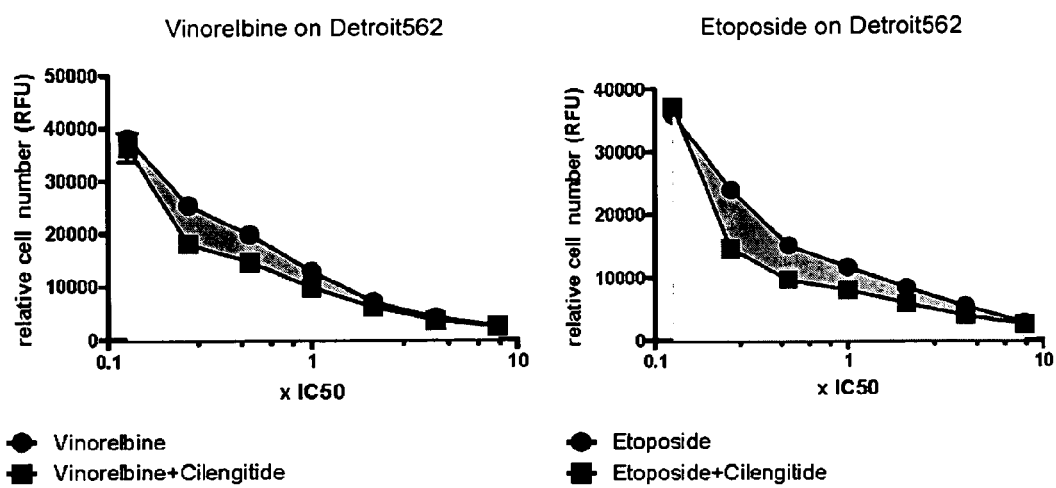
FIG. 14 shows the Effect αv integrin ligand Cilengitide in combination with vinorelbine or etoposide on SCCHN cell proliferation (Detroit562), respectively. (See Example 5).

Effect of αv Integrin Ligand Cilengitide and Paclitaxel/Vinorelbine on A498 Cell Proliferation and the Effect of αv Integrin Ligand Cilengitide and Vinorelbine/Etoposide on SCCHN (Detroit562) Cell Proliferation The graphs of FIGS. 13 and 14 show the advantagous and preferably synergistic effect of the respective combinations of Cilengitide and the combination partners in the A498/Detroit562 cell proliferation assays. Cilengitide concentration is 2 μM (constant).

Example 6

Effect of αv Integrin Ligand Cilengitide in Combination With Docetaxel/Paclitaxel on HUVEC Cell Proliferation Constant ratio assay with docetaxel/paclitaxel and Cilengitide combinations on HUVEC endothelial cells grown in complete EGM MV medium, analysis according to Chou and Talalay [1] shows synergistic effect in FIG. 13 graph and isobologram. The respective Combination Index (CI) Docetaxel-Cilengitide (CI=0.7) and Paclitaxel-Cilengitide (CI=0.1) indicates the synergistic effect of the combinations. (See FIG. 15).

Example 7

Figure 16:
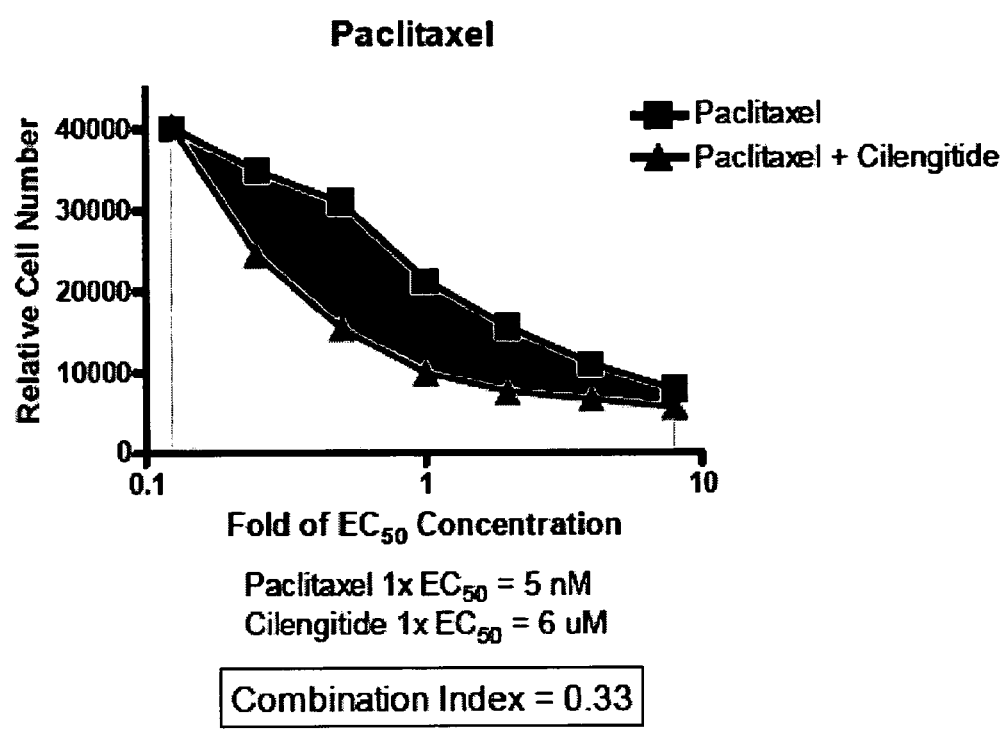
FIG. 16 shows the Effect of αv integrin ligand Cilengitide in combination with paclitaxel on A549 NSCLC cell proliferation. Combination Index (CI) <1 (here: CI=0.33) shows synergistic effect of the respective combination. (See Example 7).
Figure 17:
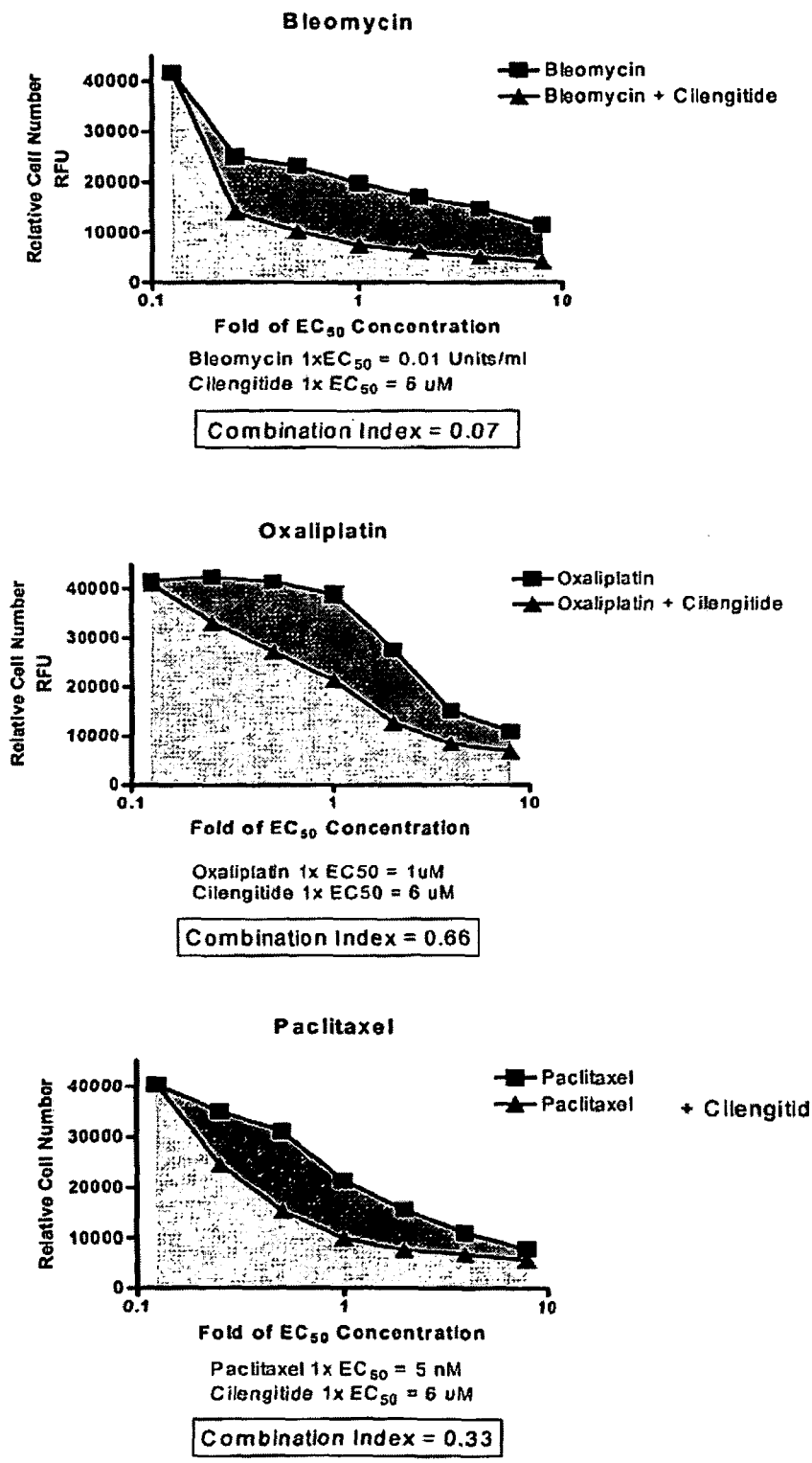
FIG. 17 shows the Effect of αv integrin ligand Cilengitide in combination with bleomycin/oxaliplatin/paclitaxel on A549 NSCLC cell proliferation. (See Example 8).

Effect of αv Integrin Ligand Cilengitide in Combination with Paclitaxel on NSCLC Cell Proliferation FIG. 16 shows A549 Constant Ratio Proliferation Assay. Cells grew on vitronectin-coated plates for 72 hours in the presence of a serially diluted chemotherapeutic with (triangles) or without (squares) Cilengitide. For the combination treatment the drugs were mixed at eight-fold the respective $EC_{50}$ concentrations and the mixture was a serially diluted. Relative cell number was determined by Alamar Blue reduction and shows the synergistic effect of the combination of paclitaxel and Cilengitide on the cell grow. The respective Combination Index (CI) Paclitaxel-Cilengitide (CI=0.33) indicates the synergistic effect of the combination.

Example 8

Figure 15:
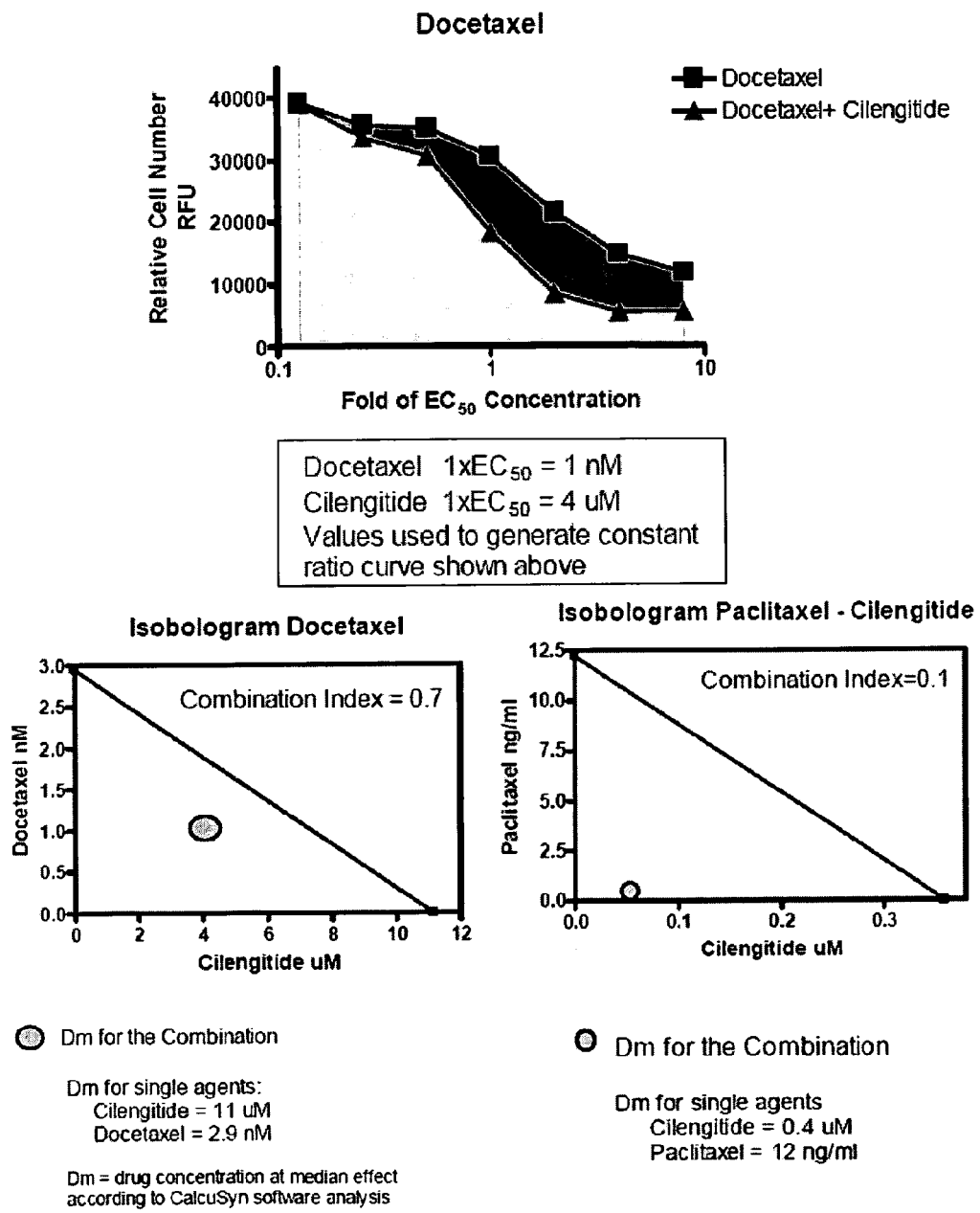
FIG. 15 shows the Effect αv integrin ligand Cilengitide in combination with docetaxel on HUVEC cell proliferation. Constant ratio assay with docetaxel/paclitaxel and Cilengitide combinations on HUVEC endothelial cells grown in complete EGM MV medium, analysis shows synergistic effect both in graph and isobologram (Combination Index (CI) <1) of the respective combination. (See Example 6).

Effect of αv Integrin Ligand Cilengitide in Combination with Bleomycin/Oxaliplatin/Paclitaxel on A549 NSCLC Cell Proliferation A549 NSCLC assay with bleomycin/oxaliplatin/paclitaxel and Cilengitide ananlysed according to Chou and Talalay [1] shows synergistic effect in all graphs shown in FIG. 15. The respective Combination Index (CI) Bleomycin-Cilengitide (CI=0.07), Oxaliplatin-Cilengitide (CI=0.66) and Paclitaxel-Cilengitide (CI=0.33) indicates the synergistic effect of the combinations. (See FIG. 17).

Example 9

Figure 18:
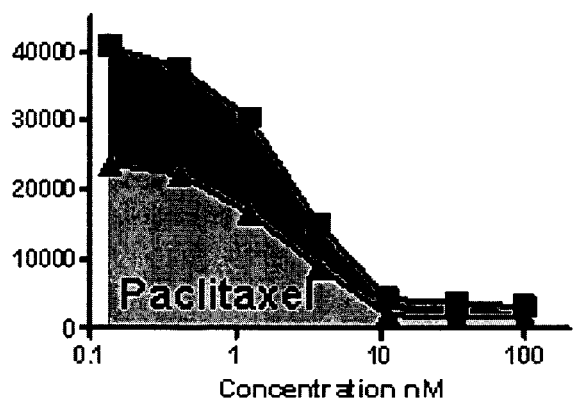
FIG. 18 shows the Effect of αv integrin ligand Cilengitide in combination with Paxlitaxel/Vinblastine on various NSCLC cell lines: Cilengitide in combination with paclitaxel on NSCLC cell line Calu 6; Cilengitide in combination with Vinblastine/Paclitaxel on NSCLC cell line H460; Serially dilute Vinblastine/Paclitaxel (squares) in presence of 10 uM cilengitide (triangles). (See Example 9).
Figure 18:
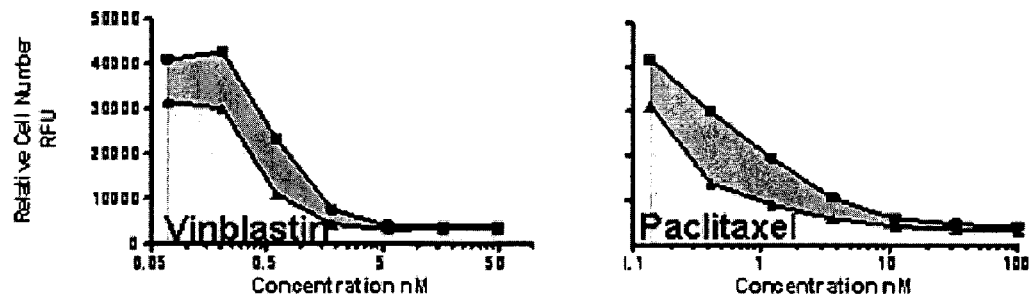

Effect of αv Integrin Ligand Cilengitide in Combination with Paxlitaxel or Vinblastine on Various NSCLC Cell Lines Calu6 NSCLC assay with paclitaxel and Cilengitide and H460 NSCLC assay with vinblastine/paclitaxel and Cilengitide show synergistic effects in all graphs shown in FIG. 18.

Example 10

Figure 19:
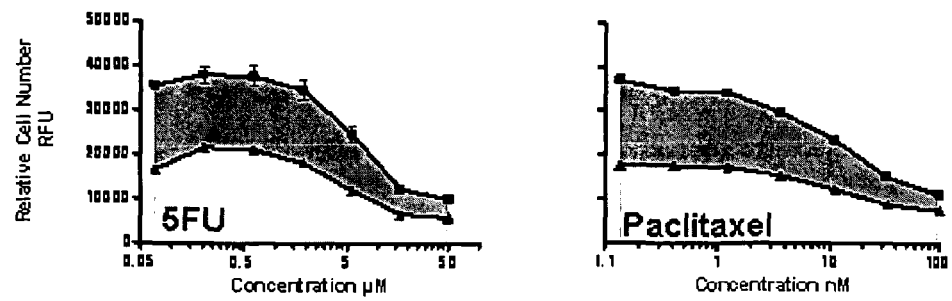
FIG. 19 shows the Effect of αv integrin ligand Cilengitide in combination with 5-FU/Paclitaxel on various EGFR dependent cell lines; Serially dilute 5-FU/Paclitaxel (squares) in presence of Cilengitide (triangles); 5-FU or Paxlitaxel on Renal cell line ACHN, Cilengitide constant at 2 µM; 5-FU or Paxlitaxel on Renal cell line A498, Cilengitide constant at 2 µM; 5-FU or Paxlitaxel on Renal cell line Caki 1, Cilengitide constant at 2 µM. (See Example 10).
Figure 19:
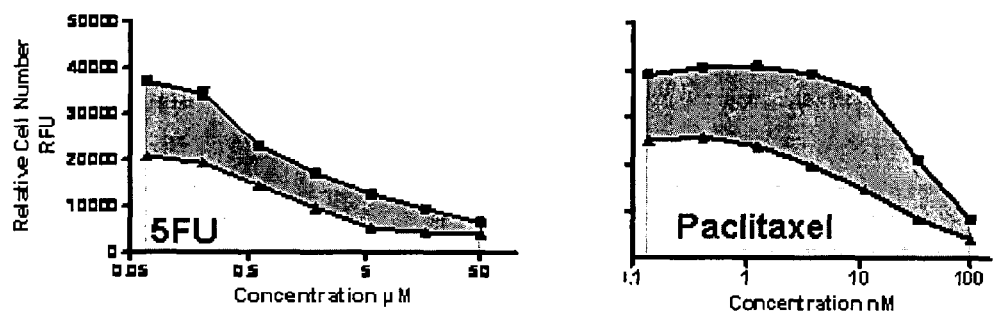
Figure 19:
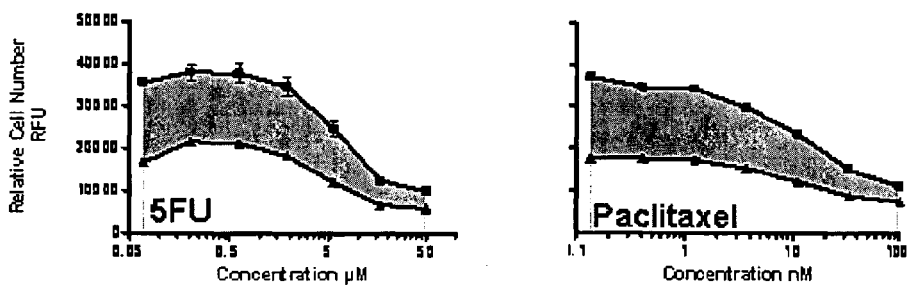

Effect of αv Integrin Ligand Cilengitide in Combination with 5-FU or Paclitaxel on Various EGFR Dependent Cell Lines Both the combinations of 5-FU with Cilengitide and Paclitaxel with Cilengitide show an advantagous and preferably synergistic effect in EGFR dependent cancers, as is shown by the results in FIG. 19, e.g. in the ACHN, A498 and Caki 1 cell proliferation assays.

Example 11

Figure 20:
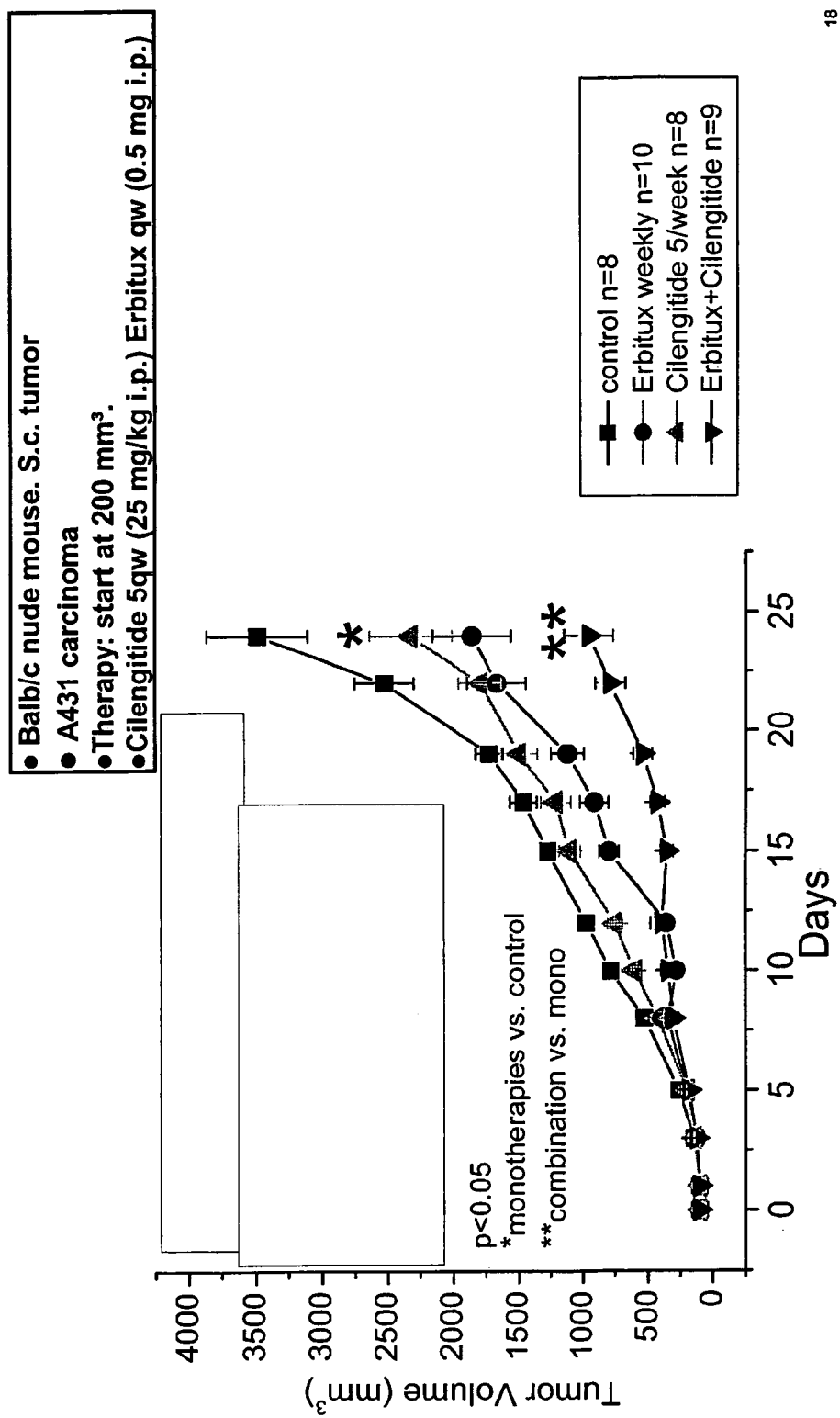
FIG. 20 shows the Effect of αv integrin ligand Cilengitide in combination with Erbitux (cetuximab) in carcinoma xenograft. (See Example 11).
Figure 21:
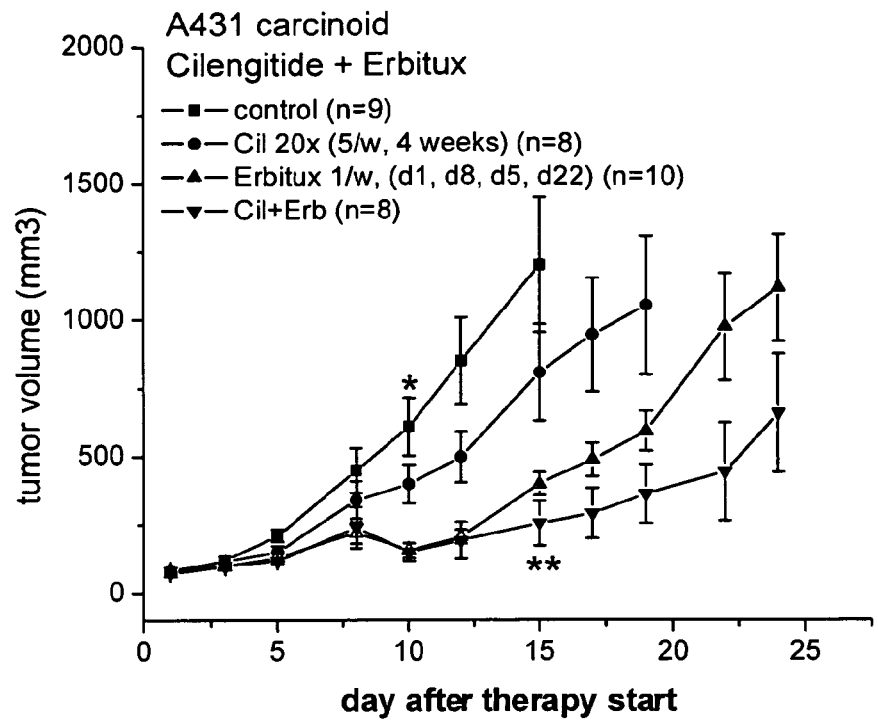
FIG. 21 shows the combination efficacy of Cilengitide & Erbitux in carcinoma xenograft, optionally in combination with Radiotherapy (Rx); A431 human epidermoid carcinoma s.c. on balb c nu nu mouse; Erbitux: 25 mg/kg (=0.5 mg/animal) i.p. d1 (4 h pre Rx), d8, d15, d22; Cilengitide: 25 mg/kg i.p. 20×5/w 1-2 h pre Rx. (See Example 11).
Figure 21:
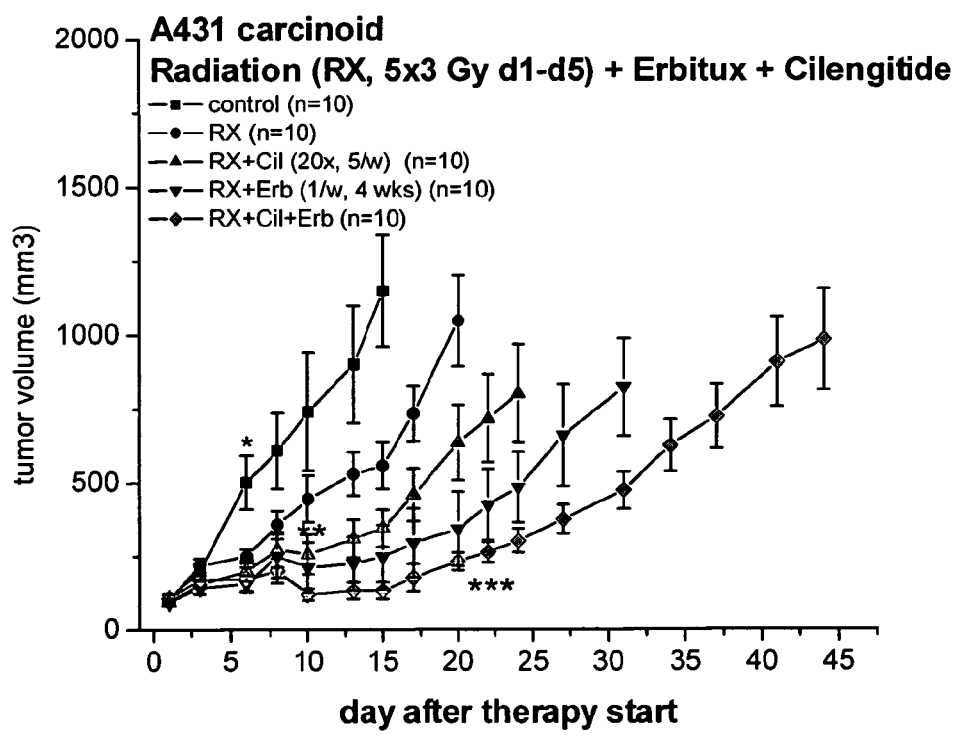

Combination Efficacy of Cilengitide & Erbitux in Carcinoma Xenograft, Optionally in Combination with Radiotherapy This example shows that combined treatment with integrin ligand Cilengitide, a potent antagonist of αvβ3, and EGFR antibody Cetuximab (Erbitux), optionally combined with Radiotherapy (preferably also referred to as RT, Rx or RTx), preferably external beam radiotherapy, are beneficial, and especially synergistically beneficial, in local tumor therapy. The results of the in vivo xenograft experiments show that radiation up-regulates αvβ3 expression in endothelial cells and consecutively phosphorylates Akt, which may provide a tumor escape mechanism from radiation injury mediated by integrin survival signaling. The studies on endothelial cell proliferation, migration, tube formation, apoptosis, and clonogenic survival also show that the radiosensitivity of endothelial cells is enhanced by the concurrent administration of the integrin antagonist. It can be shown that promissing in vitro data (shown in FIG. 22) can be successfully translated into human xenograft modells, e.g. the epidermoid (A431), xenograft model growing s.c. on BALB/c-nu/nu mice as shown in FIG. 20 and FIG. 21. Suitable reagents and methods for these experiments are known in the art.

The experiments are preferably carried out as described below or in an analogous manner thereof:

Reagents and cell culture. Primary isolated HUVECs and human dermal microvascular endothelial cells (HDMEC; Promocell, Heidelberg, Germany) are cultured up to passage 5. Cells are maintained in culture at 37jC with 5% CO2 and 95% humidity in serum reduced (5% FCS) modified Promocell medium supplemented with 2 ng/mL VEGF and 4 ng/mL basic fibroblast growth factor (bFGF; refs. 1, 30, 31). Human prostate (PC3), glioma (U87), and vulva (A431) tumor cells (Tumorbank DKFZ, Heidelberg, Germany) are cultured in DMEM medium (10% FCS). All experiments are carried out with HUVEC (up to passage 5) and a selection of experiments is confirmed using HDMEC (up to passage 6).

Matrigel invasion, migration, and coculture experiments. Invasion of HUVEC and HDMEC in vitro is measured on Matrigel-coated (0.78 mg/mL) transwell inserts with 8 Am pore size (Becton Dickinson, Heidelberg, Germany). Cells are trypsinized and 200 AL of cell suspension (3_105 cells/mL) per experiment are added to transwells in triplicate. Chemoattractant medium containing VEGF and bFGF (500 AL) is added to the lower wells. For coculture studies, PC3 cells are seeded in 24-well plates and, after irradiation of PC3 cells, Matrigel-coated transwells with endothelial cells are added to the upper compartment. After 18 hours of incubation, endothelial cells that have invaded the underside of the membrane are fixed and stained with Diff-Quik II solution (Dade Behring) and sealed on slides. Migrating cells are counted by microscopy.

Animal studies. Animal studies are done according to the rules for care and use of experimental animals and approved by the local and governmental Animal Care Committee instituted by the German government (Regierungspraesidium, Karlsruhe). For tumor growth experiments with s.c. growing human xenotransplants, athymic 8-week-old, 20 g BALB/c-nu/nu mice are obtained from Charles River Laboratories (Sulzfeld, Germany). Human PC3 prostate carcinoma cells, U87 glioblastoma cells, and A431 vulva carcinoma cells are injected s.c. into the right hind limb (1-5_106 cells in 100 AL PBS). Animals are randomized for therapy when tumor volume reaches 200 mm³ as determined thrice weekly by direct measurement with calipers and calculated by the formula volume V=length_width_width_0.5. Starting on day 0, the respective drug is administered s.c. as given below. Radiotherapy (5_2.5 Gy) is delivered on 5 consecutive days using a Co-60 source (Siemens, Gammatron, Erlangen, Germany), or as given below.

Combination efficacy of Cilengitide & Erbitux in carcinoma xenograft, optionally in combination with Radiotherapy (Rx) is preferably determined as follows:

A431 human epidermoid carcinoma s.c. on balb c nu nu mouse is treated with Erbitux (cetuximab) in an amount of 25 mg/kg (=0.5 mg/animal), administered i.p. on day 1 (4 h before radiotherapy (Rx), if the optional radiotherapy is also applied), day 8, day 15 and day 22; Cilengitide (cyclo-(Arg-Gly-Asp-DPhe-NMe-Val)) is administered i.p. in an amount of: 25 mg/kg 20 times, preferably on 5 consecutive days per week (20×5/w), preferably 1-2 h before radiotherapy (Rx), if the optional radiotherapy is also applied.

Further reference, especially with respect to the methodology, is given to the Literature given below, which is included in the disclosure of this application in its entirety by reference:

Abdollahi et al., CANCER RESEARCH 63, 8890-8898, Dec. 15, 2003

Abdollahi et al., Cancer Res 2005; 65: (9). May 1, 2005

Abdollahi et al., Clin Cancer Res 2005;11(17) Sep. 1, 2005

Hallahan et al, Int. J. Radiation Oncology Biol. Phys., Vol. 65, No. 5, pp. 1536-1543, 2006

Abdollahi et al, Clin Cancer Res 2211 2008;14(7) Apr. 1, 2008

Example 12

Figure 22:
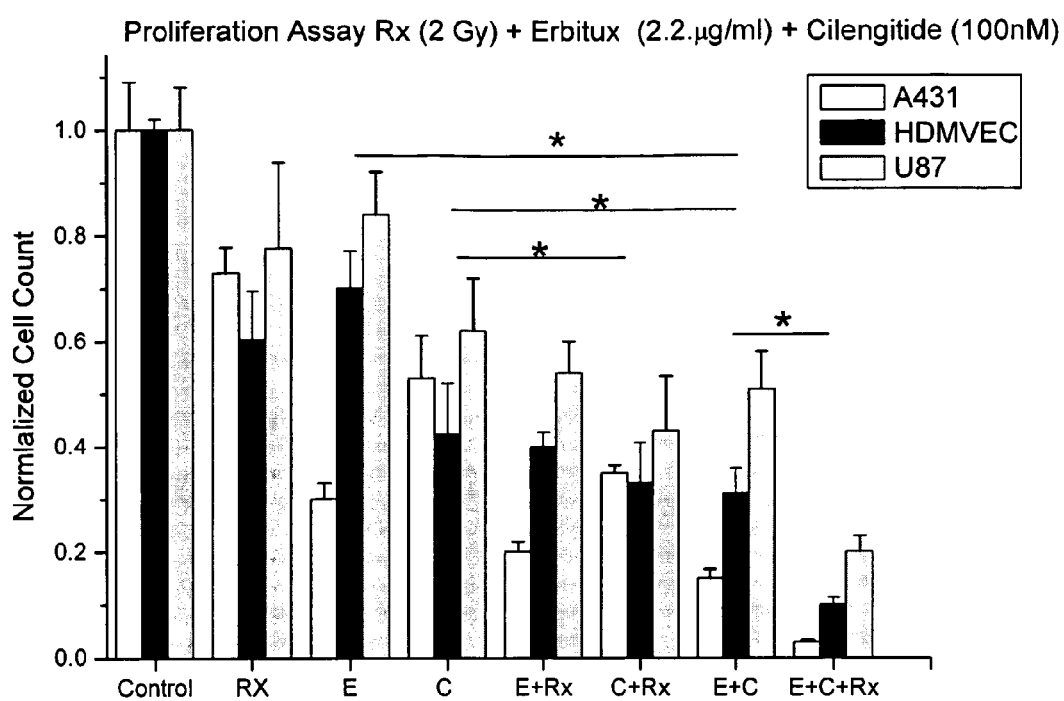
FIG. 22 shows the Combination efficacy of Cilengitide & Erbitux in A431/HDMVEC/U87 proliferation assay, optionally in combination with Radiotherapy (Rx). (See Example 12).

Combination Efficacy of Cilengitide & Erbitux in A431/HDMVEC/U87 Proliferation Assay, Optionally in Combination With Radiotherapy (Rx). These Results are Shown in FIG. 22

Cell proliferation assays were run with A431, HDMVEC and U87 cell lines, respectively, with either Erbitux (at a concentration of 2.2 μg/ml) or Cilengitide (at a concentration of 100 nM) or both, optionally in combination with radiotherapy (Rx=2 Gy), against the untreated control or radiotherapy Rx alone. FIG. 20 shows the advantageous and preferably synergistic effect of all the combinations and especially of the combination of Erbitux and Cilengitide and the combination of Erbitux, Cilengitide and radiotherapy.

Example 13

Effect of αv Integrin Ligand Cilengitide and Etoposide on HUVEC Cell Proliferation. These Results are Shown in FIG. 23

HUVEC cells were cultured on vitronectin-coated wells in Medium 199 containing 2% FSC and 10 ng/ml FGF-2 in the presence or absence of αv integrin ligand Cilengitide and the respective chemotherapeutic agent alone or in combination. Relative cell number was determined by Alamar Blue reduction.

Figure 23:
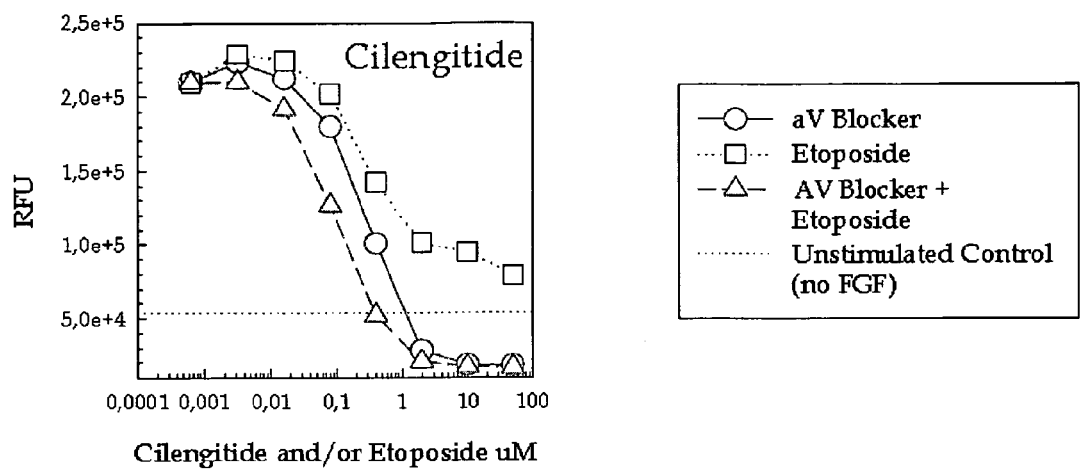
FIG. 23 shows the Effect of αv integrin ligand Cilengitide and etoposide on HUVEC cell proliferation. HUVEC cells were cultured on vitronectin-coated wells in Medium 199 containing 2% FSC and 10 ng/ml FGF-2 in the presence or absence of Cilengitide and the respective chemotherapeutic agent alone or in combination. Relative cell number was determined by Alamar Blue reduction. Cilengitide and etoposide act synergistically to inhibit HUVEC endothelial cell proliferation. Data presented in the graph is additionally represented as isobologram. Dm=drug concentration at medium effect. Combination Index (CI) <1 (here: CI=0.4) indicates synergy. (See Example 13).
Figure 23:
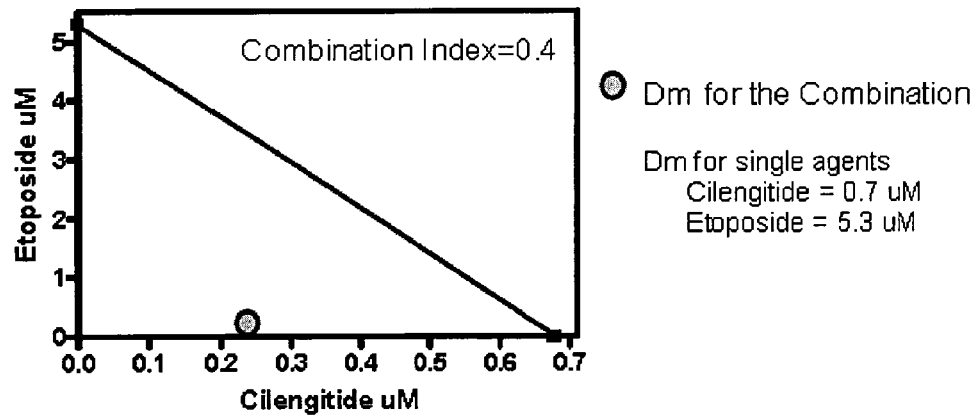

As is shown by the isobologram in FIG. 23, αv integrin ligand Cilengitide and etoposide act synergistically to inhibit HUVEC endothelial cell proliferation. The data for the eye isobologram is taken from the graph on top of FIG. 23 and is analysed according to Chou and Talalay [1]. Dm=drug concentration at medium effect. The Combination Index (CI) <1 (here CI=0.4) indicates synergy for this combination.

Example 14

Figure 24:
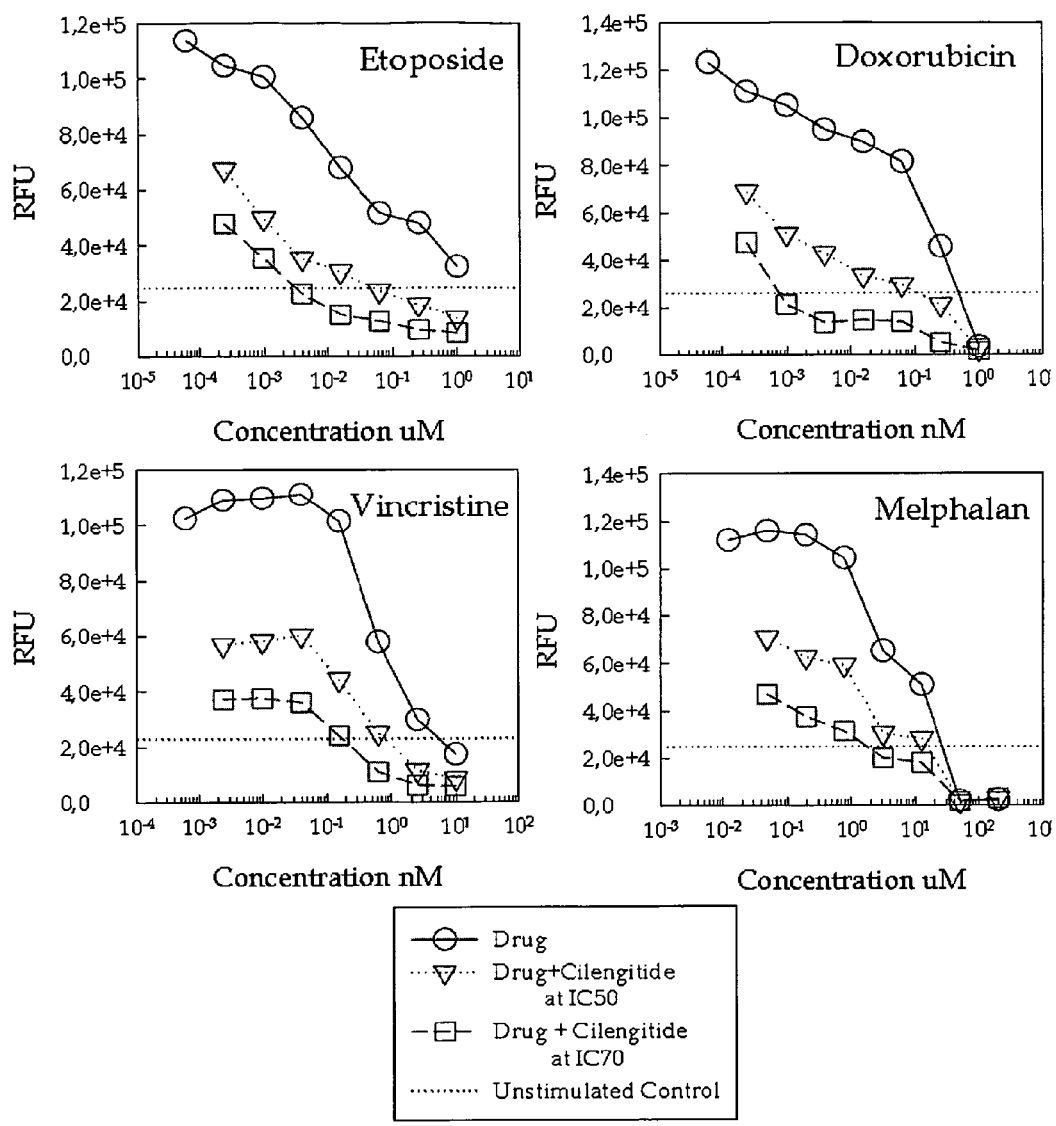
FIG. 24 shows the Effect of αv integrin ligand Cilengitide and the Drugs etoposide, doxorubicine, vincristine or melphalan on HUVEC cell proliferation. HUVEC cells were cultured on vitronectin-coated wells in Medium 199 containing 2% FSC and 10 ng/ml FGF-2 in the presence or absence of Cilengitide and the respective chemotherapeutic agents (Drug) alone or in combination with a constant concentration ($IC_{50}$ or $IC_{70}$) of Cilengitide. Related cell number was determined by Alamar Blue reduction. (See Example 14).

Effect of αv Integrin Ligand Cilengitide and the Drugs Etoposide, Doxorubicine, Vincristine or Melphalan on HUVEC Cell Proliferation. These Results are Shown in FIG. 24

HUVEC cells were cultured on vitronectin-coated wells in Medium 199 containing 2% FSC and 10 ng/ml FGF-2 in the presence or absence of αv integrin ligand Cilengitide and the respective chemotherapeutic agents (Drug) alone or in combination with a constant concentration ($IC_{50}$ or $IC_{70}$) of Cilengitide. Relative cell number was determined by Alamar Blue reduction.

Example 15

Figure 25:
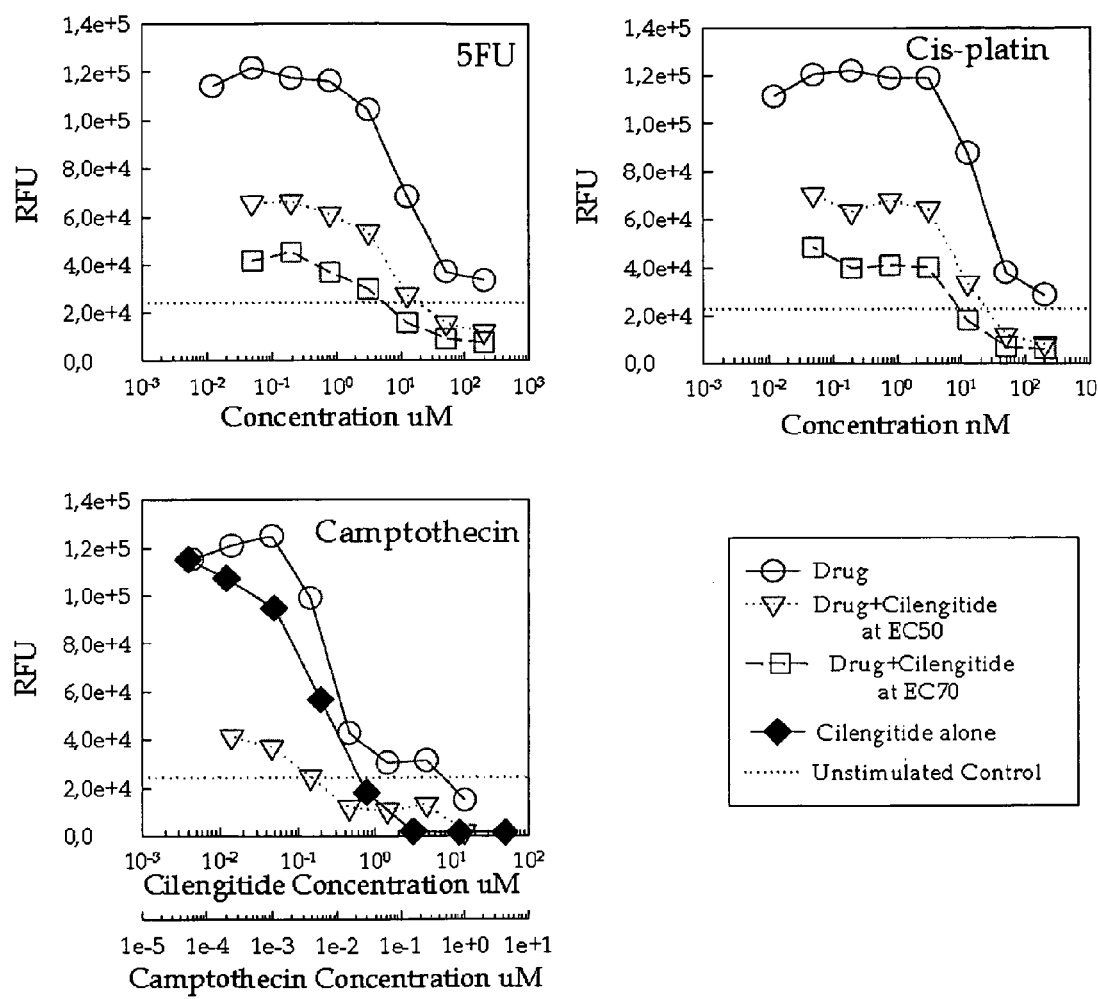
FIG. 25 shows the Effect of αv integrin ligand Cilengitide and the Drugs 5-FU, Cisplatin or Camptothecin on HUVEC cell proliferation. HUVEC cells were cultured on vitronectin-coated wells in Medium 199 containing 2% FSC and 10 ng/ml FGF-2 in the presence or absence of Cilengitide and the respective chemotherapeutic agents (Drug) alone or in combination with a constant concentration($IC_{50}$ or $IC_{70}$) of Cilengitide. Related cell number was determined by Alamar Blue reduction. (See Example 15).

Effect of αv Integrin Ligand Cilengitide and the Drugs 5-FU, Cisplatin or Camptothecin on HUVEC Cell Proliferation. These Results are Shown in FIG. 25

HUVEC cells were cultured on vitronectin-coated wells in Medium 199 containing 2% FSC and 10 ng/ml FGF-2 in the presence or absence of αv integrin ligand Cilengitide and the respective chemotherapeutic agents (Drug) alone or in combination with a constant concentration ($IC_{50}$ or $IC_{70}$) of Cilengitide. Related cell number was determined by Alamar Blue reduction.

Example 16

Figure 26:
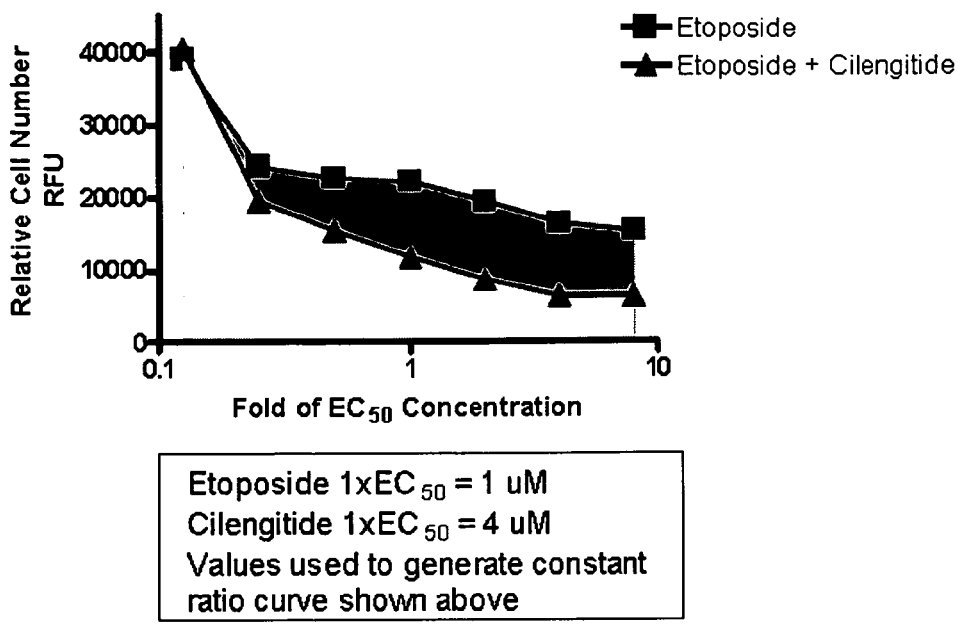
FIG. 26 shows the constant ratio assay with etoposide and Cilengitide combinations on HUVEC cells grown in complete EGM MV medium, analysis performed according to Chou and Talalay. Dm=drug concentration at median effect according to CalcuSyn software analysis. (See Example 16).
Figure 26:
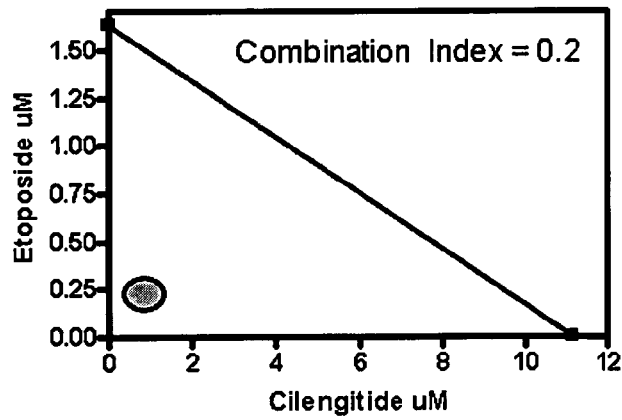

Effect of αv Integrin Ligand Cilengitide and Etoposide on HUVEC Cell Proliferation. These Results are Shown in FIG. 26

Constant ratio assay with docetaxel/paclitaxel and Cilengitide combinations on HUVEC endothelial cells grown in complete EGM MV medium, analysis according to Chou and Talalay [1] shows synergistic effect in FIG. 24 graph and isobologram (CI=0.2).

Example 17

Figure 27:
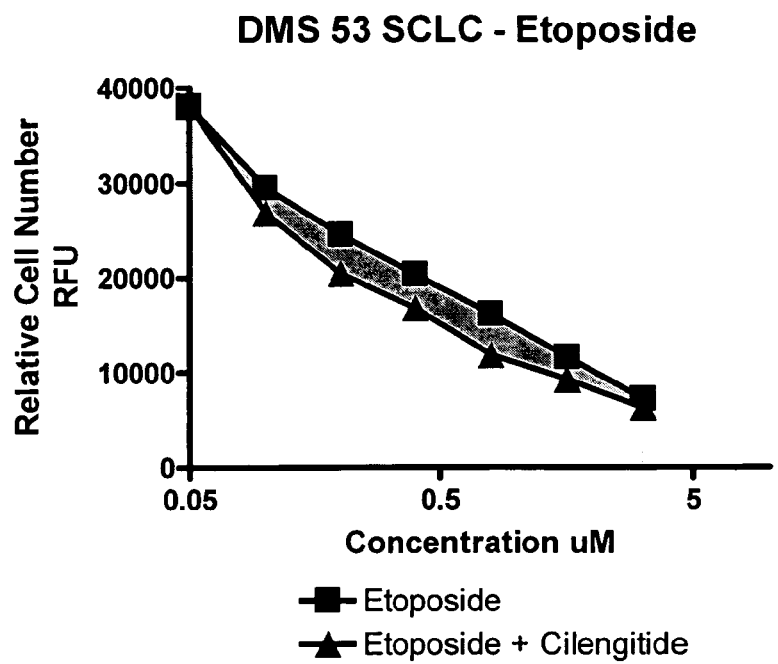
FIG. 27 shows a Constant Ratio Proliferation Assay; Cells were cultured 72 hr in the presence of etoposide or cisplatin alone or in combination with Cilengitide at a fixed ratio. Cell number was determined by Alamar Blue reduction. X-axis shows the concentration of chemotherapeutic agent used. Cilengitide concentration was in a ratio of 0.4:1 for etoposide: Cilengitide and 1:0.5 for cisplatin:Cilengitide. (See Example 17).
Figure 27:
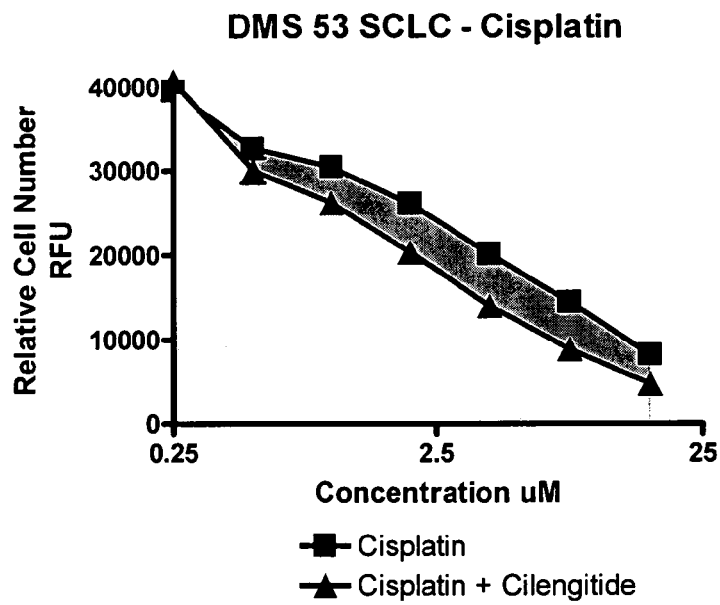

Effect of αv Integrin Ligand Cilengitide and Cisplatin or Etoposide on SCLC Cell Proliferation. These Results are Shown in FIG. 27

Constant Ratio Proliferation Assay: DMS 53 SCLC cells were cultured 72 hr in the presence of etoposide or cisplatin alone or in combination with Cilengitide at a fixed ratio. Cell number was determined by Alamar Blue reduction.
X-axis shows the concentration of chemotherapeutic agent used. The Cilengitide concentration was in a ratio of 0.4:1 for etoposide:Cilengitide and 1:0.5 for cisplatin:Cilengitide.

Example 18

Study 007: MDA-MB-468—Primary Tumor Growth

Figure 28:
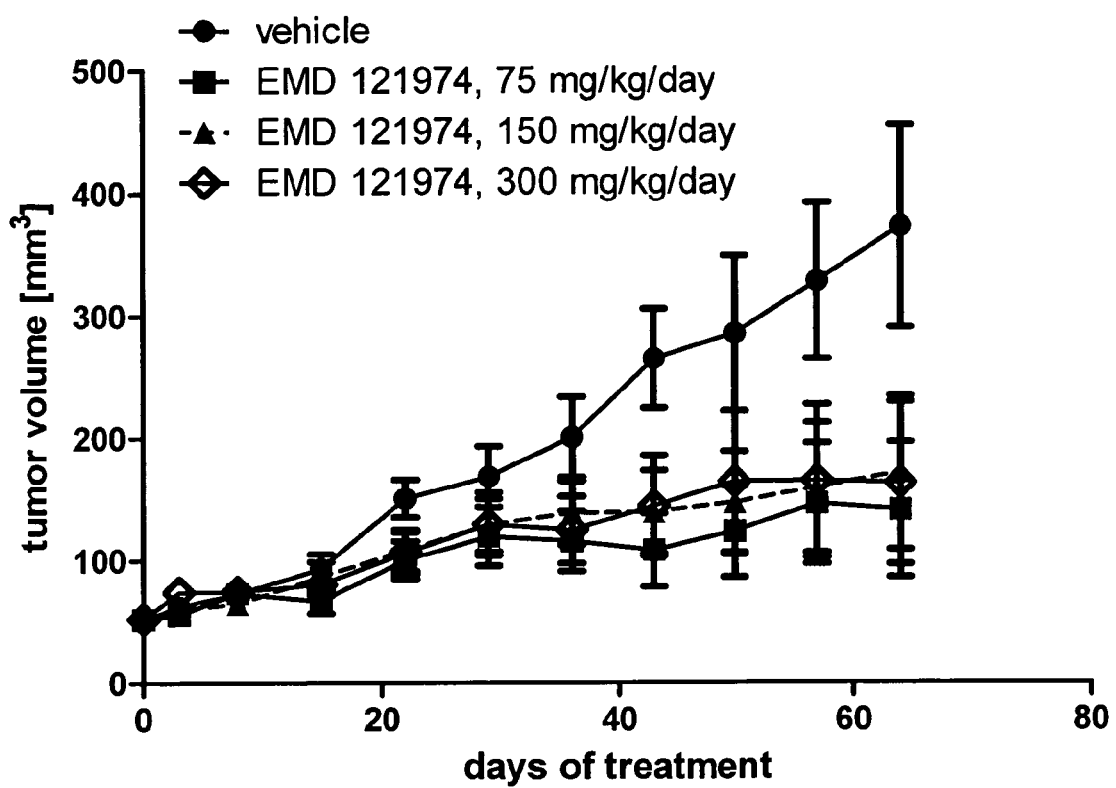
FIG. 28 shows that daily treatment with EMD 121974 (Cilengitide) inhibited primary tumour growth of MDA-MGB-468 tumors in all three dosing groups (75, 150 and 300 mg/kg). (See Example 18).

MDA-MB468 human breast tumour cells were orthotopically inoculated into the third mammary fat pad of female BALB/c nu/nu mice. The mice were randomised into groups when the tumors reached a size of approximately 40 mm³.
The mice in each group received treatment with either Vehicle Control (Placebo) or EMD 121974 (75, 150 or 300 mg/kg) by daily subcutaneous injection. Body weight and tumour volume measurements were made for all mice three times per week.
Result: Daily treatment with EMD 121974 inhibited tumor growth of MDA-MB-468 tumors (tumour volume for all three dosing groups (75, 150 or 300 mg/kg) below 200 mm³ on day 60, tumour volume for Vehicle Control higher than 350 mm³ on day 60. Results are shown in detail in FIG. 28.

The invention claimed is:

1. A method of treating bone metastasis in a subject, comprising administering to said subject a Peptide of the formula Cyclo-(Arg-Gly-Asp-DPhe-NMe-Val) and/or the pharmaceutically acceptable, solvates and/or salts thereof, and one or more cancer therapeutic agents, selected from the group consisting of: osteoclast activity modulating agents.

2. The method according to claim 1, wherein the osteoclast activity modulating agents are selected from the group consisting of bisphosphonates and RANK/RANKL/OPG modulators.

3. The method of claim 2, wherein the bisphosphonates are selected from the group consisting of: Etidronate, Clodronate, Tiludronate, Pamidronate, Neridronate, Olpadronate, Alendronate, Ibandronate, Risedronate, Zoledronate and/or the pharmaceutically acceptable solvates or salts thereof and/or the RANK/RANKL/OPG modulators are selected from the group consisting of: Denosumab and/or the pharmaceutically acceptable solvates and/or salts thereof.

4. The method according to claim 3, additionally comprising administering to the subject radiotherapy.

5. The method according to claim 1, wherein the Peptide of the formula Cyclo-(Arg-Gly-Asp-DPhe-NMe-Val) and/or the pharmaceutically acceptable solvates and/or salts thereof is administered to a subject in an amount of 250 mg to 12500 mg per week.

6. The method according to claim 1, wherein the Peptide of the formula Cyclo-(Arg-Gly-Asp-DPhe-NMe-Val) and/or the pharmaceutically acceptable derivatives, solvates and/or salts thereof is administered to a subject in an amount of 800 mg to 8000 mg per week.

7. The method according to claim 1, wherein the Peptide of the formula Cyclo-(Arg-Gly-Asp-DPhe-NMe-Val) and/or the pharmaceutically acceptable solvates and/or salts thereof is administered to a subject in an amount of 1500 mg to 7000 mg per week.

8. The method according to claim 1, wherein the Peptide of the formula Cyclo-(Arg-Gly-Asp-DPhe-NMe-Val) and/or the pharmaceutically acceptable solvates and/or salts thereof is administered to a subject in a twice weekly to four times weekly administration scheme consisting of about 500 mg or about 2000 mg per administration.

9. The method according to claim 1, wherein the Peptide of the formula Cyclo-(Arg-Gly-Asp-DPhe-NMe-Val) and/or the pharmaceutically acceptable solvates and/or salts thereof is administered to a subject in a once weekly to three times weekly administration scheme consisting of about 500 mg or about 2000 mg per administration.

10. The method according to claim 1, wherein the Peptide of the formula Cyclo-(Arg-Gly-Asp-DPhe-NMe-Val) and/or the pharmaceutically acceptable solvates and/or salts thereof is administered to a subject in a once weekly to five times weekly administration scheme consisting of about 500 mg or in a once weekly to three times weekly administration scheme consisting of about 2000 mg per administration.

11. The method according to claim 1, wherein the Peptide of the formula Cyclo-(Arg-Gly-Asp-DPhe-NMe-Val) and/or the pharmaceutically acceptable solvates and/or salts thereof is administered to a subject 1 to 20 hours prior to the application of the one or more cancer chemotherapeutic agents.

12. The method according to claim 1, said method further comprising administering to the subject radiotherapy.

13. The method according to claim 1, wherein said subject is a human subject.

* * * * *

SEQUENCE LISTING

```
<160> NUMBER OF SEQ ID NOS: 7

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
ggatatgttg ggatagtt                                                    18

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
ccaaaaaccc caaaccc                                                     17

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
tttgtgtttt gatgtttgta ggtttttgt                                        29
```

```
-continued

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
aactccacac tcttccaaaa acaaaaca                                              28

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
tttcgacgtt cgtaggtttt cgc                                                   23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gcactcttcc gaaaacgaaa cg                                                    22

<210> SEQ ID NO 7
<211> LENGTH: 5
<212> TYPE: PRT
<213> ORGANISM: Artificial Sequence
<220> FEATURE:
<223> OTHER INFORMATION: primer
<220> FEATURE:
<223> OTHER INFORMATION: cyclic peptide
<220> FEATURE:
<221> NAME/KEY: misc_feature
<222> LOCATION: (4)
<223> OTHER INFORMATION: Xaa is D-Phe and Val is N-methylated Val

<400> SEQUENCE: 7

Arg Gly Asp Xaa Val
1               5
```